(12) United States Patent
Mills

(10) Patent No.: US 9,563,746 B2
(45) Date of Patent: Feb. 7, 2017

(54) SYSTEM AND METHOD OF COMPUTING AND RENDERING THE NATURE OF DIPOLE MOMENTS, CONDENSED MATTER, AND REACTION KINETICS

(75) Inventor: Randell L. Mills, Princeton, NJ (US)

(73) Assignee: BRILLIANT LIGHT POWER, INC., Cranbury, NJ (US)

(*) Notice: Subject to any disclaimer, the term of this patent is extended or adjusted under 35 U.S.C. 154(b) by 992 days.

(21) Appl. No.: 12/567,450

(22) Filed: Sep. 25, 2009

(65) Prior Publication Data

US 2010/0121619 A1  May 13, 2010

Related U.S. Application Data

(60) Provisional application No. 61/100,103, filed on Sep. 25, 2008, provisional application No. 61/105,640, filed on Oct. 15, 2008, provisional application No. 61/114,666, filed on Nov. 14, 2008, provisional application No. 61/119,677, filed on Dec. 3, 2008, provisional application No. 61/140,403, filed on Dec. 23, 2008, provisional application No. 61/146,953, filed on Jan. 23, 2009, provisional application No. 61/155,399, filed on Feb. 25, 2009.

(51) Int. Cl.
*G01N 33/50* (2006.01)
*G06F 19/00* (2011.01)

(52) U.S. Cl.
CPC .................................. *G06F 19/701* (2013.01)

(58) Field of Classification Search
None
See application file for complete search history.

(56) References Cited

U.S. PATENT DOCUMENTS

| | | | |
|---|---|---|---|
| 6,690,705 B2 * | 2/2004 | Maksimov et al. | 372/69 |
| 7,188,033 B2 * | 3/2007 | Mills | 702/22 |
| 2007/0219768 A1 * | 9/2007 | Ekins et al. | 703/11 |

FOREIGN PATENT DOCUMENTS

JP   2002008892   *   1/2002

OTHER PUBLICATIONS

Zhigilei et al. Computer Simulations of Laser Ablation of Molecular Substrates, 2003, Chemical Reviews, No. 103, pp. 321-347.*
Kao et al. A Versatile, Efficient, and Interactive Program to Build Molecular Structures for Theoretical Calculations and Chemical Information Systems, J. Chem. Inf. Comput. Sci. 1985, 25, pp. 400-410.*

* cited by examiner

*Primary Examiner* — Jason Sims
(74) *Attorney, Agent, or Firm* — Finnegan, Henderson, Farabow, Garrett & Dunner, LLP.

(57) ABSTRACT

A method and system of physically solving the charge, mass, and current density functions of organic molecules using Maxwell's equations and computing and rendering the physical nature of the chemical bond using the solutions. The solutions can be used to solve the dipole moments in molecules or induced dipole moments between species that in turn can be used to solve condensed matter parameters and reaction kinetics. The results can be displayed on visual or graphical media. The display can be static or dynamic such that electron motion and specie's vibrational, rotational, and translational motion can be displayed in an embodiment. The displayed information is useful to anticipate reactivity and physical properties. The insight into the nature of the chemical bond of at least one species can permit the solution and display of those of other species to provide utility to anticipate their reactivity and physical properties.

23 Claims, 17 Drawing Sheets

+Y

+X

A

B

Increasing Electron Density

A

B

A    B (A)

(B)

SYSTEM AND METHOD OF COMPUTING AND RENDERING THE NATURE OF DIPOLE MOMENTS, CONDENSED MATTER, AND REACTION KINETICS

CROSS-REFERENCES TO RELATED APPLICATIONS

This application claims priority to U.S. Application Nos. 61/100,103 filed Sep. 25, 2008; 61/105,640 filed Oct. 15, 2008; 61/114,666 filed Nov. 14, 2008; 61/119,677 filed Dec. 3, 2008; 61/140,403 filed Dec. 23, 2008; 61/146,953 filed Jan. 23, 2009; 61/155,399 filed Feb. 25, 2009, the complete disclosures of which are incorporated herein by reference.

FIELD OF THE INVENTION

This invention relates to a system and method of physically solving the charge, mass, current density functions, and dipole moments of polyatomic molecules, polyatomic molecular ions, diatomic molecules, molecular radicals, molecular ions, or any portion of these species including in condensed matter and undergoing reaction, and computing and rendering the nature of these species using the solutions. The results can be displayed on visual or graphical media. The displayed information provides insight into the nature of these species and is useful to anticipate their reactivity, physical properties, and spectral absorption and emission, and permits the solution and display of other compositions of matter.

Rather than using postulated unverifiable theories that treat atomic particles as if they were not real, physical laws are now applied to atoms and ions. In an attempt to provide some physical insight into atomic problems and starting with the same essential physics as Bohr of the e⁻ moving in the Coulombic field of the proton, a classical solution to the bound electron is derived which yields a model that is remarkably accurate and provides insight into physics on the atomic level. The proverbial view deeply seated in the wave-particle duality notion that there is no large-scale physical counterpart to the nature of the electron is shown not to be correct. Physical laws and intuition may be restored when dealing with the wave equation and quantum atomic problems.

Specifically, a theory of classical physics (CP) was derived from first principles as reported previously [reference Nos. 1-13] that successfully applies physical laws to the solution of atomic problems that has its basis in a breakthrough in the understanding of the stability of the bound electron to radiation. Rather than using the postulated Schrödinger boundary condition: "$\Psi \to 0$ as $r \to \infty$", which leads to a purely mathematical model of the electron, the constraint is based on experimental observation. Using Maxwell's equations, the structure of the electron is derived as a boundary-value problem wherein the electron comprises the source current of time-varying electromagnetic fields during transitions with the constraint that the bound n=1 state electron cannot radiate energy. Although it is well known that an accelerated point particle radiates, an extended distribution modeled as a superposition of accelerating charges does not have to radiate. A simple invariant physical model arises naturally wherein the predicted results are extremely straightforward and internally consistent requiring minimal math, as in the case of the most famous equations of Newton and Maxwell on which the model is based. No new physics is needed; only the known physical laws based on direct observation are used.

Applicant's previously filed WO2005/067678 discloses a method and system of physically solving the charge, mass, and current density functions of atoms and atomic ions and computing and rendering the nature of these species using the solutions. The complete disclosure of this published PCT application is incorporated herein by reference.

Applicant's previously filed WO2005/116630 discloses a method and system of physically solving the charge, mass, and current density functions of excited states of atoms and atomic ions and computing and rendering the nature of these species using the solutions. The complete disclosure of this published PCT application is incorporated herein by reference.

Applicant's previously filed U.S. Published Patent Application No. 2005/0209788A1, relates to a method and system of physically solving the charge, mass, and current density functions of hydrogen-type molecules and molecular ions and computing and rendering the nature of the chemical bond using the solutions. The complete disclosure of this published application is incorporated herein by reference.

Applicant's previously filed WO2007/051078 discloses a method and system of physically solving the charge, mass, and current density functions of polyatomic molecules and polyatomic molecular ions and computing and rendering the nature of these species using the solutions. The complete disclosure of this published PCT application is incorporated herein by reference. This incorporated application discloses complete flow charts and written description of a computer program and systems that can be modified using the novel equations and description below to physically solve the charge, mass, and current density functions of the specific groups of molecules and molecular ions disclosed herein and computing and rendering the nature of the specific groups of molecules and molecular ions disclosed herein.

BACKGROUND OF THE INVENTION

The old view that the electron is a zero or one-dimensional point in an all-space probability wave function $\Psi(x)$ is not taken for granted. Rather, atomic and molecular physics theory, derived from first principles, must successfully and consistently apply physical laws on all scales [1-13]. Stability to radiation was ignored by all past atomic models, but in this case, it is the basis of the solutions wherein the structure of the electron is first solved and the result determines the nature of the atomic and molecular electrons involved in chemical bonds. Historically, the point at which quantum mechanics broke with classical laws can be traced to the issue of nonradiation of the one electron atom. Bohr just postulated orbits stable to radiation with the further postulate that the bound electron of the hydrogen atom does not obey Maxwell's equations—rather it obeys different physics [1-13]. Later physics was replaced by "pure mathematics" based on the notion of the inexplicable wave-particle duality nature of electrons which lead to the Schrödinger equation wherein the consequences of radiation predicted by Maxwell's equations were ignored. Ironically, Bohr, Schrödinger, and Dirac used the Coulomb potential, and Dirac used the vector potential of Maxwell's equations. But, all ignored electrodynamics and the corresponding radiative consequences. Dirac originally attempted to solve the bound electron physically with stability with respect to radiation according to Maxwell's equations with the further constraints that it was relativistically invariant and gave rise to electron spin [14]. He and many founders of QM such as Sommerfeld, Bohm, and Weinstein wrongly pursued a planetary model, were unsuccessful, and resorted to the current mathematical-probability-wave model that has many problems [1-18]. Consequently, Feynman for example, attempted to use first principles including Maxwell's equations to discover new physics to replace quantum mechanics [19].

Starting with the same essential physics as Bohr, Schrödinger, and Dirac of e_ moving in the Coulombic field of the proton and an electromagnetic wave equation and matching electron source current rather than an energy diffusion equation originally sought by Schrödinger, advancements in the understanding of the stability of the bound electron to radiation are applied to solve for the exact nature of the electron. Rather than using the postulated Schrödinger boundary condition: "Ψ→0 as r→∞", which leads to a purely mathematical model of the electron, the constraint is based on experimental observation. Using Maxwell's equations, the structure of the electron is derived as a boundary-value problem wherein the electron comprises the source current of time-varying electromagnetic fields during transitions with the constraint that the bound n=1 state electron cannot radiate energy. Although it is well known that an accelerated point particle radiates, an extended distribution modeled as a superposition of accelerating charges does not have to radiate. The physical boundary condition of nonradiation of that was imposed on the bound electron follows from a derivation by Haus [20]. The function that describes the motion of the electron must not possess spacetime Fourier components that are synchronous with waves traveling at the speed of light. Similarly, nonradiation is demonstrated based on the electron's electromagnetic fields and the Poynting power vector. A simple invariant physical model arises naturally wherein the results are extremely straightforward, internally consistent, and predictive of conjugate parameters for the first time, requiring minimal math as in the case of the most famous exact equations (no uncertainty) of Newton and Maxwell on which the model is based. No new physics is needed; only the known physical laws based on direct observation are used.

The structure of the bound atomic electron was solved by first considering one-electron atoms [1-13]. Since the hydrogen atom is stable and nonradiative, the electron has constant energy. Furthermore, it is time dynamic with a corresponding current that serves as a source of electromagnetic radiation during transitions. The wave equation solutions of the radiation fields permit the source currents to be determined as a boundary-value problem. These source currents match the field solutions of the wave equation for two dimensions plus time when the nonradiation condition is applied. Then, the mechanics of the electron can be solved from the two-dimensional wave equation plus time in the form of an energy equation wherein it provides for conservation of energy and angular momentum as given in the Electron Mechanics and the Corresponding Classical Wave Equation for the Derivation of the Rotational Parameters of the Electron section of Ref. [1]. Once the nature of the electron is solved, all problems involving electrons can be solved in principle. Thus, in the case of one-electron atoms, the electron radius, binding energy, and other parameters are solved after solving for the nature of the bound electron.

For time-varying spherical electromagnetic fields, Jackson [21] gives a generalized expansion in vector spherical waves that are convenient for electromagnetic boundary-value problems possessing spherical symmetry properties and for analyzing multipole radiation from a localized source distribution. The Green function $G(x',x)$ which is appropriate to the equation $$(\nabla^2+k^2)G(x',x)=-\delta(x'-x) \tag{1}$$

in the infinite domain with the spherical wave expansion for the outgoing wave Green function is $$G(x',x) = \frac{e^{-ik|x-x'|}}{4\pi|x-x'|} \tag{2}$$

$$= ik \sum_{l=0}^{\infty} j_l(kr_<)h_l^{(1)}(kr_>) \sum_{m=-l}^{l} Y_{l,m}^*(\theta', \phi')Y_{l,m}(\theta, \phi)$$

Jackson [21] further gives the general multipole field solution to Maxwell's equations in a source-free region of empty space with the assumption of a time dependence $e^{i\omega_n t}$:

$$B = \sum_{l,m} \left[ a_E(l, m)f_l(kr)X_{l,m} - \frac{i}{k}a_M(l, m)\nabla \times g_l(kr)X_{l,m} \right] \tag{3}$$

$$E = \sum_{l,m} \left[ \frac{i}{k} a_E(l, m)\nabla \times f_l(kr)X_{l,m} + a_M(l, m)g_l(kr)X_{l,m} \right]$$

where the cgs units used by Jackson are retained in this section. The radial functions $f_l(kr)$ and $g_l(kr)$ are of the form:

$$g_l(kr)=A_l^{(1)}h_l^{(1)}+A_l^{(2)}h_l^{(2)} \tag{4}$$

$X_{l,m}$ is the vector spherical harmonic defined by $$X_{l,m}(\theta, \phi) = \frac{1}{\sqrt{l(l+1)}} LY_{l,m}(\theta, \phi) \tag{5}$$

where $$L = \frac{1}{i}(r \times \nabla) \tag{6}$$

The coefficients $a_E(l,m)$ and $a_M(l,m)$ of Eq. (3) specify the amounts of electric (l,m) multipole and magnetic (l,m) multipole fields, and are determined by sources and boundary conditions as are the relative proportions in Eq. (4). Jackson gives the result of the electric and magnetic coefficients from the sources as $$a_E(l, m) = \frac{4\pi k^2}{i\sqrt{l(l+1)}} \int Y_l^{m*} \left\{ \begin{array}{l} \rho\frac{\partial}{\partial r}[rj_l(kr)] + \\ \frac{ik}{c}(r \cdot J)j_l(kr) - \\ ik\nabla \cdot (r \times M)j_l(kr) \end{array} \right\} d^3x \tag{7}$$

and $$a_M(l, m) = \frac{-4\pi k^2}{\sqrt{l(l+1)}} \int j_l(kr)Y_l^{m*} L \cdot \left( \frac{J}{c} + \nabla \times M \right) d^3x \tag{8}$$

respectively, where the distribution of charge $\rho(x,t)$, current $J(x,t)$, and intrinsic magnetization $M(x,t)$ are harmonically varying sources: $\rho(x)e^{-i\omega t}$, $J(x)e^{-i\omega t}$, and $M(x)e^{-i\omega t}$.

The electron current-density function can be solved as a boundary value problem regarding the time varying corresponding source current $J(x)e^{-i\omega t}$ that gives rise to the time-varying spherical electromagnetic fields during transitions between states with the further constraint that the electron is nonradiative in a state defined as the n=1 state. The potential energy, $V(r)$, is an inverse-radius-squared relationship given by given by Gauss' law which for a point charge or a two-dimensional spherical shell at a distance r from the nucleus the potential is $$V(r) = -\frac{e^2}{4\pi\varepsilon_0 r} \qquad (9)$$

Thus, consideration of conservation of energy would require that the electron radius must be fixed. Addition constraints requiring a two-dimensional source current of fixed radius are matching the delta function of Eq. (1) with no singularity, no time dependence and consequently no radiation, absence of self-interaction (See Appendix III of Ref. [1]), and exact electroneutrality of the hydrogen atom wherein the electric field is given by $$n \cdot (E_1 - E_2) = \frac{\sigma_s}{\varepsilon_0} \qquad (10)$$

where n is the normal unit vector, $E_1$ and $E_2$ are the electric field vectors that are discontinuous at the opposite surfaces, $\sigma_x$ is the discontinuous two-dimensional surface charge density, and $E_2=0$. Then, the solution for the radial electron function, which satisfies the boundary conditions is a delta function in spherical coordinates—a spherical shell [22]

$$f(r) = \frac{1}{r^2}\delta(r - r_n) \qquad (11)$$

where $r_n$ is an allowed radius. This function defines the charge density on a spherical shell of a fixed radius (See FIG. 1), not yet determined, with the charge motion confined to the two-dimensional spherical surface. The integer subscript n is determined during photon absorption as given in the Excited States of the One-Electron Atom (Quantization) section of Ref. [1]. It is shown in this section that the force balance between the electric fields of the electron and proton plus any resonantly absorbed photons gives the result that $r_n = nr_1$ wherein n is an integer in an excited state.

Given time harmonic motion and a radial delta function, the relationship between an allowed radius and the electron wavelength is given by $$2\pi r_n = \lambda_n \qquad (12)$$

Based on conservation of the electron's angular momentum of, the magnitude of the velocity and the angular frequency for every point on the surface of the bound electron are $$v_n = \frac{h}{m_e \lambda_n} = \frac{h}{m_e 2\pi r_n} = \frac{\hbar}{m_e r_n} \qquad (13)$$

$$\omega_n = \frac{\hbar}{m_e r_n^2} \qquad (14)$$

To further match the required multipole electromagnetic fields between transitions of states, the trial nonradiative source current functions are time and spherical harmonics, each having an exact radius and an exact energy. Then, each allowed electron charge-density (mass-density) function is the product of a radial delta function $$\left(f(r) = \frac{1}{r^2}\delta(r - r_n)\right),$$

two angular functions (spherical harmonic functions $Y_l^m(\theta,\phi) = P_l^m(\cos\theta)e^{im\phi}$), and a time-harmonic function $e^{im\omega_n t}$. The spherical harmonic $Y_0^0(\theta,\phi)=1$ is also an allowed solution that is in fact required in order for the electron charge and mass densities to be positive definite and to give rise to the phenomena of electron spin. The real parts of the spherical harmonics vary between −1 and 1. But the mass of the electron cannot be negative; and the charge cannot be positive. Thus, to insure that the function is positive definite, the form of the angular solution must be a superposition:

$$Y_0^0(\theta,\phi) + Y_l^m(\theta,\phi) \qquad (15)$$

The current is constant at every point on the surface for the s orbital corresponding to $Y_0^0(\theta,\phi)$. The quantum numbers of the spherical harmonic currents can be related to the observed electron orbital angular momentum states. The currents corresponding to s, p, d, f, etc. orbitals are $$l = 0 \qquad (16)$$
$$\rho(r,\theta,\phi,t) = \frac{e}{8\pi r^2}[\delta(r-r_n)][Y_0^0(\theta,\phi) + Y_l^m(\theta,\phi)]$$

$$l \neq 0 \qquad (17)$$
$$\rho(r,\theta,\phi,t) = \frac{e}{4\pi r^2}[\delta(r-r_n)]\begin{bmatrix} Y_0^0(\theta,\phi) + \\ \mathrm{Re}\{Y_l^m(\theta,\phi)e^{im\omega_n t}\} \end{bmatrix}$$

where $Y_l^m(\theta,\phi)$ are the spherical harmonic functions that spin about the z-axis with angular frequency $\omega_n$ with $Y_0^0(\theta,\phi)$ the constant function and $\mathrm{Re}\{Y_l^m(\theta,\phi)e^{im\omega_n t}\} = P_l^m(\cos\theta)\cos(m\phi + m\omega_n t)$.

The Fourier transform of the electron charge-density function is a solution of the four-dimensional wave equation in frequency space (k, ω-space). Then the corresponding Fourier transform of the current-density function $K(s,\Theta,\Phi,\omega)$ is given by multiplying by the constant angular frequency corresponding to a potentially emitted photon.

$$K(s,\Theta,\Phi,\omega) = \qquad (18)$$

$$4\pi\omega_n \frac{\sin(2s_n r_n)}{2s_n r_n} \otimes 2\pi \sum_{\nu=1}^{\infty} \frac{(-1)^{\nu-1}(\pi\sin\Theta)^{2(\nu-1)}}{(\nu-1)!(\nu-1)!} \frac{\Gamma\left(\frac{1}{2}\right)\Gamma\left(\nu+\frac{1}{2}\right)}{(\pi\cos\Theta)^{2\nu+1}2^{\nu+1}}$$

$$\frac{2\nu!}{(\nu-1)!}s^{-2\nu} \otimes 2\pi \sum_{\nu=1}^{\infty} \frac{(-1)^{\nu-1}(\pi\sin\Phi)^{2(\nu-1)}}{(\nu-1)!(\nu-1)!}$$

$$\frac{\Gamma\left(\frac{1}{2}\right)\Gamma\left(\nu+\frac{1}{2}\right)}{(\pi\cos\Phi)^{2\nu+1}2^{\nu+1}} \frac{2\nu!}{(\nu-1)!}s^{-2\nu}\frac{1}{4\pi}[\delta(\omega-\omega_n) + \delta(\omega+\omega_n)]$$

The motion on the orbitsphere is angular; however, a radial correction exists due to special relativistic effects. When the velocity is c corresponding to a potentially emitted photon $$s_n \cdot v_n = s_n \cdot c = \omega_n \qquad (19)$$

the relativistically corrected wavelength is (Eq. (1.247) of Ref. [1])

$$r_n = \lambda_n \quad (20)$$

Substitution of Eq. (20) into the sinc function results in the vanishing of the entire Fourier transform of the current-density function. Thus, spacetime harmonics of $$\frac{\omega_n}{c} = k \text{ or } \frac{\omega_n}{c}\sqrt{\frac{\varepsilon}{\varepsilon_o}} = k$$

for which the Fourier transform of the current-density function is nonzero do not exist. Radiation due to charge motion does not occur in any medium when this boundary condition is met. There is acceleration without radiation. (Also see Abbott and Griffiths and Goedecke [23-24]). Nonradiation is also shown directly using Maxwell's equations directly in Appendix 1 of Ref. [1]. However, in the case that such a state arises as an excited state by photon absorption, it is radiative due to a radial dipole term in its current-density function since it possesses spacetime Fourier transform components synchronous with waves traveling at the speed of light as shown in the Instability of Excited States section of Ref. [1]. The radiation emitted or absorbed during electron transitions is the multipole radiation given by Eq. (2) as given in the Excited States of the One-Electron Atom (Quantization) section and the Equation of the Photon section of Ref. [1] wherein Eqs. (4.18-4.23) give a macro-spherical wave in the far-field.

In Chapter 1 of Ref. [1], the uniform current density function $Y_0^0(\theta,\phi)$ (Eqs. (16-17)) that gives rise to the spin of the electron is generated from two current-vector fields (CVFs). Each CVF comprises a continuum of correlated orthogonal great circle current-density elements (one dimensional "current loops"). The current pattern comprising each CVF is generated over a half-sphere surface by a set of rotations of two orthogonal great circle current loops that serve as basis elements about each of the $$(-i_x, i_y, 0i_z) \text{ and } \left(-\frac{1}{\sqrt{2}}i_x, \frac{1}{\sqrt{2}}i_y, i_z\right) - \text{axis;}$$

the span being π radians. Then, the two CVFs are convoluted, and the result is normalized to exactly generate the continuous uniform electron current density function $Y_0^0(\theta, \phi)$ covering a spherical shell and having the three angular momentum components of $$L_{xy} = +/-\frac{\hbar}{4}(+/-\text{designates both the positive and negative vector directions}$$

along an axis in the $xy$-plane) and $L_z = \frac{\hbar}{2}$.

The z-axis view of a representation of the total current pattern of the $Y_0^0(\theta,\phi)$ orbitsphere comprising the superposition of 144 current elements is shown in FIG. 2A. As the number of great circles goes to infinity the current distribution becomes continuous and is exactly uniform following normalization. A representation of the $$\left(-\frac{1}{\sqrt{2}}i_x, \frac{1}{\sqrt{2}}i_y, i_z\right)\text{-axis}$$

view of the total uniform current-density pattern of the $Y_0^0(\phi,\theta)$ orbitsphere with 144 vectors overlaid on the continuous bound-electron current density giving the direction of the current of each great circle element is shown in FIG. 2B. This superconducting current pattern is confined to two spatial dimensions.

Thus, a bound electron is a constant two-dimensional spherical surface of charge (zero thickness and total charge=−e), called an electron orbitsphere that can exist in a bound state at only specified distances from the nucleus determined by an energy minimum for the n=1 state and integer multiples of this radius due to the action of resonant photons as shown in the Determination of Orbitsphere Radii section and Excited States of the One-Electron Atom (Quantization) section of Ref. [1], respectively. The bound electron is not a point, but it is point-like (behaves like a point at the origin). The free electron is continuous with the bound electron as it is ionized and is also point-like as shown in the Electron in Free Space section of Ref. [1]. The total function that describes the spinning motion of each electron orbitsphere is composed of two functions. One function, the spin function (see FIG. 1 for the charge function and FIG. 2 for the current function), is spatially uniform over the orbitsphere, where each point moves on the surface with the same quantized angular and linear velocity, and gives rise to spin angular momentum. It corresponds to the nonradiative n=1, l=0 state of atomic hydrogen which is well known as an s state or orbital. The other function, the modulation function, can be spatially uniform—in which case there is no orbital angular momentum and the magnetic moment of the electron orbitsphere is one Bohr magneton—or not spatially uniform—in which case there is orbital angular momentum. The modulation function rotates with a quantized angular velocity about a specific (by convention) z-axis. The constant spin function that is modulated by a time and spherical harmonic function as given by Eq. (17) is shown in FIG. 3 for several t values. The modulation or traveling charge-density wave that corresponds to an orbital angular momentum in addition to a spin angular momentum are typically referred to as p, d, f, etc. orbitals and correspond to an l quantum number not equal to zero.

It was shown previously [1-13] that classical physics gives closed form solutions for the atom including the stability of the n=1 state and the instability of the excited states, the equation of the photon and electron in excited states, the equation of the free electron, and photon which predict the wave particle duality behavior of particles and light. The current and charge density functions of the electron may be directly physically interpreted. For example, spin angular momentum results from the motion of negatively charged mass moving systematically, and the equation for angular momentum, r×p, can be applied directly to the wavefunction (a current density function) that describes the electron. The magnetic moment of a Bohr magneton, Stern Gerlach experiment, g factor, Lamb shift, resonant line width and shape, selection rules, correspondence principle, wave-particle duality, excited states, reduced mass, rotational energies, and momenta, orbital and spin splitting, spin-orbital coupling, Knight shift, and spin-nuclear coupling, and elastic electron scattering from helium atoms, are derived in closed form equations based on Maxwell's equations. The agreement between observations and predictions based on closed-form equations with fundamental constants only matches to the limit permitted by the error in the measured fundamental constants.

In contrast to the failure of the Bohr theory and the nonphysical, unpredictive, adjustable-parameter approach of quantum mechanics, multielectron atoms [1, 5] and the nature of the chemical bond [1, 6] are given by exact closed-form solutions containing fundamental constants only. Using the nonradiative electron current-density functions, the radii are determined from the force balance of the electric, magnetic, and centrifugal forces that correspond to the minimum of energy of the atomic or ionic system. The ionization energies are then given by the electric and magnetic energies at these radii. The spreadsheets to calculate the energies from exact solutions of one through twenty-electron atoms are available from the internet [25]. For 400 atoms and ions the agreement between the predicted and experimental results are remarkable [5]. Here I extend these results to the nature of the chemical bond. In this regard, quantum mechanics has historically sought the lowest energy of the molecular system, but this is trivially the case of the electrons inside the nuclei. Obviously, the electrons must obey additional physical laws since matter does not exist in a state with the electrons collapsed into the nuclei. Specifically, molecular bonding is due to the physics of Newton's and Maxwell's laws together with achieving an energy minimum.

The structure of the bound molecular electron was solved by first considering the one-electron molecule $H_2^+$ and then the simplest molecule $H_2$ [1, 6]. The nature of the chemical bond was solved in the same fashion as that of the bound atomic electron. First principles including stability to radiation requires that the electron charge of the molecular orbital is a prolate spheroid, a solution of the Laplacian as an equipotential minimum energy surface in the natural ellipsoidal coordinates compared to spheroidal in the atomic case, and the current is time harmonic and obeys Newton's laws of mechanics in the central field of the nuclei at the foci of the spheroid. There is no a priori reason why the electron position must be a solution of the three-dimensional wave equation plus time and cannot comprise source currents of electromagnetic waves that are solutions of the three-dimensional wave equation plus time. Then, the special case of nonradiation determines that the current functions are confined to two-spatial dimensions plus time and match the electromagnetic wave-equation solutions for these dimensions. In addition to the important result of stability to radiation, several more very important physical results are subsequently realized: (i) The charge is distributed on a two-dimension surface; thus, there are no infinities in the corresponding fields (Eq. (10)). Infinite fields are simply renormalized in the case of the point-particles of quantum mechanics, but it is physically gratifying that none arise in this case since infinite fields have never been measured or realized in the laboratory. (ii) The hydrogen molecular ion or molecule has finite dimensions rather than extending over all space. From measurements of the resistivity of hydrogen as a function of pressure, the finite dimensions of the hydrogen molecule are evident in the plateau of the resistivity versus pressure curve of metallic hydrogen [26]. This is in contradiction to the predictions of quantum probability functions such as an exponential radial distribution in space. Furthermore, despite the predictions of quantum mechanics that preclude the imaging of a molecule orbital, the full three-dimensional structure of the outer molecular orbital of $N_2$ has been recently tomographically reconstructed [27]. The charge-density surface observed is similar to that shown in FIG. 4 for $H_2$ which is direct evidence that MO's electrons are not point-particle probability waves that have no form until they are "collapsed to a point" by measurement. Rather they are physical, two-dimensional equipotential charge density functions as derived herein. (iii) Consistent with experiments, neutral scattering is predicted without violation of special relativity and causality wherein a point must be everywhere at once as required in the QM case. (iv) There is no electron self-interaction. The continuous charge-density function is a two-dimensional equipotential energy surface with an electric field that is strictly normal for the elliptic parameter $\xi>0$ according to Gauss' law and Faraday's law. The relationship between the electric field equation and the electron source charge-density function is given by Maxwell's equation in two dimensions [28,29] (Eq. (10)). This relation shows that only a two-dimensional geometry meets the criterion for a fundamental particle. This is the nonsingularity geometry that is no longer divisible. It is the dimension from which it is not possible to lower dimensionality. In this case, there is no electrostatic self-interaction since the corresponding potential is continuous across the surface according to Faraday's law in the electrostatic limit, and the field is discontinuous, normal to the charge according to Gauss' law [28-30]. (v) The instability of electron-electron repulsion of molecular hydrogen is eliminated since the central field of the hydrogen molecular ion relative to a second electron at $\xi>0$ which binds to form the hydrogen molecule is that of a single charge at the foci. (vi) The ellipsoidal MOs allow exact spin pairing over all time that is consistent with experimental observation. This aspect is not possible in the QM model.

Current algorithms to solve molecules are based on nonphysical models based on the concept that the electron is a zero or one-dimensional point in an all-space probability wave function $\Psi(x)$ that permits the electron to be over all space simultaneously and give output based on trial and error or direct empirical adjustment of parameters. These models ultimately cannot be the actual description of a physical electron in that they inherently violate physical laws. They suffer from the same shortcomings that plague atomic quantum theory, infinities, instability with respect to radiation according to Maxwell's equations, violation of conservation of linear and angular momentum, lack of physical relativistic invariance, and the electron is unbounded such that the edge of molecules does not exist. There is no uniqueness, as exemplified by the average of 150 internally inconsistent programs per molecule for each of the 788 molecules posted on the NIST website [31]. Furthermore, from a physical perspective, the implication for the basis of the chemical bond according to quantum mechanics being the exchange integral and the requirement of zero-point vibration, "strictly quantum mechanical phenomena," is that the theory cannot be a correct description of reality as described for even the simple bond of molecular hydrogen as reported previous [1, 6]. Even the premise that "electron overlap" is responsible for bonding is opposite to the physical reality that negative charges repel each other with an inverse-distance-squared force dependence that becomes infinite. A proposed solution based on physical laws and fully compliant with Maxwell's equations solves the parameters of molecules even to infinite length and complexity in closed form equations with fundamental constants only.

For the first time in history, the key building blocks of organic chemistry have been solved from two basic equations. Now, the true physical structure and parameters of an infinite number of organic molecules up to infinite length and complexity can be obtained to permit the engineering of new pharmaceuticals and materials at the molecular level. The solutions of the basic functional groups of organic chemistry were obtained by using generalized forms of a geometrical and an energy equation for the nature of the H—H bond. The geometrical parameters and total bond energies of about 800 exemplary organic molecules were calculated using the functional group composition. The results obtained essentially instantaneously match the experimental values typically to the limit of measurement [1]. The solved function groups are given in Table 1.

TABLE 1

Partial List of Organic Functional Groups Solved by Classical Physics.

Continuous-Chain Alkanes
Branched Alkanes
Alkenes
Branched Alkenes
Alkynes
Alkyl Fluorides
Alkyl Chlorides
Alkyl Bromides
Alkyl Iodides
Alkenyl Halides
Aryl Halides
Alcohols
Ethers
Primary Amines
Secondary Amines
Tertiary Amines
Aldehydes
Ketones
Carboxylic Acids
Carboxylic Acid Esters
Amides
N-alkyl Amides
N,N-dialkyl Amides
Urea
Carboxylic Acid Halides
Carboxylic Acid Anhydrides
Nitriles
Thiols
Sulfides
Disulfides
Sulfoxides
Sulfones
Sulfites
Sulfates
Nitroalkanes
Alkyl Nitrates
Alkyl Nitrites
Conjugated Alkenes
Conjugated Polyenes
Aromatics
Napthalene
Toluene
Chlorobenzene
Phenol
Aniline
Aryl Nitro Compounds
Benzoic Acid Compounds
Anisole
Pyrrole
Furan
Thiophene
Imidizole
Pyridine
Pyrimidine
Pyrazine
Quinoline
Isoquinoline
Indole
Adenine
Fullerene ($C_{60}$)
Graphite
Phosphines
Phosphine Oxides TABLE 1-continued Partial List of Organic Functional Groups Solved by Classical Physics.

Phosphites
Phosphates

The two basic equations that solves organic molecules, one for geometrical parameters and the other for energy parameters, were applied to bulk forms of matter containing trillions of trillions of electrons. For example, using the same alkane- and alkene-bond solutions as elements in an infinite network, the nature of the solid molecular bond for all known allotropes of carbon (graphite, diamond, $C_{60}$, and their combinations) were solved. By further extension of this modular approach, the solid molecular bond of silicon and the nature of semiconductor bond were solved. The nature of other fundamental forms of matter such as the nature of the ionic bond, the metallic bond, and additional major fields of chemistry such as that of silicon, organometallics, and boron were solved exactly such that the position and energy of each and every electron is precisely specified. The implication of these results is that it is possible using physical laws to solve the structure of all types of matter. Some of the solved forms of matter of infinite extent as well as additional major fields of chemistry are given in Table 2. In all cases, the agreement with experiment is remarkable [1].

TABLE 2

Partial List of Additional Molecules and Compositions of Matter Solved by Classical Physics.

Solid Molecular Bond of the Three Allotropes of Carbon
    Diamond
    Graphite
    Fullerene ($C_{60}$)
Solid Ionic Bond of Alkali-Hydrides
    Alkali-Hydride Crystal Structures
        Lithium Hydride
        Sodium Hydride
        Potassium Hydride
        Rubidium & Cesium Hydride
        Potassium Hydrino Hydride
Solid Metallic Bond of Alkali Metals
    Alkali Metal Crystal Structures
        Lithium Metal
        Sodium Metal
        Potassium Metal
        Rubidium & Cesium Metals
Alkyl Aluminum Hydrides
Silicon Groups and Molecules
    Silanes
    Alkyl Silanes and Disilanes
Solid Semiconductor Bond of Silicon
    Insulator-Type Semiconductor Bond
    Conductor-Type Semiconductor Bond
Boron Molecules
    Boranes
        Bridging Bonds of Boranes
    Alkoxy Boranes
    Alkyl Boranes
    Alkyl Borinic Acids
    Tertiary Aminoboranes
    Quaternary Aminoboranes
    Borane Amines
Halido Boranes Organometallic Molecular
Functional Groups and Molecules
    Alkyl Aluminum Hydrides
        Bridging Bonds of Organoaluminum Hydrides
    Organogermanium and Digermanium
    Organolead
    Organoarsenic
    Organoantimony TABLE 2-continued Partial List of Additional Molecules and Compositions of Matter Solved by Classical Physics.

Organobismuth
Organic Ions
  1° Amino
  2° Amino
  Carboxylate
  Phosphate
  Nitrate
  Sulfate
  Silicate
Proteins
  Amino Acids
  Peptide Bonds
DNA
  Bases
  2-deoxyribose
  Ribose
  Phosphate Backbone The background theory of classical physics (CP) for the physical solutions of atoms and atomic ions is disclosed in Mills journal publications [1-13], R. Mills, *The Grand Unified Theory of Classical Quantum Mechanics*, January 2000 Edition, BlackLight Power, Inc., Cranbury, N.J., ("'00 Mills GUT"), provided by BlackLight Power, Inc., 493 Old Trenton Road, Cranbury, N.J., 08512; R. Mills, *The Grand Unified Theory of Classical Quantum Mechanics*, September 2001 Edition, BlackLight Power, Inc., Cranbury, N.J., Distributed by Amazon.com ("'01 Mills OUT"), provided by BlackLight Power, Inc., 493 Old Trenton Road, Cranbury, N.J., 08512; R. Mills, *The Grand Unified Theory of Classical Quantum Mechanics*, July 2004 Edition, BlackLight Power, Inc., Cranbury, N.J., ("'04 Mills GUT"), provided by BlackLight Power, Inc., 493 Old Trenton Road, Cranbury, N.J., 08512; R. Mills, *The Grand Unified Theory of Classical Quantum Mechanics*, January 2005 Edition, BlackLight Power, Inc., Cranbury, N.J., ("'05 Mills GUT"), provided by BlackLight Power, Inc., 493 Old Trenton Road, Cranbury, N.J., 08512; R. L. Mills, "The Grand Unified Theory of Classical Quantum Mechanics", June 2006 Edition, Cadmus Professional Communications-Science Press Division, Ephrata, Pa., ISBN 0963517171, Library of Congress Control Number 2005936834, ("'06 Mills GUT"), provided by BlackLight Power, Inc., 493 Old Trenton Road, Cranbury, N.J., 08512; R. Mills, *The Grand Unified Theory of Classical Quantum Mechanics*, October 2007 Edition, BlackLight Power, Inc., Cranbury, N.J., ("'07 Mills GUT"), provided by BlackLight Power, Inc., 493 Old Trenton Road, Cranbury, N.J., 08512; R. Mills, *The Grand Unified Theory of Classical Physics*, June 2008 Edition, BlackLight Power, Inc., Cranbury, N.J., ("'08 Mills GUT-CP"); in prior published PCT applications WO2005/067678; WO2005/116630; WO2007/051078; WO2007/053486; and WO2008/085,804, and U.S. Pat. No. 7,188,033; U.S. Application No. 60/878,055, filed 3 Jan. 2007; 60/880,061, filed 12 Jan. 2007; 60/898,415, filed 31 Jan. 2007; 60/904,164, filed 1 Mar. 2007; 60/907,433, filed 2 Apr. 2007; 60/907,722, filed 13 Apr. 2007; 60/913,556, filed 24 Apr. 2007; 60/986,675, filed 9 Nov. 2007; 60/988,537, filed 16 Nov. 2007; 61/018, 595, filed 2 Jan. 2008; 61/027,977, filed 12 Feb. 2008; 61/029,712, filed 19 Feb. 2008; and 61/082,701, filed 22 Jul. 22, 2008, the entire disclosures of which are all incorporated herein by reference (hereinafter "Mills Prior Publications").

SUMMARY OF THE INVENTION

The present invention, an exemplary embodiment of which is also referred to as Millsian software and systems, stems from a new fundamental insight into the nature of the atom. Applicant's theory of Classical Physics (CP) reveals the nature of atoms and molecules using classical physical laws for the first time. As discussed above, traditional quantum mechanics can solve neither multi-electron atoms nor molecules exactly. By contrast, CP analytical solutions containing physical constants only for even the most complex atoms and molecules.

The present invention is the first and only molecular modeling program ever built on the CP framework. All the major functional groups that make up most organic molecules and the most common classes of molecules have been solved exactly in closed-form solutions with CP. By using these functional groups as building blocks, or independent units, a potentially infinite number of organic molecules can be solved. As a result, the present invention can be used to visualize the exact 3D structure and calculate the heats of formation of an infinite number of molecules, and these solutions can be used in modeling applications.

For the first time, the significant building-block molecules of chemistry have been successfully solved using classical physical laws in exact closed-form equations having fundamental constants only. The major functional groups have been solved from which molecules of infinite length can be solved almost instantly with a computer program. The predictions are accurate within experimental error for over 800 exemplary molecules, typically significantly more accuracy then those given by the current Hartree-Fock algorithm based on QM [2].

The present invention's advantages over other models includes: Rendering true molecular structures; Providing precisely all characteristics, spatial and temporal charge distributions and energies of every electron in every bond, and of every bonding atom; Facilitating the identification of biologically active sites in drugs; and Facilitating drug design.

An objective of the present invention is to solve the charge (mass) and current-density functions of specific groups of molecules and molecular ions disclosed herein or any portion of these species from first principles. In an embodiment, the solution for the molecules and molecular ions, or any portion of these species is derived from Maxwell's equations invoking the constraint that the bound electron before excitation does not radiate even though it undergoes acceleration.

Another objective of the present invention is to generate a readout, display, or image of the solutions so that the nature of the molecules and molecular ions, or any portion of these species be better understood and potentially applied to predict reactivity and physical and optical properties.

Another objective of the present invention is to apply the methods and systems of solving the nature of the atoms, molecules, and molecular ions, or any portion of these species and their rendering to numerical or graphical form to apply to proteins, 2-deoxyribonucleic acid (DNA), ribonucleic acid (RNA), and proteins.

Another objective of the present invention is to apply the methods and systems of solving the nature of the atoms, molecules, and molecular ions, or any portion of these species and their rendering to numerical or graphical form the dipole moment of functional groups and by vector additivity, the dipole moment of a molecule or molecular species comprised of the functional groups.

Another objective of the present invention is to apply the methods and systems of solving the nature of the atoms, molecules, and molecular ions, any portion of these species, their dipole moments, or induced dipole moments due to interaction between species or within species and their rendering to numerical or graphical form to solve at least one of the structure, energy, and properties of condensed matter.

Another objective of the present invention is to apply the methods and systems of solving the nature of the atoms, molecules, and molecular ions, any portion of these species, their dipole moments, or induced dipole moments due to interaction between species or within species and their rendering to numerical or graphical form to solve at least one of the structure, energy, properties, and kinetics of reaction transition states and reactions involving the atoms, molecules, and molecular ions, any portion of these species.

These objectives and other objectives are obtained by a system of computing and rendering the nature of at least one specie selected from the groups of molecules and polyatomic molecules disclosed herein, comprising physical, Maxwellian solutions of charge, mass, and current density functions of said specie, said system comprising processing means for processing physical, Maxwellian equations representing charge, mass, and current density functions of said specie; and an output device in communication with the processing means for displaying said physical, Maxwellian solutions of charge, mass, and current density functions of said specie.

Also provided is a composition of matter comprising a plurality of atoms, the improvement comprising a novel property or use discovered by calculation of at least one of (i) a bond distance between two of the atoms, (ii) a bond angle between three of the atoms, (iii) a bond energy between two of the atoms, (iv) dipole moment of at least one bond, (v) orbital intercept distances and angles, (vi) charge-density functions of atomic, hybridized, and molecular orbitals, (vii) orientations distances, and energies of species in different physical states such as solid, liquid, and gas, and (viii) reaction parameters with other species.

The parameters such as bond distance, bond angle, bond energy, species orientations and reactions being calculated from physical solutions of the charge, mass, and current density functions of atoms and atomic ions, which solutions are derived from Maxwell's equations using a constraint that a bound electron(s) does not radiate under acceleration.

The presented exact physical solutions for known species of the groups of molecules and molecular ions disclosed herein can be applied to other unknown species. These solutions can be used to predict the properties of presently unknown species and engineer compositions of matter in a manner that is not possible using past quantum mechanical techniques. The molecular solutions can be used to design synthetic pathways and predict product yields based on equilibrium constants calculated from the heats of formation. Not only can new stable compositions of matter be predicted, but now the structures of combinatorial chemistry reactions can be predicted.

Pharmaceutical applications include the ability to graphically or computationally render the structures of drugs in solution that permit the identification of the biologically active parts of the specie to be identified from the common spatial charge-density functions of a series of active species. Novel drugs can now be designed according to geometrical parameters and bonding interactions with the data of the structure of the active site of the drug.

The system can be used to calculate conformations, folding, and physical properties, and the exact solutions of the charge distributions in any given specie are used to calculate the fields. From the fields, the interactions between groups of the same specie or between groups on different species are calculated wherein the interactions are distance and relative orientation dependent. The fields and interactions can be determined using a finite-element-analysis approach of Maxwell's equations. The approach can be applied to solid, liquid, and gases phases of a species or a species present in a mixture or solution.

Embodiments of the system for performing computing and rendering of the nature of the groups of molecules and molecular ions, or any portion of these species using the physical solutions and their phases or structures in different media may comprise a general purpose computer. Such a general purpose computer may have any number of basic configurations. For example, such a general purpose computer may comprise a central processing unit (CPU), one or more specialized processors, system memory, a mass storage device such as a magnetic disk, an optical disk, or other storage device, an input means, such as a keyboard or mouse, a display device, and a printer or other output device. A system implementing the present invention can also comprise a special purpose computer or other hardware system and all should be included within its scope. A complete description of how a computer can be used is disclosed in Applicant's prior incorporated WO2007/051078 application.

Although not preferred, any of the calculated and measured values and constants recited in the equations herein can be adjusted, for example, up to ±10%, if desired.

give rise to the phenomenon of electron spin.

Figure 1:
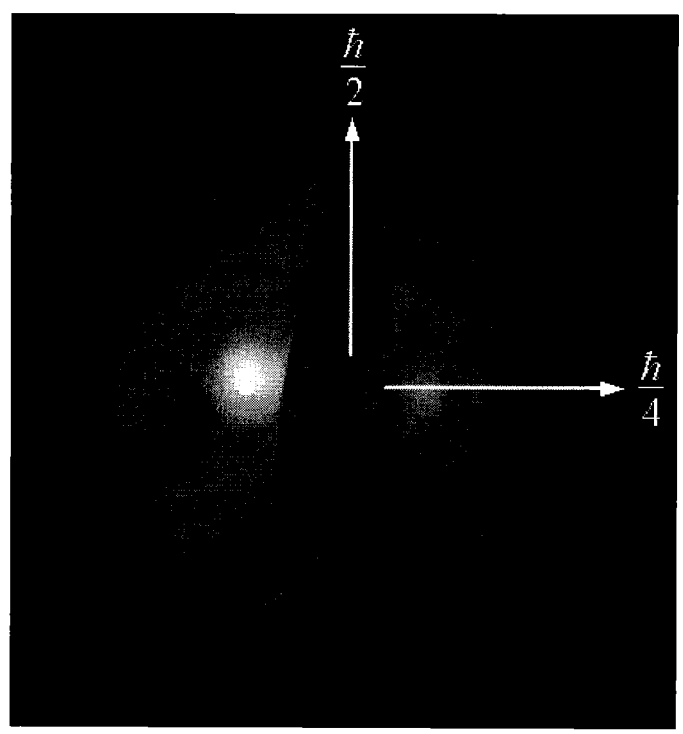
FIG. 1. A bound electron is a constant two-dimensional spherical surface of charge (zero thickness, total charge=$-e$=$-\pi$, and total mass=$m_e$), called an electron orbitsphere. The corresponding uniform current-density function having angular momentum components of $$L_{xy} = \frac{\hbar}{4} \text{ and } L_z = \frac{\hbar}{2}$$
Figure 2:
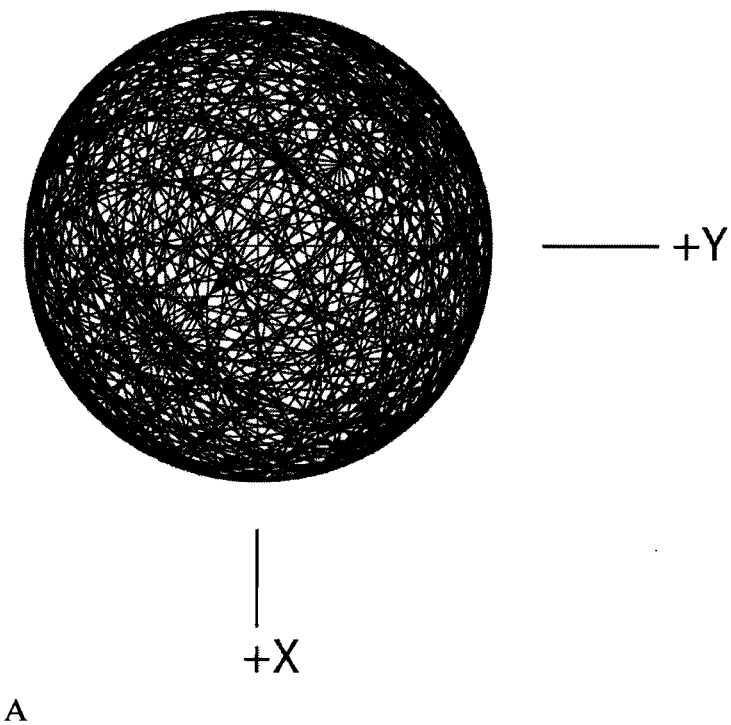
Figure 2:
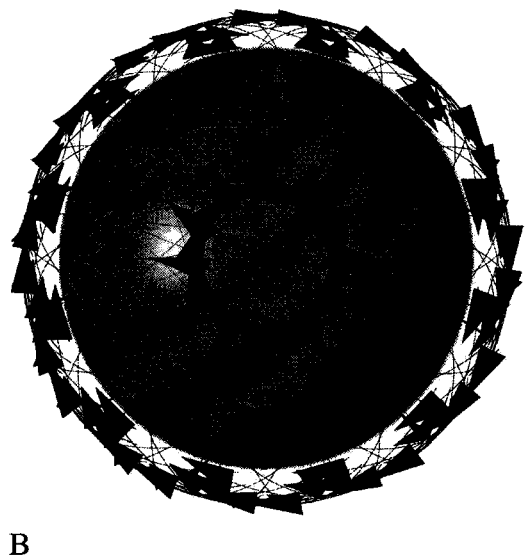

FIGS. 2A and 2B. The bound electron exists as a spherical two-dimensional supercurrent (electron orbitsphere), an extended distribution of charge and current completely surrounding the nucleus. Unlike a spinning sphere, there is a complex pattern of motion on its surface (indicated by vectors) that generates two orthogonal components of angular momentum (FIG. 1) that give rise to the phenomenon of electron spin. FIG. 2A shows a great-circle representation of the z-axis view of the total current pattern of the $Y_0^0(\phi,\theta)$ orbitsphere comprising 144 great circle current elements. FIG. 2B shows a representation of the $$\left(-\frac{1}{\sqrt{2}}i_x, \frac{1}{\sqrt{2}}i_y, i_z\right)\text{-axis}$$

view of the total uniform current-density pattern of the $Y_0^0(\phi,\theta)$ orbitsphere with 144 vectors overlaid on the continuous bound-electron current density giving the direction of the current of each great circle element (nucleus not to scale).

Figure 3:
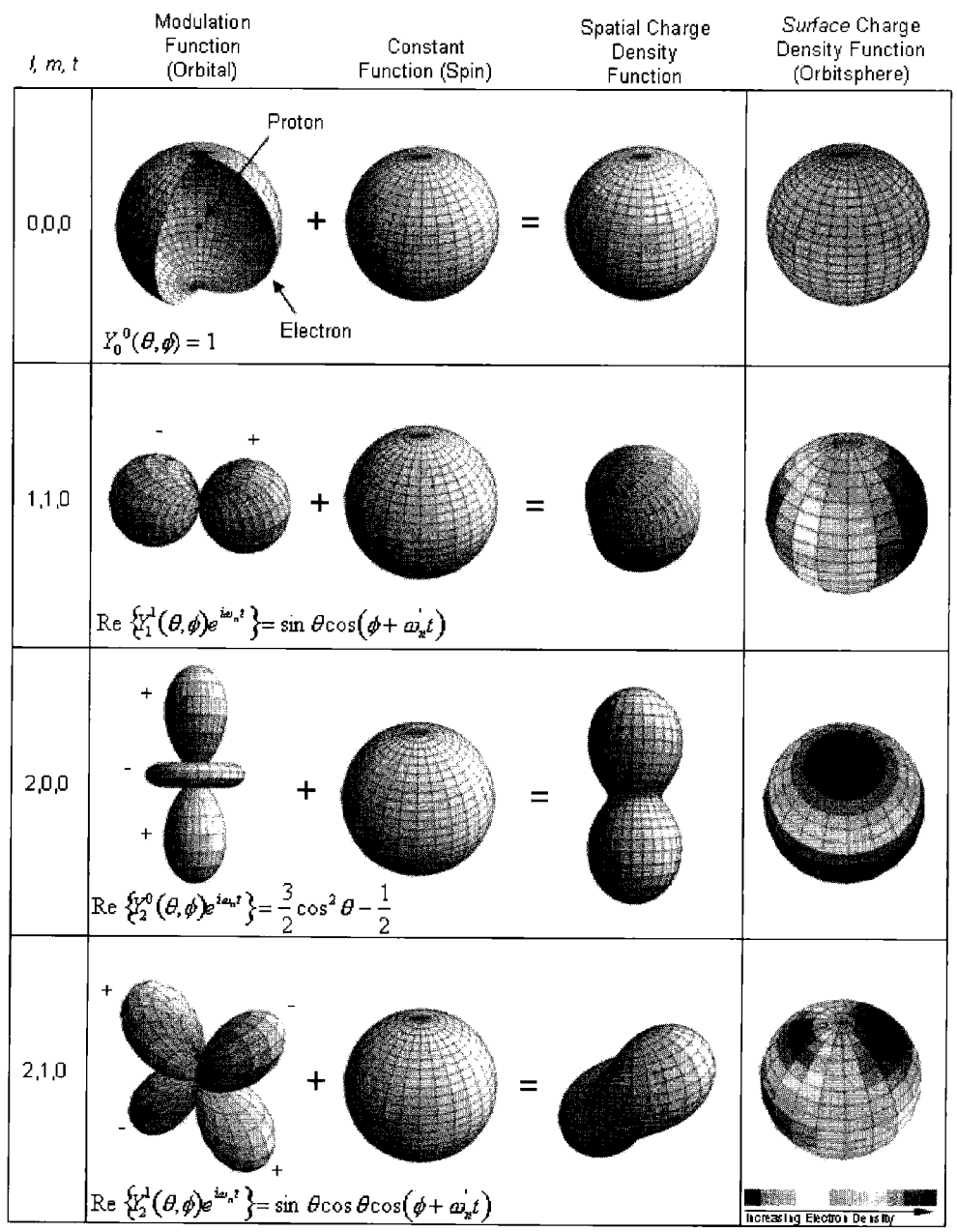

FIG. 3. The orbital function modulates the constant (spin) function, (shown for t=0; three-dimensional view).

FIGS. 4A-B. Prolate spheroidal $H_2MO$, an equipotential minimum energy two-dimensional surface of charge and current that is stable to radiation. (A) External surface showing the charge density that is proportional to the distance from the origin to the tangent to the surface with the maximum density of the MO closest to the nuclei, an energy minimum. (B) Prolate spheroid parameters of molecules and molecular ions where a is the semimajor axis, 2a is the total length of the molecule or molecular ion along the principal axis, b=c is the semiminor axis, 2b=2c is the total width of the molecule or molecular ion along the minor axis, c' is the distance from the origin to a focus (nucleus), 2c' is the internuclear distance, and the protons are at the foci.

Figure 5:
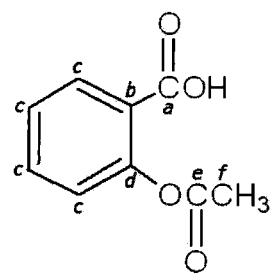

FIG. 5. Aspirin (acetylsalicylic acid)

Figure 6:
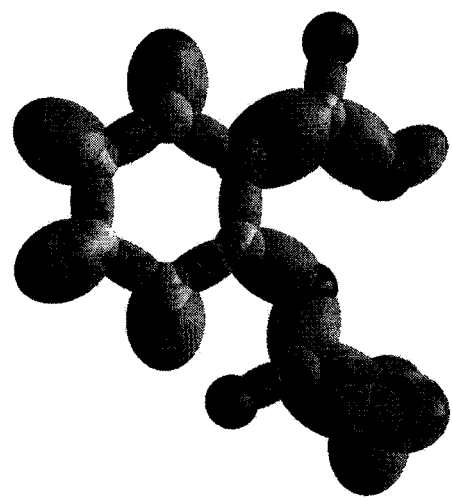

FIG. 6. Gray scale, translucent view of the charge density of aspirin showing the orbitals of the atoms at their radii, the ellipsoidal surface of each H or $H_2$-type ellipsoidal MO that transitions to the corresponding outer shell of the atom(s) participating in each bond, and the hydrogen nuclei (dark gray, not to scale).

Figure 7:
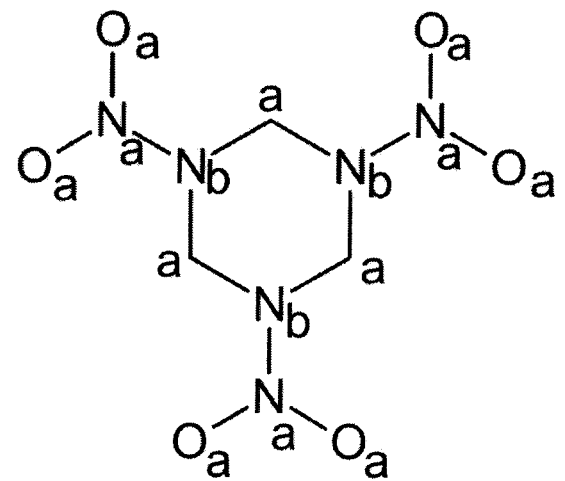

FIG. 7. Cyclotrimethylene-trinitramine (RDX)

Figure 8:
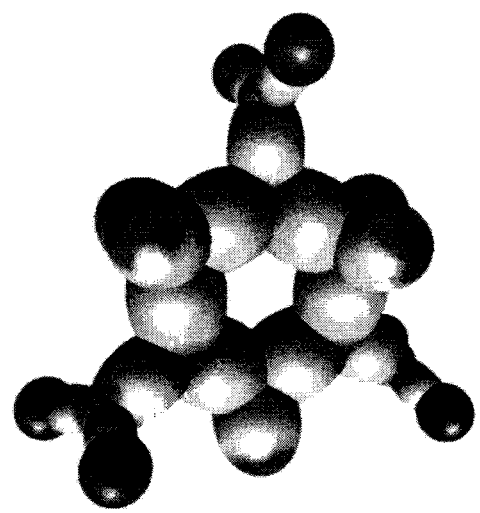

FIG. 8. Gray scale charge density of RDX showing the outer orbitals of the atoms at their radii and the ellipsoidal surface of each H or $H_2$-type ellipsoidal MO that transitions to the corresponding outer shell of the atom(s) participating in each bond.

Figure 9:
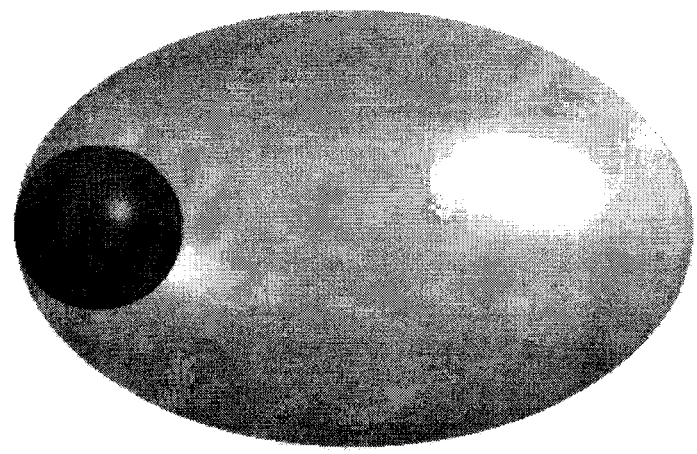

FIG. 9. Gray scale, translucent view of the charge-densities of molecular NaH showing the inner orbitals of the Na atom at their radii, the ellipsoidal surface of the $H_2$-type ellipsoidal MO formed from the outer Na3s AO and the H1s AO H, and the hydrogen nucleus (dark gray, not to scale).

Figure 10:
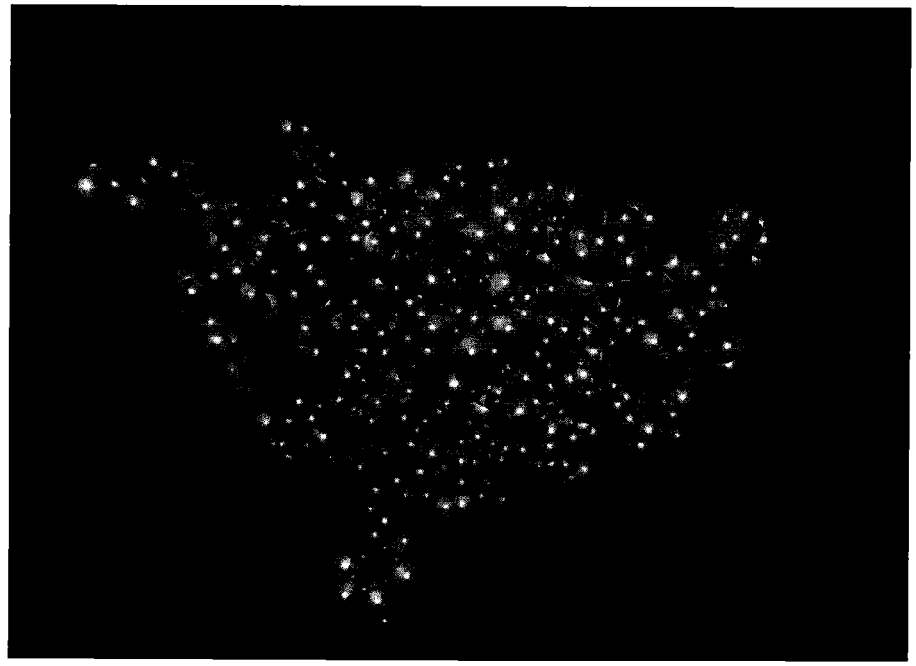

FIG. 10. Gray scale, translucent view of the charge density of insulin created and modeled using Millsian 2.0 run on a PC.

Figure 11:
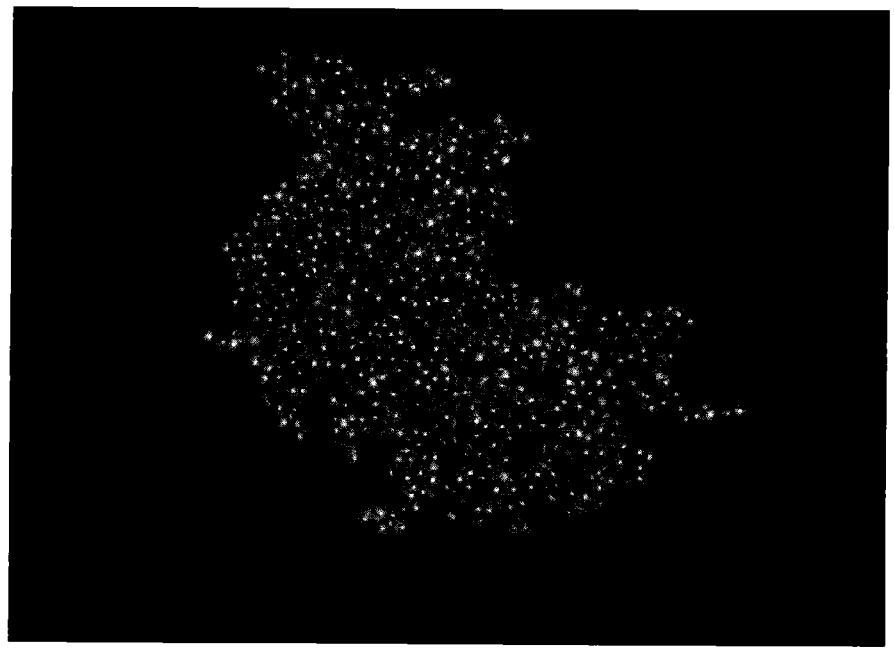

FIG. 11. Gray scale, translucent view of the charge density of lysozyme created and modeled using Millsian 2.0 run on a PC.

Figure 12:
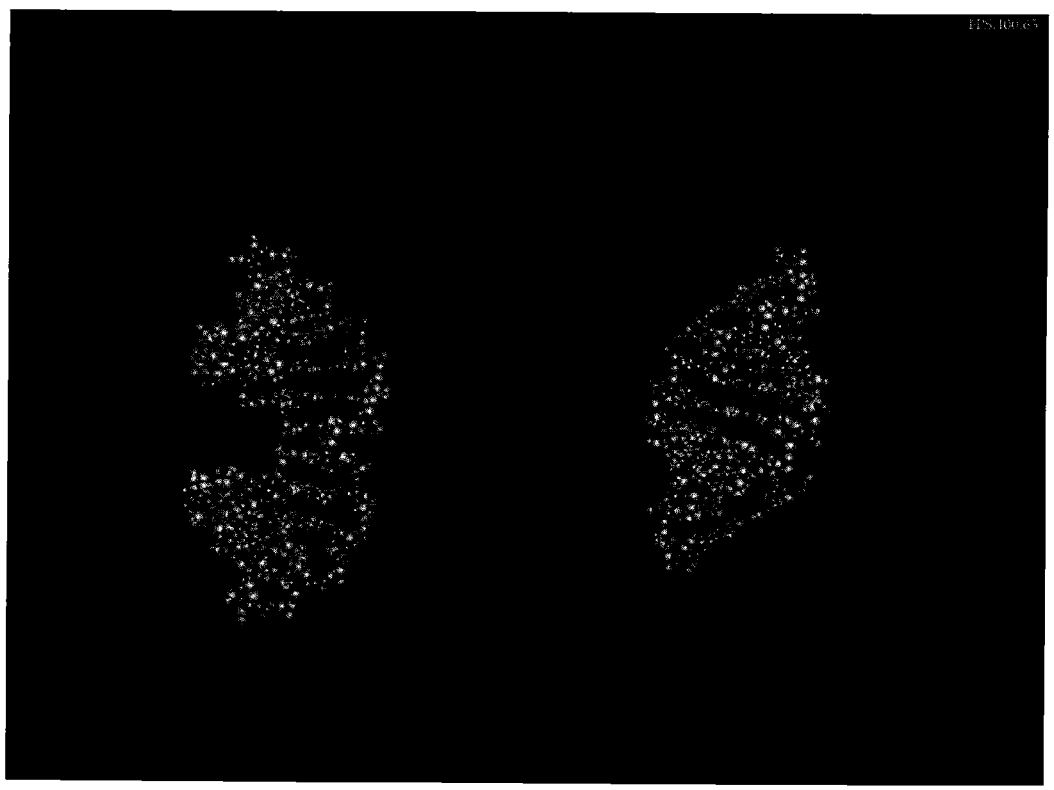

FIG. 12. Gray scale, translucent view of the charge-density of a double-stranded DNA helix created and modeled using Millsian 2.0 run on a PC.

Figure 13:
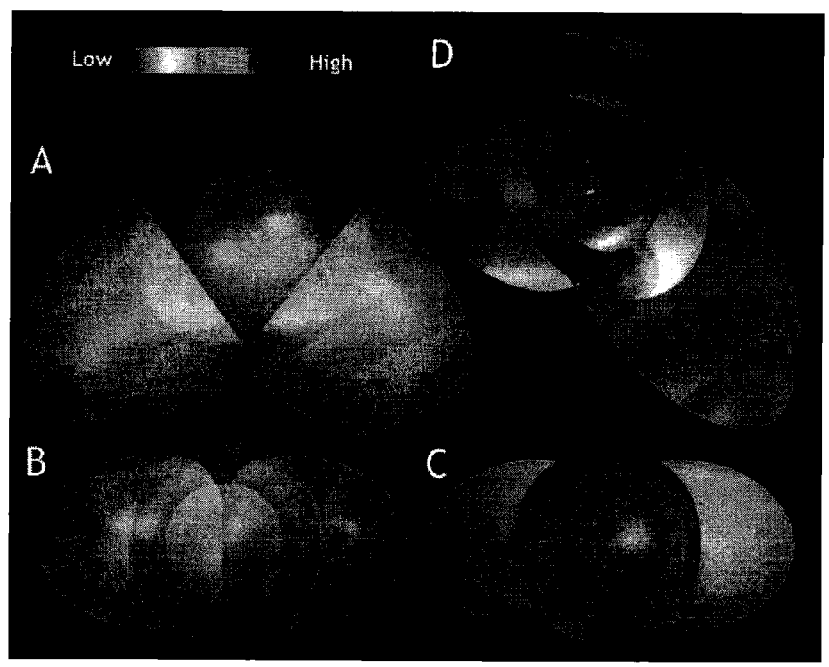

FIG. 13. $H_2O$ MO comprising the linear combination of two O—H-bond MOs. Each O—H-bond MO comprises the superposition of a $H_2$-type ellipsoidal MO and the $O2p_z$ AO or the $O2p_y$ AO. (A)-(C) Gray scale, translucent views of the charge density of the $H_2O$ MO from the top, side-on with H in foreground, and side-on with O in the foreground, respectively. For each O—H bond, the ellipsoidal surface of each $H_2$-type ellipsoidal MO transitions to the O2p AO. The O2p shell, the O2s shell, the O1s shell, and the nuclei (not to scale) are shown. (D) Cut-away view showing the inner most O1s shell, and moving radially, the O2s shell, the O2p shell, and the $H_2$-type ellipsoidal MO that transitions to the O2p AO for each O—H bond.

Figure 14:
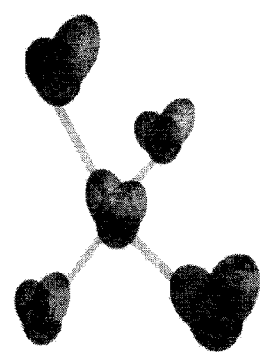

FIG. 14. Tetrahedral unit cell structure of Type I ice using the transparent gray scale charge density of each $H_2O$ MO comprising the linear combination of two O—H-bond MOs. Each dipole-dipole bond that is Coulombic in nature is depicted by connecting sticks.

Figure 15:
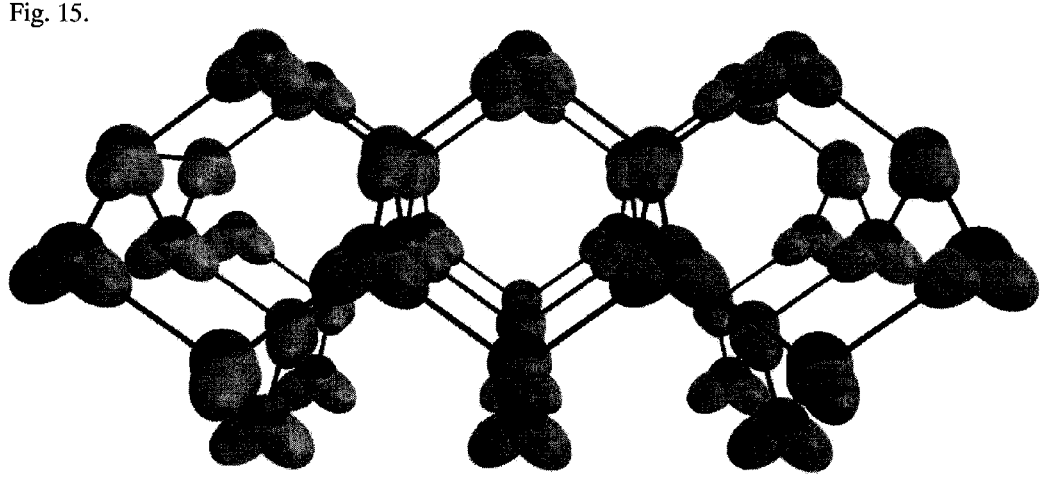

FIG. 15. C-axis view of the ideal hexagonal lattice structure of Type I ice using the opaque gray scale charge density of each $H_2O$ MO comprising the linear combination of two O—H-bond MOs. Each dipole-dipole bond that is Coulombic in nature is depicted by connecting sticks.

Figure 16:
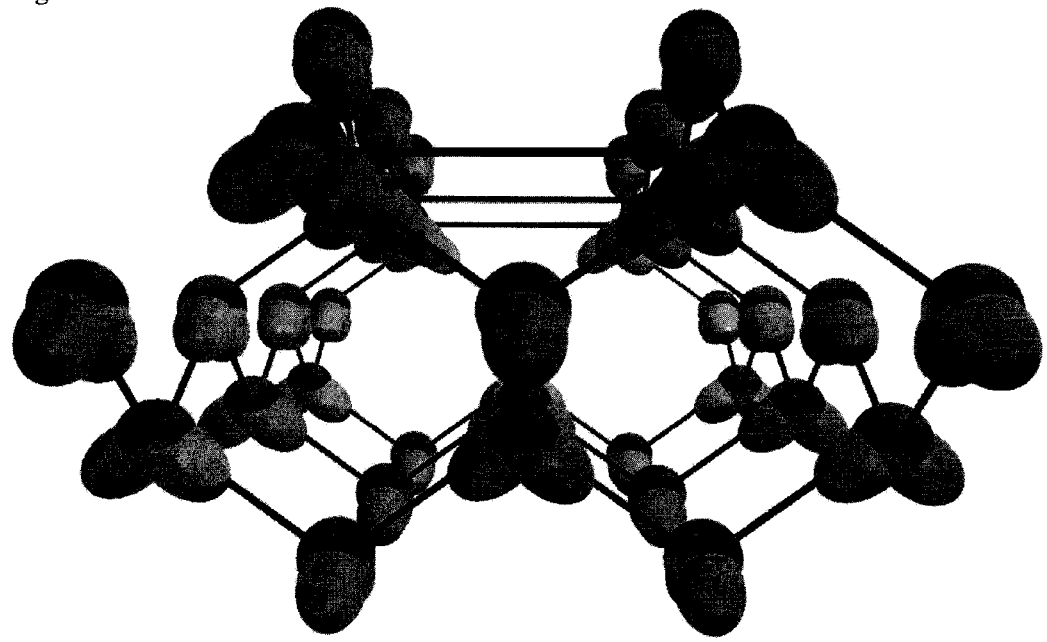

FIG. 16. An off-angle view of the ideal hexagonal lattice structure of Type I ice using the opaque gray scale charge density of each $H_2O$ MO comprising the linear combination of two O—H-bond MOs. Each dipole-dipole bond that is Coulombic in nature is depicted by connecting sticks.

Figure 17:
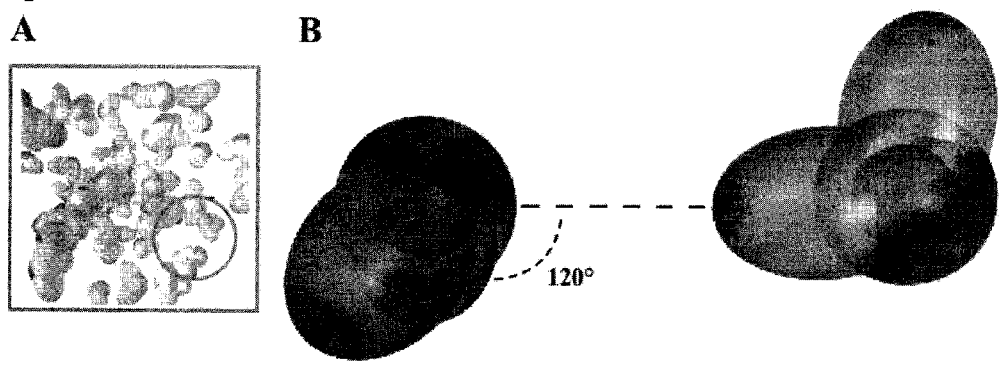

FIG. 17. Structure of steam. (A). Ensemble of gaseous water vapor molecules undergoing elastic hard-sphere collisions. (B). H-bonded water vapor molecules using the gray scale charge density of each $H_2O$ MO comprising the linear combination of two O—H-bond MOs.

Figure 18:
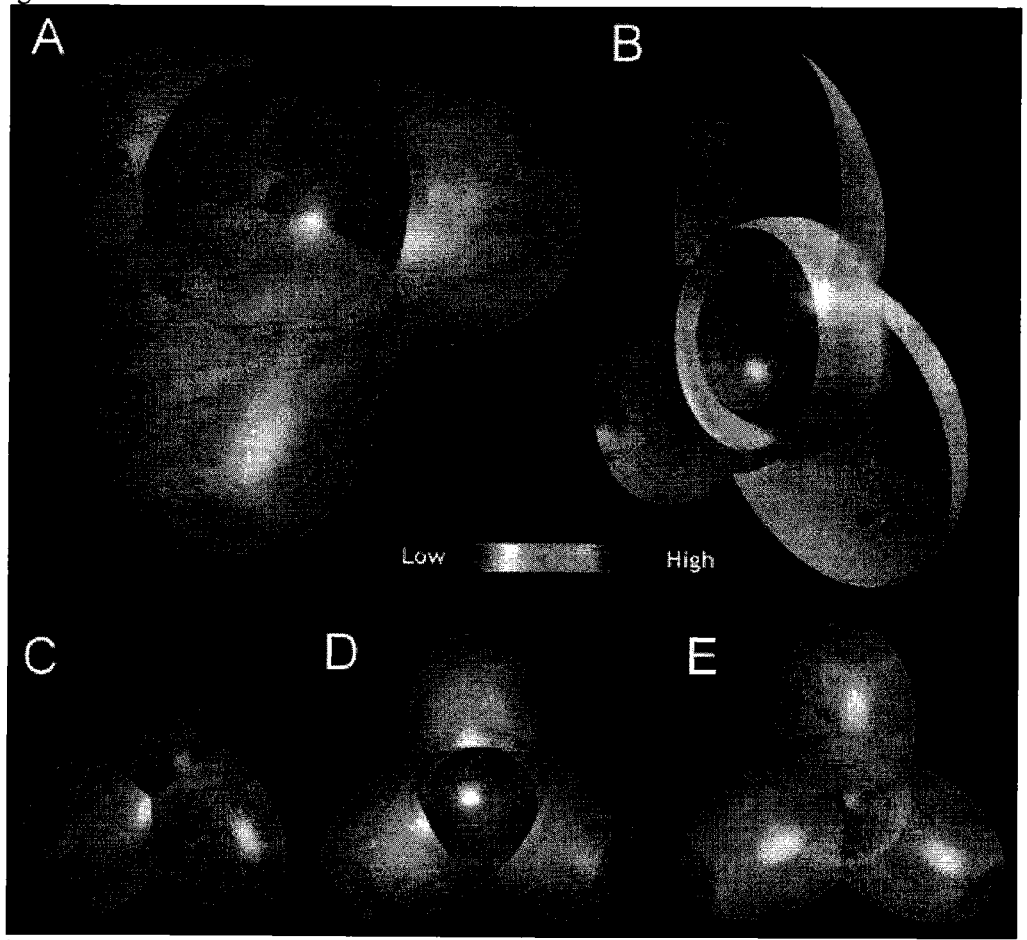

FIG. 18. $NH_3$ MO comprising the linear combination of three N—H-bonds. Each N—H-bond MO comprises the superposition of a $H_2$-type ellipsoidal MO and the $N2p_x$, $N2p_y$, or $N2p_z$ AO. (A) Gray scale, translucent view of the charge density of the $NH_3$ MO shown obliquely from the top. For each N—H bond, the ellipsoidal surface of each $H_2$-type ellipsoidal MO transitions to a N2p AO. The N2p shell, the N2s shell, the N1s shell, and the nuclei (dark gray, not to scale) are shown. (B) Off-center cut-away view showing the complete inner most N1s shell, and moving radially, the cross section of the N2s shell, the N2p shell, and the $H_2$-type ellipsoidal MO that transitions to a N2p AO for each N—H bond. (C)-(E) Gray scale, side-on, top, and bottom translucent views of the charge density of the $NH_3$ MO, respectively.

Figure 19:
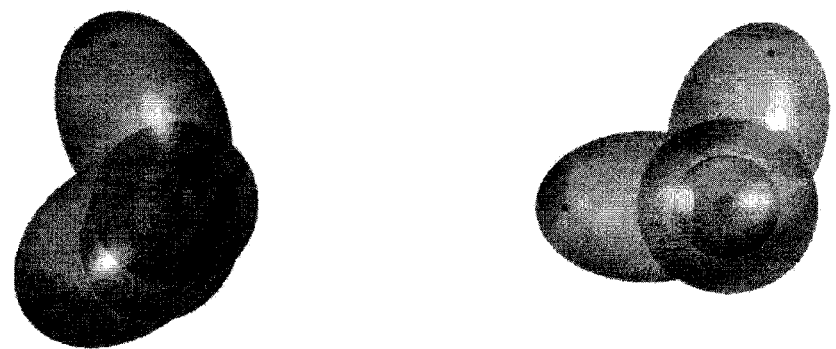

FIG. 19. Structure of the $H_3N\bullet\bullet\bullet H$—OH H bond. The H-bonded ammonia-water vapor molecular dimer using the gray scale charge density of each $NH_3$ and $H_2O$ MO comprising the linear combination of three N—H and two O—H-bond MOs, respectively.

Figure 20:
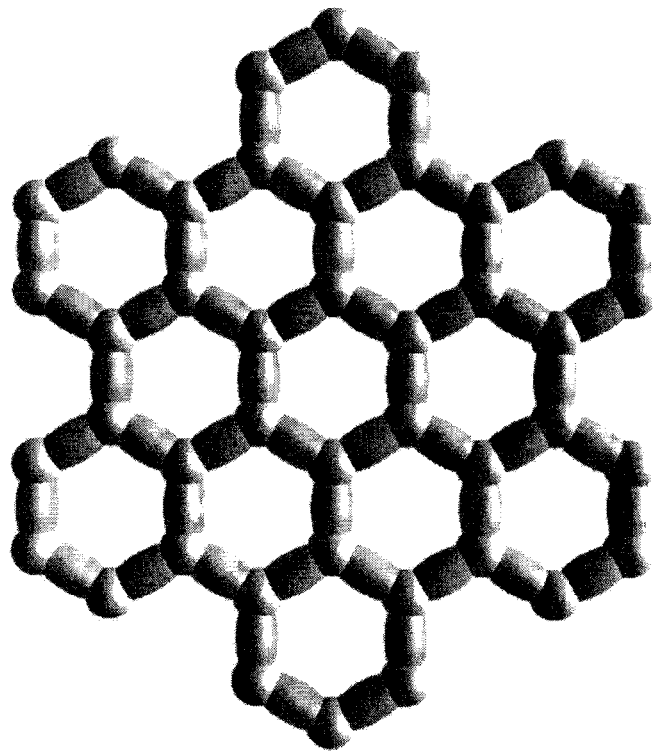
Figure 20:
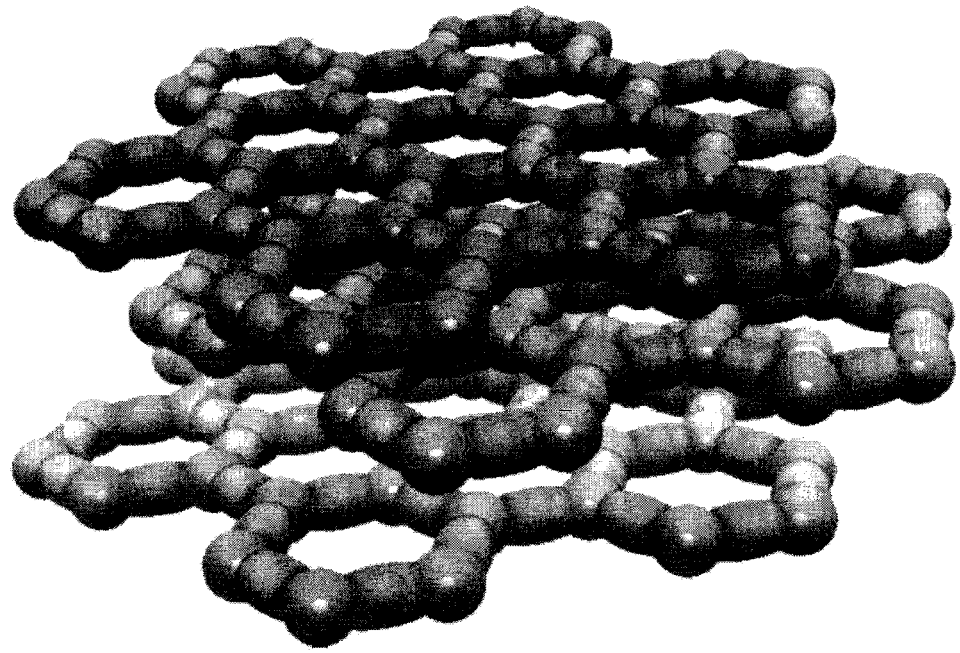

FIG. 20. The structure of graphite. (A). Single plane of macromolecule of indefinite size. (B). Layers of graphitic planes having an interplane spacing of 3.5 Å.

Figure 21:
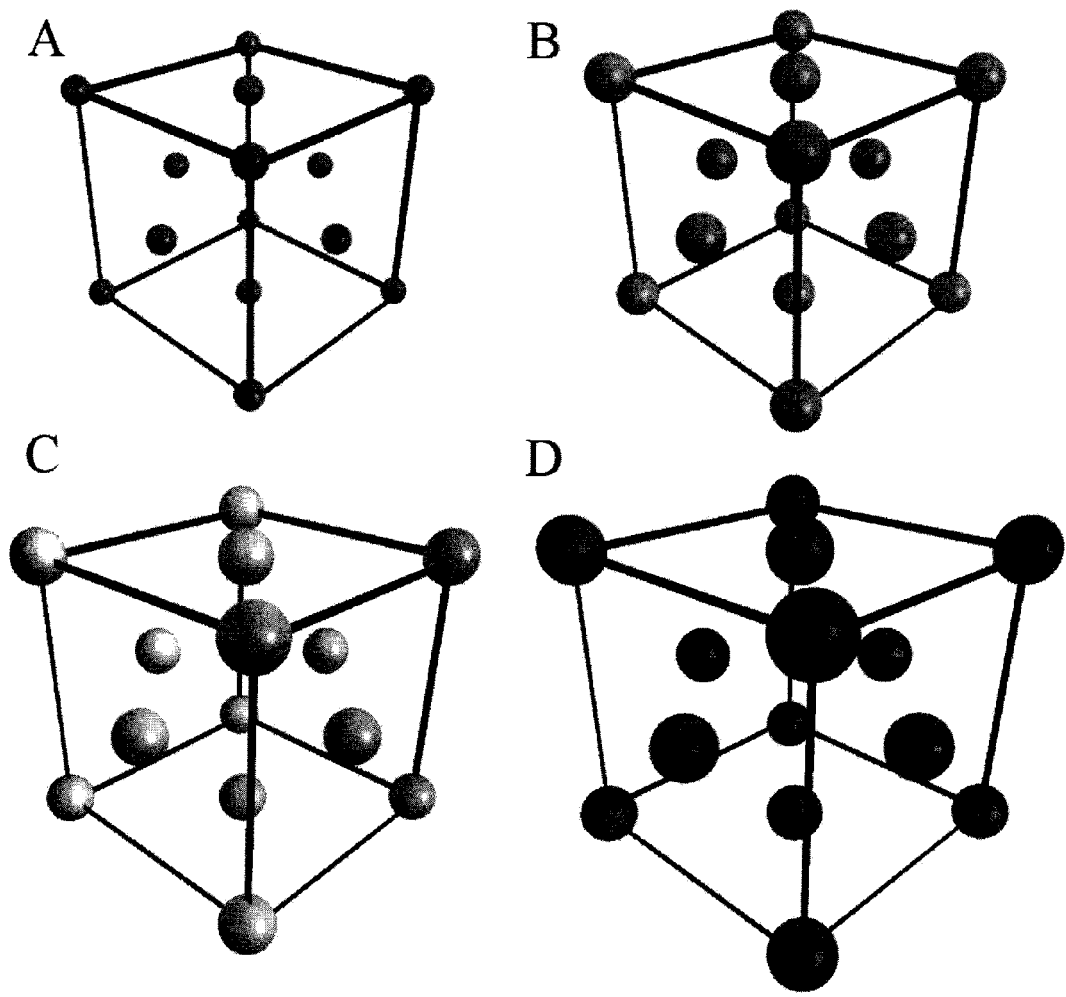

FIG. 21. The face-centered cubic crystal structures of noble gas condensates, all to the same scale. (A) The crystal structure of neon. (B) The crystal structure of argon. (C) The crystal structure of krypton. (D) The crystal structure of xenon.

Figure 22:
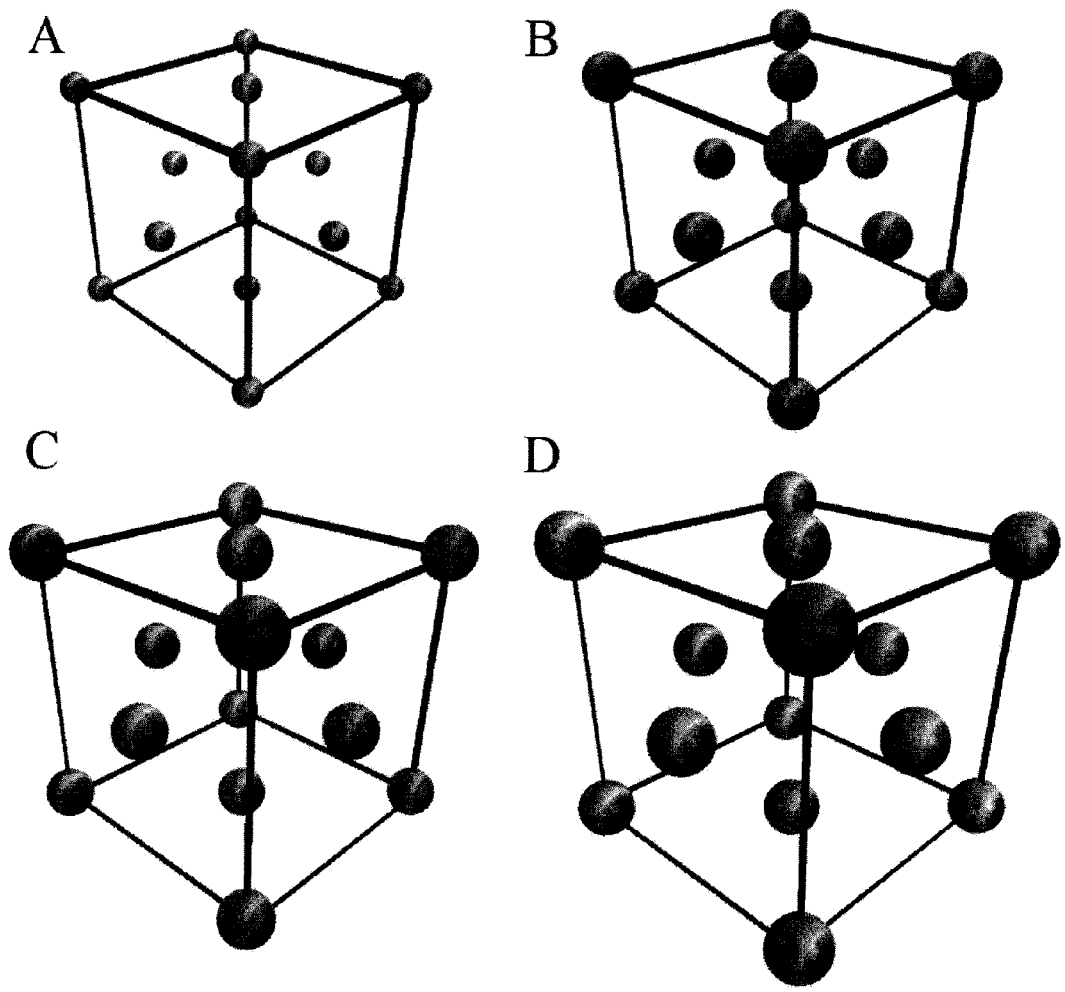

FIG. 22. The charge densities of the van der Waals dipoles and face-centered cubic crystal structures of noble gas condensates, all to the same scale. (A) The charge density and crystal structure of neon. (B) The charge density and crystal structure of argon. (C) The charge density and crystal structure of krypton. (D) The charge density and crystal structure of xenon.

Figure 23:
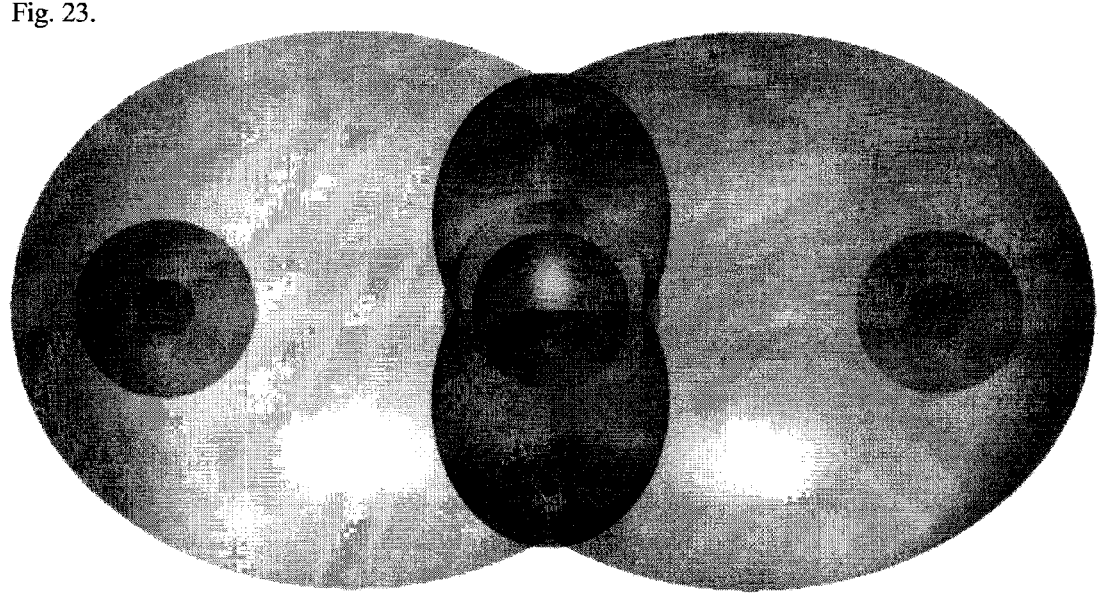

FIG. 23. Gray scale, translucent view of the chloride-ion-chloromethane transition state comprising the $Cl^{\delta+}$—C—$Cl^{\delta-}$ functional group showing the orbitals of the atoms at their radii, the ellipsoidal surface of each H or $H_2$-type ellipsoidal MO that transitions to the corresponding outer shell of the atom(s) participating in each bond, and the hydrogen nuclei (dark gray, not to scale).

Figure 24:
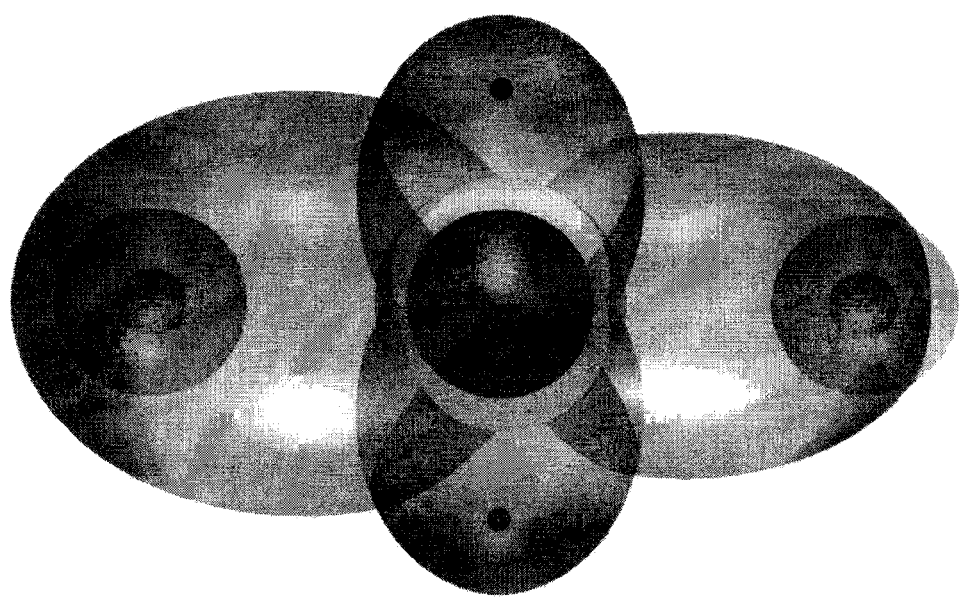

FIG. 24. Gray scale, translucent view of the negatively-charged molecular ion complex $\mathbb{C}$ comprising the $Cl^-.C^{\delta+}$ functional group showing the orbitals of the atoms at their radii, the ellipsoidal surface of each H or $H_2$-type ellipsoidal MO that transitions to the corresponding outer shell of the atom(s) participating in each bond, and the hydrogen nuclei (not to scale).

Figure 25:
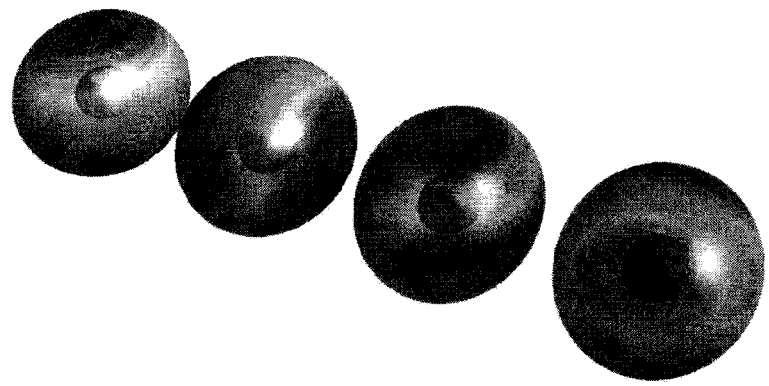

FIG. 25. Overhead-view of exemplary gray scale, translucent views of the charge-densities of the inner and outer electrons of molecular-hydrogen excited states. The outer-electron orbital function modulates the time-constant (spin) function, (shown for t=0; three-dimensional view). The inner electron is essentially that of $H_2^+$ (nuclei not to scale).

DESCRIPTION OF THE INVENTION

The present Invention comprises molecular modeling methods and systems for solving atomic and molecular structures based on applying the classical laws of physics, (Newton's and Maxwell's Laws) to the atomic scale. The functional groups such as amino acids and peptide bonds with charged functional groups, bases, 2-deoxyribose, ribose, phosphate backbone with charged functional groups, organic ions, and the functional groups of organic and other molecules have been solved in analytical equations. By using these functional groups as building blocks, or independent units, a potentially infinite number of molecules can be solved. As a result, the method and systems of the present invention can visualize the exact three-dimensional structure and calculate physical characteristics of many molecules, up to arbitrary length and complexity. Even complex proteins and DNA (the molecules that encode genetic information) may be solved in real-time interactively on a personal computer. By contrast, previous software based on traditional quantum methods must resort to approximations and run on powerful computers for even the simplest systems.

The Nature of the Chemical Bond of Hydrogen

The nature of the chemical bond of functional groups is solved by first solving the simplest molecule, molecular hydrogen as given in the Nature of the Chemical Bond of Hydrogen-Type Molecules section of Ref. [1]. The hydrogen molecule charge and current density functions, bond distance, and energies are solved from the Laplacian in ellipsoidal coordinates with the constraint of nonradiation [1,6].

$$(\eta - \zeta)R_\xi \frac{\partial}{\partial \xi}\left(R_\xi \frac{\partial \phi}{\partial \xi}\right) + \qquad (21)$$
$$(\zeta - \xi)R_\eta \frac{\partial}{\partial \eta}\left(R_\eta \frac{\partial \phi}{\partial \eta}\right) + (\xi - \eta)R_\zeta \frac{\partial}{\partial \zeta}\left(R_\zeta \frac{\partial \phi}{\partial \zeta}\right) = 0$$

a. The Geometrical Parameters of the Hydrogen Molecule

Figure 4:
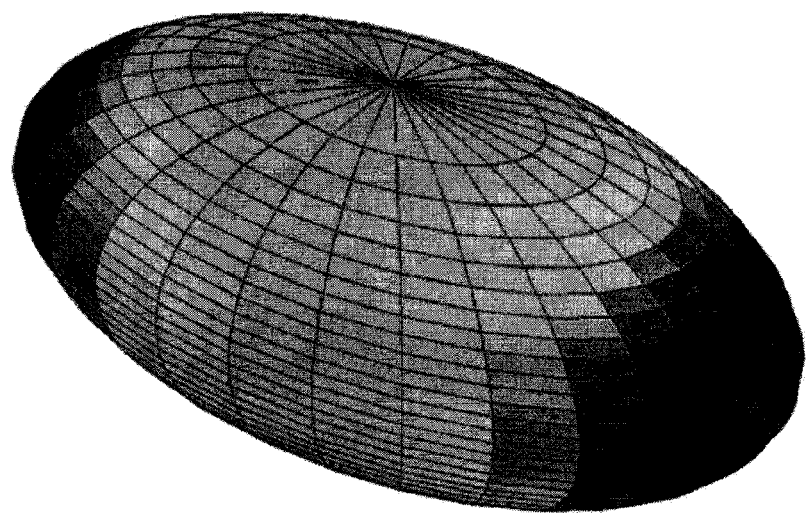
Figure 4:
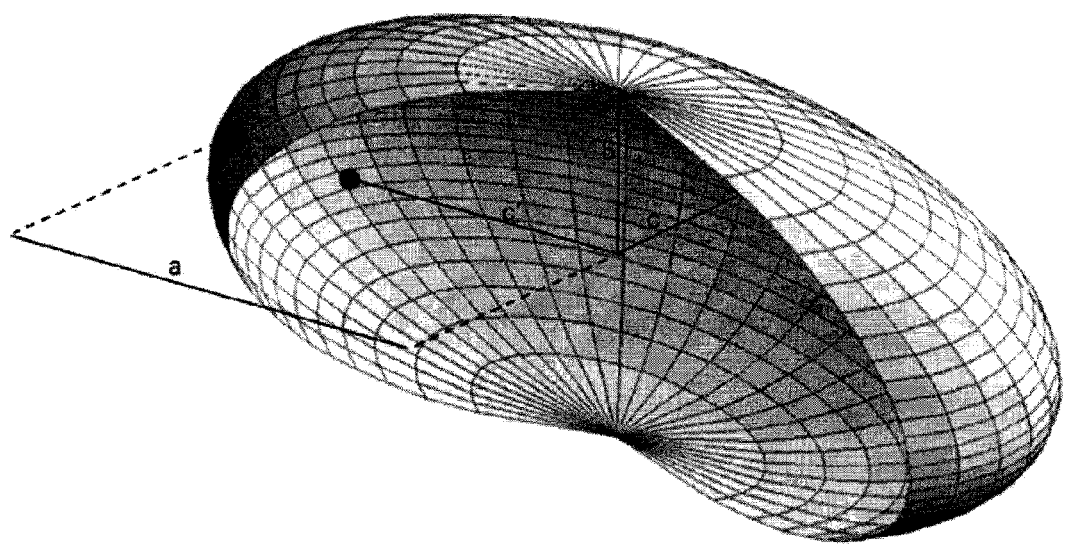

As shown in FIG. 4, the nuclei are at the foci of the electrons comprising a two-dimensional, equipotential-energy, charge- and current-density surface that obeys Maxwell's equations including stability to radiation and Newton's laws of motion. The force balance equation for the hydrogen molecule is $$\frac{\hbar^2}{m_e a^2 b^2}D = \frac{e^2}{8\pi\varepsilon_o ab^2}D + \frac{\hbar^2}{2m_e a^2 b^2}D \qquad (22)$$

where $$D = r(t) \cdot i_\xi \qquad (23)$$

is the time dependent distance from the origin to the tangent plane at a point on the ellipsoidal MO. Eq. (22) has the parametric solution $$r(t) = ia \cos \omega t + jb \sin \omega t \qquad (24)$$

when the semimajor axis, a, is $$a = a_0 \qquad (25)$$

The internuclear distance, 2c', which is the distance between the foci is $$2c' = \sqrt{2}a_0 \qquad (26)$$

The experimental internuclear distance is $\sqrt{2}a_0$. The semiminor axis is $$b = \frac{1}{\sqrt{2}}a_o \qquad (27)$$

The eccentricity, e, is $$e = \frac{1}{\sqrt{2}} \qquad (28)$$

b. The Energies of the Hydrogen Molecule

The potential energy of the two electrons in the central field of the protons at the foci is $$V_e = \frac{-2e^2}{8\pi\varepsilon_o \sqrt{a^2 - b^2}} \ln \frac{a + \sqrt{a^2 - b^2}}{a - \sqrt{a^2 - b^2}} = -67.836 \text{ eV} \qquad (29)$$

The potential energy of the two protons is $$V_p = \frac{e^2}{8\pi\varepsilon_o \sqrt{a^2 - b^2}} = 19.242 \text{ eV} \qquad (30)$$

The kinetic energy of the electrons is $$T = \frac{\hbar^2}{2m_e a \sqrt{a^2 - b^2}} \ln \frac{a + \sqrt{a^2 - b^2}}{a - \sqrt{a^2 - b^2}} = 33.918 \text{ eV} \qquad (31)$$

The energy, $V_m$, of the magnetic force between the electrons is $$V_m = \frac{-\hbar^2}{4m_e a \sqrt{a^2 - b^2}} \ln \frac{a + \sqrt{a^2 - b^2}}{a - \sqrt{a^2 - b^2}} = -16.959 \text{ eV} \qquad (32)$$

During bond formation, the electrons undergo a reentrant oscillatory orbit with vibration of the protons. The corresponding energy $\overline{E}_{osc}$ is the difference between the Doppler and average vibrational kinetic energies:

$$\overline{E}_{osc} = \overline{E}_D + \overline{E}_{Kvib} = (V_e + T + V_m + V_p)\sqrt{\frac{2\overline{E}_K}{Mc^2}} + \frac{1}{2}\hbar\sqrt{\frac{k}{\mu}} \qquad (33)$$

The total energy is $$E_T = V_e + T + V_m + V_p + \overline{E}_{osc} \qquad (34)$$

$$E_T = -\frac{e^2}{8\pi\varepsilon_o a_0}\left[\left(\frac{2\sqrt{2}}{\sqrt{2} + \frac{\sqrt{2}}{2}} - \right)\ln\frac{\sqrt{2} + 1}{\sqrt{2} - 1} - \frac{1 + \sqrt{\frac{e^2}{4\pi\varepsilon_o a_0^3}}}{\sqrt{\frac{e^2}{m_e c^2}}}\right] - \qquad (35)$$

$$\frac{1}{2}\hbar\sqrt{\frac{k}{\mu}}$$

$$= -31.686 \text{ eV}$$

The energy of two hydrogen atoms is $$E(2H[a_H]) = -27.21 \text{ eV} \qquad (36)$$

The bond dissociation energy, $E_D$, is the difference between the total energy of the corresponding hydrogen atoms (Eq. (36)) and $E_T$ (Eq. (35)).

$$E_D = E(2H[a_H]) - E_T = 4.478 \text{ eV} \tag{37}$$

The experimental energy is $E_D = 4.478$ eV. The calculated and experimental parameters of $H_2$, $D_2$, $H_2^+$, and $D_2^+$ from Ref. [6] and Chp. 11 of Ref. [1] are given in Table 3.

ber), and Eq. (14.number) will refer to the corresponding equations of Ref [1].) Additional derivations for other non-organic function groups given in Table 2 are derived in the following sections of Ref. [1]: Applications: Pharmaceuticals, Specialty Molecular Functional Groups and Molecules, Dipole Moments, and Interactions, Nature of the Solid Molecular Bond of the Three Allotropes of Carbon, Silicon Molecular Functional Groups and Molecules, Nature of the

TABLE 3

The Maxwellian closed-form calculated and experimental parameters of $H_2$, $D_2$, $H_2^+$ and $D_2^+$.

| Parameter | Calculated | Experimental |
| --- | --- | --- |
| $H_2$ Bond Energy | 4.478 eV | 4.478 eV |
| $D_2$ Bond Energy | 4.556 eV | 4.556 eV |
| $H_2^+$ Bond Energy | 2.654 eV | 2.651 eV |
| $D_2^+$ Bond Energy | 2.696 eV | 2.691 eV |
| $H_2$ Total Energy | 31.677 eV | 31.675 eV |
| $D_2$ Total Energy | 31.760 eV | 31.760 eV |
| $H_2$ Ionization Energy | 15.425 eV | 15.426 eV |
| $D_2$ Ionization Energy | 15.463 eV | 15.466 eV |
| $H_2^+$ Ionization Energy | 16.253 eV | 16.250 eV |
| $D_2^+$ Ionization Energy | 16.299 eV | 16.294 eV |
| $H_2^+$ Magnetic Moment | $9.274 \times 10^{-24}$ JT$^{-1}$ ($\mu_B$) | $9.274 \times 10^{-24}$ JT$^{-1}$ ($\mu_B$) |
| Absolute $H_2$ Gas-Phase NMR Shift | −28.0 ppm | −28.0 ppm |
| $H_2$ Internuclear Distance[a] | 0.748 Å $\sqrt{2}a_o$ | 0.741 Å |
| $D_2$ Internuclear Distance[a] | 0.748 Å $\sqrt{2}a_o$ | 0.741 Å |
| $H_2^+$ Internuclear Distance | 1.058 Å $2a_o$ | 1.06 Å |
| $D_2^+$ Internuclear Distance[a] | 1.058 Å $2a_o$ | 1.0559 Å |
| $H_2$ Vibrational Energy | 0.517 eV | 0.516 eV |
| $D_2$ Vibrational Energy | 0.371 eV | 0.371 eV |
| $H_2$ $\omega_e \chi_e$ | 120.4 cm$^{-1}$ | 121.33 cm$^{-1}$ |
| $D_2$ $\omega_e \chi_e$ | 60.93 cm$^{-1}$ | 61.82 cm$^{-1}$ |
| $H_2^+$ Vibrational Energy | 0.270 eV | 0.271 eV |
| $D_2^+$ Vibrational Energy | 0.193 eV | 0.196 eV |
| $H_2$ J = 1 to J = 0 Rotational Energy[a] | 0.0148 eV | 0.01509 eV |
| $D_2$ J = 1 to J = 0 Rotational Energy[a] | 0.00741 eV | 0.00755 eV |
| $H_2^+$ J = 1 to J = 0 Rotational Energy | 0.00740 eV | 0.00739 eV |
| $D_2^+$ J = 1 to J = 0 Rotational Energy[a] | 0.00370 eV | 0.003723 eV |

[a]Not corrected for the slight reduction in internuclear distance due to $\overline{E}_{osc}$.

Derivation of the General Geometrical and Energy Equations of Organic Chemistry

Organic molecules comprising an arbitrary number of atoms can be solved using similar principles and procedures as those used to solve alkanes of arbitrary length. Alkanes can be considered to be comprised of the functional groups of $CH_3$, $CH_2$, and C—C. These groups with the corresponding geometrical parameters and energies can be added as a linear sum to give the solution of any straight chain alkane as shown in the Continuous-Chain Alkanes section of Ref. [1]. Similarly, the geometrical parameters and energies of all functional groups such as those given in Table 1 can be solved. The functional-group solutions can be made into a linear superposition and sum, respectively, to give the solution of any organic molecule. The solutions of the functional groups can be conveniently obtained by using generalized forms of the geometrical and energy equations. The derivation of the dimensional parameters and energies of the function groups are given in the Nature of the Chemical Bond of Hydrogen-Type Molecules, Polyatomic Molecular Ions and Molecules, More Polyatomic Molecules and Hydrocarbons, and Organic Molecular Functional Groups and Molecules sections of Ref. [1]. (Reference to equations of the form Eq. (15.number), Eq. (1.number), Eq. (13.num- Solid Semiconductor Bond of Silicon, Boron Molecules, and Organometallic Molecular Functional Groups and Molecules sections.

Consider the case wherein at least two atomic orbital hybridize as a linear combination of electrons at the same energy in order to achieve a bond at an energy minimum, and the sharing of electrons between two or more such orbitals to form a MO permits the participating hybridized orbitals to decrease in energy through a decrease in the radius of one or more of the participating orbitals. The force-generalized constant k' of a $H_2$-type ellipsoidal MO due to the equivalent of two point charges of at the foci is given by:

$$k' = \frac{C_1 C_2 2e^2}{4\pi\varepsilon_0} \tag{38}$$

where $C_1$ is the fraction of the $H_2$-type ellipsoidal MO basis function of a chemical bond of the molecule or molecular ion which is 0.75 (Eq. (13.59)) in the case of H bonding to a central atom and 0.5 (Eq. (14.152)) otherwise, and $C_2$ is the factor that results in an equipotential energy match of the participating at least two molecular or atomic orbitals of the chemical bond. From Eqs. (13.58-13.63), the distance from the origin of the MO to each focus c' is given by:

$$c' = a\sqrt{\frac{\hbar^2 4\pi\varepsilon_0}{m_e e^2 2C_1 C_2 a}} = \sqrt{\frac{aa_0}{2C_1 C_2}} \quad (39)$$

The internuclear distance is $$2c' = 2\sqrt{\frac{aa_0}{2C_1 C_2}} \quad (40)$$

The length of the semiminor axis of the prolate spheroidal MO b=c is given by $$b = \sqrt{a^2 - c'^2} \quad (41)$$

And, the eccentricity, e, is $$e = \frac{c'}{a} \quad (42)$$

From Eqs. (11.207-11.212), the potential energy of the two electrons in the central field of the nuclei at the foci is $$V_e = n_1 c_1 c_2 \frac{-2e^2}{8\pi\varepsilon_o \sqrt{a^2 - b^2}} \ln\frac{a + \sqrt{a^2 - b^2}}{a - \sqrt{a^2 - b^2}} \quad (43)$$

The potential energy of the two nuclei is $$V_p = n_1 \frac{e^2}{8\pi\varepsilon_o \sqrt{a^2 - b^2}} \quad (44)$$

The kinetic energy of the electrons is $$T = n_1 c_1 c_2 \frac{\hbar^2}{2m_e a\sqrt{a^2 - b^2}} \ln\frac{a + \sqrt{a^2 - b^2}}{a - \sqrt{a^2 - b^2}} \quad (45)$$

And, the energy, $Y_m$, of the magnetic force between the electrons is $$V_m = n_1 c_1 c_2 \frac{-\hbar^2}{4m_e a\sqrt{a^2 - b^2}} \ln\frac{a + \sqrt{a^2 - b^2}}{a - \sqrt{a^2 - b^2}} \quad (46)$$

The total energy of the $H_2$-type prolate spheroidal MO, $E_{T(H_2MO)}$, is given by the sum of the energy terms:

$$E_{T(H_2MO)} = V_e + T + V_m + V_p \quad (47)$$

-continued $$E_{T(H_2MO)} = -\frac{n_1 e^2}{8\pi\varepsilon_o \sqrt{a^2 - b^2}} \left[ c_1 c_2 \left(2 - \frac{a_0}{a}\right) \ln\frac{a + \sqrt{a^2 - b^2}}{a - \sqrt{a^2 - b^2}} - 1 \right] \quad (48)$$

$$= -\frac{n_1 e^2}{8\pi\varepsilon_o c'} \left[ c_1 c_2 \left(2 - \frac{a_0}{a}\right) \ln\frac{a + c'}{a - c'} - 1 \right]$$

where $n_1$ is the number of equivalent bonds of the MO. $c_1$ is the fraction of the $H_2$-type ellipsoidal MO basis function of an MO which is 0.75 (Eqs. (13.67-13.73)) in the case of H bonding to an unhybridized central atom and 1 otherwise, and $c_2$ is the factor that results in an equipotential energy match of the participating the MO and the at least two atomic orbitals of the chemical bond. Specifically, to meet the equipotential condition and energy matching conditions for the union of the $H_2$-type-ellipsoidal-MO and the HOs or AOs of the bonding atoms, the factor $c_2$ of a $H_2$-type ellipsoidal MO may given by (i) one, (ii) the ratio of the Coulombic or valence energy of the AO or HO of at least one atom of the bond and 13.605804 eV, the Coulombic energy between the electron and proton of H, (iii) the ratio of the valence energy of the AO or HO of one atom and the Coulombic energy of another, (iv) the ratio of the valence energies of the AOs or HOs of two atoms, (v) the ratio of two $c_2$ factors corresponding to any of cases (ii)-(iv), and (vi) the product of two different $c_2$ factors corresponding to any of the cases (i)-(v). Specific examples of the factor $c_2$ of a $H_2$-type ellipsoidal MO given in previously [1] are 0.936127, the ratio of the ionization energy of N 14.53414 eV and 13.605804 eV, the Coulombic energy between the electron and proton of H;

0.91771, the ratio of 14.82575 eV, $-E_{Coulomb}(C, 2sp^3)$, and 13.605804 eV;

0.87495, the ratio of 15.55033 eV, $-E_{Coulomb}(C_{ethane}, 2sp_3)$, and 13.605804 e V;

0.85252, the ratio of 15.95955 eV, $-E_{Coulomb}(C_{ethylene}, 2sp^3)$, and 13.605804 eV;

0.85252, the ratio of 15.95955 eV, $-E_{Coulomb}(C_{benzene}, 2sp^3)$, and 13.605804 eV, and 0.86359, the ratio of 15.55033 eV, $-E_{Coulomb}(C_{alkane}, 2sp^3)$, and 13.605804 eV.

In the generalization of the hybridization of at least two atomic-orbital shells to form a shell of hybrid orbitals, the hybridized shell comprises a linear combination of the electrons of the atomic-orbital shells. The radius of the hybridized shell is calculated from the total Coulombic energy equation by considering that the central field decreases by an integer for each successive electron of the shell and that the total energy of the shell is equal to the total Coulombic energy of the initial AO electrons. The total energy $E_T$(atom,msp$^3$) (m is the integer of the valence shell) of the AO electrons and the hybridized shell is given by the sum of energies of successive ions of the atom over the n electrons comprising total electrons of the at least one AO shell.

$$E_T(\text{atom}, msp^3) = -\sum_{m=1}^{n} IP_m \quad (49)$$

where $IP_m$ is the mth ionization energy (positive) of the atom. The radius $r_{msp^3}$, of the hybridized shell is given by:

$$r_{msp^3} = \sum_{q=Z-n}^{Z-1} \frac{-(Z-q)e^2}{8\pi\varepsilon_0 E_T(\text{atom}, msp^3)} \quad (50)$$

Then, the Coulombic energy $E_{Coulomb}(\text{atom}, msp^3)$ of the outer electron of the atom $msp^3$ shell is given by $$E_{Coulomb}(\text{atom}, msp^3) = \frac{-e^2}{8\pi\varepsilon_0 r_{msp^3}} \quad (51)$$

In the case that during hybridization at least one of the spin-paired AO electrons is unpaired in the hybridized orbital (HO), the energy change for the promotion to the unpaired state is the magnetic energy E(magnetic) at the initial radius r of the AO electron:

$$E(\text{magnetic}) = \frac{2\pi\mu_0 e^2 \hbar^2}{m_e^2 r^3} = \frac{8\pi\mu_0 \mu_B^2}{r^3} \quad (52)$$

Then, the energy $E(\text{atom}, msp^3)$ of the outer electron of the atom $msp^3$ shell is given by the sum of $E_{Coulomb}(\text{atom}, msp^3)$ and E(magnetic):

$$E(\text{atom}, msp^3) = \frac{-e^2}{8\pi\varepsilon_0 r_{msp^3}} + \frac{2\pi\mu_0 e^2 \hbar^2}{m_e^2 r^3} \quad (53)$$

Consider next that the at least two atomic orbitals hybridize as a linear combination of electrons at the same energy in order to achieve a bond at an energy minimum with another atomic orbital or hybridized orbital. As a further generalization of the basis of the stability of the MO, the sharing of electrons between two or more such hybridized orbitals to form a MO permits the participating hybridized orbitals to decrease in energy through a decrease in the radius of one or more of the participating orbitals. In this case, the total energy of the hybridized orbitals is given by the sum of $E(\text{atom}, msp^3)$ and the next energies of successive ions of the atom over the n electrons comprising the total electrons of the at least two initial AO shells. Here, $E(\text{atom}, msp^3)$ is the sum of the first ionization energy of the atom and the hybridization energy. An example of $E(\text{atom}, msp^3)$ for $E(C, 2sp^3)$ is given in Eq. (14.503) where the sum of the negative of the first ionization energy of C, -11.27671 eV, plus the hybridization energy to form the $C2sp^3$ shell given by Eq. (14.146) is $E(C, 2sp^3) = -14.63489$ eV.

Thus, the sharing of electrons between two atom $msp^3$ HOs to form an atom-atom-bond MO permits each participating hybridized orbital to decrease in radius and energy. In order to further satisfy the potential, kinetic, and orbital energy relationships, each atom $msp^3$ HO donates an excess of 25% per bond of its electron density to the atom-atom-bond MO to form an energy minimum wherein the atom-atom bond comprises one of a single, double, or triple bond. In each case, the radius of the hybridized shell is calculated from the Coulombic energy equation by considering that the central field decreases by an integer for each successive electron of the shell and the total energy of the shell is equal to the total Coulombic energy of the initial AO electrons plus the hybridization energy. The total energy $E_T(\text{mol.atom}, msp^3)$ (m is the integer of the valence shell) of the HO electrons is given by the sum of energies of successive ions of the atom over the n electrons comprising total electrons of the at least one initial AO shell and the hybridization energy:

$$E_T(\text{mol. atom}, msp^3) = E(\text{atom}, msp^3) = \sum_{m=2}^{n} IP_m \quad (54)$$

where $IP_m$ is the mth ionization energy (positive) of the atom and the sum of $-IP_1$ plus the hybridization energy is $E(\text{atom}, msp^3)$. Thus, the radius $r_{msp^3}$ of the hybridized shell due to its donation of a total charge $-Qe$ to the corresponding MO is given by is given by:

$$r_{msp^3} = \left(\sum_{q=Z-n}^{Z-1}(Z-q) - Q\right)\frac{-e^2}{8\pi\varepsilon_0 E_T(\text{mol. atom}, msp^3)} \quad (55)$$

$$= \left(\sum_{q=Z-n}^{Z-1}(Z-q) - s(0.25)\right)\frac{-e^2}{8\pi\varepsilon_0 E_T(\text{mol. atom}, msp^3)}$$

where $-e$ is the fundamental electron charge and $s=1, 2, 3$ for a single, double, and triple bond, respectively. The Coulombic energy $E_{Coulomb}(\text{mol.atom}, msp^3)$ of the outer electron of the atom $msp^3$ shell is given by $$E_{Coulomb}(\text{mol} \cdot \text{atom}, msp^3) = \frac{-e^2}{8\pi\varepsilon_0 r_{msp^3}} \quad (56)$$

In the case that during hybridization at least one of the spin-paired AO electrons is unpaired in the hybridized orbital (HO), the energy change for the promotion to the unpaired state is the magnetic energy E(magnetic) at the initial radius r of the AO electron given by Eq. (52). Then, the energy $E(\text{mol.atom}, msp^3)$ of the outer electron of the atom $msp^3$ shell is given by the sum of $E_{Coulomb}(\text{mol.atom}, msp^3)$ and E(magnetic):

$$E(\text{mol.atom}, msp^3) = \frac{-e^2}{8\pi\varepsilon_0 r_{msp^3}} = \frac{2\pi\mu_0 e^2 \hbar^2}{m_e^2 r^3} \quad (57)$$

$E^T(\text{atom-atom}, msp^3)$, the energy change of each atom $msp^3$ shell with the formation of the atom-atom-bond MO is given by the difference between $E(\text{mol.atom}, msp^3)$ and $E(\text{atom}, msp^3)$:

$$E^T(\text{atom-atom}, msp^3) = E(\text{mol.atom}, msp^3) - E(\text{atom}, msp^3) \quad (58)$$

In the case of the $C2sp^3$ HO, the initial parameters (Eqs. (14.142-14.146)) are $$r_{2sp^3} = \sum_{n=2}^{5} \frac{(Z-n)e^2}{8\pi\varepsilon_0(e148.25751 \text{ eV})} \qquad (59)$$

$$= \frac{10e^2}{8\pi\varepsilon_0(e148.25751 \text{ eV})}$$

$$= 0.91771 a_0$$

-continued $$E_{Coulomb} = (C, 2sp^3) \qquad (60)$$

$$= \frac{-e^2}{8\pi\varepsilon_0 r_{2sp^3}}$$

$$= \frac{-e^2}{8\pi\varepsilon_0 0.91771 a_0}$$

$$= -14.82575 \text{ eV}$$

$$E(\text{magnetic}) = \frac{2\pi\mu_0 e^2 \hbar^2}{m_e^2 (r_3)^3} \qquad (61)$$

$$= \frac{8\pi\mu_0 \mu_B^2}{(0.84317 a_0)^3}$$

$$= 0.19086 \text{ eV}$$

$$E(C, 2sp^3) = \frac{-e^2}{8\pi\varepsilon_0 r_{2sp^3}} + \frac{2\pi\mu_0 e^2 \hbar^2}{m_e^2 (r_3)^3} \qquad (62)$$

$$= -14.82575 \text{ eV} + 0.19086 \text{ eV}$$

$$= -14.63489 \text{ eV}$$

In Eq. (55), $$\sum_{q=Z-n}^{Z-1} (Z-q) = 10 \qquad (63)$$

Eqs. (14.147) and (54) give $$E_T(\text{mol.atom}, msp^3) = E_T(C_{ethane}, 2sp^3) = -151.61569 \text{ eV} \qquad (64)$$

Using Eqs. (55-65), the final values of $r_{C2sp^3}$, $E_{Coulomb}$ ($C2sp^3$), and $E(C2sp^3)$, and the resulting $$E_T(C\underline{\overset{BO}{=}}C, C2sp^3)$$

of the MO due to charge donation from the HO to the MO where $$C\underline{\overset{BO}{=}}C$$

refers to the bond order of the carbon-carbon bond for different values of the parameter s are given in Table 4.

TABLE 4

The final values of $r_{C2sp^3}$, $E_{Coulomb}(C2sp^3)$, and $E(C2sp^3)$ and the resulting $E_T(C\underline{\overset{BO}{=}}C, C2sp^3)$ of the MO due to charge donation from the HO to the MO where $C\underline{\overset{BO}{=}}C$ refers to the bond order of the carbon-carbon bond.

| MO Bond Order (BO) | $s_1$ | $s_2$ | $r_{C2sp^3}(a_0)$ Final | $E_{Coulomb}(C2sp^3)$ (eV) Final | $E(C2sp^3)$ (eV) Final | $E_T(C\underline{\overset{BO}{=}}C, C2sp^3)$ (eV) |
|---|---|---|---|---|---|---|
| I | 1 | 0 | 0.87495 | −15.55033 | −15.35946 | −0.72457 |
| II | 2 | 0 | 0.85252 | −15.95955 | −15.76868 | −1.13379 |
| III | 3 | 0 | 0.83008 | −16.39089 | −16.20002 | −1.56513 |
| IV | 4 | 0 | 0.80765 | −16.84619 | −16.65532 | −2.02043 |

In another generalized case of the basis of forming a minimum-energy bond with the constraint that it must meet the energy matching condition for all MOs at all HOs or AOs, the energy $E(\text{mol.atom}, msp^3)$ of the outer electron of the atom $msp^3$ shell of each bonding atom must be the average of $E(\text{mol.atom}, msp^3)$ for two different values of s:

$$E(\text{mol.atom}, msp^3) = \frac{E(\text{mol.atom}(s_1), msp^3) + E(\text{mol.atom}(s_2), msp^3)}{2} \qquad (65)$$

In this case, $E_T(\text{atom-atom}, msp^3)$, the energy change of each atom $msp^3$ shell with the formation of each atom-atom-bond MO, is average for two different values of s:

$$E_T(\text{atom—atom}, msp^3) = \frac{E_T(\text{atom—atom}(s_1), msp^3) + E_T(\text{atom—atom}(s_2), msp^3)}{2} \qquad (66)$$

Consider an aromatic molecule such as benzene given in the Benzene Molecule section of Ref. [1]. Each C=C double bond comprises a linear combination of a factor of 0.75 of four paired electrons (three electrons) from two sets of two $C2sp^3$ HOs of the participating carbon atoms. Each C—H bond of CH having two spin-paired electrons, one from an initially unpaired electron of the carbon atom and the other from the hydrogen atom, comprises the linear combination of 75% $H_2$-type ellipsoidal MO and 25% $C2sp_3$ HO as given by Eq. (13.439). However, $E_T$ (atom-atom, $msp^3$) of the C—H-bond MO is given by $0.5E^T(C=C, 2sp^3)$ (Eq. (14.247)) corresponding to one half of a double bond that matches the condition for a single-bond order for C—H that is lowered in energy due to the aromatic character of the bond.

A further general possibility is that a minimum-energy bond is achieved with satisfaction of the potential, kinetic, and orbital energy relationships by the formation of an MO comprising an allowed multiple of a linear combination of H$_2$-type ellipsoidal MOs and corresponding HOs or AOs that contribute a corresponding allowed multiple (e.g. 0.5, 0.75, 1) of the bond order given in Table 4. For example, the alkane MO given in the Continuous-Chain Alkanes section of Ref. [1] comprises a linear combination of factors of 0.5 of a single bond and 0.5 of a double bond.

Consider a first MO and its HOs comprising a linear combination of bond orders and a second MO that shares a HO with the first. In addition to the mutual HO, the second MO comprises another AO or HO having a single bond order or a mixed bond order. Then, in order for the two MOs to be energy matched, the bond order of the second MO and its HOs or its HO and AO is a linear combination of the terms corresponding to the bond order of the mutual HO and the bond order of the independent HO or AO. Then, in general, $E_T$(atom-atom,msp$^3$), the energy change of each atom msp$^3$ shell with the formation of the atom-atom-bond MO is given by Eq. (56). In the case that during hybridization, at least one of the spin-paired AO electrons is unpaired in the hybridized orbital (HO), the energy change for the promotion to the unpaired state is the magnetic energy E(magnetic) (Eq. (52)) at the initial radius r of the AO electron. Then, the energy E(mol·atom,msp$^3$) of the outer electron of the atom msp$^3$ shell is given by the sum of $E_{Coulomb}$(mol.atom,msp$^3$) and E(magnetic) (Eq. (57)). $E_T$(atom-atom,msp$_3$), the energy change of each atom msp$^3$ shell with the formation of the atom-atom-bond MO is given by the difference between E(mol.atom,msp$^3$) and E(atom, msp$_3$) given by Eq. (58). Using Eq. (60) for $E_{Coulomb}$(C, 2sp$^3$) in Eq. (68), the single bond order energies given by Eqs. (55-64) and shown in Table 4, and the linear combination energies (Eqs. (65-67)), the parameters of linear combinations of bond orders and linear combinations of mixed bond orders are given in Table 5.

TABLE 5

The final values of $r_{C2sp^3}$, $E_{Coulomb}$(C2sp$^3$), and E(C2sp$^3$) and the resulting $E_T(C\underline{\underline{BO}}C, C2sp^3)$ of the MO comprising a linear combination of H$_2$-type ellipsoidal MOs and corresponding HOs of single or mixed bond order where $c_{s_n}$ is the multiple of the bond order parameter $E_T$(atom-atom(s$_n$), msp$^3$) given in Table 4.

| MO Bond Order (BO) | $s_1$ | $c_{s_1}$ | $s_2$ | $c_{s_2}$ | $s_3$ | $c_{s_3}$ | $r_{C2sp^3}^3(a_0)$ Final | $E_{Coulomb}$(C2sp$^3$) (eV) Final | E(C2sp$^3$) (eV) Final | $E_T(C\underline{\underline{BO}}C, C2sp^3)$ (eV) |
|---|---|---|---|---|---|---|---|---|---|---|
| 1/2I | 1 | 0.5 | 0 | 0 | 0 | 0 | 0.89582 | −15.18804 | −14.99717 | −0.36228 |
| 1/2II | 2 | 0.5 | 0 | 0 | 0 | 0 | 0.88392 | −15.39265 | −15.20178 | −0.56689 |
| 1/2I + 1/4II | 1 | 0.5 | 2 | 0.25 | 0 | 0.25 | 0.87941 | −15.47149 | −15.28062 | −0.64573 |
| 1/4II + 1/4(I + II) | 2 | 0.25 | 1 | 0.25 | 2 | 0.25 | 0.87363 | −15.57379 | −15.38293 | −0.74804 |
| 3/4II | 2 | 0.75 | 0 | 0 | 0 | 0 | 0.86793 | −15.67610 | −15.48523 | −0.85034 |
| 1/2I + 1/2II | 1 | 0.5 | 2 | 0.5 | 0 | 0 | 0.86359 | −15.75493 | −15.56407 | −0.92918 |
| 1/2I + 1/2III | 1 | 0.5 | 3 | 0.5 | 0 | 0 | 0.85193 | −15.97060 | −15.77974 | −1.14485 |
| 1/2I + 1/2IV | 1 | 0.5 | 4 | 0.5 | 0 | 0 | 0.83995 | −16.19826 | −16.00739 | −1.37250 |
| 1/2II + 1/2III | 2 | 0.5 | 3 | 0.5 | 0 | 0 | 0.84115 | −16.17521 | −15.98435 | −1.34946 |
| 1/2II + 1/2IV | 2 | 0.5 | 4 | 0.5 | 0 | 0 | 0.82948 | −16.40286 | −16.21200 | −1.57711 |
| I + 1/2(I + II) | 1 | 1 | 1 | 0.5 | 2 | 0.5 | 0.82562 | −16.47951 | −16.28865 | −1.65376 |
| 1/2III + 1/2IV | 3 | 0.5 | 4 | 0.5 | 0 | 0 | 0.81871 | −16.61853 | −16.42767 | −1.79278 |
| 1/2IV + 1/2IV | 4 | 0.5 | 4 | 0.5 | 0 | 0 | 0.80765 | −16.84619 | −16.65532 | −2.02043 |
| 1/2(I + II) + II | 1 | 0.5 | 2 | 0.5 | 2 | 1 | 0.80561 | −16.88873 | −16.69786 | −2.06297 | shell with the formation of each atom-atom-bond MO, is a weighted linear sum for different values of s that matches the energy of the bonded MOs, HOs, and AOs:

$$E_T(\text{atom—atom}, msp^3) = \sum_{n=1}^{N} c_{S_n} E_T(\text{atom—atom}(s_n), msp^3) \quad (67)$$

where $c_{s_n}$ is the multiple of the BO of $s_n$. The radius $r_{msp^3}$ of the atom msp$^3$ shell of each bonding atom is given by the Coulombic energy using the initial energy $E_{Coulomb}$(atom, msp$^3$) and $E_T$(atom-atom,msp$^3$), the energy change of each atom msp$^3$ shell with the formation of each atom-atom-bond MO:

$$r_{msp^3} = \frac{-e^2}{8\pi\varepsilon_0 a_0 \left( E_{Coulomb}(\text{atom}, msp^3) + E_T(\text{atom—atom}, msp^3) \right)} \quad (68)$$

where $E_{Coulomb}$(C2sp$^3$)=−14.825751 eV. The Coulombic energy $E_{Coulomb}$(mol·atom,msp$^3$) of the outer electron of the Consider next the radius of the AO or HO due to the contribution of charge to more than one bond. The energy contribution due to the charge donation at each atom such as carbon superimposes linearly. In general, the radius $r_{mol2sp^3}$ of the C2sp$^3$ HO of a carbon atom of a given molecule is calculated using Eq. (14.514) by considering $\Sigma E_{T_{mol}}$(MO, 2sp$_3$), the total energy donation to all bonds with which it participates in bonding. The general equation for the radius is given by $$r_{mol2sp^3} = \frac{-e^2}{8\pi\varepsilon_0 \left( E_{Coulomb}(C, 2sp^3) + \sum E_{T_{mol}}(MO, 2sp^3) \right)} \quad (69)$$

$$= \frac{-e^2}{8\pi\varepsilon_0 \left( e14.825751 \text{ eV} + \sum |E_{T_{mol}}(MO, 2sp^3)| \right)}$$

The Coulombic energy $E_{Coulomb}$(mol.atom,msp$^3$) of the outer electron of the atom msp$^3$ shell is given by Eq. (56). In the case that during hybridization, at least one of the spin-paired AO electrons is unpaired in the hybridized orbital (HO), the energy change for the promotion to the unpaired state is the magnetic energy E(magnetic) (Eq. (52)) at the initial radius r of the AO electron. Then, the energy $E(mol.atom,msp_3)$ of the outer electron of the atom $msp^3$ shell is given by the sum of $E_{Coulomb}(mol.atom,msp^3)$ and $E(magnetic)$ (Eq. (57)).

For example, the $C2sp^3$ HO of each methyl group of an alkane contributes $-0.92918$ eV (Eq. (14.513)) to the corresponding single C—C bond; thus, the corresponding $C2sp^3$ HO radius is given by Eq. (14.514). The $C2sp^3$ HO of each methylene group of $C_nH_{2n+2}$ contributes $-0.92918$ eV to each of the two corresponding C—C bond MOs. Thus, the radius (Eq. (69)), the Coulombic energy (Eq. (56)), and the energy (Eq. (57)) of each alkane methylene group are $$r_{alkaneC_{methylene}2sp^3} = \frac{-e^2}{8\pi\varepsilon_0 \left( E_{Coulomb}(C, 2sp^3) + \sum E_{T_{alkane}} \right)} \quad (70)$$
$$\text{(methylene C—C, } 2sp^3\text{)}$$

$$= \frac{e^2}{8\pi\varepsilon_0 \left( \begin{array}{c} e14.825751 \text{ eV} + \\ e0.93918 \text{ eV} + e0.92918 \text{ eV} \end{array} \right)}$$

$$= 0.81549 a_0$$

$$E_{Coulomb}(C_{methylene}2sp^3) = \frac{-e^2}{8\pi\varepsilon_0(0.81549a_0)} = -16.68412 \text{ eV} \quad (71)$$

$$E(C_{methylene}2sp^3) = \frac{-e^2}{8\pi\varepsilon_0(0.81549a_0)} \quad (72)$$

$$= \frac{2\pi\mu_0 e^2 \hbar^2}{m_e^2(0.84317a_0)^3}$$

$$= -16.49325 \text{ eV}$$

In the determination of the parameters of functional groups, heteroatoms bonding to $C2sp^3$ HOs to form MOs are energy matched to the $C2sp^3$ HOs. Thus, the radius and the energy parameters of a bonding heteroatom are given by the same equations as those for $C2sp^3$ HOs. Using Eqs. (52), (56-57), (61), and (69) in a generalized fashion, the final values of the radius of the HO or AO, $r_{Atom.HO.AO}$, $E_{Coulomb}(mol.atom,msp^3)$, and $E(C_{mol}2sp^3)$ are calculated using $\Sigma E_{T_{group}}(MO,2sp^3)$, the total energy donation to each bond with which an atom participates in bonding corresponding to the values of $$E_T(C^{BO}C, C2sp^3)$$

of the MO due to charge donation from the AO or HO to the MO given in Tables 4 and 5.

The energy of the MO is matched to each of the participating outermost atomic or hybridized orbitals of the bonding atoms wherein the energy match includes the energy contribution due to the AO or HO's donation of charge to the MO. The force constant k' (Eq. (38)) is used to determine the ellipsoidal parameter c' (Eq. (39)) of the each $H_2$-type-ellipsoidal-MO in terms of the central force of the foci. Then, c' is substituted into the energy equation (from Eq. (48))) which is set equal to $n_1$ times the total energy of $H_2$ where $n_1$ is the number of equivalent bonds of the MO and the energy of $H_2$, $-31.63536831$ eV, Eq. (11.212) is the minimum energy possible for a prolate spheroidal MO. From the energy equation and the relationship between the axes, the dimensions of the MO are solved. The energy equation has the semimajor axis a as it only parameter. The solution of the semimajor axis a then allows for the solution of the other axes of each prolate spheroid and eccentricity of each MO (Eqs. (40-42)). The parameter solutions then allow for the component and total energies of the MO to be determined.

The total energy, $E_{T(H_2MO)}$, is given by the sum of the energy terms (Eqs. (43-48)) plus $E_T(AO/HO)$:

$$E_T(H_2MO) = V_e + T + V_m + V_p + E_T(AO/HO) \quad (73)$$

$$E_T(H_2MO) = -\frac{n_1 e^2}{8\pi\varepsilon_o \sqrt{a^2-b^2}} \left[ \ln \frac{a+\sqrt{a^2-b^2}}{a-\sqrt{a^2-b^2}} - 1 \right] + \quad (74)$$

$$E_T(AO/HO)$$

$$= \frac{n_1 e^2}{8\pi\varepsilon_o c'} \left[ \frac{c_1 c_2 \left(2-\frac{a_0}{a}\right)}{\ln \frac{a+c'}{a-c'} - 1} \right] + E_T(AO/HO)$$

where $n_1$ is the number of equivalent bonds of the MO, $c_1$ is the fraction of the $H_2$-type ellipsoidal MO basis function of a chemical bond of the group, $c_2$ is the factor that results in an equipotential energy match of the participating at least two atomic orbitals of each chemical bond, and $E_T(AO/HO)$ is the total energy comprising the difference of the energy $E(AO/HO)$ of at least one atomic or hybrid orbital to which the MO is energy matched and any energy component $\Delta E_{H_2MO}(AO/HO)$ due to the AO or HO's charge donation to the MO.

$$E_T(AO/HO)=E(AO/HO)-\Delta E_{H_2MO}(AO/HO) \quad (75)$$

To solve the bond parameters and energies, $$c' = a\sqrt{\frac{\hbar^2 4\pi\varepsilon_0}{m_e e^2 2C_1 C_2 a}} = \sqrt{\frac{aa_0}{2C_1 C_2}}$$

(Eq. (39)) is substituted into $E_{T(H_2MO)}$ to give $$E_{T(H_2MO)} = -\frac{n_1 e^2}{8\pi\varepsilon_o \sqrt{a^2-b^2}} \left[ \ln \frac{a+\sqrt{a^2-b^2}}{a-\sqrt{a^2-b^2}} - 1 \right] + \quad (76)$$

$$E_T(AO/HO)$$

$$= \frac{n_1 e^2}{8\pi\varepsilon_o c'} \left[ \frac{c_1 c_2 \left(2-\frac{a_0}{a}\right)}{\ln \frac{a+c'}{a-c'} - 1} \right] + E_T(AO/HO)$$

$$= -\frac{n_1 e^2}{8\pi\varepsilon_o \sqrt{\frac{aa_0}{2C_1 C_2}}} \left[ \ln \frac{a+\sqrt{\frac{aa_0}{2C_1 C_2}}}{a-\sqrt{\frac{aa_0}{2C_1 C_2}}} - 1 \right] +$$

$$E_T(AO/HO)$$

The total energy is set equal to E(basis energies) which in the most general case is given by the sum of a first integer $n_1$ times the total energy of $H_2$ minus a second integer $n_2$ times the total energy of H, minus a third integer $n_3$ times the valence energy of $E(AO)$ (e.g. $E(N)=-14.53414$ eV) where the first integer can be 1, 2, 3 . . . , and each of the second and third integers can be 0, 1, 2, 3 . . . .

$$E(\text{basis energies}) = n_1(-31.63536831 \text{ eV}) - n_2(-13.605804 \text{ eV}) - n_3 E(AO) \quad (77)$$

In the case that the MO bonds two atoms other than hydrogen, E(basis energies) is $n_1$ times the total energy of $H_2$ where $n_1$ is the number of equivalent bonds of the MO and the energy of $H_2$, $-31.63536831$ eV, Eq. (11.212) is the minimum energy possible for a prolate spheroidal MO:

$$E(\text{basis energies}) = n_1(-31.63536831 \text{ eV}) \quad (78)$$

$E_T^{(H_2MO)}$, is set equal to E(basis energies), and the semimajor axis a is solved. Thus, the semimajor axis a is solved from the equation of the form:

$$-\frac{n_1 e^2}{8\pi\varepsilon_o \sqrt{\frac{aa_0}{2C_1C_2}}} \left[ \ln \frac{a + \sqrt{\frac{aa_0}{2C_1C_2}}}{a - \sqrt{\frac{aa_0}{2C_1C_2}}} - 1 \right] + E_T(\text{AO/HO}) = \quad (79)$$

$$E(\text{basis energies})$$

The distance from the origin of the $H_2$-type-ellipsoidal-MO to each focus c', the internuclear distance 2c', and the length of the semiminor axis of the prolate spheroidal $H_2$-type MO b=c are solved from the semimajor axis a using Eqs. (39-41). Then, the component energies are given by Eqs. (43-46) and (76).

The total energy of the MO of the functional group, $E_T^{(MO)}$, is the sum of the total energy of the components comprising the energy contribution of the MO formed between the participating atoms and $E_T$(atom-atom,msp$^3$.AO), the change in the energy of the AOs or HOs upon forming the bond. From Eqs. (76-77), $E_T^{(MO)}$ is $$E_T^{(MO)} = E(\text{basis energies}) + E_T(\text{atom-atom}, msp^3.AO) \quad (80)$$

During bond formation, the electrons undergo a reentrant oscillatory orbit with vibration of the nuclei, and the corresponding energy $\bar{E}_{osc}$ is the sum of the Doppler, $\bar{E}_D$, and average vibrational kinetic energies, $\bar{E}_{Kvib}$:

$$\bar{E}_{osc} = n_1(\bar{E}_D + \bar{E}_{Kvib}) = n_1 \left( E_{hv} \sqrt{\frac{2\bar{E}_K}{m_e c^2}} + \frac{1}{2}\hbar\sqrt{\frac{k}{\mu}} \right) \quad (81)$$

where $n_1$ is the number of equivalent bonds of the MO, k is the spring constant of the equivalent harmonic oscillator, and $\mu$ is the reduced mass. The angular frequency of the reentrant oscillation in the transition state corresponding to $\bar{E}_D$ is determined by the force between the central field and the electrons in the transition state. The force and its derivative are given by $$f(R) = -\frac{C_{1o}C_{2o}e^2}{4\pi\varepsilon_0 R^3} \quad (82)$$

and $$f'(a) = 2\frac{C_{1o}C_{2o}e^2}{4\pi\varepsilon_0 R^3} \quad (83)$$

such that the angular frequency of the oscillation in the transition state is given by $$\omega = \sqrt{\frac{\left[\frac{-3}{a}f(a) - f'(a)\right]}{m_e}} = \sqrt{\frac{k}{m_e}} = \sqrt{\frac{\frac{C_{1o}C_{2o}e^2}{4\pi\varepsilon_0 R^3}}{m_e}} \quad (84)$$

where R is the semimajor axis a or the semiminor axis b depending on the eccentricity of the bond that is most representative of the oscillation in the transition state. $C_{1o}$ is the fraction of the $H_2$-type ellipsoidal MO basis function of the oscillatory transition state of a chemical bond of the group, and $C_{2o}$ is the factor that results in an equipotential energy match of the participating at least two atomic orbitals of the transition state of the chemical bond. Typically, $C_{1o}=C_1$ and $C_{2o}=C_2$. The kinetic energy, $\bar{E}_K$, corresponding to $\bar{E}_D$ is given by Planck's equation for functional groups:

$$\bar{E}_K = \hbar\omega = \hbar\sqrt{\frac{\frac{C_{1o}C_{2o}e^2}{4\pi\varepsilon_0 R^3}}{m_e}} \quad (85)$$

The Doppler energy of the electrons of the reentrant orbit is $$\bar{E}_D \cong E_{hv}\sqrt{\frac{2\bar{E}_K}{m_e c^2}} = E_{hv}\sqrt{\frac{2\hbar\sqrt{\frac{C_{1o}C_{2o}e^2}{4\pi\varepsilon_0 R^3}}{m_e}}{m_e c^2}} \quad (86)$$

$\bar{E}_{osc}$ given by the sum of $\bar{E}_D$ and $\bar{E}_{Kvib}$ is $$\bar{E}_{osc(group)} = n_1(\bar{E}_D + \bar{E}_{Kvib}) \quad (87)$$

$$= n_1 \left( E_{hv} \sqrt{\frac{2\hbar\sqrt{\frac{C_{1o}C_{2o}e^2}{4\pi\varepsilon_0 R^3}}{m_e}}{m_e c^2}} + E_{vib} \right)$$

$E_{hv}$ of a group having $n_1$ bonds is given by $E_T^{(MO)}/n_1$ such that $$\bar{E}_{osc} = n_1(\bar{E}_D + \bar{E}_{Kvib}) = n_1 \left( E_{T(MO)}/n_1 \sqrt{\frac{2\bar{E}_K}{Mc^2}} + \frac{1}{2}\hbar\sqrt{\frac{k}{u}} \right) \quad (88)$$

$E_{T+osc}^{(Group)}$ is given by the sum of $E_T^{(MO)}$ (Eq. (79)) and $\bar{E}_{osc}$ (Eq. (88)):

$$E_{T+osc(Group)} = E_{T(MO)} + \bar{E}_{osc} \quad (89)$$

$$E_{T(Group)} = \left( \begin{pmatrix} -\dfrac{n_1 e^2}{8\pi\varepsilon_0 \sqrt{\dfrac{aa_0}{2C_1C_2}}} \begin{bmatrix} c_1c_2\left(2-\dfrac{a_0}{a}\right) \\ \ln\dfrac{a+\sqrt{\dfrac{aa_0}{2C_1C_2}}}{a-\sqrt{\dfrac{aa_0}{2C_1C_2}}} - 1 \end{bmatrix} \\ E_T(\text{AO/HO}) + E_T(\text{atom—atom, }msp^3 \cdot \text{AO}) \end{pmatrix} \right.$$

$$= \begin{pmatrix} E(\text{basis energies}) + \\ E_T(\text{atom—atom, }msp^3 \cdot \text{AO}) \end{pmatrix}$$

$$\left[ 1 + \sqrt{\dfrac{2\hbar\sqrt{\dfrac{C_{1o}C_{2o}e^2}{4\pi\varepsilon_0 R^3}}}{m_e c^2}} \right] + n_1 \dfrac{1}{2}\hbar\sqrt{\dfrac{k}{\mu}}$$

The total energy of the functional group $E_{T(group)}$ is the sum of the total energy of the components comprising the energy contribution of the MO formed between the participating atoms, E(basis energies), the change in the energy of the AOs or HOs upon forming the bond ($E_T$(atom-atom, $msp^3$.AO)), the energy of oscillation in the transition state, and the change in magnetic energy with bond formation, $E_{mag}$. From Eq. (89), the total energy of the group $E_{T(Group)}$ is $$E_{T(Group)} = \left( \begin{pmatrix} E(\text{basis energies}) + \\ E_T(\text{atom—atom, }msp^3 \cdot \text{AO}) \end{pmatrix} \right) \left[ 1 + \sqrt{\dfrac{2\hbar\sqrt{\dfrac{C_{1o}C_{2o}e^2}{4\pi\varepsilon_o R^3}}}{m_e c^2}} \right] + n_1 \overline{E}_{Kvib} + E_{mag} \right) \quad (90)$$

The change in magnetic energy $E_{mag}$ which arises due to the formation of unpaired electrons in the corresponding fragments relative to the bonded group is given by $$E_{mag} = c_3 \dfrac{2\pi\mu_0 e^2 \hbar^2}{m_e^2 r^3} = c_3 \dfrac{8\pi\mu_o \mu_B^2}{r^3} \quad (91)$$

where $r^3$ is the radius of the atom that reacts to form the bond and $c_3$ is the number of electron pairs.

$$E_{T(Group)} = \left( \begin{pmatrix} E(\text{basis energies}) + \\ E_T(\text{atom—atom, }msp^3 \cdot \text{AO}) \end{pmatrix} \right) \left[ 1 + \sqrt{\dfrac{2\hbar\sqrt{\dfrac{C_{1o}C_{2o}e^2}{4\pi\varepsilon_o R^3}}}{m_e c^2}} \right] + \\ n_1 \overline{E}_{Kvib} + c_3 \dfrac{8\pi\mu_o \mu_B^2}{r_n^3} \quad (92)$$

The total bond energy of the group $E_{D(Group)}$ is the negative difference of the total energy of the group (Eq. (92)) and the total energy of the starting species given by the sum of $c_4 E_{initial}(c_4$ AO/HO) and $c_5 E_{initial}(c_5$ AO/HO):

$$E_{D(Group)} = -\left( \begin{pmatrix} E(\text{basis energies}) + \\ E_T(\text{atom—atom, }msp^3 \cdot \text{AO}) \end{pmatrix} \left[ 1 + \sqrt{\dfrac{2\hbar\sqrt{\dfrac{C_{1o}C_{2o}e^2}{4\pi\varepsilon_o R^3}}}{m_e c^2}} \right] + n_1 \overline{E}_{Kvib} + \\ c_3 \dfrac{8\pi\mu_o \mu_B^2}{r_n^3} - \begin{pmatrix} c_4 E_{initial}(\text{AO/HO}) + \\ c_5 E_{initial}(c_5 \text{ AO/HO}) \end{pmatrix} \right) \quad (93)$$

In the case of organic molecules, the atoms of the functional groups are energy matched to the C2sp$^3$ HO such that $$E(AO/HO) = -14.63489 \text{ eV} \quad (94)$$

For example, of $E_{mag}$ of the C2sp$_3$ HO is:

$$E_{mag}(C2sp^3) = c_3 \dfrac{8\pi\mu_o \mu_B^2}{r^3} \quad (95)$$
$$= c_3 \dfrac{8\pi\mu_o \mu_B^2}{(0.91771a_0)^3}$$
$$= c_3 0.14803 \text{ eV}$$

Each molecule, independently of its complexity and size, is comprised of functional groups wherein each present occurs an integer number of times in the molecule. The total bond energy of the molecule is then given by the integer-weighted sum of the energies of the functions groups corresponding to the composition of the molecule. Thus, integer formulas can be constructed easily for molecules for a given class such as straight-chain hydrocarbons considered as an example infra. The results demonstrate how simply and instantaneously molecules are solved using the classical exact solutions. In contrast, quantum mechanics requires that wavefunction are nonlinear, and any sum must be squared. The results of Millsian disprove quantum mechanics in this regard, and the linearity and superposition properties of Millsian represent a breakthrough with orders of magnitude reduction in complexity in solving molecules as well as being accurate physical representations rather than pure mathematical curve-fits devoid of a connection to reality.

Total Energy of Continuous-Chain Alkanes $E_D(C_nH_{2n+2})$, the total bond dissociation energy of $C_nH_{2n+2}$, is given as the sum of the energy components due to the two methyl groups, n−2 methylene groups, and n−1 C—C bonds where each energy component is given by Eqs. (14.590), (14.625), and (14.641), respectively. Thus, the total bond dissociation energy of $C_nH_{2n+2}$ is $$E_D(C_nH_{2n+2}) = E_D(C\text{—}C)_{n-1} + 2E_{D_{alkane}}(^{12}CH_3) + \quad (96)$$
$$(n-2)E_{D_{alkane}}(^{12}CH_2)$$
$$= (n-1)(4.32754 \text{ eV}) + 2$$
$$(12.49186 \text{ eV}) + (n-2)(7.83016 \text{ eV})$$

The experimental total bond dissociation energy of $C_2H_{2n+2}$, $E_{D_{exp}}(C_nH_{2n+2})$, is given by the negative difference between the enthalpy of its formation ($\Delta H_f(C_nH_{2n+2}(gas))$) and the sum of the enthalpy of the formation of the reactant gaseous carbons ($\Delta H_f(C(gas))$) and hydrogen ($\Delta H_f(H(gas))$) atoms:

$$E_{D_{exp}}(C_nH_{2n+2}) = -\left\{\begin{array}{c}\Delta H_f(C_nH_{2n+2}(gas)) - \\ \left[\begin{array}{c}n\Delta H_f(C(gas)) + \\ (2n+2)\Delta H_f(H(gas))\end{array}\right]\end{array}\right\} \quad (97)$$

$$= -\left\{\begin{array}{c}\Delta H_f(C_nH_{2n+2}(gas)) - \\ \left[\begin{array}{c}n7.42774 \text{ eV} + \\ (2n+2)2.259353 \text{ eV}\end{array}\right]\end{array}\right\}$$

where the heats of formation atomic carbon and hydrogen gas are given by [32-33]

$$\Delta H_f(C(gas)) = 716.68 \text{ kJ/mole } (7.42774 \text{ eV/molecule}) \quad (98)$$

$$\Delta H_f(H(gas)) = 217.998 \text{ k/mole } (2.259353 \text{ eV/molecule}) \quad (99)$$

The comparison of the results predicted by Eq. (96) and the experimental values given by using Eqs. (97-99) with the data from Refs. [32-33] is given in Table 6.

TABLE 6

Summary results of n-alkanes.

| Formula | Name | Calculated Total Bond Energy (eV) | Experimental Total Bond Energy (eV) | Relative Error |
|---|---|---|---|---|
| $C_3H_8$ | Propane | 41.46896 | 41.434 | −0.00085 |
| $C_4H_{10}$ | Butane | 53.62666 | 53.61 | −0.00036 |
| $C_5H_{12}$ | Pentane | 65.78436 | 65.77 | −0.00017 |
| $C_6H_{14}$ | Hexane | 77.94206 | 77.93 | −0.00019 |
| $C_7H_{16}$ | Heptane | 90.09976 | 90.09 | −0.00013 |
| $C_8H_{18}$ | Octane | 102.25746 | 102.25 | −0.00006 |
| $C_9H_{20}$ | Nonane | 114.41516 | 114.40 | −0.00012 |
| $C_{10}H_{22}$ | Decane | 126.57286 | 126.57 | −0.00003 |
| $C_{11}H_{24}$ | Undecane | 138.73056 | 138.736 | 0.00004 |
| $C_{12}H_{26}$ | Dodecane | 150.88826 | 150.88 | −0.00008 |
| $C_{18}H_{38}$ | Octadecane | 223.83446 | 223.85 | 0.00008 |

The following list of references, which are also incorporated herein by reference in their entirety, are referred to in the above sections using [brackets]:

REFERENCES

1. R. Mills, *The Grand Unified Theory of Classical Physics*; June 2008 Edition, posted at http://www.blacklightpower.com/theory/bookdownload.shtml.
2. R. L. Mills, B. Holverstott, B. Good, N. Hogle, A. Makwana, J. Paulus, "Total Bond Energies of Exact Classical Solutions of Molecules Generated by Millsian 1.0 Compared to Those Computed Using Modern 3-21G and 6-310G* Basis Sets", submitted.
3. R. L. Mills, "Classical Quantum Mechanics", Physics Essays, Vol. 16, No. 4, December, (2003), pp. 433-498.
4. R. Mills, "Physical Solutions of the Nature of the Atom, Photon, and Their Interactions to Form Excited and Predicted Hydrino States", in press.
5. R. L. Mills, "Exact Classical Quantum Mechanical Solutions for One- Through Twenty-Electron Atoms", Physics Essays, Vol. 18, (2005), pp. 321-361.
6. R. L. Mills, "The Nature of the Chemical Bond Revisited and an Alternative Maxwellian Approach", Physics Essays, Vol. 17, (2004), pp. 342-389.
7. R. L. Mills, "Maxwell's Equations and QED: Which is Fact and Which is Fiction", Vol. 19, (2006), pp. 225-262.
8. R. L. Mills, "Exact Classical Quantum Mechanical Solution for Atomic Helium Which Predicts Conjugate Parameters from a Unique Solution for the First Time", in press.
9. R. L. Mills, "The Fallacy of Feynman's Argument on the Stability of the Hydrogen Atom According to Quantum Mechanics," Annales de la Fondation Louis de Broglie, Vol. 30, No. 2, (2005), pp. 129-151.
10. R. Mills, "The Grand Unified Theory of Classical Quantum Mechanics", Int. J. Hydrogen Energy, Vol. 27, No. 5, (2002), pp. 565-590.
11. R. Mills, The Nature of Free Electrons in Superfluid Helium—a Test of Quantum Mechanics and a Basis to Review its Foundations and Make a Comparison to Classical Theory, Int. J. Hydrogen Energy, Vol. 26, No. 10, (2001), pp. 1059-1096.
12. R. Mills, "The Hydrogen Atom Revisited", Int. J. of Hydrogen Energy, Vol. 25, Issue 12, December, (2000), pp. 1171-1183.
13. R. Mills, "The Grand Unified Theory of Classical Quantum Mechanics", Global Foundation, Inc. Orbis Scientiae entitled *The Role of Attractive and Repulsive Gravitational Forces in Cosmic Acceleration of Particles The Origin of the Cosmic Gamma Ray Bursts*, (29th Conference on High Energy Physics and Cosmology Since 1964) Dr. Behram N. Kursunoglu, Chairman, Dec. 14-17, 2000, Lago Mar Resort, Fort Lauderdale, Fla., Kluwer Academic/Plenum Publishers, New York, pp. 243-258.
14. P. Pearle, Foundations of Physics, "Absence of radiationless motions of relativistically rigid classical electron", Vol. 7, Nos. 11/12, (1977), pp. 931-945.
15. V. F. Weisskopf, Reviews of Modern Physics, Vol. 21, No. 2, (1949), pp. 305-315.
16. A. Einstein, B. Podolsky, N. Rosen, Phys. Rev., Vol. 47, (1935), p. 777.
17. H. Wergeland, "The Klein Paradox Revisited", *Old and New Questions in Physics, Cosmology, Philosophy, and Theoretical Biology*, A. van der Merwe, Editor, Plenum Press, New York, (1983), pp. 503-515.
18. F. Laloë, Do we really understand quantum mechanics? Strange correlations, paradoxes, and theorems, Am. J. Phys. 69 (6), June 2001, 655-701.
19. F. Dyson, "Feynman's proof of Maxwell equations", Am. J. Phys., Vol. 58, (1990), pp. 209-211.
20. H. A. Haus, "On the radiation from point charges", American Journal of Physics, Vol. 54, (1986), 1126-1129.
21. J. D. Jackson, *Classical Electrodynamics*, Second Edition, John Wiley & Sons, New York, (1975), pp. 739-779.
22. J. D. Jackson, *Classical Electrodynamics*, Second Edition, John Wiley & Sons, New York, (1975), p. 111.
23. T. A. Abbott and D. J. Griffiths, Am. J. Phys., Vol. 153, No. 12, (1985), pp. 1203-1211.
24. G. Goedecke, Phys. Rev 135B, (1964), p. 281.
25. http://www.blacklightpower.com/theory/theory.shtml.
26. W. J. Nellis, "Making Metallic Hydrogen," Scientific American, May, (2000), pp. 84-90.
27. J. Itatani, J. Levesque, D. Zeidler, H. Niikura, H. Pepin, J. C. Kieffer, P. B. Corkum, D. M. Villeneuve, "Tomographic imaging of molecular orbitals", Nature, Vol. 432, (2004), pp. 867-871.
28. J. A. Stratton, *Electromagnetic Theory* (McGraw-Hill Book Company, 1941), p. 195.
29. J. D. Jackson, *Classical Electrodynamics*, $2^{nd}$ Edition (John Wiley & Sons, New York, (1975), pp. 17-22.
30. H. A. Haus, J. R. Melcher, "Electromagnetic Fields and Energy," Department of Electrical Engineering and Computer Science, Massachusetts Institute of Technology, (1985), Sec. 5.3.
31. NIST Computational Chemistry Comparison and Benchmark Data Base, NIST Standard Reference Database Number 101, Release 14, September, (2006), Editor R. D. Johnson III, http://srdata.nist.gov/cccbdb.

32. D. R. Lide, *CRC Handbook of Chemistry and Physics,* 79th Edition, CRC Press, Boca Raton, Fla., (1998-9), pp. 9-63.

33. D. R. Lide, *CRC Handbook of Chemistry and Physics,* 79th Edition, CRC Press, Boca Raton, Fla., (1998-9), pp. 5-1 to 5-60.

The equation numbers and sections-referenced herein infra. are those disclosed in R. Mills, *The Grand Unified Theory of Classical Physics*; June 2008 Edition, posted at http://www.blacklightpower.com/theory/bookdownload.shtml which is herein incorporated by reference in its entirety.

General Considerations of the Bonding in Pharmaceutical and Specialty Molecules

Pharmaceutical and specialty molecules comprising an arbitrary number of atoms can be solved using similar principles and procedures as those used to solve general organic molecules of arbitrary length and complexity. Pharmaceuticals and specialty molecules can be considered to be comprised of functional groups such those of alkanes, branched alkanes, alkenes, branched alkenes, alkynes, alkyl fluorides, alkyl chlorides, alkyl bromides, alkyl iodides, alkene halides, primary alcohols, secondary alcohols, tertiary alcohols, ethers, primary amines, secondary amines, tertiary amines, aldehydes, ketones, carboxylic acids, carboxylic esters, amides, N-alkyl amides, N,N-dialkyl amides, ureas, acid halides, acid anhydrides, nitriles, thiols, sulfides, disulfides, sulfoxides, sulfones, sulfite, sulfates, nitro alkanes, nitrites, nitrates, conjugated polyenes, aromatics, heterocyclic aromatics, substituted aromatics, and others given in the Organic Molecular Functional Groups and Molecules section. The solutions of the functional groups can be conveniently obtained by using generalized forms of the geometrical and energy equations. The functional-group solutions can be made into a linear superposition and sum, respectively, to give the solution of any pharmaceutical or specialty molecule comprising these groups. The total bond energies of exemplary pharmaceutical or specialty molecules such as aspirin, RDX, and NaH are calculated using the functional group composition and the corresponding energies derived in the previous sections as well as those of any new component functional groups derived herein.

Aspirin (Acetylsalicylic Acid)

Aspirin comprises salicylic acid (ortho-hydroxybenzoic acid) with the H of the phenolic OH group replaced by an acetyl group. Thus, aspirin comprises the benzoic acid C—C(O)—OH moiety that comprises C=O and OH functional groups that are the same as those of carboxylic acids given in the corresponding section. The single bond of aryl carbon to the carbonyl carbon atom, C—C(O), is also a functional group given in the Benzoic Acid Compounds section. The aromatic

and C—H functional groups are equivalent to those of benzene given in Aromatic and Heterocyclic Compounds section. The phenolic ester C—O functional group is equivalent to that given in the Phenol section. The acetyl O—C(O)—CH₃ moiety comprises (i) C=O and C—C functional groups that are the same as those of carboxylic acids and esters given in the corresponding sections, (ii) a CH₃ group that is equivalent to that of alkanes given in the corresponding sections, (iii) and a C—O bridging the carbonyl carbon and the phenolic ester which is equivalent to that of esters given in the corresponding section.

The symbols of the functional groups of aspirin are given in Table 7. The corresponding designations of aspirin are shown in FIG. 5. The geometrical (Eqs. (15.1-15.5) and (15.51)), intercept (Eqs. (15.80-15.87)), and energy (Eqs. (15.6-15.11) and (15.17-15.65)) parameters of aspirin are given in Tables 8, 9, and 10, respectively. The total energy of aspirin given in Table 11 was calculated as the sum over the integer multiple of each $E_{D(Group)}$ of Table 10 corresponding to functional-group composition of the molecule. The bond angle parameters of aspirin determined using Eqs. (15.88-15.117) are given in Table 12. The color scale, translucent view of the charge density of aspirin comprising the concentric shells of atoms with the outer shell bridged by one or more $H_2$-type ellipsoidal MOs or joined with one or more hydrogen MOs is shown in FIG. 6.

TABLE 7

The symbols of functional groups of aspirin.

| Functional Group | Group Symbol |
|---|---|
| CC (aromatic bond) | $C\overset{3e}{=}C$ |
| CH (aromatic) | CH |
| Aryl C—C(O) | C—C(O) (i) |
| Alkyl C—C(O) | C—C(O) (ii) |
| C=O (aryl carboxylic acid) | C=O |
| Aryl (O)C—O | C—O (i) |
| Alkyl (O)C—O | C—O (ii) |
| Aryl C—O | C—O (iii) |
| OH group | OH |
| CH₃ group | CH₃ |

TABLE 8

The geometrical bond parameters of aspirin and experimental values of similar molecules [1].

| Parameter | $C\overset{3e}{=}C$ Group | CH Group | C—C(O) (i) Group | C—C(O) (ii) Group | C=O Group |
|---|---|---|---|---|---|
| a (a₀) | 1.47348 | 1.60061 | 1.95111 | 2.04740 | 1.29907 |
| c' (a0) | 1.31468 | 1.03299 | 1.39682 | 1.43087 | 1.13977 |
| Bond Length 2c' (Å) | 1.39140 | 1.09327 | 1.47833 | 1.51437 | 1.20628 |
| Exp. Bond Length (Å) | 1.399 (benzene) | 1.101 (benzene) | 1.48[2] (benzoic acid) | 1.520 (acetic acid) | 1.214 (acetic acid) |
| b, c (a₀) | 0.66540 | 1.22265 | 1.36225 | 1.46439 | 0.62331 |
| e | 0.89223 | 0.64537 | 0.71591 | 0.69887 | 0.87737 |

| Parameter | C—O (i) Group | C—O (ii) Group | C—O (iii) Group | OH Group | C—H (CH₃) Group |
|---|---|---|---|---|---|
| a (a₀) | 1.73490 | 1.73490 | 1.68220 | 1.26430 | 1.64920 |
| c' (a₀) | 1.31716 | 1.31716 | 1.29700 | 0.91808 | 1.04856 |
| Bond Length 2c' (Å) | 1.39402 | 1.39402 | 1.37268 | 0.971651 | 1.10974 |
| Exp. Bond Length (Å) | 1.393 (methyl formate) | 1.393 (avg. methyl formate) | 1.364 (phenol) | 0.972 formic acid | 1.08 (methyl formate) 1.107 (C—H propane) 1.117 (C—H butane) |
| b, c (a₀) | 1.12915 | 1.12915 | 1.07126 | 0.86925 | 1.27295 |
| e | 0.75921 | 0.75921 | 0.77101 | 0.72615 | 0.63580 |

TABLE 9

The MO to HO intercept geometrical bond parameters of aspirin. $E_T$ is $E_T$ (atom-atom, msp$^3$ · AO).

| Bond | Atom | $E_T$ (eV) Bond 1 | $E_T$ (eV) Bond 2 | $E_T$ (eV) Bond 3 | $E_T$ (eV) Bond 4 | Final Total Energy C2sp$^3$ (eV) | $r_{initial}$ ($a_0$) | $r_{final}$ ($a_0$) |
|---|---|---|---|---|---|---|---|---|
| C—H (C$_c$H) | C$_c$ | −0.85035 | −0.85035 | −0.56690 | 0 | −153.88327 | 0.91771 | 0.79597 |
| C$\overset{3e}{=}$(HOOC$_a$)C$_b$$\overset{3e}{=}$C$_c$(H) | C$_c$ | −0.85035 | −0.85035 | −0.56690 | 0 | −153.88327 | 0.91771 | 0.79597 |
| C$_b$C$_a$(O)O—H | O | −0.92918 | 0 | 0 | 0 | | 1.00000 | 0.86359 |
| C$_b$C$_a$(O)—OH | O | −0.92918 | 0 | 0 | 0 | | 1.00000 | 0.86359 |
| C$_b$C$_a$(O)—OH | C$_a$ | −0.92918 | −1.34946 | −0.64574 | 0 | −154.54007 | 0.91771 | 0.76652 |
| C$_b$C$_a$(OH)=O | O | −1.34946 | 0 | 0 | 0 | | 1.00000 | 0.84115 |
| OC$_e$(C$_f$H$_3$)=O | | | | | | | | |
| C$_b$C$_a$(OH)=O | C$_a$ | −1.34946 | −0.64574 | −0.92918 | 0 | −154.54007 | 0.91771 | 0.76652 |
| C$_b$—C$_a$(O)OH | C$_a$ | −0.64574 | −1.34946 | −0.92918 | 0 | −154.54007 | 0.91771 | 0.76652 |
| C$_b$—C$_a$(O)OH | C$_b$ | −0.64574 | −0.85035 | −0.85035 | 0 | −153.96212 | 0.91771 | 0.79232 |
| C$_c$$\overset{3e}{=}$(HOOC$_a$)C$_b$$\overset{3e}{=}$C$_c$ | C$_b$ | −0.64574 | −0.85035 | −0.85035 | 0 | −153.96212 | 0.91771 | 0.79232 |
| C$_c$$\overset{3e}{=}$(CH$_3$(O)CO)C$_d$$\overset{3e}{=}$C$_b$ | C$_d$ | −0.74804 | −0.85035 | −0.85035 | 0 | −154.06442 | 0.91771 | 0.78762 |
| C$_c$$\overset{3e}{=}$(C$_b$$\overset{3e}{=}$)C$_d$—OC(O)CH$_3$ | O | −0.74804 | −0.92918 | 0 | 0 | | 1.00000 | 0.82445 |
| C$_c$$\overset{3e}{=}$(C$_b$$\overset{3e}{=}$)C$_d$O—C(O)CH$_3$ | O | −0.92918 | −0.74804 | 0 | 0 | | 1.00000 | 0.82445 |
| O—C$_e$(O)C$_f$H$_3$ | C$_e$ | −0.92918 | −1.34946 | −0.92918 | 0 | −154.82352 | 0.91771 | 0.75447 |
| OC$_e$(C$_f$H$_3$)=O | C$_e$ | −1.34946 | −0.92918 | −0.92918 | 0 | −154.82352 | 0.91771 | 0.75447 |
| O(O)C$_e$—C$_f$H$_3$ | C$_e$ | −0.92918 | −1.34946 | −0.92918 | 0 | −154.82352 | 0.91771 | 0.75447 |
| OC$_e$(O)—C$_f$H$_3$ | C$_f$ | −0.92918 | 0 | 0 | 0 | −152.54487 | 0.91771 | 0.86359 |

| Bond | $E_{Coulomb}$(C2sp$^3$) (eV) Final | E(C2sp$^3$) (eV) Final | θ' (°) | θ$_1$ (°) | θ$_2$ (°) | d$_1$ ($a_0$) | d$_2$ ($a_0$) |
|---|---|---|---|---|---|---|---|
| C—H (C$_c$H) | −17.09334 | −16.90248 | 74.42 | 105.58 | 38.84 | 1.24678 | 0.21379 |
| C$\overset{3e}{=}$(HOOC$_a$)C$_b$$\overset{3e}{=}$C$_c$(H) | −17.09334 | −16.90248 | 134.24 | 45.76 | 58.98 | 0.75935 | 0.55533 |
| C$_b$C$_a$(O)O—H | −15.75493 | | 115.09 | 64.91 | 64.12 | 0.55182 | 0.36625 |
| C$_b$C$_a$(O)—OH | −15.75493 | | 101.32 | 78.68 | 48.58 | 1.14765 | 0.16950 |
| C$_b$C$_a$(O)—OH | −17.75013 | −17.55927 | 93.11 | 86.89 | 42.68 | 1.27551 | 0.04165 |
| C$_b$C$_a$(OH)=O | −16.17521 | | 137.27 | 42.73 | 66.31 | 0.52193 | 0.61784 |
| OC$_e$(C$_f$H$_3$)=O | | | | | | | |
| C$_b$C$_a$(OH)=O | −17.75013 | −17.55927 | 134.03 | 45.97 | 62.14 | 0.60699 | 0.53278 |
| C$_b$—C$_a$(O)OH | −17.75013 | −17.55927 | 70.34 | 109.66 | 32.00 | 1.65466 | 0.25784 |
| C$_b$—C$_a$(O)OH | −17.17218 | −16.98131 | 73.74 | 106.26 | 33.94 | 1.61863 | 0.22181 |
| C$_c$$\overset{3e}{=}$(HOOC$_a$)C$_b$$\overset{3e}{=}$C$_c$ | −17.17218 | −16.98132 | 134.09 | 45.91 | 58.79 | 0.76344 | 0.55124 |
| C$_c$$\overset{3e}{=}$(CH$_3$(O)CO)C$_d$$\overset{3e}{=}$C$_b$ | −17.27448 | −17.08362 | 100.00 | 80.00 | 46.39 | 1.16026 | 0.13674 |
| C$_c$$\overset{3e}{=}$(C$_b$$\overset{3e}{=}$)C$_d$—OC(O)CH$_3$ | −16.50297 | | 102.93 | 77.02 | 48.60 | 1.11250 | 0.18449 |
| C$_c$$\overset{3e}{=}$(C$_b$$\overset{3e}{=}$)C$_d$O—C(O)CH$_3$ | −16.50297 | | 98.22 | 81.78 | 46.27 | 1.19921 | 0.11795 |
| O—C$_e$(O)C$_f$H$_3$ | −18.03358 | −17.84271 | 91.96 | 88.04 | 41.90 | 1.29138 | 0.02578 |
| OC$_e$(C$_f$H$_3$)=O | −18.03358 | −17.84271 | 133.47 | 46.53 | 61.46 | 0.62072 | 0.51905 |
| O(O)C$_e$—C$_f$H$_3$ | −18.03358 | −17.84272 | 56.25 | 123.75 | 25.37 | 1.85002 | 0.41915 |
| OC$_e$(O)—C$_f$H$_3$ | −15.75493 | −15.56407 | 72.27 | 107.73 | 34.17 | 1.69388 | 0.26301 |

TABLE 10

The energy parameters (eV) of functional groups of aspirin.

| Parameters | $C\overset{3e}{=}C$ Group | CH Group | C—C(O) (i) Group | C—C(O) (ii) Group | C=O Group |
|---|---|---|---|---|---|
| $f_1$ | 0.75 | 1 | | | |
| $n_1$ | 2 | 1 | 1 | 1 | 2 |
| $n_2$ | 0 | 0 | 0 | 0 | 0 |
| $n_3$ | 0 | 0 | 0 | 0 | 0 |
| $C_1$ | 0.5 | 0.75 | 0.5 | 0.5 | 0.5 |
| $C_2$ | 0.85252 | 1 | 1 | 1 | 1 |
| $c_1$ | 1 | 1 | 1 | 1 | 1 |
| $c_2$ | 0.85252 | 0.91771 | 0.91771 | 0.91771 | 0.85395 |
| $c_3$ | 0 | 1 | 0 | 0 | 2 |
| $c_4$ | 3 | 1 | 2 | 2 | 4 |
| $c_5$ | 0 | 1 | 0 | 0 | 0 |
| $C_{1o}$ | 0.5 | 0.75 | 0.5 | 1 | 0.5 |
| $C_{2o}$ | 0.85252 | 1 | 1 | 1 | 1 |
| $V_e$ (eV) | −101.12679 | −37.10024 | −32.15216 | −30.19634 | −111.25473 |
| $V_p$ (eV) | 20.69825 | 13.17125 | 9.74055 | 9.50874 | 23.87467 |
| T (eV) | 34.31559 | 11.58941 | 8.23945 | 7.37432 | 42.82081 |
| $V_m$ (eV) | −17.15779 | −5.79470 | −4.11973 | −3.68716 | −21.41040 |
| E(AO/HO) (eV) | 0 | −14.63489 | −14.63489 | −14.63489 | 0 |
| $\Delta E_{H_2MO}$(AO/HO) (eV) | 0 | −1.13379 | −1.29147 | 0 | −2.69893 |
| $E_T$(AO/HO) (eV) | 0 | −13.50110 | −13.34342 | −14.63489 | 2.69893 |
| $E_T$($H_2$MO) (eV) | −63.27075 | −31.63539 | −31.63530 | −31.63534 | −63.27074 |
| $E_T$(atom-atom, $msp^3 \cdot$ AO) (eV) | −2.26759 | −0.56690 | −1.29147 | −1.85836 | −2.69893 |
| $E_T$(MO) (eV) | −65.53833 | −32.20226 | −32.92684 | −33.49373 | −65.96966 |
| $\omega$ ($10^{15}$ rad/s) | 49.7272 | 26.4826 | 10.7262 | 23.3291 | 59.4034 |
| $E_K$ (eV) | 32.73133 | 17.43132 | 7.06019 | 15.35563 | 39.10034 |
| $\overline{E}_D$ (eV) | −0.35806 | −0.26130 | −0.17309 | −0.25966 | −0.40804 |
| $\overline{E}_{Kvib}$ (eV) | 0.19649 | 0.35532 | 0.10502 | 0.10502 | 0.21077 |
| | [3] | Eq. (13.458) | [4] | [4] | [5] |
| $\overline{E}_{osc}$ (eV) | −0.25982 | −0.08364 | −0.12058 | −0.20715 | −0.30266 |
| $E_{mag}$ (eV) | 0.14803 | 0.14803 | 0.14803 | 0.14803 | 0.11441 |
| $E_T$(Group) (eV) | −49.54347 | −32.28590 | −33.04742 | −33.70088 | −66.57498 |
| $E_{initial}$($C_4$ AO/HO) (eV) | −14.63489 | −14.63489 | −14.63489 | −14.63489 | −14.63489 |
| $E_{initial}$($C_5$ AO/HO) (eV) | 0 | −13.59844 | 0 | 0 | 0 |
| $E_D$(Group) (eV) | 5.63881 | 3.90454 | 3.77764 | 4.43110 | 7.80660 |

| Parameters | C—O (i) Group | C—O (ii) Group | C—O (iii) Group | OH Group | $CH_3$ Group |
|---|---|---|---|---|---|
| $f_1$ | | | | | |
| $n_1$ | 1 | 1 | 1 | 1 | 3 |
| $n_2$ | 0 | 0 | 0 | 0 | 2 |
| $n_3$ | 0 | 0 | 0 | 0 | 0 |
| $C_1$ | 0.5 | 0.5 | 0.5 | 0.75 | 0.75 |
| $C_2$ | 1 | 1 | 1 | 1 | 1 |
| $c_1$ | 1 | 1 | 1 | 0.75 | 1 |
| $c_2$ | 0.85395 | 0.85395 | 0.79329 | 1 | 0.91771 |
| $c_3$ | 0 | 0 | 0 | 1 | 0 |
| $c_4$ | 2 | 2 | 2 | 1 | 1 |
| $c_5$ | 0 | 0 | 0 | 1 | 3 |
| $C_{1o}$ | 0.5 | 0.5 | 0.5 | 0.75 | 0.75 |
| $C_{2o}$ | 1 | 1 | 1 | 1 | 1 |
| $V_e$ (eV) | −35.08488 | −35.08488 | −34.04658 | −40.92709 | −107.32728 |
| $V_p$ (eV) | 10.32968 | 10.32968 | 10.49024 | 14.81988 | 38.92728 |
| T (eV) | 10.11150 | 10.11150 | 10.11966 | 16.18567 | 32.53914 |
| $V_m$ (eV) | −5.05575 | −5.05575 | −5.05983 | −8.09284 | −16.26957 |
| E(AO/HO) (eV) | −14.63489 | −14.63489 | −14.63489 | −13.6181 | −15.56407 |
| $\Delta E_{H_2MO}$ (AO/HO) (eV) | −2.69893 | −2.69893 | −1.49608 | 0 | 0 |
| $E_T$(AO/HO) (eV) | −11.93596 | −11.93596 | −13.13881 | −13.6181 | −15.56407 |
| $E_T$($H_2$MO) (eV) | −31.63541 | −31.63541 | −31.63532 | −31.63247 | −67.69451 |
| $E_T$(atom-atom, $msp^3 \cdot$ AO) (eV) | −1.85836 | −1.85836 | −1.49608 | 0 | 0 |
| $E_T$(MO) (eV) | −33.49373 | −33.49373 | −33.13145 | −31.63537 | −67.69450 |
| $\omega$ ($10^{15}$ rad/s) | 24.3637 | 12.7926 | 13.3984 | 44.1776 | 24.9286 |
| $E_K$ (eV) | 16.03660 | 8.42030 | 8.81907 | 29.07844 | 16.40846 |
| $\overline{E}_D$ (eV) | −0.26535 | −0.19228 | −0.19465 | −0.33749 | −0.25352 |
| $\overline{E}_{Kvib}$ (eV) | 0.14010 | 0.14965 | 0.12808 | 0.46311 | 0.35532 |
| | [6] | [7] | [8] | [9-10] | (Eq. (13.458)) |
| $\overline{E}_{osc}$ (eV) | −0.19530 | −0.11745 | −0.13061 | −0.10594 | −0.22757 |
| $\overline{E}_{mag}$ (eV) | 0.14803 | 0.14803 | 0.14803 | 0.11441 | 0.14803 |
| $E_T$(Group) (eV) | −33.68903 | −33.61118 | −33.26206 | −31.74130 | −67.92207 |
| $E_{initial}$($c_4$ AO/HO) (eV) | −14.63489 | −14.63489 | −14.63489 | −13.6181 | 14.63489 |
| $E_{initial}$($c_5$ AO/HO) (eV) | 0 | 0 | 0 | −13.59844 | −13.59844 |
| $E_D$(Group) (eV) | 4.41925 | 4.34141 | 3.99228 | 4.41035 | 12.49186 |

TABLE 11

The total bond energies of salicylic acid and aspirin calculated using the functional group composition and the energies of Table 10.

| Formula | Name | $C\overset{3e}{=}C$ Group | CH Group | C—C(O) (i) Group | C—C(O) (ii) Group | C=O Group | C—O (i) Group | C—O (ii) Group |
|---|---|---|---|---|---|---|---|---|
| $C_7H_6O_3$ | Salicylic acid | 6 | 4 | 1 | 0 | 1 | 1 | 0 |
| $C_9H_8O_4$ | Aspirin | 6 | 4 | 1 | 1 | 2 | 1 | 1 |

| Formula | Name | C—O (iii) Group | OH Group | C—H ($CH_3$) Group | Calculated Total Bond Energy (eV) | Experimental Total Bond Energy (eV) | Relative Error |
|---|---|---|---|---|---|---|---|
| $C_7H_6O_3$ | Salicylic acid | 1 | 2 | 0 | 78.26746 [11] | 78.426 | 0.00202 |
| $C_9H_8O_4$ | Aspirin | 1 | 1 | 1 | 102.92809 | | |

TABLE 12

The bond angle parameters of aspirin and experimental values [1].

| Atoms of Angle | 2c' Bond 1 ($a_0$) | 2c' Bond 2 ($a_0$) | 2c' Terminal Atoms ($a_0$) | $E_{Coulombic}$ Atom 1 | Atom 1 Hybridization Designation (Table 13) | $E_{Coulombic}$ Atom 2 | Atom 2 Hybridization Designation (Table 13) | $c_2$ Atom 1 | $c_2$ Atom 2 |
|---|---|---|---|---|---|---|---|---|---|
| ∠CCC (aromatic) | 2.62936 | 2.62936 | 4.5585 | −17.17218 | 34 | −17.17218 | 34 | 0.79232 | 0.79232 |
| ∠CCH | | | | | | | | | |
| ∠CCO (aromatic) | | | | | | | | | |
| ∠$C_aO_bH$ | 2.63431 | 1.83616 | 3.6405 | −14.82575 | 1 | −14.82575 | 1 | 1 | 0.91771 |
| ∠$C_bC_a$(O) | 2.82796 | 2.27954 | 4.4721 | −17.17218 | 34 | −13.61806 | O | 0.79232 | 0.85395 (Eq. (15.114)) |
| ∠$C_bC_a$O | 2.82796 | 2.63431 | 4.6690 | −16.40067 | 19 | −13.61806 | O | 0.82959 | 0.85395 (Eq. (15.114)) |
| ∠(O)$C_a$O | 2.27954 | 2.63431 | 4.3818 | −16.17521 (O) | 12 | −15.75493 O | 7 | 0.84115 | 0.86359 |
| ∠$C_fC_e$(O) | 2.86175 | 2.27954 | 4.5826 | −16.68411 | 24 | −13.61806 | O | 0.81549 | 0.85395 (Eq. (15.133)) |
| ∠$C_fC_e$O | 2.86175 | 2.63431 | 4.4944 | −15.75493 | 7 | −13.61806 | O | 0.86359 | 0.85395 (Eq. (15.133)) |
| ∠$OC_e$O | 2.27954 | 2.63431 | 4.3818 | −16.17521 (O) | 12 | −15.75493 O | 7 | 0.84115 | 0.86359 |
| ∠$C_dOC_e$ | 2.59399 | 2.63431 | 4.3589 | −17.27448 $C_d$ | 38 | −18.03358 $C_e$ | 53 | 0.78762 | 0.75447 |
| Methyl ∠$HC_fH$ | 2.09711 | 2.09711 | 3.4252 | −15.75493 | 7 | H | H | 0.86359 | 1 |

| Atoms of Angle | $C_1$ | $C_2$ | $c_1$ | $c'_2$ | $E_T$ (eV) | $\theta_v$ (°) | $\theta_1$ (°) | $\theta_2$ (°) | Cal. $\theta$ (°) | Exp. $\theta$ (°) |
|---|---|---|---|---|---|---|---|---|---|---|
| ∠CCC (aromatic) | 1 | 1 | 1 | 0.79232 | −1.85836 | | | | 120.19 | 120 [12-14] (benzene) |
| ∠CCH | | | | | | | 120.19 | | 119.91 | 120 [12-14] (benzene) |
| ∠CCO (aromatic) | | | | | | | | | | |
| ∠$C_aO_bH$ | 0.75 | 1 | 0.75 | 0.91771 | 0 | | | | 107.71 | |
| ∠$C_bC_a$(O) | 1 | 1 | 1 | 0.82313 | −1.65376 | | | | 121.86 | 122 [2] (benzoic acid) |
| ∠$C_bC_a$O | 1 | 1 | 1 | 0.84177 | −1.65376 | | | | 117.43 | 118 [2] (benzoic acid) |
| ∠(O)$C_a$O | 1 | 1 | 1 | 0.85237 | −1.44915 | | | | 126.03 | 122 [2] (benzoic acid) |
| ∠$C_fC_e$(O) | 1 | 1 | 1 | 0.83472 | −1.65376 | | | | 125.70 | 126.6 [1] (acetic acid) |
| ∠$C_fC_e$O | 1 | 1 | 1 | 0.85877 | −1.44915 | | | | 109.65 | 110.6 [1] (acetic acid) |
| ∠$OC_e$O | 1 | 1 | 1 | 0.85237 | −1.44915 | | | | 126.03 | |
| ∠$C_dOC_e$ | 1 | 1 | 1 | 0.77105 | −1.85836 | | | | 112.96 | 114 [1] (methyl formate) |
| Methyl ∠$HC_fH$ | 1 | 1 | 0.75 | 1.15796 | 0 | | | | 109.50 | |

$E_T$ is $E_T$(atom–atom, msp$^3$ · AO).

TABLE 13

The final values of $r_{Atom,HO,AO}$, $E_{Coulomb}$(mol.atom, msp³), and $E(C_{mol}2sp^3)$ calculated using the values of $E_T(C^{\underline{BO}}C, C2sp^3)$ given in Tables 4 and 5.

| Atom Hybridization Designation | $E_T(C^{\underline{BO}}C, C2sp^3)$ | $E_T(C^{\underline{BO}}C, C2sp^3)$ | $E_T(C^{\underline{BO}}C, C2sp^3)$ | $E_T(C^{\underline{BO}}C, C2sp^3)$ | $E_T(C^{\underline{BO}}C, C2sp^3)$ | $r_{Atom,HO,AO}$ Final | $E_{Coulomb}$ (mol.atom, msp³) (eV) Final | $E(C_{mol}2sp^3)$ (eV) Final |
|---|---|---|---|---|---|---|---|---|
| 1 | 0 | 0 | 0 | 0 | 0 | 0.91771 | −14.82575 | −14.63489 |
| 2 | −0.36229 | 0 | 0 | 0 | 0 | 0.89582 | −15.18804 | −14.99717 |
| 3 | −0.46459 | 0 | 0 | 0 | 0 | 0.88983 | −15.29034 | −15.09948 |
| 4 | −0.56689 | 0 | 0 | 0 | 0 | 0.88392 | −15.39265 | −15.20178 |
| 5 | −0.72457 | 0 | 0 | 0 | 0 | 0.87495 | −15.55033 | −15.35946 |
| 6 | −0.85034 | 0 | 0 | 0 | 0 | 0.86793 | −15.6761 | −15.48523 |
| 7 | −0.92918 | 0 | 0 | 0 | 0 | 0.86359 | −15.75493 | −15.56407 |
| 8 | −0.54343 | −0.54343 | 0 | 0 | 0 | 0.85503 | −15.91261 | −15.72175 |
| 9 | −0.18144 | −0.92918 | 0 | 0 | 0 | 0.85377 | −15.93607 | −15.74521 |
| 10 | −1.13379 | 0 | 0 | 0 | 0 | 0.85252 | −15.95955 | −15.76868 |
| 11 | −1.14485 | 0 | 0 | 0 | 0 | 0.85193 | −15.9706 | −15.77974 |
| 12 | −0.46459 | −0.82688 | 0 | 0 | 0 | 0.84418 | −16.11722 | −15.92636 |
| 13 | −1.34946 | 0 | 0 | 0 | 0 | 0.84115 | −16.17521 | −15.98435 |
| 14 | −1.3725 | 0 | 0 | 0 | 0 | 0.83995 | −16.19826 | −16.00739 |
| 15 | −0.46459 | −0.92918 | 0 | 0 | 0 | 0.83885 | −16.21952 | −16.02866 |
| 16 | −0.72457 | −0.72457 | 0 | 0 | 0 | 0.836 | −16.2749 | −16.08404 |
| 17 | −0.5669 | −0.92918 | 0 | 0 | 0 | 0.8336 | −16.32183 | −16.13097 |
| 18 | −0.82688 | −0.72457 | 0 | 0 | 0 | 0.83078 | −16.37721 | −16.18634 |
| 19 | −1.56513 | 0 | 0 | 0 | 0 | 0.83008 | −16.39089 | −16.20002 |
| 20 | −0.64574 | −0.92918 | 0 | 0 | 0 | 0.82959 | −16.40067 | −16.20981 |
| 21 | −1.57711 | 0 | 0 | 0 | 0 | 0.82948 | −16.40286 | −16.212 |
| 22 | −0.72457 | −0.92918 | 0 | 0 | 0 | 0.82562 | −16.47951 | −16.28865 |
| 23 | −0.85035 | −0.85035 | 0 | 0 | 0 | 0.82327 | −16.52645 | −16.33559 |
| 24 | −1.79278 | 0 | 0 | 0 | 0 | 0.81871 | −16.61853 | −16.42767 |
| 25 | −1.13379 | −0.72457 | 0 | 0 | 0 | 0.81549 | −16.68411 | −16.49325 |
| 26 | −0.92918 | −0.92918 | 0 | 0 | 0 | 0.81549 | −16.68412 | −16.49326 |
| 27 | −0.56690 | −0.54343 | −0.85034 | 0 | 0 | 0.81052 | −16.78642 | −16.59556 |
| 28 | −2.02043 | 0 | 0 | 0 | 0 | 0.80765 | −16.84619 | −16.65532 |
| 29 | −1.13379 | −0.92918 | 0 | 0 | 0 | 0.80561 | −16.88872 | −16.69786 |
| 30 | −0.56690 | −0.56690 | −0.92918 | 0 | 0 | 0.80561 | −16.88873 | −16.69786 |
| 31 | −0.85035 | −0.85035 | −0.46459 | 0 | 0 | 0.80076 | −16.99104 | −16.80018 |
| 32 | −0.85035 | −0.42517 | −0.92918 | 0 | 0 | 0.79891 | −17.03045 | −16.83959 |
| 33 | −0.5669 | −0.72457 | −0.92918 | 0 | 0 | 0.78916 | −17.04641 | −16.85554 |
| 34 | −1.13379 | −1.13379 | 0 | 0 | 0 | 0.79597 | −17.09334 | −16.90248 |
| 35 | −1.34946 | −0.92918 | 0 | 0 | 0 | 0.79546 | −17.1044 | −16.91353 |
| 36 | −0.46459 | −0.92918 | −0.92918 | 0 | 0 | 0.79340 | −17.14871 | −16.95784 |
| 37 | −0.64574 | −0.85034 | −0.85034 | 0 | 0 | 0.79232 | −17.17217 | −16.98131 |
| 38 | −0.85035 | −0.5669 | −0.92918 | 0 | 0 | 0.79232 | −17.17218 | −16.98132 |
| 39 | −0.72457 | −0.72457 | −0.92918 | 0 | 0 | 0.79085 | −17.20408 | −17.01322 |
| 40 | −0.75586 | −0.75586 | −0.92918 | 0 | 0 | 0.78798 | 17.26666 | 17.07580 |
| 41 | −0.74804 | −0.85034 | −0.85034 | 0 | 0 | 0.78762 | 17.27448 | 17.08362 |
| 42 | −0.82688 | −0.72457 | −0.92918 | 0 | 0 | 0.78617 | −17.30638 | −17.11552 |
| 43 | −0.72457 | −0.92918 | −0.92918 | 0 | 0 | 0.78155 | −17.40868 | −17.21782 |
| 44 | −0.92918 | −0.72457 | −0.92918 | 0 | 0 | 0.78155 | −17.40869 | −17.21783 |
| 45 | −0.54343 | −0.54343 | −0.5669 | −0.92918 | 0 | 0.78155 | −17.40869 | −17.21783 |
| 46 | −0.92918 | −0.85034 | −0.85034 | 0 | 0 | 0.77945 | −17.45561 | −17.26475 |
| 47 | −0.42517 | −0.42517 | −0.85035 | −0.92918 | 0 | 0.77945 | −17.45563 | −17.26476 |
| 48 | −0.82688 | −0.92918 | −0.92918 | 0 | 0 | 0.77699 | −17.51099 | −17.32013 |
| 49 | −0.92918 | −0.92918 | −0.92918 | 0 | 0 | 0.77247 | −17.6133 | −17.42244 |
| 50 | −0.85035 | −0.54343 | −0.5669 | −0.92918 | 0 | 0.76801 | −17.71561 | −17.52475 |
| 51 | −1.34946 | −0.64574 | −0.92918 | 0 | 0 | 0.76652 | −17.75013 | −17.55927 |
| 52 | −0.85034 | −0.54343 | −0.60631 | −0.92918 | 0 | 0.76631 | −17.75502 | −17.56415 |
| 53 | −1.1338 | −0.92918 | −0.92918 | 0 | 0 | 0.7636 | −17.81791 | −17.62705 |
| 54 | −0.46459 | −0.85035 | −0.85035 | −0.92918 | 0 | 0.75924 | −17.92022 | −17.72936 |
| 55 | −0.82688 | −1.34946 | −0.92918 | 0 | 0 | 0.75877 | −17.93128 | −17.74041 |
| 56 | −0.92918 | −1.34946 | −0.92918 | 0 | 0 | 0.75447 | −18.03358 | −17.84272 |
| 57 | −1.13379 | −1.13379 | −1.13379 | 0 | 0 | 0.74646 | −18.22712 | −18.03626 |
| 58 | −1.79278 | −0.92918 | −0.92918 | 0 | 0 | 0.73637 | −18.47690 | −18.28604 |

Cyclotrimethylene-Trinitramine ($C_3H_6N_6O_6$) 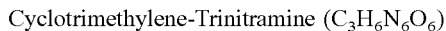

The compound cyclotrimethylene-trinitramine, commonly referred to as Cyclonite or by the code designation RDX, is a well-known explosive. RDX comprises three methylene ($CH_2$) groups joined by six alkyl C—N secondary amine functional groups given in the corresponding section. Each of the three N's of the six-membered ring shown in FIG. 7 is bonded to a $NO_2$ functional group given in the Nitroalkanes section by a N—N functional group. The latter requires hybridization of the nitrogen atoms in order to match the energies of the bridged groups.

Similar to the case of carbon, silicon, and aluminum, the bonding in the nitrogen of the N—N functional group involves four $sp_3$ hybridized orbitals formed from the outer 2p and 2s shells. In RDX, bonds form between two $N2sp^3$ HOs (N—N functional group), between a $N2sp^3$ HO and a $C2sp^3$ HO (C—N functional group), and between a $N2sp^3$ HO and a O2p AO (each N—O bond of the $NO_2$ functional group). The geometrical and energy equations of the N—N functional group are given in the Derivation of the General Geometrical and Energy Equations of Organic Chemistry section wherein the energy is matched to $E(C,2sp_3)=-14.63489$ eV (Eq. (15.25)).

The $2sp^3$ hybridized orbital arrangement after Eq. (13.422) is $$\underset{0,0}{\uparrow\downarrow} \quad \overset{2sp^3 \, state}{\underset{1,-1}{\uparrow} \quad \underset{1,0}{\uparrow} \quad \underset{1,1}{\uparrow}} \tag{16.1}$$

where the quantum numbers $(l, m_l)$ are below each electron. The total energy of the state is given by the sum over the five electrons. The sum $E_T(N, 2sp_3)$ of experimental energies [15] of N, $N^+$, $N_{2+}$, $N_{3+}$, and $N^{4+}$ is $$E_T(N, 2sp^3) = -\begin{pmatrix} 97.8902 \text{ eV} + 77.4735 \text{ eV} + \\ 47.44924 \text{ eV} + 29.6013 \text{ eV} + \\ 14.53414 \text{ eV} \end{pmatrix} \tag{16.2}$$

$$= -266.94838 \text{ eV}$$

By considering that the central field decreases by an integer for each successive electron of the shell, the radius $r_{2sp^3}$ of the $N2sp^3$ shell may be calculated from the Coulombic energy using Eq. (15.13):

$$r_{2sp^3} = \sum_{n=2}^{6} \frac{(Z-n)e^2}{8\pi\varepsilon_0(e266.94838 \text{ eV})} \tag{16.3}$$

$$= \frac{15e^2}{8\pi\varepsilon_0(e266.94838 \text{ eV})}$$

$$= 0.76452 a_0$$

where Z=7 for nitrogen. Using Eq. (15.14), the Coulombic energy $E_{Coulomb}(N, 2sp^3)$ of the outer electron of the $N2sp^3$ shell is $$E_{Coulomb}(N, 2sp^3) = \frac{-e^2}{8\pi\varepsilon_0 r_{2sp^3}} \tag{16.4}$$

$$= \frac{-e^2}{8\pi\varepsilon_0 0.76452 a_0}$$

$$= -17.79656 \text{ eV}$$

In RDX, the $C2sp^3$ HO has a hybridization factor of 0.91771 (Eq. (13.430)) with a corresponding energy of $E(C,2sp^3)=-14.63489$ eV (Eq. (15.25)), and the N HO has an energy of $E(N,2sp^3)=-17.79656$ eV (Eq. (16.4)). To meet the equipotential, minimum-energy condition of the union of the $N2sp^3$ and $C2sp^3$ HOs, $C_2=1$ in Eqs. (15.2-15.5), (15.51), and (15.61) for the N—N-bond MO, and $c_3$ given by Eqs. (15.77) and (15.79) is $$c_2 \begin{pmatrix} C2sp^3 \text{HO to } N_b 2sp^3 \text{HO} \\ \text{to } N_a 2sp^3 \text{HO} \end{pmatrix} = \frac{E(C, 2sp^3)}{E(N, 2sp^3)} c_2(C2sp^3 \text{HO}) \tag{16.5}$$

$$= \frac{-14.63489 \text{ eV}}{-17.79656 \text{ eV}}(0.91771)$$

$$= 0.75468$$

The energy of the N—N-bond MO is the sum of the component energies of the $H_2$-type ellipsoidal MO given in Eq. (15.51). Since the energy of the MO is matched to that of the $C2sp^2$ HO, E(AO/HO) in Eqs. (15.51) and (15.61) is $E(C,2sp^3)=-14.63489$ eV given by Eq. (15.25) and $E_T$(atom-atom,$msp^3$.AO) is 0 eV.

The symbols of the functional groups of RDX are given in Table 14. The geometrical (Eqs. (15.1-15.5) and (15.51)), intercept (Eqs. (15.80-15.87)), and energy (Eqs. (15.6-15.11) and (15.17-15.65)) parameters of RDX are given in Tables 15, 16, and 17, respectively. The total energy of RDX given in Table 18 was calculated as the sum over the integer multiple of each $E_D^{(Group)}$ of Table 17 corresponding to functional-group composition of the molecule. The bond angle parameters of RDX determined using Eqs. (15.88-15.117) are given in Table 19. The color scale charge density of RDX comprising atoms with the outer shell bridged by one or more $H_2$-type ellipsoidal MOs or joined with one or more hydrogen MOs is shown in FIG. 8.

TABLE 14

The symbols of functional groups of RDX.

| Functional Group | Group Symbol |
|---|---|
| $NO_2$ group | $NO_2$ |
| N—N | N—N |
| C—N (alkyl) | C—N |
| $CH_2$ group | C—H ($CH_2$) |

TABLE 15

The geometrical bond parameters of RDX and experimental values [1].

| Parameter | $NO_2$ Group | N—N Group | C—N Group | C—H ($CH_2$) Group |
|---|---|---|---|---|
| a ($a_0$) | 1.33221 | 1.68711 | 1.94862 | 1.67122 |
| c' ($a_0$) | 1.15421 | 1.29889 | 1.39593 | 1.05553 |
| Bond Length 2c' (Å) | 1.22157 | 1.37468 | 1.47739 | 1.11713 |

TABLE 15-continued

The geometrical bond parameters of RDX and experimental values [1].

| Parameter | $NO_2$ Group | N—N Group | C—N Group | C—H ($CH_2$) Group |
|---|---|---|---|---|
| Exp. Bond Length (Å) | 1.224 (nitromethane) 1.22 avg. [16] (RDX) | 1.390 [16] (RDX) | 1.468 [16] (RDX) | 1.107 (C—H propane) 1.117 (C—H butane) 1.092 [161] (RDX) |
| b, c ($a_0$) | 0.66526 | 1.07668 | 1.35960 | 1.29569 |
| e | 0.86639 | 0.76989 | 0.71637 | 0.63159 |

TABLE 16

The MO to HO intercept geometrical bond parameters of RDX.

| Bond | Atom | $E_T$ (eV) Bond 1 | $E_T$ (eV) Bond 2 | $E_T$ (eV) Bond 3 | $E_T$ (eV) Bond 4 | Final Total Energy $C2sp^3$ (eV) | $r_{initial}$ ($a_0$) | $r_{final}$ ($a_0$) |
|---|---|---|---|---|---|---|---|---|
| $N_bN_a(O)$=O | $O_a$ | −0.92918 | 0 | 0 | 0 | | 1.00000 | 0.86359 |
| $N_bN_a(O)$=O | $N_a$ | −0.92918 | −0.92918 | 0 | 0 | | 0.93084 | 0.81549 |
| $CH_2N_b$—$N_aO_2$ | $N_a$ | −0.92918 | −0.92918 | 0 | 0 | | 0.93084 | 0.81549 |
| $CH_2N_b$—$N_aO_2$ | $N_b$ | −0.56690 | −0.56690 | 0 | 0 | | 0.93084 | 0.85252 |
| C—H ($CH_2$) | $C_a$ | −0.56690 | −0.56690 | 0 | 0 | −152.74948 | 0.91771 | 0.85252 |
| —$H_2C_a$—$N_bN_a$ | $N_b$ | −0.56690 | −0.56690 | 0 | 0 | | 0.93084 | 0.85252 |
| —$H_2C_a$—$N_bN_a$ | $C_a$ | −0.56690 | −0.56690 | 0 | 0 | −152.74948 | 0.91771 | 0.85252 |

| Bond | $E_{Coulomb}$ (eV) Final | $E(C2sp^3)$ (eV) Final | θ' (°) | $θ_1$ (°) | $θ_2$ (°) | $d_1$ ($a_0$) | $d_2$ ($a_0$) |
|---|---|---|---|---|---|---|---|
| $N_bN_a(O)$=O | −15.75493 | | 135.25 | 44.75 | 66.05 | 0.54089 | 0.61333 |
| $N_bN_a(O)$=O | −16.68411 | | 133.16 | 46.84 | 63.41 | 0.59640 | 0.55781 |
| $CH_2N_b$—$N_aO_2$ | −16.68411 | | 101.80 | 78.20 | 47.85 | 1.13213 | 0.16676 |
| $CH_2N_b$—$N_aO_2$ | −15.95954 | | 104.60 | 75.40 | 50.02 | 1.08404 | 0.21485 |
| C—H ($CH_2$) | −15.95954 | −15.76868 | 73.60 | 106.40 | 39.14 | 1.29624 | 0.24071 |
| —$H_2C_a$—$N_bN_a$ | −15.95954 | | 80.95 | 99.05 | 38.26 | 1.53008 | 0.13415 |
| —$H_2C_a$—$N_bN_a$ | −15.95954 | −15.76868 | 80.95 | 99.05 | 38.26 | 1.53008 | 0.13415 |

$E_T$ is $E_T$(atom-atom, $msp^3$ · AO).

TABLE 17

The energy parameters (eV) of functional groups of RDX.

| Parameters | $NO_2$ Group | N—N Group | C—N Group | $CH_2$ Group |
|---|---|---|---|---|
| $n_1$ | 2 | 1 | 1 | 2 |
| $n_2$ | 0 | 0 | 0 | 1 |
| $n_3$ | 0 | 0 | 0 | 0 |
| $C_1$ | 0.5 | 0.5 | 0.5 | 0.75 |
| $C_2$ | 1 | 1 | 1 | 1 |
| $c_1$ | 1 | 1 | 1 | 1 |
| $c_2$ | 0.85987 | 0.75468 | 0.91140 | 0.91771 |
| $c_3$ | 0 | 0 | 0 | 1 |
| $c_4$ | 4 | 2 | 2 | 1 |
| $c_5$ | 0 | 0 | 0 | 2 |
| $C_{1o}$ | 0.5 | 0.5 | 1 | 0.75 |
| $C_{2o}$ | 1 | 1 | 1 | 1 |
| $V_e$ (eV) | −106.90919 | −32.25503 | −31.98456 | −70.41425 |
| $V_p$ (eV) | 23.57588 | 10.47496 | 9.74677 | 25.78002 |
| T (eV) | 40.12475 | 9.55926 | 8.20698 | 21.06675 |
| $V_m$ (eV) | −20.06238 | −4.77963 | −4.10349 | −10.53337 |
| E(AO/HO) (eV) | 0 | −14.63489 | −14.63489 | −15.56407 |
| $ΔE_{H_2MO}^{(AO/HO)}$ (eV) | 0 | 0 | −1.13379 | 0 |
| $E_T^{(AO/HO)}$ (eV) | 0 | −14.63489 | −13.50110 | −15.56407 |
| $E_T^{(H_2MO)}$ (eV) | −63.27093 | −31.63533 | −31.63540 | −49.66493 |
| $E_T$(atom-atom, $msp^3$ · AO) (eV) | −3.71673 | 0 | −1.13379 | 0 |
| $E_T^{(MO)}$ (eV) | −66.98746 | −31.63537 | −32.76916 | −49.66493 |
| ω ($10^{15}$ rad/s) | 19.0113 | 26.1663 | 26.0778 | 24.2751 |
| $\overline{E}_K$ (eV) | 12.51354 | 17.22313 | 17.16484 | 15.97831 |
| $\overline{E}_D$ (eV) | −0.23440 | −0.25974 | −0.26859 | −0.25017 |
| $\overline{E}_{Kvib}$ (ev) | 0.19342 [17] | 0.12770 [18] | 0.11159 [19] | 0.35532 (Eq. (13.458)) |
| $\overline{E}_{osc}$ (ev) | −0.13769 | −0.19588 | −0.21280 | −0.14502 |

TABLE 17-continued

The energy parameters (eV) of functional groups of RDX.

| Parameters | $NO_2$ Group | N—N Group | C—N Group | $CH_2$ Group |
|---|---|---|---|---|
| $E_{mag}$ (eV) | 0.11441 | 0.14803 | 0.14803 | 0.14803 |
| $E_T(Group)$ (eV) | −67.26284 | −31.83125 | −32.98196 | −49.80996 |
| $E_{initial}(c_4 AO/HO)$ (eV) | −14.63489 | −14.63489 | −14.63489 | −14.63489 |
| $E_{initial}(c_5 AO/HO)$ (eV) | 0 | 0 | 0 | −13.59844 |
| $E_D(Group)$ (eV) | 8.72329 | 2.56147 | 3.71218 | 7.83016 |
| Exp. $E_D(Group)$ (eV) | | Est. 2.86, 2.08 [20] | 3.69 [20] | |

TABLE 18

The total bond energy of gaseous-state RDX calculated using the functional group composition and the energies of Table 17.

| Formula | Name | $NO_2$ Group | N—N Group | C—N Group | $CH_2$ Group | Calculated Total bond Energy (eV) | Experimental Total Bond Energy (eV) | Relative Error |
|---|---|---|---|---|---|---|---|---|
| $C_3H_6N_6O_6$ | RDX | 3 | 3 | 6 | 3 | 79.61783 | | |

TABLE 19

The bond angle parameters of RDX and experimental values [1].

| Atoms of Angle | 2c' Bond 1 ($a_0$) | 2c' Bond 2 ($a_0$) | 2c' Terminal Atoms ($a_0$) | $E_{Coulombic}$ Atom 1 | Atom 1 Hybridization Designation (Table 13) | $E_{Coulombic}$ Atom 2 | Atom 2 Hybridization Designation (Table 13) | $c_2$ Atom 1 | $c_2$ Atom 2 |
|---|---|---|---|---|---|---|---|---|---|
| ∠$O_aNO_b$ | 2.30843 | 2.30843 | 4.1231 | −16.68411 $O_a$ | 24 | −16.68411 $O_b$ | 24 | 0.81549 | 0.81549 |
| ∠$N_bN_aO_a$ | 2.59778 | 2.27630 | 4.0988 | −17.79656 $N_b$ (Eq. (16.4)) | | −13.61806 $O_a$ | | 0.75468 (Eq. (16.5)) | 0.85987 (Eq. (15.159)) |
| ∠$CN_bN_a$ | 2.79186 | 2.59778 | 4.5826 | −16.32183 | 16 | −14.53414 | | 0.83360 | 0.91140 (Eq. (15.135)) |
| ∠CNC | 2.79186 | 2.79186 | 4.6260 | −17.04640 | 31 | −17.04640 | 31 | 0.79816 | 0.79816 |
| Methylene ∠$HC_aH$ | 2.11106 | 2.11106 | 3.4252 | −15.75493 | 7 | H | H | 0.86359 | 1 |
| ∠HCN | 2.09711 | 2.79186 | 4.0661 | −14.82575 | 1 | −14.53414 | N | 0.91771 | 0.93383 (Eq. (15.136)) |

| Atoms of Angle | $C_1$ | $C_2$ | $c_1$ | $c_2'$ | $E_T$ (eV) | $\theta_v$ (°) | $\theta_1$ (°) | $\theta_2$ (°) | Cal. $\theta$ (°) | Exp. $\theta$ (°) |
|---|---|---|---|---|---|---|---|---|---|---|
| ∠$O_aNO_b$ | 1 | 1 | 1 | 0.81549 | −1.44915 | | | | 126.52 | 125.3 (nitromethane) |
| ∠$N_bN_aO_a$ | 1 | 1 | 1 | 0.80727 | −1.44915 | | | | 114.32 | 116.8 [16] (RDX) |
| ∠$CN_bN_a$ | 1 | 1 | 1 | 0.87250 | −1.44915 | | | | 116.43 | 116.6 [16] (RDX) |
| ∠CNC | 1 | 1 | 1 | 0.79816 | −1.85836 | | | | 111.89 | 111.8 (dimethylamine) |
| Methylene ∠$HC_aH$ | 1 | 1 | 0.75 | 1.15796 | 0 | | | | 108.44 | 107 (propane) |
| ∠HCN | 0.75 | 1 | 0.75 | 1.01756 | 0 | | | | 111.76 | 112 (dimethylamine) |

Sodium Hydride Molecule (NaH)

Alkali hydride molecules each comprising an alkali metal atom and a hydrogen atom can be solved using similar principles and procedures as those used to solve organic molecules. The solutions of these molecules can be conveniently obtained by using generalized forms of the force balance equation given in the Force Balance of the σ MO of the Carbon Nitride Radical section and the geometrical and energy equations given in the Derivation of the General Geometrical and Energy Equations of Organic Chemistry section.

The bonding in the sodium atom involves the outer 3s atomic orbital (AO), and the Na—H bond forms between the Na3s AO and the H1s AO. The energy of the reactive outer electron of the sodium atom is significantly less than the Coulombic energy between the electron and proton of H given by Eq. (1.243). Consequently, the outer electron comprising the Na3s AO and the H1s AO form a σ-MO, and the inner AOs of Na remain unaltered. The MO semimajor axis of molecular sodium hydride is determined from the force balance equation of the centrifugal, Coulombic, and magnetic forces as given in the Polyatomic Molecular Ions and Molecules section and the More Polyatomic Molecules and Hydrocarbons section. Then, the geometric and energy parameters of the MO are calculated using Eqs. (15.1-15.117) wherein the distance from the origin of the $H_2$-type-ellipsoidal-MO to each focus c', the internuclear distance 2c', and the length of the semiminor axis of the prolate spheroidal $H_2$-type MO b=c are solved from the semimajor axis a.

The force balance of the centrifugal force equated to the Coulombic and magnetic forces is solved for the length of the semimajor axis. The Coulombic force on the pairing electron of the MO is $$F_{Coulomb} = \frac{e^2}{8\pi\varepsilon_0 ab^2} D i_\xi \quad (16.6)$$

The spin pairing force is $$F_{spin-pairing} = \frac{\hbar^2}{2m_e a^2 b^2} D i_\xi \quad (16.7)$$

The diamagnetic force is:

$$F_{diamagneticMO1} = -\frac{n_e \hbar^2}{4m_e a^2 b^2} D i_\xi \quad (16.8)$$

where $n_e$ is the total number of electrons that interact with the binding σ-MO electron. The diamagnetic force $F_{diamagneticMO2}$ on the pairing electron of the σ MO is given by the sum of the contributions over the components of angular momentum:

$$F_{diamagneticMO2} = -\sum_{i,j} \frac{|L_i|\hbar}{Z_j 2 m_e a^2 b^2} D i_\xi \quad (16.9)$$

where |L| is the magnitude of the angular momentum of each atom at a focus that is the source of the diamagnetism at the σ-MO. The centrifugal force is $$F_{centrifugalMO} = -\frac{\hbar^2}{m_e a^2 b^2} D i_\xi \quad (16.10)$$

The force balance equation for the σ-MO of the Na—H-bond MO with $n_e = 2$ an $$|L| = \left(2 + \sqrt{\frac{3}{4}}\right)\hbar \text{ is } \frac{\hbar^2}{m_e a^2 b^2} D \quad (16.11)$$

$$= \frac{e^2}{8\pi\varepsilon_0 ab^2} D + \frac{\hbar^2}{2m_e a^2 b^2} D - \left(\frac{2}{2} + \frac{2}{Z} + \frac{\sqrt{\frac{3}{4}}}{Z}\right)$$

$$\frac{\hbar^2}{2m_e a^2 b^2} D$$

$$a = \left(2 + \frac{2}{Z} + \frac{\sqrt{\frac{3}{4}}}{Z}\right) a_0 \quad (16.12)$$

With Z=11, the semimajor axis of the Na—H-bond MO is $$a = 2.26055 a_0 \quad (16.13)$$

Using the semimajor axis, the geometric and energy parameters of the MO are calculated using Eqs. (15.1-15.117) in the same manner as the organic functional groups given in the Organic Molecular Functional Groups and Molecules section. For the Na—H-bond MO of the NaH, $c_1=1$, $c_2=1$ and $C_2=1$ in both the geometry relationships (Eqs. (15.2-15.5)) and the energy equation (Eq. (15.61)). In NaH the molecule, the Na3s AO has an energy of E(Na3s)=−5.139076 eV [15] and the H AO has an energy of E(H)=−13.59844 eV [15]. To meet the equipotential condition of the union of the Na3s AO and the H1s AO, $c_2$ and $C_2$ of Eqs. (15.2-15.5) and Eq. (15.61) for the Na—H-bond MO given by Eq. (15.77) is $$C_2(\text{Na3sAO to H1sAO}) = c_2(\text{Na3sAO to H1sAO}) \quad (16.14)$$

$$= \frac{-5.139076 \text{ eV}}{-13.59844 \text{ eV}}$$

$$= 0.37792$$

The energy of the MO is matched to that of the Na2p AO with which in intersects such that E(AO/HO) is E(Na2p)=−47.2864 eV [15]; thus, $E_{initial}(c_4 \text{ AO/HO})$ (eV) is given by the sum of E(Na2p)=−47.2864 eV and E(Na3s)=−5.139076 eV.

The symbol of the functional group of molecular NaH is given in Table 20. The geometrical (Eqs. (15.1-15.5) and (16.11-16.14)), intercept (Eqs. (15.80-15.87)), and energy (Eqs. (15.61-15.65) and (16.13-16.14)) parameters of molecular NaH are given in Tables 21, 22, and 23, respectively. The color scale, translucent view of the charge-densities of molecular NaH comprising the concentric shells of the inner AOs of the Na atom and an outer MO formed from the outer Na3s AO and the H1s AO are shown in FIG. 9.

TABLE 20

The symbol of the functional group of molecular NaH.

| Functional Group | Group Symbol |
|---|---|
| NaH group | Na—H |

TABLE 21

The geometrical bond parameters of molecular NaH and experimental values [20].

| Parameter | Na—H Group |
|---|---|
| a ($a_0$) | 2.26055 |
| c' ($a_0$) | 1.72939 |
| Bond Length 2c' (Å) | 1.83031 |
| Exp. Bond Length (Å) | 1.88654 (NaH) |
| b, c ($a_0$) | 1.45577 |
| e | 0.76503 |

TABLE 22

The MO to Na2p AO intercept geometrical bond parameters of NaH.

| Bond | Atom | $E_T$ (eV) Bond 1 | $E_T$ (eV) Bond 2 | $E_T$ (eV) Bond 3 | $E_T$ (eV) Bond 4 |
|---|---|---|---|---|---|
| Na—H (NaH) | Na | 0 | 0 | 0 | 0 |

| Bond | Final Total Energy Na2p (eV) | $r_{initial}$ ($a_0$) | $r_{final}$ ($a_0$) | $E_{Coulomb}$(Na2p) (eV) Final | E(Na2p) (eV) Final |
|---|---|---|---|---|---|
| Na—H (NaH) | | 2.65432 | 0.56094 | | −47.2864 |

| Bond | $\theta'$ (°) | $\theta_1$ (°) | $\theta_2$ (°) | $d_1$ ($a_0$) | $d_2$ ($a_0$) |
|---|---|---|---|---|---|
| Na—H (NaH) | 28.66 | 151.34 | 10.65 | 2.22161 | 0.49221 |

TABLE 23

The energy parameters (eV) of the Na—H functional group of molecular NaH.

| Parameters | Na—H Group |
|---|---|
| $n_1$ | 1 |
| $n_2$ | 0 |
| $n_3$ | 0 |
| $C_1$ | 0.37792 |
| $C_2$ | 1 |
| $c_1$ | 1 |
| $c_2$ | 1 |
| $c_3$ | 0 |
| $c_4$ | 1 |
| $c_5$ | 1 |
| $C_{1o}$ | 0.37792 |
| $C_{2o}$ | 1 |
| $V_e$ (eV) | −31.72884 |
| $V_p$ (eV) | 7.86738 |
| $T$ (eV) | 7.01795 |
| $V_m$ (eV) | −3.50898 |
| E(AO/HO) (eV) | −47.2864 |
| $\Delta E_{H_2MO}(AO/HO)$ (eV) | 0 |
| $E_T(AO/HO)$ (eV) | −47.2864 |
| $E_T(H_2MO)$ (eV) | −67.63888 |
| $E_T$(atom-atom, msp$^3$ · AO) (eV) | 0 |
| $E_T(MO)$ (eV) | −67.63888 |
| $\omega$ ($10^{15}$ rad/s) | 14.4691 [20] |
| $E_K$ (eV) | 9.52384 |
| $\overline{E}_D$ (eV) | −0.41296 |
| $\overline{E}_{Kvib}$ (eV) | 0.14534 |
| $\overline{E}_{osc}$ (eV) | −0.34029 |
| $E_{mag}$ (eV) | 0.11441 |
| $E_T(Group)$ (eV) | −67.97917 |
| $E_{initial}(c_4 AO/HO)$ (eV) | −52.425476 |
| $E_{initial}(c_5 AO/HO)$ (eV) | −13.59844 |
| $E_D(Group)$ (eV) | 1.95525 |
| Exp. $E_D(Group)$ (eV) | 1.92451 (Na—H [21]) |

Bond and Dipole Moments

The bond moment of a functional group may be calculated by considering the charge donation between atoms of the functional group. Since the potential of an MO is that of a point charge at infinity (Eq. (11.36)), an asymmetry in the distribution of charge between nonequivalent HOs or AOs of the MO occurs to maintain an energy match of the MO with the bridged orbitals. The charge must redistribute between the spherical orbitals to achieve a corresponding current-density that maintains constant current at the equivalent-energy condition according to the energy-matching factor such as $c_2$ or $C_2$ of Eqs. (15.51) and (15.61). Since the orbital energy and radius are reciprocally related, the contribution scales as the square of the ratio (over unity) of the energy of the resultant net positively-charged orbital and the initial matched energy of the resultant net negatively-charged orbital of the bond multiplied by the energy-matching factor (e.g. $c_2$ or $C_2$). The partial charges on the HOs or AOs corresponding to the charge contribution are equivalent to point charges centered on the nuclei. Due to symmetry, the bond moment µ of each functional group is along the internuclear axis and is calculated from the partial changes at the separation distance, the internuclear distance.

Using the reciprocal relationship between the orbital energies and radii, the dependence of the orbital area on the radius squared, and the relationship of the partial charge q to the areas with energy matching for each electron of the MO, the bond moment µ along the internuclear axis of A-B wherein A is the net positively-charged atom is given by $$\mu = qd = n_1 ce\left(1 - \left(\frac{E_A(\text{valence})}{E_B(\text{valence})}\right)^2\right) 2c' \quad (16.15)$$

wherein $n_1$ is the number of equivalent bonds of the MO, c is energy-matching factor su as $c_1$, $c_2$, $C_1$, or $C_2$ of Eqs. (15.51) and (15.61) where $c_1$ and $C_2$ may correspond to both electrons of a MO localized on one AO or HO such as when the magnitude of the valence or Coulombic energy of the AO or HO is less than that of $E_{Coulomb}(H) = -13.605804$ eV or when the orbital may contain paired or shared electrons in a linear combination with the partner orbital, and d is the charge-separation distance, the internuclear distance 2c'. $E_B$(valence) is the initial matched energy of the resultant net negatively-charged orbital of the bond that is further lowered by bonding (Eqs. (15.32) and (15.16)) to atom A having an energy $E_A$(valence). Typically, $E_B$(valence) of a carbon-heteroatom bond is −14.63489 eV, the initial C2sp$^3$ HO (Eq. (15.25)) energy to which the heteroatom is energy matched. Functional group bond moments determined using Eq. (16.15) are given in Table 24.

$$E(\text{atom, msp}^3) = \frac{-e^2}{8\pi\varepsilon_0 r_{msp^3}} + \frac{2\pi\mu_0 e^2 \hbar^2}{m_e^2 r^3} \quad (15.16)$$

$$E(C, 2sp^3) = \frac{-e^2}{8\pi\varepsilon_0 r_{2sp^3}} + \frac{2\pi\mu_0 e^2 \hbar^2}{m_e^2 (r_3)^3} \quad (15.25)$$

$$= -14.82575 \text{ eV} + 0.19086 \text{ eV}$$

$$= -14.63489 \text{ eV}$$

$$r_{mol2sp^3} = \frac{-e^2}{8\pi\varepsilon_0 \left(E_{Coulomb}(C, 2sp^3) + \sum E_{T_{mol}}(MO, 2sp^3)\right)} \quad (15.32)$$

$$= \frac{e^2}{8\pi\varepsilon_0 \left(e14.825751 \text{ eV} + \sum |E_{T_{mol}}(MO, 2sp^3)|\right)}$$

$$-\frac{n_1 e^2}{8\pi\varepsilon_0 \sqrt{\frac{aa_0}{2C_1C_2}}} \left[\frac{c_1c_2\left(2-\frac{a_0}{a}\right)\ln\left[\frac{a+\sqrt{\frac{aa_0}{2C_1C_2}}}{a-\sqrt{\frac{aa_0}{2C_1C_2}}}\right]-1\right] + E_T(AO/HO) = \quad (15.51)$$

$$E(\text{basis energies})$$

$$E_{T+osc}(\text{Group}) = E_T(MO) + \overline{E}_{osc} \quad (15.61)$$

$$= \left(\left[-\frac{n_1 e^2}{8\pi\varepsilon_0 \sqrt{\frac{aa_0}{2C_1C_2}}}\left[\frac{c_1c_2\left(2-\frac{a_0}{a}\right)\ln\left[\frac{a+\sqrt{\frac{aa_0}{2C_1C_2}}}{a-\sqrt{\frac{aa_0}{2C_1C_2}}}\right]-1\right]+\right.\right.$$
$$\left.\left.E_T(AO/HO) + E_T(\text{atom} - \text{atom}, msp^3 \cdot AO)\right]\right.$$
$$\left.\left[1+\sqrt{\frac{2\hbar\sqrt{\frac{C_{1o}C_{2o}e^2}{4\pi\varepsilon_o R^3}}}{m_e c^2}}\right] + n_1 \frac{1}{2}\hbar\sqrt{\frac{k}{\mu}}\right)$$

$$= (E(\text{basis energies}) + E_T(\text{atom} - \text{atom}, msp^3 \cdot AO))$$

$$\left[1+\sqrt{\frac{2\hbar\sqrt{\frac{C_{1o}C_{2o}e^2}{4\pi\varepsilon_o R^3}}}{m_e c^2}}\right] + n_1 \frac{1}{2}\hbar\sqrt{\frac{k}{\mu}}$$

TABLE 24

The bond moments of functional groups compared to experimental value [22-87] wherein the parameters correspond to those given previously except as indicated.

| Functional Group[a] | $n_1$ | $(c_1)c_2$ | $(C_1)C_2$ | $E_B$(valence) | $E_A$(valence) | $\frac{q}{e}$ | Bond Length $2c'$ (Å) | Bond Moment $\mu$ (D) | Exp. Bond Moment $\mu$ (D) |
|---|---|---|---|---|---|---|---|---|---|
| H—C (alkyl) | 1 | 0.91771 | 1 | 14.63489 | 15.35946 | 0.070 | 1.11713 | 0.37 | 0.4 |
| H—C (aromatic) | 1 | 0.91771 | 1 | 15.95955 | 15.95955 | 0 | 1.09327 | 0 | 0 |
| H—N[b] (amine) | 1 | 0.78896 | 1 | 13.59844 | 15.81768 | 0.279 | 1.00343 | 1.34 | 1.31 |
| H—N[c] (ammonia) | 1 | 0.74230 | 1 | 13.59844 | 15.81768 | 0.262 | 1.03677 | 1.30 | 1.31 |
| H—O[d] (alcohol) | 1 | 0.91771 | 1 | 13.59844 | 15.81768 | 0.324 | 0.97165 | 1.51 | 1.51 |
| H—O[e] (water) | 1 | 0.71419 | 1 | 13.59844 | 15.81768 | 0.323 | 0.97157 | 1.51 | 1.51 |
| C—N | 1 | 0.91140 | 1 | 14.53414 | 14.82575 | 0.037 | 1.46910 | 0.26 | 0.22 |
| C—O | 1 | 0.85395 | 1 | 14.63489 | 15.56407 | 0.112 | 1.41303 | 0.76 | 0.74 |
| C—F[f] | 1 | 1.09254[b] | 1 | 14.63489 | 15.98435 | 0.211 | 1.38858 | 1.41 | 1.41 |
| C—Cl | 1 | 1 | (2)0.81317 | 14.63489 | 15.35946 | 0.165 | 1.79005 | 1.42 | 1.46 |
| C—Br | 1 | 1 | (2)0.74081 | 14.63489 | 15.35946 | 0.150 | 1.93381 | 1.40 | 1.38 |
| C—I[g] | 1 | 1 | (2)0.65537 | 14.63489 | 15.28545 | 0.119 | 2.13662 | 1.22 | 1.19 |
| C=O | 2 | 0.85395 | 1 | 14.63489 | 16.20002 | 0.385 | 1.20628 | 2.23 | 2.3 |
| C≡N | 3 | 0.91140 | 1 | 14.63489 | 16.20002 | 0.616 | 1.16221 | 3.44 | 3.5 |
| H—S[h] | 1 | 0.69878 | 1 | 14.63489 | 15.81768 | 0.118 | 1.34244 | 0.76 | 0.69 |
| C—S | 1 | 1 | 0.91771 | 14.63489 | 15.35946 | 0.093 | 1.81460 | 0.81 | 0.9 |
| S—O | 1 | 1 | 0.77641 | 14.63489 | 15.76868 | 0.125 | 1.56744 | 0.94 | 1.0 |
| S=O[i] | 2 | 0.82897 | 1 | 10.36001 | 11.57099 | 0.410 | 1.49118 | 2.94 | 2.93 |
| N—O | 1 | 1.06727 | 1 | 14.53414 | 14.82575 | 0.043 | 1.40582 | 0.29 | 0.30 |
| N=O (nitro) | 2 | 0.91140 | 1 | 14.63489 | 15.95955 | 0.345 | 1.22157 | 2.02 | 2.01 |
| C—P | 1 | 1 | 0.73885 | 14.63489 | 15.35946 | 0.075 | 1.86534 | 0.67 | 0.69 |
| P—O | 1 | 0.79401 | 1 | 14.63489 | 15.35946 | 0.081 | 1.61423 | 0.62 | 0.60 |
| P=O[j] | 2 | 1.25942 | 1 | 14.63489 | 15.76868 | 0.405 | 1.46521 | 2.85 | 2.825 |
| Si—H | 1 | 1 | 0.75800 | 10.25487 | 11.37682 | 0.131 | 1.48797 | 0.94 | 0.99 |
| Si—C | 1 | 1 | 0.70071 | 14.63489 | 15.35946 | 0.071 | 1.87675 | 0.64 | 0.60 |
| Si—O[k] | 1 | 1 | 1.32796 | 10.25487 | 10.87705 | 0.166 | 1.72480 | 1.38 | 1.38 |
| B—H[l] | 1 | 1.14361 | 1 | 11.80624 | 12.93364 | 0.172 | 1.20235 | 0.99 | 1.0 |
| B—C | 1 | 0.80672 | 1 | 14.63489 | 15.35946 | 0.082 | 1.57443 | 0.62 | 0.69 |
| B—O (alkoxy) | 1 | 1 | 0.79562 | 11.80624 | 12.93364 | 0.159 | 1.37009 | 1.05 | 0.93 |
| B—N | 1 | 1 | 0.81231 | 11.89724 | 14.53414 | 0.400 | 1.36257 | 2.62 | 2.68 |
| B—F[m] | 1 | 0.85447 | 1 | 14.88734 | 17.42282 | 0.316 | 1.29621 | 1.97 | 1.903 |
| B—Cl | 1 | 1 | 0.91044 | 11.80624 | 12.93364 | 0.182 | 1.76065 | 1.54 | 1.58 |

[a]The more positive atom is on the left.
[b]$c_2$ from Eqs. (15.77), (15.79), and Eq. (13.430) and $E_A$(valence) is given by 1/2 two $H_2$-type ellipsoidal MOs (Eq. (11.212)).
[c]$c_2$ from Eqs. (15.77), (15.79), and the product of 0.936127 (Eq. (13.248)) and 0.92235 given by 13.59844 eV/(13.59844 eV + 0.25 · $E_D$) where $E_D$ is the N—H bond energy $E_D(^{14}NH_3)$ = 4.57913 eV given by Eq. (13.404) and the energy of H is 13.59844 eV; $E_A$(valence) is given by 1/2 two $H_2$-type ellipsoidal MOs (Eq. (11.212)).
[d]$E_A$(valence) is given by 1/2 two $H_2$-type ellipsoidal MOs (Eq. (11.212)).
[e]$c_2$ from Eqs. (15.77) given by 13.59844 eV/(13.59844 eV + 0.25 · $E_D$) where $E_D$ is the O—H bond energy $E_D(H^{16}OH)$ = 5.1059 eV given by Eq. (13.222)) and the energy of H is 13.59844 eV; $E_A$(valence) is given by 1/2 two $H_2$-type ellipsoidal MOs (Eq. (11.212)).
[f]Eq. (15.129) with the inverse energy ratio of E(F) = −17.42282 eV and E(C, $2sp^3$) = −14.63489 eV corresponding to higher binding energy of the former.
[g]$E_A$(valence) is given by 15.35946 eV − 1/2$E_{mag}$ (Eqs. (14.150) and (15.67)).
[h]$c_1$ from Eqs. (15.79), (15.145), and (13.430); $E_A$(valence) is given by 1/2 two $H_2$-type ellipsoidal MOs (Eq. (11.212)).

TABLE 24-continued

The bond moments of functional groups compared to experimental value [22-87] wherein the parameters correspond to those given previously except as indicated.

| Functional Group[a] | $n_1$ | $(c_1)c_2$ | $(C_1)C_2$ | $E_B$(valence) | $E_A$(valence) | $\frac{q}{e}$ | Bond Length 2c' (Å) | Bond Moment μ (D) | Exp. Bond Moment μ (D) |
|---|---|---|---|---|---|---|---|---|---|

[i]$c_2$ from the reciprocal of Eq. (15.147), $E_A$(valence) is given by Eq. (15.139), and $E_B$(valence) is $E(S) = -10.36001$ eV.
[j]$c_2$ from the reciprocal of Eq. (15.182).
[k]$c_2$ from the reciprocal of Eq. (20.49).
[l]$c_2$ from the reciprocal of Eq. (22.29).
[m]$c_2$ from Eq. (15.77) using $E(F) = -17.42282$ eV and $E(B_{B-Fborane}, 2sp^3) = -14.88734$ eV (Eq. (22.61)).

The dipole moment of a given molecule is then given by the vector sum of the bond moments in the molecule. Thus, the dipole moment is given by taking into account the magnitude and direction of the bond moment of each functional group wherein the function-group bond moment stays constant from molecule to molecule and is in the vector direction of the internuclear axis. The dipole moments of water and ammonia to compare to the experimental values are given from the corresponding moments in Table 24. The calculated dipole moment of $H_2O$ is $$\mu_{H_2O} = 2(1.51)\cos\left(\frac{106°}{2}\right) = 1.8128D \quad (16.16)$$

where the angle between the O—H bond is 106° given by Eq. (13.242). The experimental dipole moment of $H_2O$ is [23]

$$\mu_{H_2O} = 1.8546D \quad (16.17)$$

The calculated dipole moment of $NH_3$ is $$\mu_{NH_3} = 3(1.30)\cos(68°) = 1.467D \quad (16.18)$$

where the angle between each N—H bond and the z-axis is 68° given by Eq. (13.417). The experimental dipole moment of $NH_3$ is [23]

$$\mu_{NH_3} = 1.4718D \quad (16.19)$$

The charge distributions of the functional groups given in Table 24 facilitate the rendering of the charge distribution of molecules of unlimited complexity comprised of these functional groups. What was previously impossible to achieve using supercomputers can be readily accomplished on a personal computer (PC). The rendering of the true charge densities of the exemplary proteins insulin and lysozyme are shown in color scale, translucent view in FIGS. 10 and 11, respectively. The color scale, translucent view of the charge-density of an exemplary double-stranded RNA helix is shown in FIG. 12.

Nature of the Dipole Bond: Dipole-Dipole, Hydrogen, and Van Der Waals Bonding

The boundless number and length of permutations of the functional groups can form a correspondingly infinite number of molecules. The intermolecular forces instill upon molecules their inherent properties such as state—being solid, liquid, or gas, the temperatures at which phase transitions occur, and the energy content change required to change the state. However, the types of bonding are relatively few even though the breadth of molecular compositions is infinite. Since all molecules comprise nuclei that behave on the scale of molecules as electrostatic point charges, and electrically charged electrons exist as charge and current densities that obey Maxwell's equations, the binding is determined by electrical and electrodynamics forces. These typically dominate over any magnetic forces since the latter is a relativistic effect of the former and is thus negligible as the norm. Thus, essentially all molecular bonding is Coulombic in nature. The extreme case involves ions, and ionic bonding between charged functional groups of molecules obeys the same physical principles as inorganic ions as given in the Nature of the Solid Ionic Bond of Alkali Hydrides and Halides section. Similarly, the charge-density distributions of negatively-charged electrons relative to the positively-charged nuclei of neutral molecules gives rise to Coulombic-based bonding that can be grouped into two main categories, bonding that comprises permanent dipole-dipole interactions further including an extreme case, hydrogen bonding, and bonding regarding reversible mutually induced dipole fields in near-neighbor molecules called van der Waals bonding.

The H bond is exemplary of the extreme of dipole-dipole interactions as the source of bond energy and rises from the extremely high dipole moments of H bound to F, O, or N as shown in the Bond and Dipole Moments section. The bond energies of these types of bonds are large due to the very high Coulombic energy associated with the dipole-dipole interaction between H-bonded molecules compared to those having much lower dipole moments. Still H-bond energies are typically small by the standards of covalent bonds. The differences are also reflected in the relative bond lengths. In water for example, the O—H bond distance and energy are $2c'=0.970\pm0.005$ Å (Eq. (13.186)) and $E_D(H^{16}OH)=5.1059$ eV (Eq. 13.222), respectively; whereas, those of the hydrogen bond of water are $2c_{O\cdots H}'=1.78$ Å (Eq. (16.27)) and $E_{vapor,0°C}=0.233$ eV/H-bond (Eq. (16.57)), respectively. On the other end of the spectrum, van der Waals bonds are also Coulombic in nature and are between dipoles. However, the dipoles are mutually induced rather than permanent, and the mutual induction is typically small. Thus, the bond distances are on the order of angstroms and the energies in the 10's of meV's range. The bonding between molecules gives rise to condensed matter, and the classical theory of condensed matter based on these forms of bonding is treated next.

Condensed Matter Physics

Condensed matter comprises liquids and solids of atoms and molecules. It is shown infra that the geometrical parameters, energies, and properties of the latter can be solved using the same equations as those used to solved the geometrical parameters and component energies of the individual molecules as given in the Organic Molecular Functional Groups and Molecules section.

The structure and properties of liquids can be solved by first solving the unit cell of the corresponding condensed solid. The unit cell may be solved by first determining the packing that minimizes the lattice energy. In nature, there are a small, finite number of packing arrangements. The particular arrangement relates to the most efficient one giving the most objects packed into a given space with the size and shape limitations. The water molecule, for example, is small compared to the unit cell of ice; so, it will naturally assume a tetrahedral structure and hexagonal packing given the geometry of its electric dipoles with a partial positive on the H's and partial negative on the O. In general, a reiterative algorithm is used that optimizes the packing of the molecules and tests that packing against the unit cell parameters and lattice energy until an optimum is found. The lattice parameters can be verified by X-ray crystallography and neutron diffraction. The lattice energy can be measured using calorimetry; so, the model can be directly tested.

Bonding in neutral condensed solids and liquids arises from interactions between molecules wherein the molecules of the lattice have multipoles that give rise to corresponding Coulombic or magnetic interactions. Typically, the multipoles are electric or magnetic dipoles. Consider the former case. Since the separated partial charges that give rise to bond moments are equivalent to point charges centered on the bond nuclei as given in the Bond and Dipole Moments section, the maximum interaction energy between interacting species can be calculated using Coulomb's law with the corresponding partial monopole charges and separation distance. The energy from the interaction of the partial charges increases as the separation decreases, but concomitantly, the energy of a bond that may form between the interacting species increases as well. The equilibrium separation distance corresponds to the occurrence of the balance between the Coulombic potential energy of the interacting atoms and the energy of the bond whose formation involves the interacting atoms. Thus, the balance is at the energy threshold for the formation of a nascent bond that would replace the interacting partial charges while also destabilizing the standard bonds of the interacting molecules. Then, an optimal lattice structure corresponds to an energy minimum with an associated energy. The minimum energy structure corresponds to the highest density of interacting dipoles in their minimum energy state. A convenient method to calculate the lattice energy is to determine the electric or magnetic field in the material having an electric or magnetic polarization density, and in turn, the energy can be calculated from the energy of each dipole in the corresponding field using the electrostatic or magnetostatic form of Gauss' or Amperes' equation, respectively.

Once the a, b, and c parameters of the unit cell are solved from the energy (force) balance between the electric monopoles and the nascent bond energy, the unit cell is determined. Then, the unit cell can be proliferated to arbitrary scale to render the solid. Typically, only one lattice parameter needs to be determined since the additional distances can be determined from geometrical relations based on the unit cell structure. The lattice energy may be calculated from the potential between dipoles using the cell parameters. The dielectric constant and other properties may also be calculated using Maxwell's equations and other first principles.

The structures of liquids can be modeled as linear combinations of unit cells comprising perturbations of the solid unit cell. In one approach, increasing disorder is added to the solid structure in the transition from solid to liquid to gas. Complete disorder or statistical gas behavior applies in the ideal gas limit. Thus, liquid states may be modeled by adding more cells with increasing loss of order of the solid unit cell as the temperature of the liquid is increased. The disorder is due to population of translational, rotational, and vibrational levels to match the internal energy at a given temperature. Consider thermodynamics. In principle, it is possible to classically calculate the fields over all space, the exact field interactions, and the position, trajectory, momentum, and energy of every particle of a material at each instance. Then, the material properties can be determined from these parameters. However, in practice, it is impossible computationally. For the same reason, simple underlying physical principles are applied to derive statistical properties for large ensembles of particles as given in the Statistical Mechanics section. The same statistical thermodynamic methods may be applied to modeling liquids and gases using the exact solutions of the individual molecules. Using the molecular geometrical parameters, charge distributions, and corresponding interactions as input, unit cells can be computed based on the solid unit cell. Working with increasing numbers of unit cells of increasing randomness and populating the unit cells based on appropriate statistical models such as Boltzmann statistics for increasing enthalpy input and temperature, accurate models of liquids are provided. The corresponding liquid properties can be solved from each liquid structure.

A preferred approach to solving the energy and geometric parameters of ice, considered next, is to solve the separation distance of the electric monopoles comprising a partial positive on each H and a partial negative charge on each O as the balance between the Coulombic attraction energy between the partial charges and the repulsion energy due to the formation of a nascent H—O bond between the hydrogen-bonded atoms. The nascent bond substitutes for the hydrogen bond while also removing electron density and stability from the standard water molecule bonds. Thus, it offsets the Coulombic energy and establishes the equilibrium minimum approach distance of the interacting atoms of the water molecules. Then, using Gauss's law, the energy per water molecule is calculated as the dipole energy in the electric field of the lattice of electric dipoles.

Geometrical Parameters and Energies of the Hydrogen Bond of $H_2O$ in the Ice Phase The extraordinary properties of water are determined by hydrogen (H) bonds, designated by the dotted bond O—H•••O, each between a participating H of one water molecule and an O of another. The structure of each phase of water is then determined by the number of H bonds on average per water molecule. As shown in the Bond and Dipole Moments section, the O—H bond has a bond moment $\mu$ of 1.51 D corresponding to a partial charge on each H of +0.323e and a component of partial charge on each O per bond moment of −0.323e. The thermodynamic basis of the H bond is the minimization of the Coulombic energy between the H and O of the hydrogen bond, limited by the formation of a nascent bond between these atoms that destabilizes the initial O—H bond. The sum of the torques and forces are zero at force balance to achieve a hexagonal crystal structure that is an energy minimum. The maximum electrostatic energy of the partial charges is calculated for the components along the H-bond axis. This energy is balanced by the total energy of the nascent bond that can form between the H•••O atoms of the H bond. The bond length of the H bond, the internuclear distance between the H and O of the H•••O bond, is calculated by a similar method as that used to determine the bond angle given in the Bond Angle of $H_2O$ section.

The $H_2O$ MO comprises a linear combination of two O—H-bond MOs. Each O—H-bond MO comprises the superposition of a $H_2$-type ellipsoidal MO and the $O2p_z$ AO or the $O2p_y$ AO with a relative H partial orbital contribution to the MO of 0.75; otherwise, the O2p orbitals are the same as those of the oxygen atom. The solution of the geometrical parameters and component energies are given in the Water Molecule ($H_2O$) section and the color scale charge density of the $H_2O$ MO is show in FIG. 13.

Rather than consider the possible bond between the two H atoms of the O—H bonds in the determination of the bond angle, consider that the hydrogen bond may achieve a partial bond order or partial three-centered O—H—O bond as given in the Bridging Bonds of Organoaluminum Hydrides (Al—H—Al and Al—C—Al) and Bridging Bonds of Boranes (B—H—B and B—B—B) sections, and the H can become mobile between water molecules corresponding to H exchange. Such exchange of O•••H—O to O—H•••O bonding would decrease the initial O—H-bond strength since electron density would be shifted from the O—H bonds to the O•••H bond. Concomitantly, the Coulombic energy of the H bond would be eliminated. Thus, the equilibrium distance $r_e$ or internuclear bond distance of O•••H designated as $2c'_{O\cdots H}=r_e$ is determined by the condition that the total energy of the nascent $H_2$-type ellipsoidal MO formed from the atoms of the O•••H bond is equal to the maximum Coulombic energy between the partial charges of the H and O atoms of the H bond.

The O—H bond moments superimpose at the central O. The minimum energy corresponds to the maximum separation of the $\delta^-$ of each bond moment on the O atom that occurs in space and time with $\pi$ phase. The corresponding distance is the hypotenuse of the right triangle having the distance $2c'_{O\cdots H}$ between the H and O nuclei of the H•••O bond as one side and the radius of the oxygen atom, $r_{O2p}=0$ (Eq. (10.162)), as the other. Then, the maximum Coulomb energy $E_{Coulomb}$(H-bond) between the atoms of the O•••H bond due to the two separated $\delta^-$'s on the oxygen atom with the $\delta^+$ centered on the nucleus of hydrogen is $$E_{Coulomb}(\text{H-bond}) = \frac{-2\delta^2 e^2}{4\pi\varepsilon_0 \sqrt{(2c'_{O-H})^2 + (r_{O2p})^2}} \quad (16.20)$$

Since each H bond is between two $H_2O$ molecules and there are four H bonds per $H_2O$ molecule, the Coulomb energy per $H_2O$ $E_{Coulomb}(H_2O)$ is equivalent to two times $E_{Coulomb}$(H-bond) (Eq. (16.20)):

$$E_{Coulomb}(H_2O) = \frac{-4\delta^2 e^2}{4\pi\varepsilon_0 \sqrt{(2c'_{O-H})^2 + (r_{O2p})^2}} \quad (16.21)$$

Eq. (16.21) is the energy to be equated to that of the nascent covalent bonds involving the atoms of the H bonds of the water molecule. Using Eq. (15.3), the internuclear distance of this bond, $2c_{O\cdots H}'=r_e$, in terms of the corresponding semimajor axis $a_{O\cdots H}$ is $$2c'_{O-H} = 2\sqrt{\frac{a_{O-H} a_0}{2C_1 C_2}} \quad (16.22)$$

The length of the semiminor axis of the prolate spheroidal MO b=c is given by $$b_{O\cdots H} = \sqrt{(a_{O\cdots H})^2 - (c_{O\cdots H}')^2} \quad (16.23)$$

And, the eccentricity, e, is $$e_{O-H} = \frac{c'_{O-H}}{a_{O-H}} \quad (16.24)$$

The semimajor axis $a_{O\cdots H}$ of the O•••H bond is determined using the general equation for determination of the bond angle between terminal atoms given by Eqs. (15.93) and (15.99) with Eqs. (15.46-15.47) except that the MO energy is matched to the Coulombic energy of the H bond (Eq. (16.21) with substitution of Eq. (15.3)) rather than being set equal to zero for zero interaction energy in the case of the bond-angle determination:

$$\frac{-4\delta^2 e^2}{4\pi\varepsilon_0 \sqrt{\left(2\sqrt{\frac{a_{O-H} a_0}{2C_1 C_2}}\right)^2 + (r_{O2p})^2}} = \quad (16.25)$$

$$\left[\left(-\frac{n_1 e^2}{8\pi\varepsilon_0 \sqrt{\frac{aa_0}{2C_1 C_2}}}\left[\frac{c_1 c_2 \left(2 - \frac{a_0}{a}\right)\ln\frac{a + \sqrt{\frac{aa_0}{2C_1 C_2}}}{a - \sqrt{\frac{aa_0}{2C_1 C_2}}} - 1\right]\right) + \right.$$

$$\left. E_T(AO/HO) + E_T(\text{atom---atom}, msp^3 \cdot AO)\right]$$

$$\left[1 + \sqrt{\frac{2\hbar \sqrt{\frac{C_{1o} C_{2o} e^2}{4\pi\varepsilon_0 R^3}}}{m_e c^2}}\right] +$$

$$n_1 \frac{1}{2} \hbar \sqrt{\frac{\frac{c_1 c_2 e^2}{8\pi\varepsilon_o a^3} - \frac{e^2}{8\pi\varepsilon_o \left(a + \sqrt{\frac{aa_0}{2C_1 C_2}}\right)^3}}{\mu}}$$

where $n_1$ is the number of equivalent bonds of the MO, $c_1$ is the fraction of the $H_2$-type ellipsoidal MO basis function, $c_2$ is the factor that results in an equipotential energy match of the participating at least two atomic orbitals of each chemical bond, $C_{1o}$ is the fraction of the $H_2$-type ellipsoidal MO basis function of the oscillatory transition state of a chemical bond of the group, and $C_{2o}$ is the factor that results in an equipotential energy match of the participating at least two atomic orbitals of the transition state of the chemical bond, $E_T$(AO/HO) is the total energy comprising the difference of the energy E(AO/HO) of at least one atomic or hybrid orbital to which the MO is energy matched and any energy component $\Delta E_{H_2MO}$ (AO/HO) due to the AO or HO's charge donation to the MO, $E_T$(atom-atom,$msp^3$.AO) is the change in the energy of the AOs or HOs upon forming the bond, and $\mu$ is the reduced mass.

For the determination of the H-bond distance, the energy parameters are the same as those of water given in the Water Molecule ($H_2O$) section except that any parameters due to matching AO's, $E_T$ (AO/HO) and $E_T$(atom-atom,$msp^3$.AO), is zero since only the energies of the MO electrons to form the O•••H MO are considered. The partial charge $\delta=q/e$ from Table 24 is 0.323, and the reduced mass is $$\mu = \frac{16}{17}.$$

The parameters are summarized in Table 16.18 and Eq. (16.26).

TABLE 25

The energy parameters (eV) of the O•••H functional group of the hydrogen bond of Type I ice.

| Parameters | O•••H Group |
|---|---|
| $\delta$ | 0.323 |
| $n_1$ | 2 |
| $C_1$ | 0.75 |
| $C_2$ | 1 |
| $c_1$ | 0.75 |
| $c_2$ | 1 |
| $c_{1o}$ | 1.5 |
| $C_{2o}$ | 1 |
| $V_e$ (eV) | −20.30177 |
| $V_p$ (eV) | 16.15958 |
| $T$ (eV) | 2.38652 |
| $V_m$ (eV) | −1.19326 |
| $E(AO/HO)$ (eV) | 0 |
| $\Delta E_{H_2MO}(AO/HO)$ (eV) | 0 |
| $E_T(AO/HO)$ (eV) | 0 |
| $E_T(H_2MO)$ (eV) | −2.94892 |
| $E_T(\text{atom-atom, msp}^3 \cdot AO)$ (eV) | 0 |
| $E_T(MO)$ (eV) | −2.94892 |
| $\omega$ ($10^{15}$ rad/s) | 6.55917 |
| $E_K$ (eV) | 4.31736 |
| $\overline{E}_D$ (eV) | −0.012122 |
| $\overline{E}_{Kvib}$ (eV) | 0.03263 |
| $\overline{E}_{osc}$ (eV) | 0.004191 |
| $E_T(Group)$ (eV) | −2.94054 |

Substitution of the parameters of Table 25, the internuclear distance $2c_{O-H}'$ given by Eq. (13.185), and R given by Eq. (16.23) and (16.22) into Eq. (16.25) gives $$\frac{-4(0.323)^2 e^2}{4\pi\varepsilon_0 \sqrt{\left(2\sqrt{\frac{a_{O-H}a_0}{2(0.75)}}\right)^2 + (5.2917706 \times 10^{-11} \text{ m})^2}} = \quad (16.26)$$

$$\left\{ \frac{-e^2}{4\pi\varepsilon_0 \sqrt{\frac{a_{O-H}a_0}{2(0.75)}}} \left( \ln \frac{a_{O-H} + \sqrt{\frac{a_{O-H}a_0}{2(0.75)}}}{a_{O-H} - \sqrt{\frac{a_{O-H}a_0}{2(0.75)}}} \left(\frac{3}{2} - \frac{3}{8}\frac{a_0}{a_{O-H}}\right) - 1 \right) \right.$$

$$\left. 1 + 2\sqrt{\frac{2\hbar \sqrt{\frac{3}{2} \frac{\frac{e^2}{4\pi\varepsilon_0} \sqrt{\left(\frac{(a_{O-H})^2 - }{2\sqrt{\frac{a_{O-H}a_0}{2(0.75)}}}\right)^2}^3}{m_e}}}{m_e c^2}} \right\} +$$

$$2\left(\frac{1}{2}\right)\hbar \sqrt{\frac{\frac{0.75 e^2}{8\pi\varepsilon_o (a_{O-H})^3} - \frac{e^2}{8\pi\varepsilon_o \left(a_{O-H} + \sqrt{\frac{a_{O-H}a_0}{2(0.75)}}\right)^3}}{\frac{16}{17}}}$$

From the energy relationship given by Eq. (16.26) and the relationships between the axes given by Eqs. (16.22-16.24), the dimensions of the O•••H MO can be solved.

The most convenient way to solve Eq. (16.26) is by the reiterative technique using a computer. The result to within the round-off error with five-significant figures is $$a_{O\cdots H} = 4.25343 a_0 = 2.25082 \times 10^{10} \text{ m} \quad (16.27)$$

The component energy parameters at this condition are given in Table 25. Substitution of Eq. (16.27) into Eq. (16.22) gives $$c_{O\cdots H}' = 1.68393 a_0 = 8.91097 \times 10^{-11} \text{ m} \quad (16.28)$$

and internuclear distance of the H bond:

$$2c_{O\cdots H}' = 3.36786 a_0 = 1.78219 \times 10^{-10} \text{ m} = 1.78219 \text{ Å} \quad (16.29)$$

The internuclear distance of the O—H given by Eq. (13.185) is $$2c' = 1.83601 a_0 = 9.71574 \times 10^{-11} \text{ m} \quad (16.30)$$

The internuclear distance $2c_{O\cdots H}'$ of the O—H bond added to $2c_{O\cdots H}'$ gives the internuclear distance $2c_{O\cdots HO}'$ between the oxygen atoms of the group O—H•••O:

$$2c_{O\cdots HO}' = 2c_{O\cdots H}' + 2c_{O-H}' \quad (16.31)$$

Substitution of $2c_{O\cdots H}'$ (Eq. (16.29)) and $2c_{O-H}'$ (Eq. (13.185)) into Eq. (16.31) gives the nearest-neighbor separation, the internuclear distance $2c_{O\cdots HO}'$ between the oxygen atoms of the O—H•••O bond in Type I ice:

$$2c'_{O-H} = 2c'_{O-H} + 2c'_{O-H} \quad (16.32)$$
$$= 1.78219 \times 10^{-10} \text{ m} + 9.71574 \times 10^{-11} \text{ m}$$
$$= 2.75377 \times 10^{-10} \text{ m}$$
$$= 2.75377 \text{ Å}$$

The experimental oxygen nearest-neighbor separation distance $2c_{O\cdots HO}'$ is [88]

$$2c_{O\cdots HO}' = 2.75 \text{ Å} \quad (16.33)$$

The experimental internuclear distance of the O—H bond of $H_2O$ is [89]

$$2c'=9.70\pm0.005\times10^{-11} \text{ m} \tag{16.34}$$

Using Eqs. (16.33) and (16.34), the experimental H bond distance $2c_{O\cdots HO}'$ in Type I ice is [88-89]

$$2c_{O\cdots H}'=1.78 \text{ Å} \tag{16.35}$$

The other H-bond MO parameters can also be determined by the relationships among the parameters. Substitution of Eqs. (16.27) and (16.28) into Eq. (16.23) gives $$b_{O\cdots H}=c_{O\cdots H}=3.90590a_0=2.06691\times10^{-10} \text{ m} \tag{16.36}$$

Substitution of Eqs. (16.27) and (16.28) into Eq. (16.24) gives $$e_{O\cdots H}=0.39590 \tag{16.37}$$

Since water is a hexagonal crystal system in common with the carbon allotrope diamond, the internuclear distance of the two terminal O atoms of a set of three $H_2O$'s corresponding to the hexagonal lattice parameter $a_1$ is calculated using the same approach as that given by Eqs. (17.1-17.3) using the law of cosines:

$$s_1^2+s_2^2-2s_1s_2 \cos\theta=s_3^2 \tag{16.38}$$

where $s_3=a_1$ is the hypotenuse of the isosceles triangle having equivalent sides of length equal to $2c_{O\cdots HO}'$. With the bond angle between three water molecules formed by the two corresponding H bonds given by $\theta_{\angle H_2O,H_2O,H_2O}=109.5$ ([90] and $s_1=s_2=2c_{O\cdots HO}'$ given by Eq. (16.32), the distance between the oxygen atoms of the terminal water molecules along the hypotenuse, $s_3=2c_{H_2O-H_2O}'=a_1$, is $$a_l = 2c'_{H_2O-H_2O} \tag{16.39}$$
$$= \sqrt{2(2c'_{O-HO})^2(1-\cos(109.5°))}$$
$$= \sqrt{2(2.75377 \text{ Å})^2(1-\cos(109.5°))}$$
$$= 4.49768 \text{ Å}$$

Due to the tetrahedral structure shown in FIG. 14, four water molecules form a pyramidal structure with a central $H_2O(1)$ at the apex designated as on the z-axis, and the three other water molecules, $H_2O(n)$ n=2, 3, 4, form the base in the xy-plane. As further shown in FIG. 14, a fifth $H_2O(5)$ is positioned a distance $2c_{O\cdots HO}'$ along the z-axis. Twice the height along the z-axis from the base of the pyramid to the fifth $H_2O$ comprises the Type I ice unit cell parameter c which is determined next using Eqs. (13.412-13.417).

Since any two O—H•••O bonds having the internuclear distance $2c_{O\cdots HO}'$ between the oxygen atoms of in Type I ice form an isosceles triangle having the hypotenuse $a_1$ between the terminal oxygen's, the distance $d_{origin-O}$ from the origin of the pyramidal base to the nucleus of a terminal oxygen atom is given by $$d_{origin-O} = \frac{a_l}{2\sin 60°} \tag{16.40}$$

Substitution of Eq. (16.39) into Eq. (16.40) gives $$d_{origin-O}=2.59674a_0 \tag{16.41}$$

The height $d_{height}$ along the z-axis of the pyramid from the origin to the O nucleus of $H_2O(1)$ is given by $$d_{height}=\sqrt{(2c_{O\cdots HO}')^2-(d_{origin\cdots O})^2} \tag{16.42}$$

Substitution of Eqs. (16.32) and (16.41) into Eq. (16.42) gives $$d_{height}=0.91662a_0 \tag{16.43}$$

The angle $\theta_v$ of each O—H•••O bond from the z-axis is given by $$\theta_v = \tan^{-1}\left(\frac{d_{origin-O}}{d_{height}}\right) \tag{16.44}$$

Substitution of Eqs. (16.41) and (16.43) into Eq. (16.44) gives $$\theta_v=70.560 \tag{16.45}$$

Using Eqs. (16.32) and (16.43), the hexagonal lattice parameter $c_1$ for Type I ice given by twice the height along the z-axis from the base of the pyramid to the fifth water, $H_2O(5)$, is $$c_l = 2(c'_{O-H} + d_{height}) \tag{16.46}$$
$$= 2(2.75377 \text{ Å} + 0.91662 \text{ Å})$$
$$= 7.34077 \text{ Å}$$

The experimental lattice parameters $a_1$ and $c_1$ for Type I ice are [90, 91]

$$a_1=4.49 \text{ Å}$$
$$a_1=4.5212 \text{ Å} \tag{16.47}$$

and [91, 92]

$$c_1=7.31 \text{ Å}$$
$$c_1=7.3666 \text{ Å}$$

The tetrahedral unit cell and the ideal hexagonal lattice structure of Type I ice are shown in FIGS. 14-16, using the color scale charge density of each water molecule.

A convenient method to calculate the lattice energy is to determine the electric field in ice having an electric polarization density corresponding to the aligned molecular water dipoles moments, and in turn, the energy can be calculated from the energy of each dipole in the corresponding field using the electrostatic form of Gauss' equation. The electric field inside of a material having a uniform polarization density $P_0$ given by Eq. (6.3.3.15) of Haus and Melcher [93] is $$E(H_2O) = \frac{P_0}{3\varepsilon_0}(-\cos\theta i_r + \sin\theta i_\theta) \tag{16.49}$$

The polarization density $P_0$ given by Eq. (6.3.3.3) of Haus and Melcher [93] is $$P_0=N\mu_{H_2O} \tag{16.50}$$

where $\mu_{H_2O}$ is the dipole moment of water and N is the number density of water dipoles given by the density $\rho_{ice}$ divided by the molecular weight MW and multiplied by the Avogadro constant $N_A$:

$$N = \frac{\rho_{ice}}{\text{MW}} N_A \tag{16.51}$$

Substitution of Eqs. (16.50) and (16.51) into Eq. (16.49) gives $$E(\text{H}_2\text{O}) = \frac{\mu_{H_2O} \frac{\rho_{ice}}{\text{MW}} N_A}{3\varepsilon_0}(-\cos\theta i_r + \sin\theta i_\theta) \tag{16.52}$$

The energy of forming the condensed phase is that of the alignment of the water dipoles each comprised of two O—H component dipoles where the angular dependence along the z-axis in ice is unity, and this condition applies even in the case of the local order in water. The corresponding energy $U(\text{H}_2\text{O})$ per water dipole due to the polarization electric field of the lattice of hexagonal dipoles is given by $$U(\text{H}_2\text{O}) = 2\mu_{H_2O} \cdot E(\text{H}_2\text{O}) = \frac{-2(\mu_{H_2O})^2 \frac{\rho_{ice}}{\text{MW}} N_A}{3\varepsilon_0} \tag{16.53}$$

Substitution of the density of ice $$\rho = \frac{0.92 \text{ g}}{1 \times 10^{-6} \text{ m}^3}$$

[92], the MW=18 g/mole, $N_A$=6.0221415×$10^{23}$ molecules/mole, and the water dipole moment given by Eq. (16.16) with the predicted and experimental hexagonal bond angle of ice, $\theta_{\angle H_2O}$=109.5° [90]:

$$\mu_{H_2O}=2(1.51)\cos(109.5/2°)=5.79898 \times 10^{-30} \text{ C·m} \tag{16.54}$$

into Eq. (16.53) gives $$U(\text{H}_2\text{O}) = \frac{-2\left(\frac{5.79898 \times}{10^{-30} \text{ C·m}}\right)^2 \frac{0.92 \text{ g}}{1 \times 10^{-6} \text{ m}^3} 6.0221415 \times \frac{10^{23} \text{ molecules/mole}}{18 \text{ g/mole}}}{3\varepsilon_0} \tag{16.55}$$

$$= -0.48643 \text{ eV}(-46.934 \text{ kJ/mole})$$

$U(\text{H}_2\text{O})$ is also the negative of $E_{vapor,0°\ C.}$, the energy of water initially at 0° C. or the energy of vaporization of water at 0° C.:

$$E_{vapor,0°\ C.}=-U(\text{H}_2\text{O})=0.48643 \text{ eV } (46.934 \text{ kJ/mole}) \tag{16.56}$$

The experimental energy of vaporization of water at 0° C. (Type I ice) is [94]

$$E_{vapor,0°\ C.}=45.054 \text{ kJ/mole} \tag{16.57}$$

The calculated results based on first principles and given by analytical equations are summarized in Table 26.

TABLE 26

The calculated and experimental geometrical and energy parameters of the H bond of water of Type I ice.

| Parameter | Calculated | Experimental | Ref. for Exp. |
|---|---|---|---|
| H Bond Length $2c'_{O\cdots H}$ Nearest Neighbor Separation Distance | 1.78219 Å | 1.78 Å | 88, 89 |
| $2c'_{O\cdots H}$ | 2.75377 Å | 2.75 Å | 88 |
|  |  | 4.49 Å | 90 |
| $H_2O$ Lattice Parameter $a_1$ | 4.49768 Å | 4.5212 Å | 91 |
| $H_2O$ Lattice Parameter $c_1$ | 7.34077 Å | 7.31 Å | 92 |
|  |  | 7.3666 Å | 91 |
| Energy of Vaporization of Water at 0° C. | 46.934 kJ/mole | 45.054 kJ/mole | 94 |

As the temperature increases, the corresponding molecular kinetic energy can excite a vibrational mode along the H bond axis. Concomitantly, the O—H bond elongates and decreases in energy. As a consequence, the hydrogen bond achieves a partial bond order or partial three-centered O—H—O bond, and the H can undergo exchange between water molecules. The time-average effect of exchange is to decrease the statistical equilibrium separation distance of water molecules. In competition with the separation-distance decreasing effect of exchange is the increasing effect due to collisional impact and recoil as a function of increasing temperature. The former effect dominates from the temperature of ice to 4° C. at which point water assumes a maximum density. Thereafter, the momentum imparted with water-water collisions overwhelms the decrease due to exchange, and the molecular separation statistically increases with temperature until a totally gaseous state is achieved at atmospheric pressure at 100° C. Unit cells with increasing entropy can be derived from the ice unit cell by populating translational, rotational, and vibrational levels of molecules within the cells to match the internal energy at a given temperature. Using statistical mechanical models such as Boltzmann statistics to populate an increasing number of basis units cells of increasing disorder and based on the ice unit cell, the behavior of water as a function of temperature can be modeled over the range of states from ice to liquid to steam. The structure of each phase of water is then determined by the number of H bonds on average per water molecule. Based on the 10% energy change in the heat of vaporization in going from ice at 0° C. to water at 100° C. [94], the average number of H bonds per water molecule in boiling water is 3.6. The H bond distance is calculated next using the enthalpy to form steam from boiling water.

Geometrical Parameters and Energies of the Hydrogen Bond of $H_2O$ in the Vapor Phase Two or more water molecules can interact along the O•••H or H bond axis. In the gas phase, the maximum energy of interaction between water molecules of steam is equivalent to the negative of the heat of vaporization of water at the boiling point, 100° C.; otherwise, water vapor would form the corresponding condensed state. For the determination of the H-bond distance, the energy parameters, partial charge, and reduced mass are the same as those of the water molecules of ice given in Eq. (16.26) except that the negative of the experimental $E_{vapor,100°\ C.}$=0.42137 eV (40.657 kJ/mole) [94] is equated to the nascent covalent bond energy. The parameters are summarized in Table 27 and Eq. (16.58).

TABLE 27

The energy parameters (eV) of the O···H functional group of the hydrogen bond of water vapor.

| Parameters | O···H Group |
|---|---|
| δ | 0.323 |
| $n_1$ | 2 |
| $C_1$ | 0.75 |
| $C_2$ | 1 |
| $c_1$ | 0.75 |
| $c_2$ | 1 |
| $c_{1o}$ | 1.5 |
| $C_{2o}$ | 1 |
| $V_e$ (eV) | −15.20020 |
| $V_p$ (eV) | 14.08285 |
| $T$ (eV) | 1.35707 |
| $V_m$ (eV) | −0.67853 |
| $E(AO/HO)$ (eV) | 0 |
| $\Delta E_{H_2MO}(AO/HO)$ (eV) | 0 |
| $E_T(AO/HO)$ (eV) | 0 |
| $E_T(H_2MO)$ (eV) | −0.43882 |
| $E_T$(atom-atom, msp³·AO) (eV) | 0 |
| $E_T(MO)$ (eV) | −0.43882 |
| ω ($10^{15}$ rad/s) | 4.20131 |
| $E_K$ (eV) | 2.76538 |
| $\overline{E}_D$ (eV) | 0.001444 |
| $\overline{E}_{Kvib}$ (eV) | 0.02033 |
| $\overline{E}_{osc}$ (eV) | 0.008724 |
| $E_T(Group)$ (eV) | −0.42137 |

Substitution of the parameters of Table 16.20 and $-E_{vapor,0°C}$ (Eq. (16.57)) into Eq. (16.26) gives $$e(0.42137 \text{ eV}) = \tag{16.58}$$

$$\left\{ \left( \frac{-e^2}{4\pi\varepsilon_0 \sqrt{\frac{a_{O-H}a_0}{2(0.75)}}} \right) \left( \left( \frac{3}{2} - \frac{3}{8}\frac{a_0}{a_{O-H}} \right) \ln \frac{a_{O-H} + \sqrt{\frac{a_{O-H}a_0}{2(0.75)}}}{a_{O-H} - \sqrt{\frac{a_{O-H}a_0}{2(0.75)}}} - 1 \right) \right\}$$

$$\left( 1 + 2\sqrt{\frac{2\hbar\sqrt{\frac{3}{2}\frac{e^2}{4\pi\varepsilon_0\left(\sqrt{(a_{O-H})^2 - \left(2\sqrt{\frac{a_{O-H}a_0}{2(0.75)}}\right)^2}\right)^3}}}{m_e c^2}} \right) +$$

$$2\left(\frac{1}{2}\right)\hbar \sqrt{\frac{\frac{0.75 e^2}{8\pi\varepsilon_0(a_{O-H})^3} - \frac{e^2}{8\pi\varepsilon_0\left(a_{O-H} + \sqrt{\frac{a_{O-H}a_0}{2(0.75)}}\right)^3}}{\frac{16}{17}}}$$

From the energy relationship given by Eq. (16.58) and the relationships between the axes given by Eqs. (16.22-16.24), the dimensions of the O•••H MO can be solved.

The most convenient way to solve Eq. (16.58) is by the reiterative technique using a computer. The result to within the round-off error with five-significant figures is $$a_{O\cdots H} = 5.60039 a_0 = 2.96360 \times 10^{-10} \text{ m} \tag{16.59}$$

The component energy parameters at this condition are given in Table 27. Substitution of Eq. (16.59) into Eq. (16.22) gives $$c_{O\cdots H}' = 1.93225 a_0 = 1.02250 \times 10^{-10} \text{ m} \tag{16.60}$$

and internuclear distance of the H bond:

$$2c_{O\cdots H}' = 3.86450 a_0 = 2.04501 \times 10^{-10} \text{ m} \tag{16.61}$$

The experimental H bond distance $2c_{O\cdots H}'$ in the gas phase is [95]

$$2c_{O\cdots H}' = 2.02 \times 10^{-10} \text{ m} \tag{16.62}$$

and [96]

$$2c_{O\cdots H}' = 2.05 \times 10^{-10} \text{ m} \tag{16.63}$$

The other H-bond MO parameters can also be determined by the relationships among the parameters. Substitution of Eqs. (16.59) and (16.60) into Eq. (16.23) gives $$b_{O\cdots H} = c_{O\cdots H} = 5.25650 a_0 = 2.78162 \times 10^{-10} \text{ m} \tag{16.64}$$

Substitution of Eqs. (16.59) and (16.60) into Eq. (16.24) gives $$e_{O\cdots H} = 0.34502 \tag{16.65}$$

Substitution of $2c_{O\cdots H}'$ (Eq. (16.61)) and $2c_{O-H}'$ (Eq. (13.185)) into Eq. (16.31) gives the nearest neighbor separation, the internuclear distance $2c_{O\cdots HO}'$ between the oxygen atoms of the O—H•••O bond in Type I ice:

$$2c'_{O-HO} = 2c'_{O-H} + 2c'_{O-H} \tag{16.66}$$

$$= 2.04501 \times 10^{-10} \text{ m} + 9.71574 \times 10^{-11} \text{ m}$$

$$= 3.01658 \times 10^{-10} \text{ m}$$

$$= 3.01658 \text{ Å}$$

Using Eqs. (16.31), (16.34), and (16.63), the experimental nearest neighbor separation $2c_{O-HO}'$ is [89, 96]

$$2c'_{O-HO} = 2c'_{O-H} + 2c'_{O-H} \tag{16.67}$$

$$= 2.05 \times 10^{-10} \text{ m} + 9.70 \times 10^{-11} \text{ m}$$

$$= 3.02 \times 10^{-10} \text{ m}$$

$$= 3.02 \text{ Å}$$

H-bonded water vapor molecules in steam are shown in FIGS. 17A-B using the color scale charge density of each water molecule.

The calculated results based on first principles and given by analytical equations are summarized in Table 28.

TABLE 28

The calculated and experimental geometrical and energy parameters of the H bond of steam.

| Parameter | Calculated | Experimental | Ref. for Exp. |
|---|---|---|---|
| H Bond Length $2c'_{O\cdots H}$ | 2.04501 Å | 2.02 Å<br>2.05 Å | 95, 96 |
| Nearest Neighbor Separation Distance | | | |
| $2c'_{O\cdots H}$ | 3.01658 Å | 3.02 Å | 89, 96 |

Geometrical Parameters and Energies of the Hydrogen Bond of $H_2O$ and $NH_3$

Similar to the water molecule, the ammonia molecule has a strong dipole moment along each of its N—H-bonds. The $NH_3$ MO comprises the linear combination of three N—H- bond MOs. Each N—H-bond MO comprises the superposition of a H-type ellipsoidal MO and the N2$p_x$, N2$p_y$, or N2$p_z$ AO with a relative H partial orbital contribution to the MO of 0.75. The solution of the geometrical parameters and component energies are given in the Ammonia (NH$_3$) section, and the color scale charge density of the NH$_3$ MO is show in FIG. 18.

Due to the interacting dipoles, hydrogen bonds also form between the nitrogen of ammonia and the hydrogen of water molecules. Water hydrogen bonds to ammonia molecules by interaction along the N•••HO or H bond axis. As shown in the Bond and Dipole Moments section, each N—H bond of ammonia has a bond moment μ of 1.30 D corresponding to a N component of partial charge of –0.262e, and the O—H bond has a bond moment μ of 1.51 D corresponding to a H partial charge of +0.323e. The thermodynamic basis of the H bond is the minimization of the Coulombic energy between the hydrogen bonded H of H$_2$O and N of ammonia, limited by the formation of a nascent N—H bond between these atoms that destabilizes the initial O—H bond of the water molecule partner. As in the case of ice, the maximum electrostatic energy of the partial charges is calculated for the components along the H-bond axis. This energy is balanced by the total energy of the nascent bond that can form between the N•••H atoms of the H bond. The bond length of the H bond, the internuclear distance between the N and H of the N•••H bond, is calculated using Eq. (16.25) by a similar method as that used to calculate the O•••H bond distance of ice. According to the method given in the Geometrical Parameters and Energies of the hydrogen Bond of H$_2$O section, the equilibrium distance $r_e$ or internuclear bond distance of N•••H designated as $2c_{N\cdots H}'=r_e$ is determined by the condition that the total energy of the nascent H$_2$-type ellipsoidal MO formed from the atoms of the N•••H bond is equal to the maximum Coulombic energy between the partial charges of the N and H atoms of the H bond.

The maximum Columbic energy corresponds to the minimum separation distance of N and H atoms corresponding to the alignment along the N•••H bond axis. The corresponding distance from the $\delta^+$ of the H$_2$O H and the NH$_3$ N is the distance $2c_{N\cdots H}'$ between the N and H nuclei of the N•••H bond. Then, the maximum Coulomb energy $E_{Coulomb}$(H-bond) between the atoms of the N•••H bond due to the $\delta^-$ on the nitrogen atom with the $\delta^+$ centered on the nucleus of hydrogen is $$E_{Coulomb}(H\text{-bond}) = \frac{-\delta_N^- \delta_H^+ e^2}{4\pi\varepsilon_0 2c'_{N-H}} \quad (16.68)$$

Eq. (16.68) is the energy to be equated to that of the nascent bonds involving the atoms of the H bond.

For the determination of the H-bond distance, the energy parameters of the nascent N—H bond are the same as those of ammonia given in the Ammonia (NH$_3$) section except that any parameter due to matching AO's, $E_T$(AO/HO) and $E_T$(atom-atom,msp$^3$.AO), is zero since only the energies of the MO electrons to form the N•••H MO are considered. The energy of Eq. (16.68) is multiplied by three to match the total energy of the three N—H bond MOs of ammonia. The partial charges $\delta=q/e$ from Table 24 are –0.262 and +0.323, and the reduced mass is $$\mu = \frac{14}{15}.$$

The parameters are summarized in Table 29 and Eq. (16.69).

TABLE 29

The energy parameters (eV) of the N•••H functional group of the hydrogen bond of the ammonia-water molecular dimer.

| Parameters | N•••H Group |
|---|---|
| $\delta_N^-$ | 0.262 |
| $\delta_H^+$ | 0.323 |
| $n_1$ | 3 |
| $C_1$ | 0.75 |
| $C_2$ | 0.93613 |
| $c_1$ | 0.75 |
| $c_2$ | 1 |
| $C_{1o}$ | 1.5 |
| $C_{2o}$ | 1 |
| $V_e$ (eV) | –23.60741 |
| $V_p$ (eV) | 20.75035 |
| $T$ (eV) | 2.17246 |
| $V_m$ (eV | –1.08623 |
| E(AO/HO) (eV) | 0 |
| $\Delta E_{H_2MO}$(AO/HO) (eV) | 0 |
| $E_T$(AO/HO) (eV) | 0 |
| $E_T$(H$_2$MO) (eV) | –1.77083 |
| $E_T$(atom-atom, msp$^3$ · AO) (eV) | 0 |
| $E_T$(MO) (eV) | –1.77083 |
| ω (10$^{15}$ rad/s) | 4.44215 |
| $E_K$ (eV) | 2.92390 |
| $\overline{E}_D$ (eV) | –0.00599 |
| $\overline{E}_{Kvib}$ (eV) | 0.021843 |
| $\overline{E}_{osc}$ (eV) | 0.00493 |
| $E_T$(Group) (eV) | 1.75603 |
| $E_T$(Group) (eV) N—H | 0.58534 |

Substitution of the parameters of Table 29 into Eq. (16.25) with $R=a_{N\cdots H}$ gives $$\frac{-3(0.262)(0.323)e^2}{4\pi\varepsilon_0 \left(2\sqrt{\frac{a_{N-H}a_0}{2(0.75)(0.93613)}}\right)} = \quad (16.69)$$

$$\left\{\left(\frac{-3e^2}{8\pi\varepsilon_0\sqrt{\frac{a_{N-H}a_0}{2(0.75)(0.93613)}}}\right)\left(\ln\frac{a_{N-H}+\sqrt{\frac{a_{N-H}a_0}{2(0.75)(0.93613)}}}{a_{N-H}-\sqrt{\frac{a_{N-H}a_0}{2(0.75)(0.93613)}}}-1\right)\left(\frac{3}{2}-\frac{3}{8}\frac{a_0}{a_{N-H}}\right)\right.$$

$$\left.\left(1+3\frac{2\hbar\sqrt{\frac{3}{2}\frac{e^2}{4\pi\varepsilon_0\left(\sqrt{(a_{N-H})^2-\left(2\sqrt{\frac{a_{N-H}a_0}{2(0.75)}}\right)^2}\right)^3}}}{m_e c^2}\right)\right.$$

$$\left.+3\left(\frac{1}{2}\right)\hbar\sqrt{\frac{\frac{0.75 e^2}{8\pi\varepsilon_o(a_{N-H})^3}-\frac{e^2}{8\pi\varepsilon_o\left(a_{N-H}+\sqrt{\frac{a_{N-H}a_0}{2(0.75)(0.93613)}}\right)^3}}{\frac{14}{15}}}\right\}$$

From the energy relationship given by Eq. (16.69) and the relationships between the axes given by Eqs. (16.22-16.24), the dimensions of the N•••H MO can be solved.

The most convenient way to solve Eq. (16.69) is by the reiterative technique using a computer. The result to within the round-off error with five-significant figures is $$a_{N\cdots H}=5.43333a_0=2.87519\times10^{-10} \text{ m} \quad (16.70)$$

The component energy parameters at this condition are given in Table 29. Substitution of Eq. (16.70) into Eq. (16.22) gives $$c'_{N\cdots H}=1.96707a_0=1.04093\times10^{-10} \text{ m} \quad (16.71)$$

and internuclear distance of the H bond:

$$2c_{N\cdots H}'=3.93414a_0=2.08186\times10^{-10} \text{ m}=2.08186 \text{ Å} \quad (16.72)$$

The experimental H bond distance $2c_{N\cdots H}'$ in the gas phase is [96, 97]

$$2c_{N\cdots HO}'=2.02\times10^{-10} \text{ m} \quad (16.73)$$

The other H-bond MO parameters can also be determined by the relationships among the parameters. Substitution of Eqs. (16.70) and (16.71) into Eq. (16.23) gives $$b_{N\cdots H}=c_{N\cdots H}=5.06475a_0=2.68015\times10^{-10} \text{ m} \quad (16.74)$$

Substitution of Eqs. (16.70) and (16.71) into Eq. (16.24) gives $$e_{N\cdots H}=0.36204 \quad (16.75)$$

The addition of $2c_{N\cdots H}'$ (Eq. (16.72)) and $2c_{O-H}'$ (Eq. (13.185)) gives the nearest neighbor separation, the internuclear distance $2c_{N\cdots HO}'$ between the nitrogen and oxygen atoms of the N•••H—O bond of the ammonia-water molecular dimer.

$$2c'_{N-HO} = 2c'_{N-H} + 2c'_{O-H} \quad (16.76)$$
$$= 2.08186\times10^{-10} \text{ m} + 9.71574\times10^{-11} \text{ m}$$
$$= 3.05343\times10^{-10} \text{ m}$$
$$= 3.05343 \text{ Å}$$

The addition of the experimental $2c_{N\cdots H}'$ (Eq. (16.73)) and $2c_{O-H}'$ (Eq. (13.185)) gives the experimental nearest neighbor separation $2c_{N\cdots HO}'$ [96, 89]:

$$2c'_{N-HO} = 2c'_{N-H} + 2c'_{O-H} \quad (16.77)$$
$$= 2.02\times10^{-10} \text{ m} + 9.70\times10^{-11} \text{ m}$$
$$= 2.99\times10^{-10} \text{ m}$$
$$= 2.99 \text{ Å}$$

H-bonded ammonia-water molecular dimer is shown in FIG. 19 using the color scale charge density of each molecule. The energy of forming the dimer in the gas phase is that of the alignment of the ammonia dipole moment in the electric field of the H—O water dipole. Using $\mu_{NH_3}=1.467\text{D}=4.89196\times10^{-30}$ C·m (Eq. (16.18)), $\mu_{H-O,H_2O}=1.51\text{ D}=5.02385\times10^{-30}$ C·m (Table 24), and the N•••H distance, $2c_{N\cdots H}'=2.08186\times10^{-10}$ m (Eq. (16.72)), the N•••H bond dissociation energy $E_D(N•••H)$ of the ammonia-water molecular dimer is $$E_D(N \ldots H) = \mu_{H_3N} \cdot \frac{2\mu_{H-O,H_2O}}{4\pi\varepsilon_0(2c'_{N-H})^3} \quad (16.78)$$

-continued
$$= \frac{(4.89196\times10^{-30} \text{ C·m})(5.02385\times10^{-30} \text{ C·m})}{4\pi\varepsilon_0(2.08186\times10^{-10} \text{ m})^2}$$
$$= 29.48 \text{ kJ}$$

The experimental N•••H bond dissociation energy between amino N and hydroxyl H is approximately [98]

$$E_D(N•••H)=29 \text{ kJ} \quad (16.79)$$

The calculated results based on first principles and given by analytical equations are summarized in Table 30.

TABLE 30

The calculated and experimental geometrical and energy parameters of the H-bonded ammonia-water vapor molecular dimer.

| Parameter | Calculated | Experimental | Ref. for Exp. |
|---|---|---|---|
| H Bond Length $2c'_{N\cdots H}$ | 2.08186 Å | 2.02 Å | 96, 97 |
| Nearest Neighbor Separation Distance | 3.05343 Å | 2.99 Å | 96, 89 |
| $2c'_{N\cdots HO}$ N•••H Bond Dissociation Energy | 29.48 kJ/mole | 29 kJ/mole | 98 |

Geometrical Parameters Due to the Interplane Van Der Waals Cohesive Energy of Graphite Eq. (16.25) can be applied to other solids such as graphite. Graphite is an allotrope of carbon that comprises planar sheets of covalently bound carbon atoms arranged in hexagonal aromatic rings of a macromolecule of indefinite size. The structure of graphite is shown in FIGS. 20A and B. The structure shown in FIG. 20 has been confirmed directly by TEM imaging, and the Pi cloud predicted by quantum mechanics has been dispatched [99].

As given in the Graphite section, the structure of the indefinite network of aromatic hexagons of a sheet of graphite is solved using a linear combination of aromatic $$C \stackrel{3e}{=} C$$

aromatic bonds comprising (0.75)(4)=3 electrons according to Eq. (15.161). In graphite, the minimum energy structure with equivalent carbon atoms wherein each carbon forms bonds with three other such carbons requires a redistribution of charge within an aromatic system of bonds. Considering that each carbon contributes four bonding electrons, the sum of electrons of graphite at a vertex-atom comprises four from the vertex atom plus two from each of the two atoms bonded to the vertex atom where the latter also contribute two each to the juxtaposed bond. These eight electrons are distributed equivalently over the three bonds of the group such that the electron number assignable to each bond is 8/3. Thus, the $$C \stackrel{8/3c}{=} C$$

functional group of graphite comprises the aromatic bond with the exception that the electron-number per bond is 8/3. The sheets, in turn, are bound together by weaker intermolecular van der Waals forces. The geometrical and energy parameters of graphite are calculated using Eq. (16.25) with the van der Waals energy equated to the nascent bond energy.

The van der Waals energy is due to mutually induced nonpermanent dipoles in near-neighbor bonds. Albeit, the $$C \overset{8/3e}{=} C$$

functional group is symmetrical such that it lacks a permanent dipole moment, a reversible dipole can be induced upon van der Waals bonding. The parameters of the $$C \overset{8/3e}{=} C$$

functional group are the same as those of the aromatic $$C \overset{3e}{=} C$$

functional group, the basis functional group of aromatics, except that the bond order is $$8/3 \left( \text{e.g. } 2c'_{C \overset{8/3e}{=} C} = 2c'_{C \overset{3e}{=} C} \right).$$

Using Eq. (16.15) wherein $C_2$ of Eq. (15.51) for the aromatic $$C \overset{3e}{=} C - \text{bond } MO$$

is $C_2(\text{aromaticC2sp}^3\text{HO})=c_2(\text{aromaticC2sp}^3\text{HO})=0.85252$ (Eq. (15.162)) and $E_{Coulomb}(C_{benzene},2sp^3)$ is 15.95955 eV (Eq. (14.245)), $E(C,2sp^3)=-14.63489$ eV (Eq. (14.143)) and $2c'=1.39140\times10^{-10}$ m (Table 15.214), the van der Waals dipole of graphite is given in Table 31.

TABLE 31

The parameters and van der Waals dipole bond moment of the $C \overset{8/3e}{=} C$ functional group of graphite.

| Functional Group | $n_1$ | $(c_1)c_2$ | $(C_1)C_2$ | $E_B$(valence) | $E_A$(valence) | $\frac{q}{e}$ | Bond Length 2c' (Å) | Bond Moment μ (D) |
|---|---|---|---|---|---|---|---|---|
| $C \overset{8/3e}{=} C$ | $\frac{8}{3}$ | 0.85252 | 1 | 14.82575 | 15.95955 | 0.36101 | 1.3914 | 2.41270 |

The interaction between a dipole in one plane with the nearest neighbor in another plane is zero in the case that the aromatic rings of one layer are aligned such that they would superimpose as the interlayer separation goes to zero. But, the energy of interaction is nonzero when one plane is translated relative to a neighboring plane. A minimum equal-energy is achieved throughout the graphite structure when each layer is displaced by $$2c'_{3e}, \\ C=C$$

the bond length of $$C \overset{3e}{=} C$$

along an intra-planar $C_2$ axis relative to the next as shown in FIG. 20B. Then, a pair of dipoles exists for each dipole of a given plane with one dipole above and one below in neighboring planes such that all planes can be equivalently bound by van der Waals forces. In this case, the distance $r_{\mu_1 \ldots \mu_2}$ between dipole $\mu_1$ in one plane and its nearest neighbor $\mu_2$ above or below on a neighboring and $$2c'_{C \overset{3e}{=} C} - \text{displaced plane is } r_{\mu_1 \ldots \mu_2} = \sqrt{\left(2c'_{C \overset{3e}{=} C}\right)^2 + (2c'_{C \ldots C})^2} \quad (16.80)$$

where $2c_{C \cdots C}'$ is the interplane distance. The alignment angle $\theta_{\mu_1 \ldots \mu_2}$ between the dipoles is $$\theta_{\mu_1 \ldots \mu_2} = \sin^{-1} \frac{2c'_{C \ldots C}}{r_{\mu_1 \ldots \mu_2}} \quad (16.81)$$

$$= \sin^{-1} \frac{2c'_{C \ldots C}}{\sqrt{\left(2c'_{C \overset{3e}{=} C}\right)^2 + (2c'_{C \ldots C})^2}}$$

The van der Waals energy is the potential energy between interacting neighboring pairs of $$C \overset{8/3e}{=} C$$

induced dipoles. Using Eqs. (16.80-16.81), $$\mu_{C \overset{8/3e}{=} C} = 2.41270D = 8.04790 \times 10^{-30} C \cdot m (\text{Table 31}),$$

and the $C \overset{8/3e}{=} C$ distance, $$2c'_{C \overset{8/3e}{=} C} = 1.39140 \times 10^{-10} m (\text{Table 15.214}),$$

the van der Waals energy of graphite between two planes at a vertex atom is $$E_{van\,der\,Waals}(\text{graphite}) = (3)\frac{2(\mu_{C\overset{813e}{=}C})^2}{4\pi\varepsilon_0(r_{\mu_1\ldots\mu_2})^3}\cos\theta_{\mu_1\ldots\mu_2} \quad (16.82)$$

$$= \left(\frac{6(8.04790\times10^{-30}\,C\cdot m)^2}{4\pi\varepsilon_0\left(\left(1.39140\times10^{-10}\,m\right)^2 + \left(2\sqrt{\frac{a_{C\ldots C}a_0}{2C_1C_2}}\right)^2\right)^{1.5}}\right.$$

$$\left.\cos\sin^{-1}\frac{2\sqrt{\frac{a_{C\ldots C}a_0}{2C_1C_2}}}{\sqrt{(1.39140\times10^{-10}\,m)^2 + \left(2\sqrt{\frac{a_{C\ldots C}a_0}{2C_1C_2}}\right)^2}}\right)$$

where there are three bonds at each vertex atom.

The graphite inter-plane distance of 3.5 Å [100] is calculated using Eq. (16.25) with the van der Waals energy (Eq. (16.82)) between dipoles of two neighboring planes equated to the nascent bond energy. The energy matching parameter $c_2$ is the same that of the graphite sheet corresponding to the aromatic carbons as given in the Graphite section, and the reduced mass is $\mu = 6$. The parameters are summarized in Table 32 and Eq. (16.83).

TABLE 32

The energy parameters (eV) of the graphite interplanar functional group ($C_{aromatic}\cdots C_{aromatic}$).

| Parameters | $C_{aromatic}\cdots C_{aromatic}$ Group |
|---|---|
| $n_1$ | 1 |
| $C_1$ | 0.5 |
| $C_2$ | 1 |
| $c_1$ | 1 |
| $c_2$ | 0.85252 |
| $C_{1o}$ | 0.5 |
| $C_{2o}$ | 1 |
| $V_e$ (eV) | −4.35014 |
| $V_p$ (eV) | 4.10093 |
| $T$ (eV) | 0.19760 |
| $V_m$ (eV) | −0.09880 |
| $E(AO/HO)$ (eV) | 0 |
| $\Delta E_{H_2MO}(AO/HO)$ (eV) | 0 |
| $E_T(AO/HO)$ (eV) | 0 |
| $E_T(H_2MO)$ (eV) | −0.15042 |
| $E_T(\text{atom-atom, msp}^3\cdot AO)$ (eV) | 0 |
| $E_T(MO)$ (eV) | −0.15042 |
| $\omega$ ($10^{15}$ rad/s) | 0.800466 |
| $E_K$ (eV) | 0.52688 |
| $\bar{E}_D$ (eV) | −0.00022 |
| $\bar{E}_{Kvib}$ (eV) | 0.00317 |
| $\bar{E}_{osc}$ (eV) | 0.00137 |
| $E_T(Group)$ (eV) | −0.14905 |

Substitution of the parameters of Table 32 and the interlayer cohesive energy of graphite (Eq. (16.82)) into Eq. (16.25) with $R = a_{C\cdots C}$ gives $$\frac{-6(8.04790\times10^{-30}\,C\cdot m)^2}{4\pi\varepsilon_0\left(\left(1.39140\times10^{-10}\,m\right)^2 + \left(2\sqrt{\frac{a_{C\ldots C}a_0}{2(0.5)}}\right)^2\right)^{1.5}} \quad (16.83)$$

$$\cos\sin^{-1}\frac{2\sqrt{\frac{a_{C\ldots C}a_0}{2(0.5)}}}{\sqrt{(1.39140\times10^{-10}\,m)^2 + \left(2\sqrt{\frac{a_{C\ldots C}a_0}{2(0.5)}}\right)^2}} =$$

$$\left\{\frac{-e^2}{8\pi\varepsilon_0\sqrt{\frac{a_{C\ldots C}a_0}{2(0.5)}}}\left(\ln\frac{a + \sqrt{\frac{a_{C\ldots C}a_0}{2(0.5)}}}{a - \sqrt{\frac{a_{C\ldots C}a_0}{2(0.5)}}} - 1\right)\left((0.85252)\left(2 - \frac{1}{2}\frac{a_0}{a_{C\ldots C}}\right)\right)\right.$$

$$\left. + \left(\frac{1}{2}\right)\hbar\sqrt{\frac{(0.5)\frac{e^2}{4\pi\varepsilon_o(a_{C\ldots C})^3}}{m_e}}\left(1 + 2\sqrt{\frac{2\hbar\sqrt{\frac{(0.5)\frac{e^2}{4\pi\varepsilon_o(a_{C\ldots C})^3}}{m_e}}}{m_ec^2}}\right) + \right.$$

$$\left.\frac{(0.85252)e^2}{8\pi\varepsilon_o(a_{C\ldots C})^3} - \frac{e^2}{8\pi\varepsilon_o\left(a_{C\ldots C} + \sqrt{\frac{a_{C\ldots C}a_0}{2(0.5)}}\right)^3}\right\}$$

From the energy relationship given by Eq. (16.83) and the relationships between the axes given by Eqs. (16.22-16.24), the dimensions of the C•••C MO can be solved.

The most convenient way to solve Eq. (16.83) is by the reiterative technique using a computer. The result to within the round-off error with five-significant figures is $$a_{C\cdots C} = 11.00740 a_0 = 5.82486\times10^{-10}\,m \quad (16.84)$$

The component energy parameters at this condition are given in Table 32. Substitution of Eq. (16.84) into Eq. (16.22) gives $$c_{C\cdots C}' = 3.31774 a_0 = 1.75567\times10^{-10}\,m \quad (16.85)$$

and internuclear distance of the graphite interplane bond at vacuum ambient pressure:

$$2c_{C\cdots C}' = 6.63548 a_0 = 3.51134\times10^{-10}\,m = 3.51134\,Å \quad (16.86)$$

The experimental graphite interplane distance $2c_{C\cdots C}'$ is [100]

$$2c_{C\cdots C}' = 3.5\times10^{-10}\,m = 3.5\,Å \quad (16.87)$$

The other interplane bond MO parameters can also be determined by the relationships among the parameters. Substitution of Eqs. (16.84) and (16.85) into Eq. (16.23) gives $$b_{C\cdots C} = c_{C\cdots C}' = 10.49550 a_0 = 5.55398\times10^{-10}\,m \quad (16.88)$$

Substitution of Eqs. (16.84) and (16.85) into Eq. (16.25) gives $$e_{C\cdots C} = 0.30141 \quad (16.89)$$

Using Eqs. (16.80) and (16.86), the distance $r_{\mu_1 \ldots \mu_2}$ between dipole $\mu_1$ on one plane and its nearest neighbor $\mu_2$ above or below on a juxtaposed and $$2c'_{\underset{C=C}{3e}} - \text{displaced plane is } r_{\mu_1 \ldots \mu_2} = 3.77697 \times 10^{-10} m \quad (16.90)$$

Using Eqs. (16.81) and (16.86), the alignment angle $\theta_{\mu_1 \ldots \mu_2}$ between the dipoles is $$\theta_{\mu_1 \ldots \mu_2} = 68.38365° \quad (16.91)$$

Using Eqs. (16.82) and (16.90-91), the van der Waals energy per carbon atom is $$E_{van\ der\ Waals}(\text{graphite}/C) = 0.04968 \text{ eV} \quad (16.92)$$

The experimental van der Waals energy per carbon atom is [101]

$$E_{van\ der\ Waals}(\text{graphite}/C) = 0.052 \text{ eV} \quad (16.93)$$

The calculated results based on first principles and given by analytical equations are summarized in Table 33.

TABLE 33

The calculated and experimental geometrical parameters and interplane van der Waals cohesive energy of graphite.

| Parameter | Calculated | Experimental | Ref. for Exp. |
|---|---|---|---|
| Graphite Interplane Distance $2c'_{C \ldots C}$ | 3.51134 Å | 3.5 Å | 100 |
| van der Waals Energy per Carbon Atom | 0.04968 eV | 0.052 eV | 101 |

Graphite has a high cohesive energy due to its significant van der Waals dipole bond moment of 2.41270D. Other species such as atoms and molecules having mirror symmetry and consequently no permanent dipole moment also form reversible van der Waals dipole bond moments. Different phases can be achieved according to the extent of the van der Waals dipole bonding as the internal energy as a function of temperature and pressure changes analogously to the H-bonded system water that can exist as ice, water, and steam. Thus, the factors in the van der Waals bonding can give rise to numerous material behaviors. In the case of atoms such as noble gas atoms and certain diatomic molecules such as hydrogen, the moments, their interaction energies, and the corresponding nascent bond energies are much smaller. Thus, except at cryogenic temperatures, these elements exist as gases, and even at temperatures approaching absolute zero, solidification of helium has not been achieved in the absence of high pressure. This is due to the nature of the induced dipoles and van der Waals phenomena in helium. Since this system is a good example of van der Waals forces in atoms, it will be treated next.

Geometrical Parameters and Energies Due to the Interatomic Van Der Waals Cohesive Energy of Liquid Helium Noble gases such as helium are typically gaseous and comprised of non-interacting atoms having no electric or magnetic multipoles. But, at very low temperatures it is possible to form diffuse diatomic molecules, or alternatively, these gases may be condensed with the formation of mutually induced van der Waals dipole interactions. As a measure of the nascent bond between two noble gas atoms used to calculate the limiting separation for condensation, consider that the experimental bond energies of diatomic molecules of helium and argon, for example, are only 49.7 meV and 49 meV, respectively [21]. This is a factor of about 100 smaller than the bond energy of a carbon-carbon bond that is the form of nascent bond in graphite. Thus, the corresponding energy of the interspecies interaction is smaller and the van der Waals spacing is larger, except wherein the nascent bond energy as a function of separation distance mitigates this relationship to some extent. The nature of the helium bonding is solved using the same approach as that of other functional groups given in the Organic Molecular Functional Groups and Molecules section.

Helium is a two-electron neutral atom with both electrons paired as mirror-image current densities in a shell of radius $0.566987a_0$ (Eq. (7.35)). Thus, in isolation or at sufficient separation, there is no energy between helium atoms. The absence of any force such as so-called long-range London forces having a $r^{-n}$; $n > 2$ dependency is confirmed by elastic electron scattering from helium atoms as shown in the Electron Scattering Equation for the Helium Atom Based on the Orbitsphere Model section. However, reversible mutual van der Waals dipoles may be induced by collisions when the atoms are in close proximity such that helium gas can condense into a liquid. The physics is similar to the case of graphite except that the dipoles are atomic rather than molecular, and in both cases the limiting separation is based on the formation of a nascent bond to replace the dipole-dipole interaction. Thus, Eq. (16.25) can also be applied to atoms such as helium.

The van der Waals bonding in the helium atom involves hybridizing the one 1s AO into $1s^1$ HO orbitals containing two electrons. The total energy of the state is given by the sum over the two electrons. The sum $E_T(\text{He},1s^1)$ of experimental energies [15] of He and He$^+$ is $$E_T(\text{He}, 1s^1) = 54.41776 \text{ eV} + 24.587387 \text{ eV} \quad (16.94)$$
$$= 79.005147 \text{ eV}$$

By considering that the central field decreases by an integer for each successive electron of the shell, the radius $r_{1s^1}$ of the He$1s^1$ shell may be calculated from the Coulombic energy using Eq. (15.13):

$$r_{1s^1} = \sum_{n=0}^{1} \frac{(Z-n)e^2}{8\pi\varepsilon_0(e79.005147 \text{ eV})} \quad (16.95)$$
$$= \frac{3e^2}{8\pi\varepsilon_0(e79.005147 \text{ eV})}$$
$$= 0.51664 a_0$$

where $Z=2$ for helium. Using Eq. (15.14), the Coulombic energy $E_{Coulomb}(\text{He},1s^1)$ of the outer electron of the van der Waals bound He$1s^1$ shell is $$E_{Coulomb}(\text{He}, 1s^1) = \frac{-e^2}{8\pi\varepsilon_0 r_{1s^1}} \quad (16.96)$$
$$= \frac{-e^2}{8\pi\varepsilon_0 0.51664 a_0}$$
$$= -26.335049 \text{ eV}$$

To meet the equipotential condition of the union of the two He$1s^1$ HOs in a nascent bond, $c_2$ of Eqs. (15.2-15.5) and Eq.

(15.61) for the nascent He—He-bond MO is given by Eq. (15.75) as the ratio of the valance energy of the He AO, $E(He) = -24.587387$ eV and the magnitude of $E_{Coulomb}(He, 1s^1)$ (Eq. (16.96)):

$$c_2(He\text{—}He, He1s^1HO) = \frac{24.587387 \text{ eV}}{26.33505 \text{ eV}} = 0.93364 \quad (16.97)$$

The opposite charges distributions act as symmetrical point charges at the point of maximum separation, each being centered at ½ the He-atom radius from the origin. Using the parameters of Eq. (16.97) and $2c' = 0.51664a_0 = 2.73395 \times 10^{-11}$ m (Eq. (16.95)), the van der Waals dipole of helium is given in Table 34.

TABLE 34

The parameters and van der Waals dipole bond moment of the He functional group of liquid helium.

| Functional Group | $n_1$ | $(c_1)c_2$ | $(C_1)C_2$ | $E_B$(valence) | $E_A$(valence) | $\frac{q}{e}$ | Bond Length $2c'$ (Å) | Bond Moment $\mu$ (D) |
|---|---|---|---|---|---|---|---|---|
| He | 1 | 0.93364 | 1 | 24.587387 | 26.33505 | 0.13744 | 0.273395 | 0.18049 |

As in the case with graphite, the van der Waals energy is the potential energy between interacting neighboring induced dipoles. Using $\mu_{He} = 0.18049$ D $= 6.02040 \times 10^{-31}$ C·m (Table 34), the van der Waals energy is $$E_{van\ der\ Waals}(He) = 2\frac{2(\mu_{He})^2}{4\pi\varepsilon_0(r_{He\ ...\ He})^3} \quad (16.98)$$

$$= \left(\frac{2(6.02040 \times 10^{-31} \text{ C} \cdot \text{m})^2}{4\pi\varepsilon_0\left(2\sqrt{\frac{a_{He\ ...\ He}a_0}{2C_1C_2}}\right)^3}\right)$$

where there are two bonds at each vertex atom.

The helium interatomic distance is calculated using Eq. (16.25) with the van der Waals energy (Eq. (16.98)) between neighboring dipoles equated to the nascent bond energy. The energy matching parameter $c_2$ is the same that of the helium dipole, and the reduced mass is $\mu = 2$. The parameters are summarized in Table 35 and Eq. (16.99).

TABLE 35

The energy parameters (eV) of the helium functional group (He . . . He).

| Parameters | He . . . He Group |
|---|---|
| $n_1$ | 1 |
| $C_1$ | 0.5 |
| $C_2$ | $0.93364^{-1}$ |
| $c_1$ | 1 |
| $c_2$ | 0.93364 |
| $C_{1o}$ | 0.5 |
| $C_{2o}$ | $0.93364^{-1}$ |
| $V_e$ (eV) | −3.96489 |
| $V_p$ (eV) | 3.88560 |
| $T$ (eV) | 0.15095 |
| $V_m$ (eV) | −0.07548 |
| $E$(AO/HO) (eV) | 0 |
| $\Delta E_{H_2MO}^{(AO/HO)}$ (eV) | 0 |
| $E_T^{(AO/HO)}$ (eV) | 0 |
| $E_T^{(H_2MO)}$ (eV) | −0.00382 |

TABLE 35-continued

The energy parameters (eV) of the helium functional group (He . . . He).

| Parameters | He . . . He Group |
|---|---|
| $E_T$(atom-atom, msp³·AO) (eV) | 0 |
| $E_T^{(MO)}$ (eV) | −0.00382 |
| $\omega$ ($10^{15}$ rad/s) | 0.635696 |
| $E_K$ (eV) | 0.41843 |
| $\overline{E}_D$ (eV) | 0.00000 |
| $\overline{E}_{Kvib}$ (eV) | 0.00443 |
| $\overline{E}_{osc}$ (eV) | 0.00221 |
| $E_T^{(Group)}$ (eV) | −0.00160 |

Substitution of the parameters of Table 35 and the interatomic cohesive energy of helium (Eq. (16.89)) into Eq. (16.25) with $R = a_{He\cdots He}$ gives $$\frac{-4(6.02040 \times 10^{-31} \text{ C} \cdot \text{m})^2}{4\pi\varepsilon_0\left(2\sqrt{\frac{a_{He\ ...\ He}a_0}{2(0.5)(0.93364)^{-1}}}\right)^3} = \quad (16.99)$$

$$\left\{\begin{pmatrix}\frac{-e^2}{8\pi\varepsilon_0\sqrt{\frac{a_{He\ ...\ He}a_0}{2(0.5)(0.93364)^{-1}}}}\\ (0.93364)\left(2 - \frac{1}{2}\frac{a_0}{a_{He\ ...\ He}}\right)\\ \ln\frac{a + \sqrt{\frac{a_{He\ ...\ He}a_0}{2(0.5)(0.93364)^{-1}}}}{a - \sqrt{\frac{a_{He\ ...\ He}a_0}{2(0.5)(0.93364)^{-1}}}} - 1\end{pmatrix}\right.$$

$$\left.\left(1 + 2\hbar\sqrt{\frac{(0.5)(0.93364)^{-1}\frac{e^2}{4\pi\varepsilon_0(a_{He\ ...\ He})^3}}{m_e c^2}}\right) +$$

$$\left(\frac{1}{2}\right)\hbar\sqrt{\frac{\frac{(0.93364)e^2}{8\pi\varepsilon_o(a_{He\ ...\ He})^3} - \frac{e^2}{8\pi\varepsilon_o\left(a_{He\ ...\ He} + \sqrt{\frac{a_{He\ ...\ He}a_0}{2(0.5)(0.93364)^{-1}}}\right)^3}}{2}}\right\}$$

From the energy relationship given by Eq. (16.99) and the relationships between the axes given by Eqs. (16.22-16.24), the dimensions of the He•••He MO can be solved.

The most convenient way to solve Eq. (16.99) is by the reiterative technique using a computer. The result to within the round-off error with five-significant figures is $$a_{He\cdots He}=13.13271a_0=6.94953\times10^{-10}\text{ m} \quad (16.100)$$

The component energy parameters at this condition are given in Table 35. Substitution of Eq. (16.100) into Eq. (16.22) gives $$c'_{He\cdots He}=3.50160a_0=1.85297\times10^{-10}\text{ m} \quad (16.101)$$

and internuclear distance between neighboring helium atoms:

$$2c'_{He\cdots He}=7.00320a_0=3.70593\times10^{-10}\text{ m}=3.70593\text{ Å} \quad (16.102)$$

The experimental helium interatomic distance $2c_{C\cdots C}'$ at 4.24K and <2.25 K are [102]

$$2c'_{He\cdots He}(4.24\text{K})=3.72\times10^{-10}\text{ m}=3.72\text{ Å} \quad$$

$$2c'_{He\cdots He}(<2.25\text{K})=3.70\times10^{-10}\text{ m}=3.70\text{ Å} \quad (16.103)$$

The other interatomic bond MO parameters can also be determined by the relationships among the parameters. Substitution of Eqs. (16.100) and (16.101) into Eq. (16.23) gives $$b_{He\cdots He}=c_{He\cdots He}=12.65729a_o=6.69795\times10^{-10}\text{ m} \quad (16.104)$$

Substitution of Eqs. (16.100) and (16.101) into Eq. (16.25) gives $$e_{He\cdots He}=0.26663 \quad (16.105)$$

Using Eqs. (16.89) and (16.102) and the relationship that there are two van der Waals bonds per helium atom and two atoms per bond, the van der Waals energy per helium atom is $$E_{van\ der\ Waals}(\text{liquid He/He})=0.000799\text{ eV} \quad (16.106)$$

The experimental van der Waals energy calculated from the heat of vaporization per helium atom is [103]

$$E_{van\ der\ Waals}(\text{liquid He})=E_{vapor,4.221K}=0.0829$$
$$\text{kJ/mole}=0.000859\text{ eV/He} \quad (16.107)$$

At 1.7 K, the viscosity of liquid helium is close to zero, and a characteristic roton scattering dominates over phonon scattering at this temperature and below [104]. The van der Waals bond energy is also equivalent to the roton energy [105, 106]

$$E_{roton}(\text{liquid He})=8.7\text{ K}=0.00075\text{ eV} \quad (16.108)$$

and the roton is localized within a region of radius ≈3.7-4.0 Å [104, 106-108] that matches the He•••He van der Waals bond distance (Eq. (16.102)). The origin of the roton energy and its cross section as belonging to the van der Waals bond resolves its nature. Independent of this result, the modern view of the roton is that it is not considered associated with the excitation of vorticity as it was historically; rather it is considered to be due to short-wavelength phonon excitations [105]. Its role in scattering free electrons in superfluid helium is discussed in the Free Electrons in Superfluid Helium are Real in the Absence of Measurement Requiring a Connection of ψ to Physical Reality section. The calculated results based on first principles and given by analytical equations are summarized in Table 36.

TABLE 36

The calculated and experimental geometrical parameters and interatomic van der Waals cohesive energy of liquid helium.

| Parameter | Calculated | Experimental | Ref. for Exp. |
|---|---|---|---|
| Liquid Helium Interatomic Distance $2c'_{C\cdots C}$ | 3.70593 Å | 3.72 Å (T = 4.24 K)<br>3.70 (T < 2.25 K) | 102 |
| Roton Length Scale | 3.70593 Å | 3.7-4.0 Å | 104, 106-108 |
| van der Waals Energy per Helium Atom (4.221 K) | 0.000799 eV | 0.000859 eV | 103 |
| Roton Energy | 0.000799 eV | 0.00075 eV | 105, 106 |

Helium, exhibits unique behavior due to its possible phases based on the interplay of the factors that determine the van der Waals bonding at a given temperature and pressure to achieve an energy minimum. In extreme cases of sufficient ultra-low temperatures with the atoms driven in phase with an external excitation field such that the formation of a van der Waals-dipole-bound macromolecular state or other forms of bonding, such as metallic bonding in the case of alkali metals or van der Waals bonding in meta-stable helium atoms, are suppressed, a pure statistical thermodynamic state called a Bose-Einstein condensate [109] (BEC)[1] can form having a predominant population of the atoms in a single, lowest-energy translational state in the trap. Since helium has only two electrons in an outer s-shell having a small diameter, the dipole moment too very weak to form transverse dipoles associated with packing. Specifically, with the angular dependence of packed dipoles interactions, the van der Waals energy $E_{van\ der\ Waals}$(He) (Eqs. (16.98) and (16.99)) between neighboring dipoles becomes less than the vibrational energy in the transition state ($\overline{E}_{Kvib}$ term of Eq. (16.99) from Eq. (15.53)). Consequently, helium can only mutually induce and form linear dipole-dipole bonds having end-to-end interactions as an energy minimum. Interposed atoms can form a non-bonded phase having correlated translational motion and obeying Bose-Einstein statistics. This phase forms a Bose-Einstein condensate (BEC) as an energy minimum wherein the translations are synchronous. Since a phase comprised of linearly ordered unit cells held together by dipole interactions, specifically van der Waals dipole interactions, can exist with a BEC phase, superfluidity can arise wherein the lines of bound dipoles move without friction relative to the BEC phase having correlated-translational motion. The linear bonding is also the origin of quantized vortex rings that enter as quantized vortex lines to form rings.

[1] The BEC is incorrectly interpreted as a single large atom having a corresponding probability wave function of quantum mechanics. Since excitation occurs in units of $\hbar$ in order of to conserve angular momentum as shown previously for electronic (Chapter 2), vibrational (Chapter 11), rotational (Chapter 12), and translational excitation (Chapter 3) and Bose-Einstein statistics arise from an underlying deterministic physics (Chapter 24), this state comprised of an ensemble of individual atoms is predicted classically using known equations [110]. As in the case of the coherent state of photons in a laser cavity (Chapter 4), the coherency of the BEC actually disproves the inherent Heisenberg Uncertainty Principle (HUP) of quantum mechanics since the atomic positions and energies are precisely determined simultaneously. Furthermore, it is possible to form a BEC comprising molecules in addition to atoms [111] wherein the molecules lack zero-order vibration in contradiction to the HUP. The classical physics underlying Bose-Einstein statistics was covered in the Statistical Mechanics section.

The van der Waals bonds undergo breakage and formation and exist on a time-average basis depending on the internal energy and pressure as in the case of liquid water. The van der Waals bonding exhibits a maximum extent as the temperature is lowered below the boiling point, and the BEC phase comprises the balance of the atoms as the temperature is further lowered to absolute zero. Helium cannot form a solid without application of high pressure to decrease the interatomic separation and permit energetically favorable transverse dipole interactions as well as linear ones. In contrast, other noble gases such as Ne, Ar, Kr, and Xe each possess additional shells including an outer p-shell having a relatively larger radius that gives rise to a significant bond moment supportive of dipole packing interactions; thus, these gases can form solids without the application of high pressure.

Geometrical Parameters and Energies Due to the Interatomic Van Der Waals Cohesive Energy of Solid Neon Neon is a ten-electron neutral atom having the electron configuration $1s^2 2s^2 2p^6$ with the electrons of each shell paired as mirror-image current densities in a shell wherein the radius of the outer shell is $r_{10}=0.63659 a_0$ (Eq. (10.202)). Thus, in isolation or at sufficient separation, there is no energy between neon atoms. However, reversible mutual van der Waals dipoles may be induced by collisions when the atoms are in close proximity such that neon gas can condense into a liquid and further solidify at sufficiently low temperatures due to the strong dipole moment that accommodates close packing. As in the case of helium, the dipoles are atomic rather than molecular, and the limiting separation is based on the formation of a nascent bond to replace the dipole-dipole interaction. Thus, Eq. (16.25) can also be applied to neon atoms.

The van der Waals bonding in the neon atom involves hybridizing the three 2p AOs into $2p^3$ HO orbitals containing six electrons. The total energy of the state is given by the sum over the six electrons. The sum $E_T(Ne, 2p^3)$ of experimental energies [15] of Ne, $Ne^+$, $Ne^{2+}$, $Ne^{3+}$, $Ne^{4+}$, and $Ne^{5+}$ is $$E_T(Ne, 2p^3) = \begin{pmatrix} 157.93 \text{ eV} + 126.21 \text{ eV} + 97.12 \text{ eV} + \\ 63.45 \text{ eV} + 40.96296 \text{ eV} + \\ 21.56454 \text{ eV} \end{pmatrix} \quad (16.109)$$

$$= 507.2375 \text{ eV}$$

By considering that the central field decreases by an integer for each successive electron of the shell, the radius $r_{2p^3}$ of the $Ne2p^3$ shell may be calculated from the Coulombic energy using Eq. (15.13):

$$r_{2p^3} = \sum_{n=4}^{9} \frac{(Z-n)e^2}{8\pi\varepsilon_0(e507.2375 \text{ eV})} \quad (16.110)$$

$$= \frac{21 e^2}{8\pi\varepsilon_0(e507.2375 \text{ eV})}$$

$$= 0.56329 a_0$$

where $Z=10$ for neon. Using Eq. (15.14), the Coulombic energy $E_{Coulomb}(Ne, 2p^3)$ of the outer electron of the van der Waals bound $Ne2p^3$ shell is $$E_{Coulomb}(Ne, 2p^3) = \frac{-e^2}{8\pi\varepsilon_0 r_{2p^3}} \quad (16.111)$$

$$= \frac{-e^2}{8\pi\varepsilon_0 0.56329 a_0}$$

$$= -24.154167 \text{ eV}$$

To meet the equipotential condition of the union of the two $Ne2p^3$ HOs in a nascent bond, $c_2$ of Eqs. (15.2-15.5) and Eq. (15.61) for the nascent Ne—Ne-bond MO is given by Eq. (15.75) as the ratio of the valance energy of the Ne AO, $E(Ne)=-21.56454$ eV and the magnitude of $E_{Coulomb}(Ne, 2p^3)$ (Eq. (16.111)):

$$c_2(Ne—Ne, Ne2p^3 HO) = \frac{21.56454 \text{ eV}}{24.154167 \text{ eV}} = 0.89279 \quad (16.112)$$

The opposite charges distributions act as symmetrical point charges at the point of maximum separation, each being centered at ½ the Ne-atom radius from the origin. Using the parameters of Eq. (16.112) and $2c'=0.56329 a_0=2.98080 \times 10^{-11}$ m (Eq. (16.110)), the van der Waals dipole of neon is given in Table 37.

TABLE 37

The parameters and van der Waals dipole bond moment of the Ne functional group of solid neon.

| Functional Group | $n_1$ | $(c_1)c_2$ | $(C_1)C_2$ | $E_B$(valence) | $E_A$(valence) | $\frac{q}{e}$ | Bond Length 2c' (Å) | Bond Moment μ (D) |
|---|---|---|---|---|---|---|---|---|
| Ne | 1 | 0.89279 | 1 | 21.56454 | 24.15417 | 0.22730 | 0.298080 | 0.32544 |

The minimum-energy packing of neon dipoles is face-centered cubic also called cubic close packing. In this case, each neon atom has 12 nearest neighbors and the angle between the aligned dipoles is $$\frac{\pi}{4}$$

radians. As in the case with graphite, the van der Waals energy is the potential energy between interacting neighboring induced dipoles. Using $\mu_{Ne}=0.32544$ D$=1.08554 \times 10^{-10}$ C·m (Table 37), the van der Waals energy is $$E_{van\,der\,Waals}(Ne) = 12\frac{2(\mu_{Ne})^2}{4\pi\varepsilon_0(r_{Ne\ldots Ne})^3}\cos\left(\frac{\pi}{4}\right) \quad (16.113)$$

$$= \left(\frac{24(1.08554\times 10^{-30}\,C\cdot m)^2}{4\pi\varepsilon_0\left(2\sqrt{\frac{a_{Ne\ldots Ne}a_0}{2C_1C_2}}\right)^3}\right)\cos\left(\frac{\pi}{4}\right)$$

The neon interatomic distance is calculated using Eq. (16.25) with the van der Waals energy (Eq. (16.113)) between neighboring dipoles equated to the nascent bond energy. The energy matching parameter $c_2$ is the same that of the neon dipole, and the reduced mass is $\mu=10$. The parameters are summarized in Table 38 and Eq. (16.114).

TABLE 38

The energy parameters (eV) of the neon functional group (Ne ... Ne).

| Parameters | Ne ... Ne Group |
|---|---|
| $n_1$ | 1 |
| $C_1$ | 0.5 |
| $C_2$ | $0.89279^{-1}$ |
| $c_1$ | 1 |
| $c_2$ | 0.89279 |
| $C_{1o}$ | 0.5 |
| $C_{2o}$ | $0.89279^{-1}$ |
| $V_e$ (eV) | −4.40464 |
| $V_p$ (eV) | 4.27694 |
| $T$ (eV) | 0.19429 |
| $V_m$ (eV) | −0.09714 |
| $E(AO/HO)$ (eV) | 0 |
| $\Delta E_{H_2MO}(AO/HO)$ (eV) | 0 |
| $E_T(AO/HO)$ (eV) | 0 |
| $E_T(H_2MO)$ (eV) | −0.03055 |
| $E_T$(atom-atom, msp$^3$ · AO) (eV) | 0 |
| $E_T(MO)$ (eV) | −0.03055 |
| $\omega$ ($10^{15}$ rad/s) | 0.810674 |
| $E_K$ (eV) | 0.53360 |
| $\overline{E}_D$ (eV) | −0.00004 |
| $\overline{E}_{Kvib}$ (eV) | 0.00240 |
| $\overline{E}_{osc}$ (eV) | 0.00116 |
| $E_T(Group)$ (eV) | −0.02939 |

Substitution of the parameters of Table 38 and the interatomic cohesive energy of neon (Eq. (16.113)) into Eq. (16.25) with $R = a_{Ne\cdots Ne}$ gives $$\frac{-24(1.08554\times 10^{-30}\,C\cdot m)^2}{4\pi\varepsilon_0\left(2\sqrt{\frac{a_{Ne\ldots Ne}a_0}{2(0.5)(0.89279)^{-1}}}\right)^3}\cos\left(\frac{\pi}{4}\right) = \quad (16.114)$$

$$\left\{\left(\frac{-e^2}{8\pi\varepsilon_0\sqrt{\frac{a_{Ne\ldots Ne}a_0}{2(0.5)(0.89279)^{-1}}}}\right)\left((0.89279)\left(2 - \frac{1}{2}\frac{a_0}{a_{Ne\ldots Ne}}\right)\ln\frac{a+\sqrt{\frac{a_{Ne\ldots Ne}a_0}{2(0.5)(0.89279)^{-1}}}}{a-\sqrt{\frac{a_{Ne\ldots Ne}a_0}{2(0.5)(0.89279)^{-1}}}} - 1\right)\right\}$$

$$\left(1 + 2\sqrt{\frac{(0.5)(0.89279)^{-1}\frac{e^2}{4\pi\varepsilon_0(a_{Ne\ldots Ne})^3}}{m_e}}\right) +$$

$$\left(\frac{1}{2}\right)\hbar\sqrt{\frac{\frac{(0.89279)e^2}{8\pi\varepsilon_0(a_{Ne\ldots Ne})^3} - \frac{e^2}{8\pi\varepsilon_0\left(a_{Ne\ldots Ne} + \sqrt{\frac{a_{Ne\ldots Ne}a_0}{2(0.5)(0.89279)^{-1}}}\right)^3}}{10}}\right\}$$

From the energy relationship given by Eq. (16.114) and the relationships between the axes given by Eqs. (16.22-16.24), the dimensions of the Ne•••Ne MO can be solved.

The most convenient way to solve Eq. (16.114) is by the reiterative technique using a computer. The result to within the round-off error with five-significant figures is $$a_{Ne\cdots Ne} = 11.33530a_0 = 5.99838\times 10^{-10}\,m \quad (16.115)$$

The component energy parameters at this condition are given in Table 38. Substitution of Eq. (16.115) into Eq. (16.22) gives $$c'_{Ne\cdots Ne} = 3.18120a_0 1.68342\times 10^{-10}\,m \quad (16.116)$$

and internuclear distance between neighboring neon atoms:

$$2c'_{Ne\cdots Ne} = 6.36239a_0 = 3.36683\times 10^{-10}\,m = 3.36683\,\text{Å} \quad (16.117)$$

The experimental neon interatomic distance $2c'_{C\cdots C}$ at the melting point of 24.48 K is [112, 113]

$$2c'_{Ne\cdots Ne}(24.48K) = 3.21\times 10^{-10}\,m = 3.21\,\text{Å} \quad (16.118)$$

The other interatomic bond MO parameters can also be determined by the relationships among the parameters. Substitution of Eqs. (16.115) and (16.116) into Eq. (16.23) gives $$b_{Ne\cdots Ne}c_{Ne\cdots Ne} = 10.87975a_0 = 5.75732\times 10^{-10}\,m \quad (16.119)$$

Substitution of Eqs. (16.115) and (16.116) into Eq. (16.25) gives $$e_{Ne\cdots Ne} = 0.28065 \quad (16.120)$$

A convenient method to calculate the lattice energy is to determine the electric field in solid neon having an electric polarization density corresponding to the aligned dipoles moments, and in turn, the energy can be calculated from the energy of each dipole in the corresponding field using the electrostatic form of Gauss' equation. Substitution of the density of solid neon at the melting point $$\rho = \frac{1.433\,g}{1\times 10^{-6}\,m^3}, \quad [113]$$

the MW=20.179 g/mole, $N_A$=6.0221415×10$^{23}$ molecules/mole, and the neon dipole moment given in Table 37 into Eq. (16.53) gives:

$$U(Ne) = \frac{-2(\mu_{Ne})^2 \frac{\rho_{solid\,Ne}}{MW} N_A}{3\varepsilon_0} \quad (16.121)$$

$$= \frac{-2(1.08554 \times 10^{-30}\ C \cdot m)^2 \frac{1.433\ g}{1 \times 10^{-6}\ m^3}}{20.179\ g/mole}$$

$$\frac{6.0221415 \times 10^{23}\ molecules/mole}{3\varepsilon_0}$$

$$= -0.02368\ eV(-2.285\ kJ/mole)$$

U(Ne) is also the negative of $E_{van\ der\ Waals}$, the van der Waals energy per neon atom:

$$E_{van\ der\ Waals}(solid\ Ne/Ne)=0.02368\ eV=2.285\ kJ/mole \quad (16.122)$$

The experimental van der Waals energy calculated from the heat of vaporization and fusion per neon atom at the boiling point and triple point, respectively, is [103]

$$E_{van\ der\ Waals}(solid\ Ne)=E_{vapor}+E_{fusion}=0.02125\ eV/Ne=2.0502\ kJ/mole \quad (16.123)$$

The calculated results based on first principles and given by analytical equations are summarized in Table 39. Using neon the atomic radius (Eq. (16.110)) and the nearest-neighbor distance (Eq. (16.117)), the lattice structure of neon is shown in FIG. 21A. The charge density of the van der Waals dipoles of the crystalline lattice is shown in FIG. 22A.

TABLE 39

The calculated and experimental geometrical parameters and interatomic van der Waals cohesive energy of solid neon.

| Parameter | Calculated | Experimental | Ref. for Exp. |
|---|---|---|---|
| Solid Neon Interatomic Distance 2c'$_{C...C}$ | 3.36683 Å | 3.21 Å (T = 24.48 K) | 113 |
| van der Waals Energy per Neon Atom | 0.02368 eV | 0.02125 eV | 103 |

Geometrical Parameters and Energies Due to the Interatomic Van Der Waals Cohesive Energy of Solid Argon Argon is an eighteen-electron neutral atom having the electron configuration 1s$_2$2s$^2$2p$^6$3s$^2$3p$^6$ with the electrons of each shell paired as mirror-image current densities in a shell wherein the radius of the outer shell is $r_{18}$=0.86680a$_0$ (Eq. (10.386)). Thus, in isolation or at sufficient separation, there is no energy between argon atoms. However, reversible mutual van der Waals dipoles may be induced by collisions when the atoms are in close proximity such that argon gas can condense into a liquid and further solidify at sufficiently low temperatures due to the strong dipole moment that accommodates close packing. As in the case of helium, the dipoles are atomic rather than molecular, and the limiting separation is based on the formation of a nascent bond to replace the dipole-dipole interaction. Thus, Eq. (16.25) can also be applied to argon atoms.

The van der Waals bonding in the argon atom involves hybridizing the three 3p AOs into 3p$^3$ HO orbitals containing six electrons. The total energy of the state is given by the sum over the six electrons. The sum $E_T(Ar,3p^3)$ of experimental energies [15] of Ar, Ar$^+$, Ar$^{2+}$, Ar$^{3+}$, Ar$^{4+}$, and Ar$^{5+}$ is $$E_T(Ar, 3p^3) = \begin{pmatrix} 91.009\ eV + 75.02\ eV + 59.81\ eV + \\ 40.74\ eV + 27.62966\ eV + \\ 15.75961\ eV \end{pmatrix} \quad (16.124)$$

$$= 309.96827\ eV$$

By considering that the central field decreases by an integer for each successive electron of the shell, the radius $r_{3p^3}$ of the Ar3p$^3$ shell may be calculated from the Coulombic energy using Eq. (15.13):

$$r_{3p^3} = \sum_{n=12}^{17} \frac{(Z-n)e^2}{8\pi\varepsilon_0(e309.96827\ eV)} \quad (16.125)$$

$$= \frac{21e^2}{8\pi\varepsilon_0(e309.96827\ eV)}$$

$$= 0.92178a_0$$

where Z=18 for argon. Using Eq. (15.14), the Coulombic energy $E_{Coulomb}(Ar,3p^3)$ of the outer electron of the van der Waals bound Ar3p$^3$ shell is $$E_{Coulomb}(Ar, 3p^3) = \frac{-e^2}{8\pi\varepsilon_0 r_{3p^3}} \quad (16.126)$$

$$= \frac{-e^2}{8\pi\varepsilon_0 0.92178a_0}$$

$$= -14.760394\ eV$$

To meet the equipotential condition of the union of the two Ar3p$^3$ HOs in a nascent bond, $c_2$ of Eqs. (15.2-15.5) and Eq. (15.61) for the nascent Ar— Ar-bond MO is given by Eq. (15.75) as the ratio of the valance energy of the Ar AO, E(Ar)=−15.75961 eV and the magnitude of $E_{Coulomb}(Ar, 3p^3)$ (Eq. (16.126)):

$$c_2(Ar-Ar, Ar3p^3HO) = \frac{14.760394\ eV}{15.75961\ eV} = 0.93660 \quad (16.127)$$

Since the outer Ar3p$^3$ HO shell is at a lower energy and greater radius than the non-polarized 3p shell, the inner shells are polarized as well. The dipole of the outer shell can polarize the inner shells to the limit that the sum of the primary and secondary dipoles is twice the primary scaled by the energy matching factors of the van der Waals bond given in Eq. (16.15). Thus, the limiting dipole due to polarization of the inner shells is given by $$\mu_{Ar} < 2c_1^{-1} qC_2 2c' = 2(0.93660)^{-1}(0.13110)e(0.93660)^{-1} \quad (16.128)$$

$$(4.87784 \times 10^{-11}\ m)$$

$$= 2.49410 \times 10^{-30}\ C \cdot m$$

$$= 0.74771\ D$$

The condition of Eq. (16.128) is matched by the participation of the outer four shells as given in Table 40. At each shell, opposite charges distributions act as symmetrical point charges at the point of maximum separation, each being centered at ½ the shell radius from the origin. Using the parameters of Eq. (16.127) and 2c'=0.92178a$_0$=4.87784×10$^{-11}$ m (Eq. (16.125)) as well as the radii of the inner shells of argon (Table 10.17), the van der Waals dipole of argon is given in Table 40 as the sum of the moments of each participating shell.

TABLE 40

The parameters and van der Waals dipole bond moment of the Ar functional group of solid argon.

| Functional Group | $n_1$ | $(c_1)c_2$ | $(C_1)C_2$ | $E_B$(valence) | $E_A$(valence) | $\frac{q}{e}$ | Bond Length 2c' (Å) | Bond Moment $\mu$ (D) |
|---|---|---|---|---|---|---|---|---|
| Ar | 1 | 0.93660 | 1 | 14.76039 | 15.75961 | 0.13110 | Ar3p³ HO 0.48778<br>Ar3s AO 0.41422<br>Ar2p AO 0.15282<br>Ar2s AO 0.12615 | 0.74366 |

The minimum-energy packing of argon dipoles is face-centered cubic also called cubic close packing. In this case, each argon atom has 12 nearest neighbors and the angle between the aligned dipoles is $$\frac{\pi}{4}$$

radians. As in the case with graphite, the van der Waals energy is the potential energy between interacting neighboring induced dipoles. Using $\mu_{Ar}=0.74366$ D$=2.48058\times10^{-30}$ C·m (Table 40), the van der Waals energy is $$E_{van\,der\,Waals}(Ar) = 12\frac{2(\mu_{Ar})^2}{4\pi\varepsilon_0(r_{Ar\ldots Ar})^3}\cos\left(\frac{\pi}{4}\right) \quad (16.129)$$

$$= \left(\frac{24(2.48058\times10^{-30}\,\text{C·m})^2}{4\pi\varepsilon_0\left(2\sqrt{\frac{a_{Ar\ldots Ar}a_0}{2C_1C_2}}\right)^3}\right)\cos\left(\frac{\pi}{4}\right)$$

The argon interatomic distance is calculated using Eq. (16.25) with the van der Waals energy (Eq. (16.129)) between neighboring dipoles equated to the nascent bond energy. The energy matching parameter $c_2$ is the same that of the argon dipole, and the reduced mass is $\mu=20$. The parameters are summarized in Table 41 and Eq. (16.130).

TABLE 41

The energy parameters (eV) of the argon functional group (Ar . . . Ar).

| Parameters | Ar . . . Ar Group |
|---|---|
| $n_1$ | 1 |
| $C_1$ | 0.5 |
| $C_2$ | $0.93660^{-1}$ |
| $c_1$ | 1 |
| $c_2$ | 0.93660 |
| $C_{1o}$ | 0.5 |
| $C_{2o}$ | $0.93660^{-1}$ |
| $V_e$ (eV) | −4.18356 |
| $V_p$ (eV) | 3.97600 |
| $T$ (eV) | 0.16731 |
| $V_m$ (eV) | −0.08365 |
| E(AO/HO) (eV) | 0 |
| $\Delta E_{H_2MO}^{(AO/HO)}$ (eV) | 0 |
| $E_T^{(AO/HO)}$ (eV) | 0 |
| $E_T^{(H_2MO)}$ (eV) | −0.12391 |
| $E_T$(atom-atom, msp³·AO) (eV) | 0 |
| $E_T^{(MO)}$ (eV) | −0.12391 |
| $\omega$ ($10^{15}$ rad/s) | 0.683262 |
| $E_K$ (eV) | 0.44974 |
| $\overline{E}_D$ (eV) | −0.00016 |
| $\overline{E}_{Kvib}$ (eV) | 0.00153 |

TABLE 41-continued

The energy parameters (eV) of the argon functional group (Ar . . . Ar).

| Parameters | Ar . . . Ar Group |
|---|---|
| $\overline{E}_{osc}$ (eV) | 0.00060 |
| $E_T^{(Group)}$ (eV) | −0.12331 |

Substitution of the parameters of Table 1 and the interatomic cohesive energy of argon (Eq. (16.129)) into Eq. (16.25) with R=$a_{Ar\cdots Ar}$ gives $$\frac{-24(2.48058\times10^{-30}\,\text{C·m})^2}{4\pi\varepsilon_0\left(2\sqrt{\frac{a_{Ar\ldots Ar}a_0}{2(0.5)(0.93660)^{-1}}}\right)^3}\cos\left(\frac{\pi}{4}\right) = \quad (16.130)$$

$$\left\{\begin{pmatrix}\dfrac{-e^2}{8\pi\varepsilon_0\sqrt{\dfrac{a_{Ar\ldots Ar}a_0}{2(0.5)(0.93660)^{-1}}}}\\ \\ (0.93660)\left(2-\dfrac{1}{2}\dfrac{a_0}{a_{Ar\ldots Ar}}\right)\ln\dfrac{a+\sqrt{\dfrac{a_{Ar\ldots Ar}a_0}{2(0.5)(0.93660)^{-1}}}}{a-\sqrt{\dfrac{a_{Ar\ldots Ar}a_0}{2(0.5)(0.93660)^{-1}}}}-1\end{pmatrix}\right.$$

$$\left. \left(1+2\hbar\sqrt{\dfrac{(0.5)(0.93660)^{-1}\dfrac{e^2}{4\pi\varepsilon_0(a_{Ar\ldots Ar})^3}}{m_e}}\right)+\right.$$

$$\left.\left(\dfrac{1}{2}\right)\hbar\sqrt{\dfrac{(0.93660)e^2}{8\pi\varepsilon_o(a_{Ar\ldots Ar})^3}-\dfrac{e^2}{8\pi\varepsilon_o\left(a_{Ar\ldots Ar}+\sqrt{\dfrac{a_{Ar\ldots Ar}a_0}{2(0.5)(0.93660)^{-1}}}\right)^3}}{20}\right\}$$

From the energy relationship given by Eq. (16.130) and the relationships between the axes given by Eqs. (16.22-16.24), the dimensions of the Ar•••Ar MO can be solved.

The most convenient way to solve Eq. (16.130) is by the reiterative technique using a computer. The result to within the round-off error with five-significant figures is $$a_{Ar\cdots Ar}=12.50271a_0=6.61615\times10^{-10}\,\text{m} \quad (16.131)$$

The component energy parameters at this condition are given in Table 41. Substitution of Eq. (16.131) into Eq. (16.22) gives $$c_{Ar\cdots Ar}'=3.42199a_0=1.81084\times10^{-10}\text{ m} \quad (16.132)$$

and internuclear distance between neighboring argon atoms:

$$2c_{Ar\cdots Ar}'(0\text{ K})=6.84397a_0 3.62167\times10^{-10}\text{ m}=3.62167\text{ Å} \quad (16.133)$$

The experimental argon interatomic distance $2c_{C\cdots C}'$ is [114]

$$2c_{Ar\cdots Ar}'(4.2\text{ K})=3.71\times10^{-10}\text{ m}=3.71\text{ Å} \quad (16.134)$$

The other interatomic bond MO parameters can also be determined by the relationships among the parameters. Substitution of Eqs. (16.131) and (16.132) into Eq. (16.23) gives $$b_{Ar\cdots Ar}=c_{Ar\cdots Ar}=12.02530a_0=6.36351\times10^{-10}\text{ m} \quad (16.135)$$

Substitution of Eqs. (16.131) and (16.132) into Eq. (16.25) gives $$e_{Ar\cdots Ar}=0.27370 \quad (16.136)$$

A convenient method to calculate the lattice energy is to determine the electric field in solid argon having an electric polarization density corresponding to the aligned dipoles moments, and in turn, the energy can be calculated from the energy of each dipole in the corresponding field using the electrostatic form of Gauss' equation. Substitution of the density of solid argon at 402 K $$\rho = \frac{1.83\text{ g}}{1\times 10^{-6}\text{ m}^3}, \quad [114]$$

the MW=39.948 g/mole, $N_A$=6.0221415×10$^{23}$ molecules/mole, and the argon dipole moment given in Table 40 into Eq. (16.53) gives:

$$U(\text{Ar}) = \frac{-2(\mu_{Ar})^2 \frac{\rho_{\text{solid Ar}}}{MW} N_A}{3\varepsilon_0} \quad (16.137)$$

$$= \frac{-2(2.48058\times 10^{-30}\text{ C}\cdot\text{m})^2 \frac{1.83\text{ g}}{1\times 10^{-6}\text{ m}^3}{39.948\text{ g/mole}} 6.0221415\times 10^{23}\text{ molecules/mole}}{3\varepsilon_0}$$

$$= -0.07977\text{ eV}(-7.697\text{ kJ/mole})$$

U(Ar) is also the negative of $E_{\text{van der Waals}}$, the van der Waals energy per argon atom:

$$E_{\text{van der Waals}}(\text{solid Ar},4.2\text{ K/Ar})=0.07977\text{ eV}=7.697\text{ kJ/mole} \quad (16.138)$$

The experimental van der Waals energy is the cohesive energy [115]:

$$E_{\text{van der Waals}}(\text{solid Ar},0\text{ K})=0.08022\text{ eV/Ar}=7.74\text{ kJ/mole} \quad (16.139)$$

The calculated results based on first principles and given by analytical equations are summarized in Table 42. Using argon the atomic radius (Eq. (16.125)) and the nearest-neighbor distance (Eq. (16.133)), the lattice structure of argon is shown in FIG. 21B. The charge density of the van der Waals dipoles of the crystalline lattice is shown in FIG. 22B.

TABLE 42

The calculated and experimental geometrical parameters and interatomic van der Waals cohesive energy of solid argon.

| Parameter | Calculated | Experimental | Ref. for Exp. |
|---|---|---|---|
| Solid Argon Interatomic Distance $2c'_{C\cdots C}$ | 3.62167 Å (T = 0 K) | 3.71 Å (T = 4.2 K) | 114 |
| van der Waals Energy per Argon Atom | 0.07977 eV (T = 4.2 K) | 0.08022 eV (T = 0 K) | 115 |

Geometrical Parameters and Energies Due to the Interatomic Van Der Waals Cohesive Energy of Solid Krypton Krypton is a thirty-six-electron neutral atom having the electron configuration $1s_2 2s^2 2p_6 3s_2 3p^6 3d^{10} 4s^2 4p^6$ with the electrons of each shell paired as mirror-image current densities in a shell wherein the radius of the outer shell is $r_{36}=0.97187a_0$ (Eq. (10.102)). Thus, in isolation or at sufficient separation, there is no energy between krypton atoms. However, reversible mutual van der Waals dipoles may be induced by collisions when the atoms are in close proximity such that krypton gas can condense into a liquid and further solidify at sufficiently low temperatures due to the strong dipole moment that accommodates close packing. As in the case of helium, the dipoles are atomic rather than molecular, and the limiting separation is based on the formation of a nascent bond to replace the dipole-dipole interaction. Thus, Eq. (16.25) can also be applied to krypton atoms.

The van der Waals bonding in the krypton atom involves hybridizing the three 4p AOs into 4p$^3$ HO orbitals containing six electrons. The total energy of the state is given by the sum over the six electrons. The sum $E_T(\text{Kr},4p^3)$ of experimental energies [15, 116-119] of Kr, $$E_T(\text{Kr}, 4p^3) = \begin{pmatrix} 78.5\text{ eV} + 64.7\text{ eV} + 52.5\text{ eV} + \\ 36.950\text{ eV} + 24.35984\text{ eV} + \\ 13.99961\text{ eV} \end{pmatrix} \quad (16.140)$$

$$= 271.00945\text{ eV}$$

By considering that the central field decreases by an integer for each successive electron of the shell, the radius $r_{4p^3}$ of the Kr4p$^3$ shell may be calculated from the Coulombic energy using Eq. (15.13):

$$r_{4p^3} = \sum_{n=30}^{35} \frac{(Z-n)e^2}{8\pi\varepsilon_0(e271.00945\text{ eV})} \quad (16.141)$$

$$= \frac{21e^2}{8\pi\varepsilon_0(e271.00945\text{ eV})}$$

$$= 1.05429a_0$$

where Z=36 for krypton. Using Eq. (15.14), the Coulombic energy $E_{Coulomb}(\text{Kr},4p^3)$ of the outer electron of the van der Waals bound Kr4p$^3$ shell is $$E_{Coulomb}(\text{Kr}, 4p^3) = \frac{-e^2}{8\pi\varepsilon_0 r_{rp^3}} \quad (16.142)$$

$$= \frac{-e^2}{8\pi\varepsilon_0 1.05429a_0}$$

$$= -12.905212\text{ eV}$$

To meet the equipotential condition of the union of the two $Kr4p^3$ HOs in a nascent bond, $c_2$ of Eqs. (15.2-15.5) and Eq. (15.61) for the nascent Kr—Kr-bond MO is given by Eq. (15.75) as the ratio of the valence energy of the Kr AO, $E(Kr)=-13.99961$ eV and the magnitude of $E_{Coulomb}(Kr, 4p_3)$ (Eq. (16.142)):

$$c_2(\text{Kr---Kr, Kr}4p^3\text{HO}) = \frac{12.905212 \text{ eV}}{13.99961 \text{ eV}} = 0.92183 \quad (16.143)$$

Since the outer $Kr4p^3$ HO shell is at a lower energy and greater radius than the non-polarized 4p shell, the inner shells are polarized as well. The dipole of the outer shell can polarize the inner shells to the limit that the sum of the primary and secondary dipoles is twice the primary scaled by the energy matching factors of the van der Waals bond given in Eq. (16.15). Thus, the limiting dipole due to polarization of the inner shells is given by $$\mu_{Kr} < 2c_1^{-1}qC_2 2c' = 2(0.16298)e(0.92183)^{-1} \quad (16.144)$$

$$(5.57905 \times 10^{-11} \text{ m})$$

$$= 3.42870 \times 10^{-30} \text{ C} \cdot \text{m} = 1.02790D$$

The condition of Eq. (16.144) is matched by the participation of the outer three shells as given in Table 43. At each shell, opposite charges distributions act as symmetrical point charges at the point of maximum separation, each being centered at ½ the shell radius from the origin. Using the parameters of Eq. (16.143) and $2c'=1.05429a_0=5.57905 \times 10^{-11}$ m (Eq. (16.141)) as well as the radii of the inner shells of krypton (Eq. (10.102)), the van der Waals dipole of krypton is given in Table 16.36 as the sum of the moments of each participating shell.

$$E_{van\ der\ Waals}(\text{Kr}) = 12 \frac{2(\mu_{Kr})^2}{4\pi\varepsilon_0 (r_{Kr...Kr})^3} \cos\left(\frac{\pi}{4}\right) \quad (16.145)$$

$$= \left(\frac{24(3.37329 \times 10^{-30} \text{ C} \cdot \text{m})^2}{4\pi\varepsilon_0 \left(2\sqrt{\frac{a_{Kr...Kr}a_0}{2C_1C_2}}\right)^3}\right) \cos\left(\frac{\pi}{4}\right)$$

The krypton interatomic distance is calculated using Eq. (16.25) with the van der Waals energy (Eq. (16.145)) between neighboring dipoles equated to the nascent bond energy. The energy matching parameter $c_2$ is the same that of the krypton dipole, and the reduced mass is $\mu=42$. The parameters are summarized in Table 44 and Eq. (16.146).

TABLE 44

The energy parameters (eV) of the krypton functional group (Kr . . . Kr).

| Parameters | Kr . . . Kr Group |
| --- | --- |
| $n_1$ | 1 |
| $C_1$ | 0.5 |
| $C_2$ | 0.92183 |
| $c_1$ | 1 |
| $c_2$ | 0.92183 |
| $C_{1o}$ | 0.5 |
| $C_{2o}$ | 0.92183 |
| $V_e$ (eV) | -3.75058 |
| $V_p$ (eV) | 3.52342 |
| $T$ (eV) | 0.13643 |
| $V_m$ (eV) | -0.06821 |
| E(AO/HO) (eV) | 0 |
| $\Delta E_{H_2MO}(AO/HO)$ (eV) | 0 |
| $E_T(AO/HO)$ (eV) | 0 |
| $E_T(H_2MO)$ (eV) | -0.15895 |
| $E_T$(atom-atom, msp$^3$ · AO) (eV) | 0 |
| $E_T(MO)$ (eV) | -0.15895 |
| ω (10$^{15}$ rad/s) | 0.550731 |

TABLE 43

The parameters and van der Waals dipole bond moment of the Kr functional group (FG) of solid krypton.

| FG | $n_1$ | $(c_1)c_2$ | $(C_1)C_2$ | $E_B$(valence) | $E_A$(valence) | q/e | Ion/IP/Z [116-119] | Bond Length 2c' (Å) (Eqs. (16.141) and (10.102)) | Bond Moment μ (D) |
| --- | --- | --- | --- | --- | --- | --- | --- | --- | --- |
| Kr | 1 | 0.92183 | 1 | 12.90521 | 13.99961 | 0.16298 | Kr$^{6+}$ 111.07 | Kr4p$^3$ HO 0.55790 Kr4s AO | 1.01129 |
| | | | | | | | Kr$^{8+}$ 231.59 | 0.45405 Kr3d AO 0.27991 | |

The minimum-energy packing of krypton dipoles is face-centered cubic also called cubic close packing. In this case, each krypton atom has 12 nearest neighbors and the angle between the aligned dipoles is $$\frac{\pi}{4}$$

radians. As in the case with graphite, the van der Waals energy is the potential energy between interacting neighboring induced dipoles. Using $\mu_{Kr}$=1.01129 D=3.37329×10$^{-30}$ C·m (Table 43), the van der Waals energy is TABLE 44-continued The energy parameters (eV) of the krypton functional group (Kr . . . Kr).

| Parameters | Kr . . . Kr Group |
| --- | --- |
| $E_K$ (eV) | 0.36250 |
| $\overline{E}_D$ (eV) | -0.00019 |
| $\overline{E}_{Kvib}$ (eV) | 0.00091 |
| $\overline{E}_{osc}$ (eV) | 0.00026 |
| $E_T(Group)$ (eV) | -0.15869 |

Substitution of the parameters of Table 44 and the interatomic cohesive energy of krypton (Eq. (16.145)) into Eq. (16.25) with $R=a_{Kr\cdots Kr}$ gives $$\frac{-24(3.37329\times 10^{-31}\text{ C}\cdot\text{m})^2}{4\pi\varepsilon_0\left(2\sqrt{\frac{a_{Kr\cdots Kr}a_0}{2(0.5)(0.92183)}}\right)^3}\cos\left(\frac{\pi}{4}\right)= \quad (16.146)$$

$$\left\{\left(\frac{-e^2}{8\pi\varepsilon_0\sqrt{\frac{a_{Kr\cdots Kr}a_0}{2(0.5)(0.92183)}}}\right)\left(\ln\left(\frac{a+\sqrt{\frac{a_{Kr\cdots Kr}a_0}{2(0.5)(0.92183)}}}{a-\sqrt{\frac{a_{Kr\cdots Kr}a_0}{2(0.5)(0.92183)}}}\right)-1\right)\left((0.92183)\left(2-\frac{1}{2}\frac{a_0}{a_{Kr\cdots Kr}}\right)\right)\right\}$$

$$+\left(1+2\hbar\sqrt{\frac{(0.5)(0.92183)\frac{e^2}{4\pi\varepsilon_o(a_{Kr\cdots Kr})^3}}{m_e}}\right)+$$

$$\left(\frac{1}{2}\right)\hbar\sqrt{\frac{\frac{(0.92183)e^2}{8\pi\varepsilon_o(a_{Kr\cdots Kr})^3}-\frac{e^2}{8\pi\varepsilon_o\left(a_{Kr\cdots Kr}+\sqrt{\frac{a_{Kr\cdots Kr}a_0}{2(0.5)(0.92183)}}\right)^3}}{42}}$$

From the energy relationship given by Eq. (16.146) and the relationships between the axes given by Eqs. (16.22-16.24), the dimensions of the Kr•••Kr MO can be solved.

The most convenient way to solve Eq. (16.146) is by the reiterative technique using a computer. The result to within the round-off error with five-significant figures is $$a_{Kr\cdots Kr}=13.74580a_0=7.27396\times 10^{-10}\text{ m} \quad (16.147)$$

The component energy parameters at this condition are given in Table 44. Substitution of Eq. (16.147) into Eq. (16.22) gives $$c_{Kr\cdots Kr}'=3.86154a_0=2.04344\times 10^{-10}\text{ m} \quad (16.148)$$

and internuclear distance between neighboring krypton atoms:

$$2c_{Kr\cdots Kr}'=(0\text{ K})=7.72308a_0=4.08688\times 10^{-10}\text{ m}=4.08688\text{ Å} \quad (16.149)$$

The experimental krypton interatomic distance $2c_{C\cdots C}'$ is [113]

$$2c_{Kr\cdots Kr}'(0\text{ K})=3.992\times 10^{-10}\text{ m}=3.992\text{ Å} \quad (16.150)$$

The other interatomic bond MO parameters can also be determined by the relationships among the parameters. Substitution of Eqs. (16.147) and (16.148) into Eq. (16.23) gives $$b_{Kr\cdots Kr}, c_{Kr\cdots Kr}=13.19225a_0=6.98104\times 10^{-10}\text{ m} \quad (16.151)$$

Substitution of Eqs. (16.147) and (16.148) into Eq. (16.25) gives $$e_{Kr\cdots Kr}=0.28092 \quad (16.152)$$

A convenient method to calculate the lattice energy is to determine the electric field in solid krypton having an electric polarization density corresponding to the aligned dipoles moments, and in turn, the energy can be calculated from the energy of each dipole in the corresponding field using the electrostatic form of Gauss' equation. Substitution of the density of solid krypton at 4.2 K $$\rho=\frac{3.094\text{ g}}{1\times 10^{-6}\text{ m}^3}, \quad [113]$$

the MW=83.80 g/mole, $N_A$=6.0221415×10$^{23}$ molecules/mole, and the krypton dipole moment given in Table 43 into Eq. (16.53) gives:

$$U(Kr)=\frac{-2(\mu_{Kr})^2\frac{\rho_{solid\ Kr}}{MW}N_A}{3\varepsilon_0} \quad (16.153)$$

$$=\frac{-2(3.37329\times 10^{-30}\text{ C}\cdot\text{m})^2\frac{1\times 10^{-6}\text{ m}^3}{83.80\text{ g/mole}}\cdot 6.0221415\times 10^{23}\text{ molecules/mole}}{3\varepsilon_0}$$

$$=-0.11890\text{ eV }(-11.472\text{ kJ/mole})$$

U(Ar) is also the negative of $E_{van\ der\ Waals}$, the van der Waals energy per krypton atom:

$$E_{van\ der\ Waals}(\text{solid Kr},0\text{ K/Kr})=0.11890\text{ eV}=11.472\text{ kJ/mole} \quad (16.154)$$

The experimental van der Waals energy is the cohesive energy [120]:

$$E_{van\ der\ Waals}(\text{solid Kr},0\text{ K/Kr})=0.11561\text{ eV}=11.15454\text{ kJ/mole} \quad (16.155)$$

The calculated results based on first principles and given by analytical equations (0 K) are summarized in Table 45. Using krypton the atomic radius (Eq. (16.141)) and the nearest-neighbor distance (Eq. (16.149)), the lattice structure of krypton is shown in FIG. 21C. The charge density of the van der Waals dipoles of the crystalline lattice is shown in FIG. 22C.

TABLE 45

The calculated and experimental geometrical parameters and interatomic van der Waals cohesive energy (0 K) of solid krypton.

| Parameter | Calculated | Experimental | Ref. for Exp. |
|---|---|---|---|
| Solid Krypton Interatomic Distance $2c'_{C\ldots C}$ | 4.08688 Å | 3.992 Å | 113 |
| van der Waals Energy per Krypton Atom | 0.11890 eV | 0.11561 eV | 120 |

Geometrical Parameters and Energies Due to the Interatomic Van Der Waals Cohesive Energy of Solid Xenon Xenon is a fifty-four-electron neutral atom having the electron configuration $1s^22s^22p^63s^23p^63d^{10}4s^24p^64d^{10}5s^25p^6$ with the electrons of each shell paired as mirror-image current densities in a shell wherein the radius of the outer shell is $r_{54}=1.12168a_0$ (Eq. (10.102)). Thus, in isolation or at sufficient separation, there is no energy between xenon atoms. However, reversible mutual van der Waals dipoles may be induced by collisions when the atoms are in close proximity such that xenon gas can condense into a liquid and further solidify at sufficiently low temperatures due to the strong dipole moment that accommodates close packing. As in the case of helium, the dipoles are atomic rather than molecular, and the limiting separation is based on the formation of a nascent bond to replace the dipole-dipole interaction. Thus, Eq. (16.25) can also be applied to xenon atoms.

The van der Waals bonding in the xenon atom involves hybridizing the three 5p AOs into 5p³ HO orbitals containing six electrons. The total energy of the state is given by the sum over the six electrons. The sum $E_T(Xe,5p_3)$ of experimental energies [15, 121-122] of Xe, Xe$^+$, Xe$^{2+}$, Xe$^{3+}$, Xe$^{4+}$, and Xe$^{5+}$ is $$E_T(Xe, 5p^3) = \begin{pmatrix} 66.703 \text{ eV} + 54.14 \text{ eV} + 40.9 \text{ eV} + \\ 31.050 \text{ eV} + 20.975 \text{ eV} + \\ 12.129842 \text{ eV} \end{pmatrix} \quad (16.156)$$

$$= 225.89784 \text{ eV}$$

By considering that the central field decreases by an integer for each successive electron of the shell, the radius $r_{5p^3}$ of the Xe5p³ shell may be calculated from the Coulombic energy using Eq. (15.13):

$$r_{5p^3} = \sum_{n=48}^{53} \frac{(Z-n)e^2}{8\pi\varepsilon_0(e225.897842 \text{ eV})} \quad (16.157)$$

$$= \frac{21e^2}{8\pi\varepsilon_0(e225.897842 \text{ eV})}$$

$$= 1.26483 a_0$$

where Z=54 for xenon. Using Eq. (15.14), the Coulombic energy $E_{Coulomb}(Xe,5p^3)$ of the outer electron of the van der Waals bound Xe5p³ shell is $$E_{Coulomb}(Xe, 5p^3) = \frac{-e^2}{8\pi\varepsilon_0 r_{5p^3}} \quad (16.158)$$

$$= \frac{-e^2}{8\pi\varepsilon_0 1.26483 a_0}$$

$$= -10.757040 \text{ eV}$$

To meet the equipotential condition of the union of the two Xe5p³ HOs in a nascent bond, $c_2$ of Eqs. (15.2-15.5) and Eq. (15.61) for the nascent Xe—Xe-bond MO is given by Eq. (15.75) as the ratio of the valance energy of the Xe AO, E(Xe)=−12.129842 eV and the magnitude of $E_{Coulomb}$(Xe, 5p³) (Eq. (16.158)):

$$c_2(Xe-Xe, Xe5p^3HO) = \frac{10.75704 \text{ eV}}{12.129842 \text{ eV}} = 0.88682 \quad (16.159)$$

Since the outer Xe5p³ HO shell is at a lower energy and greater radius than the non-polarized 5p shell, the inner shells are polarized as well. The dipole of the outer shell can polarize the inner shells to the limit that the sum of the primary and secondary dipoles is twice the primary scaled by the energy matching factors of the van der Waals bond given in Eq. (16.15). Thus, the limiting dipole due to polarization of the inner shells is given by $$\mu_{Xe} < 2c_1^{-1}qC_2 2c' = 2(0.24079)e(0.88682) \quad (16.160)$$

$$(6.69318 \times 10^{-11} \text{ m})$$

$$= 5.16444 \times 10^{-30} \text{ C} \cdot \text{m} = 1.54826 D$$

The condition of Eq. (16.160) is matched by the participation of the outer two shells as given in Table 46. At each shell, opposite charges distributions act as symmetrical point charges at the point of maximum separation, each being centered at ½ the shell radius from the origin. Using the parameters of Eq. (16.159) and $2c'=1.26483a_o=6.69318\times10^{-11}$ m (Eq. (16.157)) as well as the radius of the inner 5s shell of xenon (Eq. (10.102)), the van der Waals dipole of xenon is given in Table 46 as the sum of the moments of each participating shell.

TABLE 46

The parameters and van der Waals dipole bond moment of the Kr functional group (FG) of solid xenon.

| FG | $n_1$ | $(c_1)c_2$ | $(C_1)C_2$ | $E_B$(valence) | $E_A$(valence) | $\frac{q}{e}$ | Ion/IP/Z [121-122] | Bond Length 2c' (Å) (Eqs. (16.157) and (10.102)) | Bond moment μ (D) |
|---|---|---|---|---|---|---|---|---|---|
| Xe | 1 | 0.88682 | 1 | 10.75704 | 12.12984 | 0.24079 | Xe$^{6+}$ 91.67 | Xe5p³ HO 0.66932 Xe5s AO 0.55021 | 1.41050 |

The minimum-energy packing of xenon dipoles is face-centered cubic also called cubic close packing. In this case, each xenon atom has 12 nearest neighbors and the angle between the aligned dipoles is $$\frac{\pi}{4}$$

radians. As in the case with graphite, the van der Waals energy is the potential energy between interacting neighboring induced dipoles. Using $\mu_{Xe}$=1.41050 D=4.70492×10$^{-30}$ C·m (Table 46), the van der Waals energy is $$E_{van\ der\ Waals}(Xe) = 12 \frac{2(\mu_{Xe})^2}{4\pi\varepsilon_0(r_{Xe\ldots Xe})^3} \cos\left(\frac{\pi}{4}\right) \quad (16.161)$$

$$= \left(\frac{24(4.70492 \times 10^{-30} \text{ C} \cdot \text{m})^2}{4\pi\varepsilon_0 \left(2\sqrt{\frac{a_{Xe...Xe}a_0}{2C_1C_2}}\right)^3}\right) \cos\left(\frac{\pi}{4}\right)$$

The xenon interatomic distance is calculated using Eq. (16.25) with the van der Waals energy (Eq. (16.161)) between neighboring dipoles equated to the nascent bond energy. The energy matching parameter $c_2$ is the same that of the xenon dipole, and the reduced mass is $\mu=65$. The parameters are summarized in Table 47 and Eq. (16.162).

TABLE 47

The energy parameters (eV) of the xenon functional group (Xe ... Xe).

| Parameters | Xe ... Xe Group |
|---|---|
| $n_1$ | 1 |
| $C_1$ | 0.5 |
| $C_2$ | 0.88682 |
| $c_1$ | 1 |
| $c_2$ | 1 |
| $C_{1o}$ | 0.5 |
| $C_{2o}$ | 0.88682 |
| $V_e$ (eV) | −3.49612 |
| $V_p$ (eV) | 3.20821 |
| $T$ (eV) | 0.10960 |
| $V_m$ (eV) | −0.05480 |
| $E(AO/HO)$ (eV) | 0 |
| $\Delta E_{H_2MO(AO/HO)}$ (eV) | 0 |
| $E_{T(AO/HO)}$ (eV) | 0 |
| $E_{T(H_2MO)}$ (eV) | −0.23311 |
| $E_T$(atom-atom, msp³ · AO) (eV) | 0 |
| $E_{T(MO)}$ (eV) | −0.23311 |
| $\omega$ ($10^{15}$ rad/s) | 0.432164 |
| $E_K$ (eV) | 0.28446 |
| $\overline{E}_D$ (eV) | −0.00025 |
| $\overline{E}_{Kvib}$ (eV) | 0.00062 |
| $\overline{E}_{osc}$ (eV) | 0.00006 |
| $E_{T(Group)}$ (eV) | −0.23305 |

Substitution of the parameters of Table 47 and the interatomic cohesive energy of xenon (Eq. (16.161)) into Eq. (16.25) with $R=a_{Xe...Xe}$ gives $$\frac{-24(4.70492 \times 10^{-31} \text{ C} \cdot \text{m})^2}{4\pi\varepsilon_0 \left(2\sqrt{\frac{a_{Xe...Xe}a_0}{2(0.5)(0.88682)}}\right)^3} \cos\left(\frac{\pi}{4}\right) = \quad (16.162)$$

$$\left\{\left(\frac{-e^2}{8\pi\varepsilon_0\sqrt{\frac{a_{Xe...Xe}a_0}{2(0.5)(0.88682)}}}\right)\left(\ln\frac{a+\sqrt{\frac{a_{Xe...Xe}a_0}{2(0.5)(0.88682)}}}{a-\sqrt{\frac{a_{Xe...Xe}a_0}{2(0.5)(0.88682)}}}-1\right)\left(2-\frac{1}{2}\frac{a_0}{a_{Xe...Xe}}\right)\right\}$$

$$+\left(1+2\sqrt{\frac{2\hbar\sqrt{(0.5)(0.88682)\frac{e^2}{4\pi\varepsilon_o(a_{Xe...Xe})^3}}}{m_ec^2}}\right)+\left(\frac{1}{2}\right)$$

$$\hbar\sqrt{\frac{\frac{e^2}{8\pi\varepsilon_o(a_{Xe...Xe})^3}-\frac{e^2}{8\pi\varepsilon_o\left(a_{Xe...Xe}+\sqrt{\frac{a_{Xe...Xe}a_0}{2(0.5)(0.88682)}}\right)^3}}{65}}\right\}$$

From the energy relationship given by Eq. (16.162) and the relationships between the axes given by Eqs. (16.22-16.24), the dimensions of the Xe•••Xe MO can be solved.

The most convenient way to solve Eq. (16.162) is by the reiterative technique using a computer. The result to within the round-off error with five-significant figures is $$a_{Xe\text{···}Xe}=15.94999a_0=8.44037\times10^{-10} \text{ m} \quad (16.163)$$

The component energy parameters at this condition are given in Table 47. Substitution of Eq. (16.163) into Eq. (16.22) gives $$c'_{Xe\text{···}Xe}=4.24093a_0=2.24420\times10^{-10} \text{ m} \quad (16.164)$$

and internuclear distance between neighboring xenon atoms:

$$2c'_{Xe\text{···}Xe}(0 \text{ K})=8.48187a_0=4.48841\times10^{-10}$$
$$\text{m}=4.48841 \text{ Å} \quad (16.165)$$

The experimental xenon interatomic distance $2c_{C\text{···}C}'$ at the melting point of 161.35 K is [112, 113]

$$2c_{Xe\text{···}Xe}'(161.35 \text{ K})=4.492\times10^{-10} \text{ m}=4.492 \text{ Å} \quad (16.166)$$

The other interatomic bond MO parameters can also be determined by the relationships among the parameters. Substitution of Eqs. (16.163) and (16.164) into Eq. (16.23) gives $$b_{Xe\text{···}Xe}=c_{Xe\text{···}Xe}=15.37585a_0=8.13655\times10^{-10} \text{ m} \quad (16.167)$$

Substitution of Eqs. (16.163) and (16.164) into Eq. (16.25) gives $$e_{Xe\text{···}Xe}=0.26589 \quad (16.168)$$

A convenient method to calculate the lattice energy is to determine the electric field in solid xenon having an electric polarization density corresponding to the aligned dipoles moments, and in turn, the energy can be calculated from the energy of each dipole in the corresponding field using the electrostatic form of Gauss' equation. Substitution of the density of solid xenon at 0 K $$\rho = \frac{3.780 \text{ g}}{1\times10^{-6} \text{ m}^3}, \quad [113]$$

the MW=131.29 g mole, $N_A=6.0221415\times10^{23}$ molecules/mole, and the xenon dipole moment given in Table 46 into Eq. (16.53) gives:

$$U(Xe) = \frac{-2(\mu_{Xe})^2 \frac{\rho_{solid\ Xe}}{MW} N_A}{3\varepsilon_0} \quad (16.169)$$

$$= \frac{-2\left(\frac{4.70492 \times}{10^{-30}\ C \cdot m}\right)^2 \frac{\frac{3.780\ g}{1 \times 10^{-6}\ m^3}}{131.29\ g/mole} 6.0221415 \times}{3\varepsilon_0}$$

$$= -0.18037\ eV\ (-17.403\ kJ/mole)$$

$U(Xe)$ is also the negative of $E_{van\ der\ Waals}$, the van der Waals energy per xenon atom:

$$E_{van\ der\ Waals}(solid\ Xe, 0\ K/Xe) = 0.18037\ eV = 17.403\ kJ/mole \quad (16.170)$$

The experimental van der Waals energy is the cohesive energy [123]:

$$E_{van\ der\ Waals}(solid\ Xe, 0\ K) = 0.16608\ eV/Xe = 16.02472\ kJ/mole \quad (16.171)$$

The calculated results based on first principles and given by analytical equations are summarized in Table 48. Using xenon the atomic radius (Eq. (16.157)) and the nearest-neighbor distance (Eq. (16.165)), the lattice structure of xenon is shown in FIG. 21D. The charge density of the van der Waals dipoles of the crystalline lattice is shown in FIG. 22BD.

TABLE 48

The calculated and experimental geometrical parameters and interatomic van der Waals cohesive energy of solid xenon.

| Parameter | Calculated | Experimental | Ref. for Exp. |
|---|---|---|---|
| Solid Xenon Interatomic Distance $2c'_{C...C}$ | 4.4884 Å (T = 0 K) | 4.492 Å (T = 161.35 K) | 113 |
| van der Waals Energy per Xenon Atom (0 K) | 0.18037 eV | 0.16608 eV | 123 |

Reaction Kinetics and Thermodynamics

Reaction kinetics may be modeled using the classical solutions of reacting species and their interactions during collisions wherein the bond order of the initial and final bonds undergo a decreasing and increasing bond order, respectively, with conservation of charge and energy. Collisions can be modeled starting with the simple hard sphere model with conservation of energy and momentum. The energy distribution may be modeled using the appropriate statistical thermodynamics model such as Maxwell-Boltzmann statistics. Low-energy collisions are elastic, but for sufficiently high energy, a reaction may occur. Hot reacting species such as molecules at the extreme of the kinetic energy distribution can achieve the transition state, the intermediate species at the cross over point in time and energy between the reactants and products. The rate function to form the transition state may depend on the collisional orientation as well as the collisional energy. Bond distortion conserves the energy and momentum of the collision from the trajectories of the reactants. For sufficient distortion due to a sufficiently energetic collision at an appropriate relative orientation, a reaction occurs wherein the products exiting the collision event are different from the reactants entering the collision. The initial reactant energy and momentum as well as those arising from any bonding energy changes are conserved in the translational, rotational, and vibrational energies of the products. The bond energy changes are given by the differences in the energies of the product and reactants molecules wherein the geometrical parameters, energies, and properties of the latter can be solved using the same equations as those used to solved the geometrical parameters and component energies of the individual molecules as given in the Organic Molecular Functional Groups and Molecules section. The bond energy changes at equilibrium determine the extent of a reaction according to the Gibbs free energy of reaction. Whereas, the corresponding dynamic reaction-trajectory parameters of translational, rotational, and vibrational energies as well as the time dependent electronic energy components such as the electron potential and kinetic energies of intermediates correspond to the reaction kinetics. Each aspect will be treated next in turn.

Consider the gas-phase reaction of two species A and B comprising the reactants that form one or more products $C_n$ where n is an integer:

$$A + B \leftrightharpoons C_1 + \ldots + C_N \quad (16.172)$$

Arising from collisional probabilities, the concentrations (denoted [A],[B], ... ) as a function of time can be fitted to a second-order rate law $$-\frac{d[A]}{dt} = k[A][B] - k' \prod_{i=1}^{n} [C_i] \quad (16.173)$$

where k and k' are the forward and reverse rate constants. The equilibrium constant K corresponding to the balance between the forward and reverse reactions is given by the quotient of the forward and reverse rate constants:

$$K = \frac{k}{k'} \quad (16.174)$$

The relationship between the temperature-dependent equilibrium constant and the standard Gibbs free energy of reaction $\Delta G_T^0(T)$ at temperature T is $$K = Q_K(T) e^{\frac{-\Delta G_T^0(T)}{RT}} \quad (16.175)$$

where R is the ideal gas constant, $$Q_K(T) = \frac{\prod_{i=1}^{n} [C_i]}{[A][B]} \quad (16.176)$$

is the reaction quotient at the standard state, and $$\Delta G_T^0(T) = \Delta H_T^0(T) - T\Delta S_T^0 \quad (16.177)$$

where $\Delta H_T^0(T)$ and $\Delta S_T^0$ are the standard-state enthalpy and entropy of reaction, respectively. Rearranging Eq. (16.175) gives the free energy change upon reaction:

$$\Delta G = RT \ln \frac{Q_K}{K} \quad (16.178)$$

If the instantaneous free energy change is zero, then the reaction is at equilibrium. An exergonic or work-producing reaction corresponds to the cases with $\Delta G_T^0(T)$ or $\Delta G$ negative, and endergonic or work consuming reactions corresponds to positive values. The enthalpy of reaction or heat of reaction at constant pressure is negative for an exothermic (heat releasing) reaction, and is positive for an endothermic (heat absorbing) reaction. The enthalpy of reaction may be calculated by Hess's law as the difference of the sum of the heats of formation of the products minus the sum of the heats of formation of the reactants wherein the individual heats of the molecules are solved using the equations given in the Organic Molecular Functional Groups and Molecules section.

Transition State Theory

Transition state theory (TST) has been widely validated experimentally. It entails the application classical trajectory calculations that allow the study of the dynamics at the microscopic level such as differential cross sections, total cross sections, and product energy distributions, as well as at the macroscopic level for the determination of thermal rate constants by solving the classical equations of motion with the formation of the transition state. The reaction trajectory parameters give rise to terms of a classical thermodynamic kinetics equation discovered in 1889 by Arrhenius and named after him. The data of the variation of the rate constant k with temperature of many reactions fit the Arrhenius equation given by $$k = Ae^{\frac{-E_a}{RT}} \qquad (16.179)$$

where $E_a$ is the activation energy and A is a preexponential or frequency factor that may have a relatively small temperature dependence compared to the exponential term of Eq. (16.179). For reactions that obey the Arrhenius equation, when ln k is plotted versus 1/T in a so-called Arrhenius plot, the slope is the constant $-E_a/R$, and the intercept is A. Eq. (16.179) confirms that typically two colliding molecules require a certain minimum kinetic energy of relative motion to sufficiently distort initial reactant bonds and concomitantly allow nascent bonds to form. The cross over species from reactants to products called the transition state will proceed through the minimum energy complex involving the reactants. Thus, the activation energy can be interpreted as the minimum energy that the reactants must have in order to form the transition state and transform to product molecules. $E_a$ can be calculated from the total energy of the transition state relative to that of the reactants and is achieved when the thermal energy of the reactants overcomes the energy deficit between the energy of the reactants and that of the transition state. The preexponential factor corresponds to the collision frequency and energy of collisions upon which the formation of the transition state is dependent.

For bimolecular reactions, transition state theory yields [124]

$$k(T) = \frac{1}{(k_B T)h} \gamma(T) K^\circ \exp(-\Delta G_T^{\ddagger \circ}/RT) \qquad (16.180)$$

where $\Delta G_T^{\ddagger \circ}$ is the quasi-thermodynamic free energy of activation, $\gamma(T)$ is a transmission coefficient, $K^\circ$ is the reciprocal of the concentration, h is Planck's constant, and $k_B$ is the Boltzmann constant. The factor $$\frac{1}{(k_B T)h}$$

is obtained by dynamical classical equations of motion involving species trajectories having a statistical mechanical distribution. Specifically, the reactant molecular distribution is typically a Maxwell-Boltzmann distribution. The classical derivation of the preexponential term of the Arrhenius equation can be found in textbooks and review articles such as section 2.4 of Ref. [124]. Typically the A term can be accurately determined from the Maxwell-Boltzmann-distribution-constrained classical equations of motion by sampling or by using Monte Carlo methods on many sets (usually more than ten thousand) of initial conditions for the coordinates and momenta involving the trajectories. The translational levels are a continuous distribution, and the rotational and vibrational levels are quantized according to the classical equations given, for example, in the Vibration of the Hydrogen Molecular Ion section and the Diatomic Molecular Rotation section.

$S_N^2$ Reaction of Cl⁻ with $CH_3Cl$

Consider the $S_N2$ (bimolecular nucleophilic substitution) gas-phase reaction of Cl⁻ with chloromethane through a transition state:

$$Cl^- + CH_3Cl \rightarrow ClCH_3 + Cl^- \qquad (16.181)$$

The corresponding Arrhenius equation for the reaction given by Eq. (16.179) is $$k(T) = \frac{k_B T}{h} \frac{Q^\ddagger}{\Phi^R} e^{\frac{-\Delta E^\ddagger}{k_B T}} \qquad (16.182)$$

where $k_B$ is the Boltzmann constant, h is Planck's constant, $\Delta E^\ddagger$ is the activation energy of the transition state $\ddagger$, T is the temperature, $\Phi^R$ is the reaction partition per unit volume, and $Q^\ddagger$ is the coordinate independent transition-state partition function. The preexponential factor $$\frac{k_B T}{h} \frac{Q^\ddagger}{\Phi^R}$$

has previously been calculated classically and shown to be in agreement with the experimental rate constant [125]. Then, only the transition state need be calculated and its geometry and energy compared to observations to confirm that classical physics is predictive of reaction kinetics. The activation energy can be calculated by determining the energy at the point that the nascent bond with the chloride ion is the same as that of the leaving chlorine wherein the negative charge is equally distributed on the chlorines. The rearrangement of bonds and the corresponding electron MOs of the reactants and products can be modeled as a continuous transition of the bond orders of the participating bonds from unity to zero and vice versa, respectively, wherein the transition state is a minimum-energy molecule having bonds between all of the reactants, Cl⁻ and $CH_3Cl$.

Transition State

The reaction proceeds by back-side attack of $Cl^-$ on $CH_3Cl$. Based on symmetry, the reaction pathway passes through a $D_{3h}$ configuration having $Cl^{\delta-}$—C—$Cl^{\delta\delta}$ on the $C_3$ axis. The hydrogen atoms are in the $\sigma_h$ plane with the bond distances the same as those of the $CH_3$ functional group given in the Alkyl Chlorides section, since this group is not involved in the substitution reaction. The transition-state group $Cl^{\delta-}$—C—$Cl^{\delta\delta}$ is treated as a three-centered-bond functional group that comprises a linear combination of $Cl^-$ and the C—Cl group of chloromethane (C—Cl (i) given in Table 15.33). It is solved using the Eq. (15.51) with the total energy matched to the sum of the $H_2$-type ellipsoidal MO total energy, $-31.63536831$ eV given by Eq. (11.212) as in the case of chloromethane, and the energy of the two outer electrons of $Cl^-$, $E(Cl^-) = -IP_1 - IP_2 - 12.96764\ eV - 3.612724\ eV = -16.58036\ eV$ [15, 126]. These electrons are contributed to form the back-side-attack bond. Then, the corresponding parameter $E_T^{(AO/HO)}$ (eV) is $-14.63489\ eV - 16.58036\ eV = -31.21525\ eV$ due to the match of the MO energy to both $E(C,2sp_3) = -14.63489\ eV$ (Eq. (15.25)) and $E(Cl^-)$, and $E_{initial}^{(c_5 AO/HO)}$ (eV) is $-16.58036\ eV$ corresponding to the initial energy of the $Cl^-$ electrons. Also, due to the two C—Cl bonds of the $Cl^{\delta-}$—C—$Cl^{\delta-}$ functional group $n_1 = 2$. Otherwise all of the parameters of Eq. (15.51) remain the same as those of chloromethane given in Table 15.36. The geometrical (Eqs. (15.1-15.5) and (15.51)), intercept (Eqs. (15.80-15.87)), and energy (Eqs. (15.6-15.11) and (15.17-15.65)) parameters are given in Tables 49, 50, and 51, respectively. The color scale, translucent view of the charge density of the chloride-ion-chloromethane transition state comprising the $Cl^{\delta-}$—C—$Cl^{\delta-}$ functional group is shown in FIG. 23. The transition state bonding comprises two paired electrons in each $Cl^{\delta-}$—C MO with two from $Cl^-$, one from Cl and one from $CH_3$. As a symmetrical three-centered bond, the central bonding species are two Cl bound to a central $CH_3^+$ per $Cl^{\delta-}$—C MO with a continuous current onto the C—H MO at the intersection of each $Cl^{\delta-}$—C MO with the $CH_3^+$ group. Due to the four electrons and the valence of the chlorines, the latter possess a partial negative charge of $-0.5e$ distributed on each $Cl^{\delta-}$—C MO such that the far field is equivalent to that of the corresponding point charge at each Cl nucleus.

TABLE 49

The geometrical bond parameters of the $Cl^{\delta-}$—C—$Cl^{\delta-}$ and $CH_3$ functional groups of the chloride-ion-chloromethane transition state.

| Parameter | $Cl^{\delta-}$—C—$Cl^{\delta-}$ Group | C—H ($CH_3$) Group |
|---|---|---|
| a ($a_0$) | 3.70862 | 1.64920 |
| c' ($a_0$) | 2.13558 | 1.04856 |
| Bond Length 2c' (Å) | 2.26020 | 1.10974 |
| Literature Bond Length (Å) | 2.3-2.4 [125, 127] | 1.06-1.07 [125] |
| b, c ($a_0$) | 3.03202 | 1.27295 |
| e | 0.57584 | 0.63580 |

TABLE 50

The MO to HO and AO intercept geometrical bond parameters of the $Cl^{\delta-}$—C—$Cl^{\delta-}$ and $CH_3$ functional groups of the chloride-ion-chloromethane transition state.

| Bond | Atom | $E_T$ (eV) Bond 1 | $E_T$ (eV) Bond 2 | $E_T$ (eV) Bond 3 | $E_T$ (eV) Bond 4 | Final Total Energy $C2sp^3$ (eV) | $r_{initial}$ ($a_0$) |
|---|---|---|---|---|---|---|---|
| $Cl^{\delta-}$—C—$Cl^{\delta-}$ | C | −0.36229 | −0.36229 | 0 | 0 | −152.34026 | 0.91771 |
| $Cl_a^{\delta-}$—C—$Cl_b^{\delta-}$ | $Cl_a^{\delta-}$ | −0.36229 | 0 | 0 | 0 | | 2.68720 |
| $Cl_a^{\delta-}$—C—$Cl_b^{\delta-}$ | $Cl_b^{\delta-}$ | −0.36229 | 0 | 0 | 0 | | 1.05158 |
| C—H ($CH_3$) | C | −0.36229 | −0.36229 | 0 | 0 | −152.34026 | 0.91771 |

| Bond | $r_{final}$ ($a_0$) | $E_{Coulomb}(C2sp^3)$ (eV) Final | $E(C2sp^3)$ (eV) Final | $\theta'$ (°) | $\theta_1$ (°) | $\theta_2$ (°) | $d_1$ ($a_0$) | $d_2$ ($a_0$) |
|---|---|---|---|---|---|---|---|---|
| $Cl^{\delta-}$—C—$Cl^{\delta-}$ | 0.87495 | −15.55033 | −15.35946 | | | | | |
| $Cl_a^{\delta-}$—C—$Cl_b^{\delta-}$ | 0.89582 | −15.18804 | | | | | | |
| $Cl_a^{\delta-}$—C—$Cl_b^{\delta-}$ | 0.89582 | −15.18804 | | | | | | |
| C—H ($CH_3$) | 0.87495 | −15.55033 | −15.35946 | 78.85 | 101.15 | 42.40 | 1.21777 | 0.16921 |

$E_T$ is $E_T$(atom-atom, $msp^3 \cdot AO$).

TABLE 51

The energy parameters (eV) of the $Cl^{\delta-}$—C—$Cl^{\delta-}$ and $CH_3$ functional groups of the chloride-ion-chloromethane transition state.

| Parameters | $Cl^{\delta-}$—C—$Cl^{\delta-}$ Group | $CH_3$ Group |
|---|---|---|
| $n_1$ | 2 | 3 |
| $n_2$ | 0 | 2 |
| $n_3$ | 1 | 0 |
| $C_1$ | 0.5 | 0.75 |
| $C_2$ | 0.81317 | 1 |
| $c_1$ | 1 | 1 |
| $c_2$ | 1 | 0.91771 |
| $c_3$ | 1 | 0 |
| $c_4$ | 2 | 1 |
| $c_5$ | 1 | 3 |
| $C_{1o}$ | 0.5 | 0.75 |
| $C_{2o}$ | 0.81317 | 1 |
| $V_e$ (eV) | −33.44629 | −107.32728 |
| $V_p$ (eV) | 12.74200 | 38.92728 |
| $T$ (eV) | 4.50926 | 32.53914 |
| $V_m$ (eV) | −2.25463 | −16.26957 |
| $E(AO/HO)$ (eV) | −31.21525 | −15.56407 |
| $\Delta E_{H_2MO}^{(AO/HO)}$ (eV) | −1.44915 | 0 |
| $E_T^{(AO/HO)}$ (eV) | −29.76611 | −15.56407 |
| $E_{T(n_3AO/HO)}$ (eV) | −16.58036 | 0 |
| $E_{T(H_2MO)}$ (eV) | −48.21577 | −67.69451 |
| $E_T$(atom-atom, $msp^3 \cdot AO$) (eV) | −1.44915 | 0 |
| $E_{T(MO)}$ (eV) | −49.66491 | −67.69450 |
| $\omega$ ($10^{15}$ rad/s) | 3.69097 | 24.9286 |
| $E_K$ (eV) | 2.42946 | 16.40846 |
| $\overline{E}_D$ (eV) | −0.07657 | −0.25352 |
| $\overline{E}_{Kvib}$ (eV) | 0.08059 [5] | 0.35532 (Eq. (13.458)) |

TABLE 51-continued

The energy parameters (eV) of the $Cl^{\delta-}$—C—$Cl^{\delta-}$ and $CH_3$ functional groups of the chloride-ion-chloromethane transition state.

| Parameters | $Cl^{\delta-}$—C—$Cl^{\delta-}$ Group | $CH_3$ Group |
|---|---|---|
| $\overline{E}_{osc}$ (eV) | −0.03628 | −0.22757 |
| $E_{mag}$ (eV) | 0.14803 | 0.14803 |
| $E_T^{(Group)}$ (eV) | −49.73747 | −67.92207 |
| $E_{initial}^{(c_4AO/HO)}$ (eV) | −14.63489 | −14.63489 |
| $E_{initial}^{(c_5AO/HO)}$ (eV) | −16.58036 | −13.59844 |
| $E_D^{(Group)}$ (eV) | 3.73930 | 12.49186 |

The bond energy of the C—Cl group of chloromethane from Table 15.36 is $E_D^{(Group)}$ (eV)=3.77116 eV compared to the bond energy of the $Cl^{\delta-}$—C—$Cl^{\delta-}$ functional group of the chloride-ion-chloromethane transition state of $E_D^{(Group)}$ (eV)=3.73930 eV (Table 16.44). Since the energies of the $CH_3$ functional groups are unchanged, the chloride-ion-chloromethane transition state is $\Delta E$=+0.03186 eV (+0.73473 kcal/mole) higher in energy than chloromethane. Experimentally, the transition state is about 1±1 kcal/mole higher [128]. Using this energy as the corresponding activation energy $\Delta E^{\ddagger}$ of Eq. (16.182) with the classically determined preexponential factor $$\frac{k_B T}{h} \frac{Q^{\ddagger}}{\Phi^R}$$

predicts the experimental reaction rate very well [125]. Negatively-Charged Molecular Ion Complex C In addition to the nature and energy of the transition state designated by $\ddagger$, experimental gas-phase rate constants indicate that the reaction of $Cl^-$ with $CH_3Cl$ passes through a bound state comprising the attachment of $Cl_-$ to the positive dipole of $CH_3Cl$ [125, 127-128] (the dipole moment of the C—Cl functional group is given in the Bond and Dipole Moments section). This negatively-charged molecular ion complex designated $\mathbb{C}$ exists as a more stable state in between the reactants and the transition state, and by equivalence of the chlorines, it also exists between the transition state and the products. Experimentally $\mathbb{C}$ is 12.2±2 kcal/mole more stable than the isolated reactants and products, $Cl^-$ and $CH_3Cl$. Thus, an energy well corresponding to $\mathbb{C}$ occurs on either side of the energy barrier of the transition state $\ddagger$ that is about 1±1 kcal/mole above the reactants and products [125, 128]. Thus, the combination of the depth of this well and the barrier height yields an intrinsic barrier to nucleophilic substitution given by the reaction of Eq. (16.181) of 13.2 4±2.2 kcal/mole [125, 128].

The negatively-charged molecular ion complex $\mathbb{C}$ comprises the functional groups of $CH_3Cl$ (C—Cl (i) and $CH_3$ given in Table 15.33 of the Alkyl Chlorides section) and a $Cl_-.C^{\delta+}$ functional group wherein $Cl^-$ is bound to the $CH_3Cl$ moiety by an ion-dipole bond. As given in the case of the dipole-dipole bonding of ice, liquid water, and water vapor as well as the van der Waals bonding in graphite and noble gasses given in the Condensed Matter Physics section, the bond energy and bond distance of the $Cl^-.C^{\delta+}$ functional group are determined by the limiting energy and distance of the formation of a corresponding nascent $Cl^-$—$CH_3Cl$ covalent bond that destabilizes the C—Cl bond of the $CH_3Cl$ moiety by involving charge density of its electrons in the formation the nascent bond. Subsequently, the higher energy $Cl^{\delta-}$—C—$Cl^{\delta-}$ functional group of the transition state is formed.

The energy and geometric parameters of the $Cl^-.C^{\delta+}$ functional group are solved using Eq. (15.51) with the total energy matched to the $H_2$-type ellipsoidal MO total energy, −31.63536831 eV. The parameter $E_T(AO/HO)$ (eV) is −14.63489 eV-3.612724 eV=−18.24761 eV due to the match of the MO energy to both $E(C,2sp^3)$=−14.63489 eV (Eq. (15.25)) and the outer electron of $E(Cl^-)$ (−$IP_1$=3.612724 eV) [126] that forms the nascent bond by the involving the electrons of the C—Cl group of the $CH_3Cl$ moiety. Then, $E_{initial}^{(c_5AO/HO)}$ (eV) is −3.612724 eV corresponding to the initial energy of the outer $Cl^-$ electron. Also, $E_T$(atom-atom,msp$^3$.AO) in Eq. (15.61) is −1.85836 eV due to the charge donation from the C HO to the MO based on the energy match between the $C2sp^3$ HOs corresponding to the energy contribution of methylene, −0.92918 eV (Eq. (14.513). $E_{mag}$=0 since the $Cl^-$ electrons are paired upon dissociation, and the vibrational energy of the transition state is appropriate for $Cl^-.C^{\delta+}$. Otherwise, all of the parameters of Eq. (15.51) remain the same as those of chloromethane given in Table 15.36. The geometrical (Eqs. (15.1-15.5) and (15.51)), intercept (Eqs. (15.80-15.87)), and energy (Eqs. (15.6-15.11) and (15.17-15.65)) parameters are given in Tables 52, 53, and 54, respectively. The color scale, translucent view of the charge density of the negatively-charged molecular ion complex $\mathbb{C}$ comprising the $Cl^-.C^{\delta+}$ functional group is shown in FIG. 24. The bonding in the $\mathbb{C}$ complex comprises two paired electrons in the $Cl^-.C^{\delta+}$ MO with ½ of the charge density from $Cl^-$ and the other half from $CH_3$. The central bonding species are a Cl bound to a central $CH_3^+$ with a continuous current onto the C—H MO at the intersection of the $Cl^-.C^{\delta+}$ MO with the $CH_3^+$ group. Due to the two electrons and the valence of the chlorine, the latter possess a negative charge of −e distributed on the $Cl^-.C^{\delta+}$ MO such that the far field is equivalent to that of the corresponding point charge at the Cl nucleus. The bonding in the $CH_3Cl$ moiety is equivalent to that of chloromethane except that the C—H bonds are in a plane to accommodate the $Cl^-.C^{\delta+}$ MO.

TABLE 52

The geometrical bond parameters of the $Cl^- \bullet C^{\delta+}$, C—Cl, and $CH_3$ functional groups of the negatively-charged molecular ion complex $\mathbb{C}$.

| Parameter | $Cl^- \bullet C^{\delta+}$ Group | C—H ($CH_3$) Group | C—Cl (i) Group |
|---|---|---|---|
| a ($a_0$) | 2.66434 | 1.64920 | 2.32621 |
| c' ($a_0$) | 1.81011 | 1.04856 | 1.69136 |
| Bond Length 2c' (Å) | 1.91574 | 1.10974 | 1.79005 |
| Literature Bond Length (Å) | >1.80 curve fit [127] | 1.06-1.07 [1] | 1.785 [1] (methyl chloride) |
| b, c ($a_0$) | 1.95505 | 1.27295 | 1.59705 |
| e | 0.67938 | 0.63580 | 0.72709 |

TABLE 53

The MO to HO and AO intercept geometrical bond parameters of the $Cl^- \cdot Cl^{\delta+}$, C—Cl, and $CH_3$ functional groups of the negatively-charged molecular ion complex C.

| Bond | Atom | $E_T$ (eV) Bond 1 | $E_T$ (eV) Bond 2 | $E_T$ (eV) Bond 3 | $E_T$ (eV) Bond 4 | Final Total Energy $C2sp^3$ (eV) |
|---|---|---|---|---|---|---|
| $Cl^- \cdot C^{\delta+}$ | C | −0.82688 | −0.72457 | 0 | 0 | |
| $Cl^- \cdot C^{\delta+}$ | $Cl^-$ | −0.82688 | 0 | 0 | 0 | |
| C—Cl | C | −0.82688 | −0.72457 | 0 | 0 | −153.16714 |
| C—Cl | Cl | −0.72457 | 0 | 0 | 0 | |
| C—H ($CH_3$) | C | −0.82688 | −0.72457 | 0 | 0 | −153.16714 |

| Bond | $r_{initial}$ ($a_0$) | $r_{final}$ ($a_0$) | $E_{Coulomb}(C2sp^3)$ (eV) Final | $E(C2sp^3)$ (eV) Final |
|---|---|---|---|---|
| $Cl^- \cdot C^{\delta+}$ | 0.91771 | 0.83078 | −16.37720 | −16.18634 |
| $Cl^- \cdot C^{\delta+}$ | 2.68720 | 0.86923 | −15.65263 | |
| C—Cl | 0.91771 | 0.83078 | −16.37720 | −16.18634 |
| C—Cl | 1.05158 | 0.87495 | −15.55033 | |
| C—H ($CH_3$) | 0.91771 | 0.83078 | −16.37720 | −16.18634 |

| Bond | $\theta'$ (°) | $\theta_1$ (°) | $\theta_2$ (°) | $d_1$ ($a_0$) | $d_2$ ($a_0$) |
|---|---|---|---|---|---|
| $Cl^- \cdot C^{\delta+}$ | | | | | |
| $Cl^- \cdot C^{\delta+}$ | 16.80 | 163.20 | 7.38 | 2.64225 | 0.83214 |
| C—Cl | 63.91 | 116.09 | 27.85 | 2.05675 | 0.36539 |
| C—Cl | 69.62 | 110.38 | 30.90 | 1.99599 | 0.30463 |
| C—H ($CH_3$) | 73.30 | 106.70 | 38.69 | 1.28725 | 0.23869 |

$E_T$ is $E_T$(atom-atom, $msp^3 \cdot$ AO).

TABLE 54

The energy parameters (eV) of the $Cl^- \bullet C^{\delta+}$, C—Cl, and $CH_3$ functional groups of the negatively-charged molecular ion complex C.

| Parameters | $Cl^- \bullet C^{\delta+}$ Group | $CH_3$ Group | C—Cl (i) Group |
|---|---|---|---|
| $n_1$ | 1 | 3 | 1 |
| $n_2$ | 0 | 2 | 0 |
| $n_3$ | 0 | 0 | 0 |
| $C_1$ | 0.5 | 0.75 | 0.5 |
| $C_2$ | 0.81317 | 1 | 0.81317 |
| $c_1$ | 1 | 1 | 1 |
| $c_2$ | 1 | 0.91771 | 1 |
| $c_3$ | 0 | 0 | 1 |
| $c_4$ | 2 | 1 | 2 |
| $c_5$ | 1 | 3 | 0 |
| $C_{1o}$ | 0.5 | 0.75 | 0.5 |
| $C_{2o}$ | 0.81317 | 1 | 0.81317 |
| $V_e$ (eV) | −24.89394 | −107.32728 | −29.68411 |
| $V_p$ (eV) | 7.51656 | 38.92728 | 8.04432 |
| $T$ (eV) | 4.67169 | 32.53914 | 6.38036 |
| $V_m$ (eV) | −2.33584 | −16.26957 | −3.19018 |
| $E$(AO/HO) (eV) | −18.24761 | −15.56407 | −14.63489 |
| $\Delta E_{H_2MO}^{(AO/HO)}$ (eV) | −1.65376 | 0 | −1.44915 |
| $E_T^{(AO/HO)}$ (eV) | −16.59386 | −15.56407 | −13.18574 |
| $E_T^{(H_2MO)}$ (eV) | −31.63537 | −67.69451 | −31.63536 |
| $E_T$(atom-atom, $msp^3 \cdot$ AO) (eV) | −1.65376 | 0 | −1.44915 |
| $E_T^{(MO)}$ (eV) | −33.28913 | −67.69450 | −33.08452 |
| $\omega$ ($10^{15}$ rad/s) | 6.06143 | 24.9286 | 7.42995 |
| $E_K$ (eV) | 3.98974 | 16.40846 | 4.89052 |
| $\bar{E}_D$ (eV) | −0.13155 | −0.25352 | −0.14475 |
| $\bar{E}_{Kvib}$ (eV) | 0.02790 [129] | 0.35532 (Eq. (13.458)) | 0.08059 [5] |
| $\bar{E}_{osc}$ (eV) | −0.11760 | −0.22757 | −0.10445 |
| $E_{mag}$ (eV) | 0 | 0.14803 | 0.14803 |
| $E_T^{(Group)}$ (eV) | −33.40672 | −67.92207 | −33.18897 |
| $E_{initial}^{(c_4AO/HO)}$ (eV) | −14.63489 | −14.63489 | −14.63489 |
| $E_{initial}^{(c_5AO/HO)}$ (eV) | −3.612724 | −13.59844 | 0 |
| $E_D^{(Group)}$ (eV) | 0.52422 | 12.49186 | 3.77116 |

The bond energies of the $CH_3Cl$ moiety are unchanged to the limit of the formation of the $Cl^- \cdot C^{\delta+}$ functional group of the negatively-charged molecular ion complex C. Thus, the energy of stabilization of forming the ion-dipole complex is equivalent to the bond energy of the $Cl^- \cdot C^{\delta+}$ functional group. Experimentally C is 12.2±2 kcal/mole more stable than the isolated reactants and products [125, 127-128], $Cl^-$ and $CH_3Cl$. The bond energy of the $Cl^- \cdot C^{\delta+}$ functional group of the negatively-charged molecular ion complex C of $E_D^{(Group)}$=12.08900 kcal/mole (0.52422 eV) given in Table 16.47 matches the experimental stabilization energy very well. A simulation of the reaction of Eq. (16.181) is available on the internet [130].

Excited States of the Hydrogen Molecule
Force Balance of the Excited States of the Hydrogen Molecule In the mathematical limit, as the eccentricity goes to zero the hydrogen molecule becomes the helium atom. The excited states of the hydrogen molecule are determined by the same physics as those of the helium atom. It was shown in the Excited States of Helium section that the inner atomic orbital is essentially that of $He^+$ for all excited states with the exact result upon ionization. The infinite $H_2$ excited state corresponds to a free electron with the inner MO and protons comprising $H_2^+$. Implicit in the calculation of the energy of the outer electron of each $H_2$ excited state is that the inner electron has the geometrical parameters, component energies, and the total energy of $H_2^+$ as shown to very good approximation for the inner atomic electron of helium exited states. For $H_2$, the excited-state photon's two-dimensional ellipsoidal electric field at the outer electron superimposes that of the field of the nuclei at the foci of the inner MO and inner MO charge such that the resultant electric field has a magnitude $e/n$ in the direction of $i_\xi$ at the outer electron where $n=2, 3, 4, \ldots$ for excited states. Then, the force balance of the outer excited-state electron is given by balance between the centrifugal force, the central Coulombic force corresponding to the effective central field due to the superposition of photon field at the outer electron and the net field of the protons at the foci of the inner MO, and the magnetic forces for the particular spin and orbital state. The geometrical parameters for $H_2$ are determined from the semimajor axis given by the force balance and the relationships among the ellipsoidal parameters. The energies corresponding to the excited electron are given by the prolate spheroidal energy equations given in the Derivation of the General Geometrical and Energy Equations of Organic Chemistry section except for a ½ correction corresponding to a single electron, and the electric terms are scaled according to the effective central field of $1/n$.

Singlet Excited States $l=0$

The force balance between the electric, magnetic, and centrifugal forces of the outer electron given by Eqs. (9.10) and (11.285) is $$\frac{\hbar^2}{m_e a^2 b^2} D = \frac{1}{n} \frac{e^2}{8\pi\varepsilon_o a b^2} D + \frac{1}{n} \frac{2m}{3} \frac{1}{2} \frac{\hbar^2}{2m_e a^2 b^2} D \qquad (12.37)$$

where the geometrical factor due to the rotation about the semimajor axis is given by Eq. (11.391) and m is a positive or negative integer due to the symmetry of the angular momentum components as given in the Force Balance of Hydrogen-Type Molecules section. The parametric solution given by Eq. (11.83) occurs when semimajor axis, a, is $$a = a_0 \left( 2n - \frac{m}{3} \right) \qquad (12.38)$$

The internuclear distance, 2c', which is the distance between the foci is given by Eq. (11.79) where $p=1/n$.

$$2c' = 2\sqrt{\frac{aa_0}{2p}} = 2a_0 \sqrt{\frac{n\left(2n - \frac{m}{3}\right)}{2}} \qquad (12.39)$$

The semiminor axis is given by Eq. (11.80).

$$b = \sqrt{a^2 - c'^2} = a_0 \left(2n - \frac{m}{3}\right)\sqrt{1 - \frac{n}{2\left(2n - \frac{m}{3}\right)}} \qquad (12.40)$$

The eccentricity, e is given by Eq. (11.67).

$$e = \frac{c'}{a} = \sqrt{\frac{n}{2\left(2n - \frac{m}{3}\right)}} \qquad (12.41)$$

$l \neq 0$

The exited singlet states of the hydrogen molecule for $l \neq 0$ are solved using the same approach as those of the excited states of the helium atom given in the corresponding section, wherein the force balance due to the $a_{Mag}(l,m)$ terms corresponding to prolate spheroid geometry rather than spherical are also associated Legendre functions or spherical harmonics with regard to the semimajor axis as given by Li, Kang, and Leong [131].

The magnetic forces comprise the component of Eq. (12.37) corresponding to the nondynamic current and the $a_{Mag}(l,m)$ component due to the time dynamic modulation current and its interaction with electron spin. The force balance between the electric, magnetic, and centrifugal forces of the outer electron given by Eqs. (12.37) and (9.52) is $$\frac{\hbar^2}{m_e a^2 b^2} D = \frac{1}{n} \frac{e^2}{8\pi\varepsilon_o a b^2} D + \frac{1}{n} \frac{m}{3} \frac{\hbar^2}{2m_e a^2 b^2} D - \qquad (12.42)$$

$$\frac{1}{n} \frac{\frac{3}{2}}{(2l+1)!!} \left(\frac{l+1}{l}\right)^{1/2} \frac{1}{l+2} \frac{1}{2} \frac{\hbar^2}{m_e a^2 b^2} \left(1 - \sqrt{\frac{l}{l+1}}\right) D$$

where the $\sqrt{3/4}$ and $r^{-3}$ terms are replaced by one and $Da^{-2}b^{-2}$ as given in the Force Balance of Hydrogen-Types Molecules section. The parametric solution given by Eq. (11.83) occurs when semimajor axis, a, is $$a = a_0 \left( 2n - \frac{m}{3} + \frac{\frac{3}{2}}{(2l+1)!!} \left(\frac{l+1}{l}\right)^{1/2} \frac{1}{l+2} \left(1 - \sqrt{\frac{l}{l+1}}\right) \right) \qquad (12.43)$$

The internuclear distance, 2c', which is the distance between the foci is given by Eq. (11.79) where $p=1/n$.

$$2c' = 2\sqrt{\frac{aa_0}{2p}} = 2a_0 \sqrt{\frac{n\left(n - \frac{m}{3} + \frac{\frac{3}{2}}{(2l+1)!!}\left(\frac{l+1}{l}\right)^{1/2} 2\frac{1}{l+2}\left(1 - \sqrt{\frac{l}{l+1}}\right)\right)}{2}} \qquad (12.44)$$

The semiminor axis is given by Eq. (11.80).

$$b = \sqrt{a^2 - c'^2} \qquad (12.45)$$

-continued $$= a_0 \left( \frac{\left(2n - \frac{m}{3} + \frac{\frac{3}{2}}{(2l+1)!!}\left(\frac{l+1}{l}\right)^{1/2}\right)}{\frac{1}{l+2}\left(1 - \sqrt{\frac{l}{l+1}}\right)} \right)$$

The eccentricity, e, is given by Eq. (11.67).

$$e = \frac{c'}{a} = \sqrt{\frac{n}{2\left(2n - \frac{m}{3} + \frac{\frac{3}{2}}{(2l+1)!!}\left(\frac{l+1}{l}\right)^{1/2}\right)\frac{1}{l+2}\left(1 - \sqrt{\frac{l}{l+1}}\right)}} \quad (12.46)$$

Triplet Excited States
l=0

The force-balance equation and semimajor-axis solution of triplet excited states for l=0 are equivalent to those of the corresponding singlet excited states given by Eqs. (12.37-12.38). However, due to the triplet spin state, the magnetic force in Eq. (12.37) is increased by a factor of two as in the case of the corresponding helium exited states given in Eq. (9.31). Thus, m is replaced by 2 m. Then, the force balance between the electric, magnetic, and centrifugal forces of the outer electron is $$\frac{\hbar^2}{m_e a^2 b^2}D = \frac{1}{n}\frac{e^2}{8\pi\varepsilon_o ab^2}D + \frac{1}{n}\frac{4m}{3}\frac{1}{2}\frac{\hbar^2}{2m_e a^2 b^2}D \quad (12.47)$$

The parametric solution given by Eq. (11.83) occurs when semimajor axis, a, is $$a = a_0\left(2n - \frac{2m}{3}\right) \quad (12.48)$$

The internuclear distance, 2c', which is the distance between the foci is given by Eq. (11.79) where p=1/n.

$$2c' = 2\sqrt{\frac{aa_0}{2p}} = 2a_0\sqrt{\frac{n\left(2n - \frac{2m}{3}\right)}{2}} \quad (12.49)$$

The semiminor axis is given by Eq. (11.80).

$$b = \sqrt{a^2 - c'^2} = a_0\left(2n - \frac{2m}{3}\right)\sqrt{1 - \frac{n}{2\left(2n - \frac{2m}{3}\right)}} \quad (12.50)$$

The eccentricity, e, is given by Eq. (11.67).

$$e = \frac{c'}{a} = \sqrt{\frac{n}{2\left(2n - \frac{2m}{3}\right)}} \quad (12.51)$$

l≠0

The magnetic forces of triplet excited molecular states having l≠0 comprise the nondynamic-current component of Eq. (12.42) with the parameter m of the magnetic force of Eq. (12.37) increased by a factor of two and the $a_{Mag}(l,m)$ component due to the time dynamic modulation current and its interaction with electron spin. The latter is solved using the same approach as that of the triplet excited states of the helium atom given in the corresponding section. The force balance between the electric, magnetic, and centrifugal forces of the outer electron given by Eqs. (12.47) and (9.63) is $$\frac{\hbar^2}{m_e a^2 b^2}D = \frac{1}{n}\frac{e^2}{8\pi\varepsilon_o ab^2}D + \frac{1}{n}\frac{2m}{3}\frac{\hbar^2}{2m_e a^2 b^2}D + \quad (12.52)$$

$$\frac{1}{n}\frac{\frac{3}{2}}{(2l+1)!!}\left(\frac{l+1}{l}\right)^{1/2}\frac{1}{l+2}\frac{1}{2}\frac{\hbar^2}{m_e a^2 b^2}\left(2 - \sqrt{\frac{l}{l+1}}\right)D$$

where the $\sqrt{3/4}$ and $r^{-3}$ terms are replaced by one and $Da^{-2}b^{-2}$ as given in the Force Balance of Hydrogen-Types Molecules section. The parametric solution given by Eq. (11.83) occurs when semimajor axis, a, is $$a = a_0\left(2n - \frac{2m}{3} - \frac{\frac{3}{2}}{(2l+1)!!}\left(\frac{l+1}{l}\right)^{1/2}\frac{1}{l+2}\left(2 - \sqrt{\frac{l}{l+1}}\right)\right) \quad (12.53)$$

The internuclear distance, 2c', which is the distance between the foci is given by Eq. (11.79) with the 2 factor and p=1/n.

$$2c' = 2\sqrt{\frac{aa_0}{2p}} \quad (12.54)$$

$$= 2a_0\sqrt{\frac{n\left(2n - \frac{2m}{3} - \frac{\frac{3}{2}}{(2l+1)!!}\left(\frac{l+1}{l}\right)^{1/2}\frac{1}{l+2}\left(2 - \sqrt{\frac{l}{l+1}}\right)\right)}{2}}$$

The semiminor axis is given by Eq. (11.80).

$$b = \sqrt{a^2 - c'^2} \quad (12.55)$$

-continued $$= a_0 \left\{ \frac{\left(2n - \frac{2m}{3} - \frac{\frac{3}{2}}{(2l+1)!!}\left(\frac{l+1}{l}\right)^{1/2}\right)}{\frac{1}{l+2}\left(2 - \sqrt{\frac{l}{l+1}}\right)} \right\}$$

$$\left\{ 1 - \frac{n}{\sqrt{2\left[\frac{\left(2n - \frac{2m}{3} - \frac{\frac{3}{2}}{(2l+1)!!}\left(\frac{l+1}{l}\right)^{1/2}\right)}{\frac{1}{l+2}\left(2 - \sqrt{\frac{l}{l+1}}\right)}\right]}} \right\}$$

The eccentricity, e, is given by Eq. (11.67).

$$e = \frac{c'}{a} = \sqrt{\frac{n}{2\left[\frac{\left(2n - \frac{2m}{3} - \frac{\frac{3}{2}}{(2l+1)!!}\left(\frac{l+1}{l}\right)^{1/2}\right)}{\frac{1}{l+2}\left(2 - \sqrt{\frac{l}{l+1}}\right)}\right]}} \quad (12.56)$$

Energies of the Excited States of the Hydrogen Molecule

The component energies of the outer electron of the hydrogen molecule of the excited state corresponding to quantum number n are given by Eqs. (11.290-11.293) and (11.233-11.236) where the energies are each multiplied by a factor of ½ since the outer MO comprises only one electron, and those corresponding to charge are multiplied by effective-charge factor of 1/n:

$$V_e = \frac{1}{n}\frac{1}{2}\frac{-2e^2}{8\pi\varepsilon_o\sqrt{a^2 - b^2}}\ln\frac{a + \sqrt{a^2 - b^2}}{a - \sqrt{a^2 - b^2}} \quad (12.57)$$

$$V_p = 0 \quad (12.58)$$

$$T = \frac{1}{2}\frac{\hbar^2}{2m_e a\sqrt{a^2 - b^2}}\ln\frac{a + \sqrt{a^2 - b^2}}{a - \sqrt{a^2 - b^2}} \quad (12.59)$$

$$V_m = \frac{1}{n}\frac{1}{2}\frac{-\hbar^2}{4m_e a\sqrt{a^2 - b^2}}\ln\frac{a + \sqrt{a^2 - b^2}}{a - \sqrt{a^2 - b^2}} \quad (12.60)$$

$$\overline{E}_{osc}(H_2) = \overline{E}_D + \overline{E}_{Kvib} \quad (12.61)$$

$$= -(V_e + T + V_m + V)\sqrt{\frac{2\hbar\sqrt{\frac{1}{n^4}\frac{1}{2}\frac{e^2}{4\pi\varepsilon_o a_0^3}}}{m_e c^2}} + \overline{E}_{Kvib}$$

where with regard to Eq. (12.61), the angular frequency of reentrant oscillation ω and corresponding energies $E_K$, $\overline{E}_D$, and $\overline{E}_{osc}$ are given by Eqs. (11.233-11.236) with p=1n and the factor of ½ was applied since the outer MO comprises only one electron. The potential energy, $V_p$, due to proton-proton repulsion (Eq. 12.58)) is zero. The repulsive term applies only to the total energy of $H_2^+$ which is implicit in the calculation of the energy of the outer electron of the $H_2$ excited state as in the case with the energy of the helium exited states given in the Excited States of Helium section. The total energy, $E_T$, for the hydrogen molecular excited state given by Eqs. (11.239-11.240) is $$E_T = V_e + T + V_m + V_p + \overline{E}_{osc} \quad (12.62)$$

$$E_T = -\left\{ \left(\frac{-e^2}{8\pi\varepsilon_o} - \frac{n\hbar^2}{4m_e a} + \frac{\hbar^2}{8m_e a}\right)\frac{1}{n\sqrt{a^2 - b^2}}\ln\frac{a + \sqrt{a^2 - b^2}}{a - \sqrt{a^2 - b^2}}\left[1 + \sqrt{\frac{2\hbar\sqrt{\frac{e^2}{n^4 8\pi\varepsilon_o a_0^3}}}{m_e c}}\right] - \overline{E}_{Kvib} \right\} \quad (12.63)$$

The negative of Eq. (12.63) is the ionization energy of the excited state of $H_2$. The energy $T_c$ from the n=1 state (also referred to as the state X) to the energy of the $n^{th}$ excited state is given by the sum of $E_T$ given by Eq. (12.63) and $IP_1$ of $H_2$ given by Eq. (11.298):

$$T_3(H_2) = E_T + 15.4248 \text{ eV} \quad (12.64)$$

The geometrical (Eqs. (12.37-12.54) and energy (Eqs. (12.55-12.61)) parameters of singlet and triplet excited states of molecular hydrogen are given in Tables 55 and 56, respectively, where $\overline{E}_{Kvib}$ was given to very good approximation by $\omega_e$ of $H_2^+$ (the n=∞ state) since there is a close match with $\omega_e$ of each excited state [132]. The color scale, translucent views of the charge densities of exemplary ellipsoidal spherical harmonics that modulate the time-independent spin function are shown in FIG. 25. The modulation functions propagate about the major axis as spatially and temporally harmonic charge-density waves.

TABLE 55

The geometrical and energy parameters of the singlet excited states of molecular hydrogen compared to the experimental energies [9].

| n | m | l | a ($a_0$) | a (m) | b, c (m) | c' (m) | 2c' (m) | e | $V_e$ (eV) | $V_p$ (eV) |
|---|---|---|---|---|---|---|---|---|---|---|
| 2 | 4 | 1 | 2.73570 | 1.44767E-10 | 1.15312E-10 | 8.75257E-11 | 1.75051E-10 | 0.60460 | -5.76118 | 0 |
| 2 | 1 | 1 | 3.73570 | 1.97685E-10 | 1.69169E-10 | 1.02279E-10 | 2.04558E-10 | 0.51739 | -4.03193 | 0 |
| 2 | 0 | 0 | 4.00000 | 2.11671E-10 | 1.83312E-10 | 1.05835E-10 | 2.11671E-10 | 0.50000 | -3.73688 | 0 |
| 2 | -2 | 0 | 4.66667 | 2.46949E-10 | 2.18897E-10 | 1.14315E-10 | 2.28631E-10 | 0.46291 | -3.15548 | 0 |
| 3 | 4 | 0 | 4.66667 | 2.46949E-10 | 2.03426E-10 | 1.40007E-10 | 2.80014E-10 | 0.56695 | -2.20446 | 0 |
| 3 | 4 | 1 | 4.73570 | 2.50603E-10 | 2.07146E-10 | 1.41039E-10 | 2.82078E-10 | 0.56280 | -2.16761 | 0 |
| 3 | 3 | 0 | 5.00000 | 2.64589E-10 | 2.21371E-10 | 1.44921E-10 | 2.89842E-10 | 0.54772 | -2.03734 | 0 |
| 3 | 3 | 2 | 5.00562 | 2.64886E-10 | 2.21673E-10 | 1.45003E-10 | 2.90005E-10 | 0.54742 | -2.03474 | 0 |
| 3 | 3 | 1 | 5.06904 | 2.68242E-10 | 2.25081E-10 | 1.45918E-10 | 2.91836E-10 | 0.54398 | -2.00588 | 0 |
| 3 | 2 | 0 | 5.33333 | 2.82228E-10 | 2.39270E-10 | 1.49674E-10 | 2.99348E-10 | 0.53033 | -1.89402 | 0 |
| 3 | 2 | 1 | 5.40237 | 2.85881E-10 | 2.42973E-10 | 1.50639E-10 | 3.01279E-10 | 0.52693 | -1.86685 | 0 |

TABLE 55-continued

The geometrical and energy parameters of the singlet excited states of molecular hydrogen compared to the experimental energies [9].

| | | | | | | | | | | |
|---|---|---|---|---|---|---|---|---|---|---|
| 3 | 1 | 0 | 5.66667 | 2.99867E−10 | 2.57134E−10 | 1.54280E−10 | 3.08561E−10 | 0.51450 | −1.76971 | 0 |
| 3 | 1 | 1 | 5.73570 | 3.03520E−10 | 2.60830E−10 | 1.55217E−10 | 3.10434E−10 | 0.51139 | −1.74599 | 0 |
| 3 | −3 | 1 | 7.06904 | 3.74077E−10 | 3.32025E−10 | 1.72316E−10 | 3.44633E−10 | 0.46064 | −1.38755 | 0 |
| 4 | 4 | 1 | 6.73570 | 3.56438E−10 | 2.98872E−10 | 1.94226E−10 | 3.88452E−10 | 0.54491 | −1.13268 | 0 |
| 4 | 1 | 2 | 7.67229 | 4.06000E−10 | 3.49094E−10 | 2.07290E−10 | 4.14580E−10 | 0.51057 | −0.97861 | 0 |
| 4 | 1 | 1 | 7.73570 | 4.09356E−10 | 3.52488E−10 | 2.08145E−10 | 4.16290E−10 | 0.50847 | −0.96969 | 0 |
| 4 | −1 | 0 | 8.33333 | 4.40981E−10 | 3.84438E−10 | 2.16036E−10 | 4.32071E−10 | 0.48990 | −0.89305 | 0 |
| 4 | −1 | 1 | 8.40237 | 4.44634E−10 | 3.88126E−10 | 2.16929E−10 | 4.33857E−10 | 0.48788 | −0.88497 | 0 |

| n | m | l | T (eV) | $V_m$ (eV) | $E_{T^{(H_2MO)}}$ (eV) | $\overline{E}_{Kvib}$ (eV) | $\omega$ ($10^{15}$ rad/s) | $E_K$ (eV) | $\overline{E}_D$ (eV) |
|---|---|---|---|---|---|---|---|---|---|
| 2 | 4 | 1 | 2.10592 | −0.52648 | −4.18174 | 0.28479 | 7.30819 | 4.81038 | −1.81447E−02 |
| 2 | 1 | 1 | 1.07930 | −0.26982 | −3.22245 | 0.28479 | 7.30819 | 4.81038 | −1.39823E−02 |
| 2 | 0 | 0 | 0.93422 | −0.23355 | −3.03621 | 0.28479 | 7.30819 | 4.81038 | −1.31742E−02 |
| 2 | −2 | 0 | 0.67618 | −0.16904 | −2.64835 | 0.28479 | 7.30819 | 4.81038 | −1.14913E−02 |
| 3 | 4 | 0 | 0.70858 | −0.11810 | −1.61398 | 0.28479 | 3.24809 | 2.13795 | −4.66874E−03 |
| 3 | 4 | 1 | 0.68657 | −0.11443 | −1.59546 | 0.28479 | 3.24809 | 2.13795 | −4.61517E−03 |
| 3 | 3 | 0 | 0.61120 | −0.10187 | −1.52801 | 0.28479 | 3.24809 | 2.13795 | −4.42004E−03 |
| 3 | 3 | 2 | 0.60974 | −0.10162 | −1.52663 | 0.28479 | 3.24809 | 2.13795 | −4.41606E−03 |
| 3 | 3 | 1 | 0.59357 | −0.09893 | −1.51124 | 0.28479 | 3.24809 | 2.13795 | −4.37155E−03 |
| 3 | 2 | 0 | 0.53269 | −0.08878 | −1.45011 | 0.28479 | 3.24809 | 2.13795 | −4.19471E−03 |
| 3 | 2 | 1 | 0.51834 | −0.08639 | −1.43490 | 0.28479 | 3.24809 | 2.13795 | −4.15070E−03 |
| 3 | 1 | 0 | 0.46845 | −0.07808 | −1.37933 | 0.28479 | 3.24809 | 2.13795 | −3.98998E−03 |
| 3 | 1 | 1 | 0.45661 | −0.07610 | −1.36548 | 0.28479 | 3.24809 | 2.13795 | −3.94992E−03 |
| 3 | −3 | 1 | 0.29443 | −0.04907 | −1.14219 | 0.28479 | 3.24809 | 2.13795 | −3.30401E−03 |
| 4 | 4 | 1 | 0.33632 | −0.04204 | −0.83840 | 0.28479 | 1.82705 | 1.20259 | −1.81892E−03 |
| 4 | 1 | 2 | 0.25510 | −0.03189 | −0.75539 | 0.28479 | 1.82705 | 1.20259 | −1.63883E−03 |
| 4 | 1 | 1 | 0.25070 | −0.03134 | −0.75032 | 0.28479 | 1.82705 | 1.20259 | −1.62783E−03 |
| 4 | −1 | 0 | 0.21433 | −0.02679 | −0.70551 | 0.28479 | 1.82705 | 1.20259 | −1.53061E−03 |
| 4 | −1 | 1 | 0.21065 | −0.02633 | −0.70066 | 0.28479 | 1.82705 | 1.20259 | −1.52008E−03 |

| n | m | l | $\overline{E}_{osc}$ (eV) | $IP_1(H_2)$ (eV) | Cal. $T_e$ (eV) | Exp. $T_e$ (eV) | State | Exp. $T_e$ (cm$^{-1}$) | Relative Error |
|---|---|---|---|---|---|---|---|---|---|
| 2 | 4 | 1 | 0.12425 | 15.424814 | 11.3673 | 11.36819 | B | 91689.9 | 0.00008 |
| 2 | 1 | 1 | 0.12841 | 15.424814 | 12.3308 | 12.40385 | C | 100043.0 | 0.00589 |
| 2 | 0 | 0 | 0.12922 | 15.424814 | 12.5178 | 12.40631 | E | 100062.8 | −0.00899 |
| 2 | −2 | 0 | 0.13091 | 15.424814 | 12.9074 | 12.82999 | F | 103480 | −0.00603 |
| 3 | 4 | 0 | 0.13773 | 15.424814 | 13.9486 | 13.96780 | K | 112657 | 0.00138 |
| 3 | 4 | 1 | 0.13778 | 15.424814 | 13.9671 | 13.98466 | G | 112793 | 0.00125 |
| 3 | 3 | 0 | 0.13798 | 15.424814 | 14.0348 | 14.01839 | I | 113065 | −0.00117 |
| 3 | 3 | 2 | 0.13798 | 15.424814 | 14.0362 | 14.02818 | Q | 113144 | −0.00057 |
| 3 | 3 | 1 | 0.13803 | 15.424814 | 14.0516 | 14.06042 | J | 113404 | 0.00063 |
| 3 | 2 | 0 | 0.13820 | 15.424814 | 14.1129 | 14.12043 | D | 113888 | 0.00053 |
| 3 | 2 | 1 | 0.13825 | 15.424814 | 14.1282 | 14.12055 | H | 113889 | −0.00054 |
| 3 | 1 | 0 | 0.13841 | 15.424814 | 14.1839 | 14.19631 | L | 114500 | 0.00087 |
| 3 | 1 | 1 | 0.13845 | 15.424814 | 14.1978 | 14.21540 | M | 114654 | 0.00124 |
| 3 | −3 | 1 | 0.13909 | 15.424814 | 14.4217 | 14.41551 | N | 116268 | −0.00043 |
| 4 | 4 | 1 | 0.14058 | 15.424814 | 14.7270 | 14.71581 | R | 118690 | −0.00076 |
| 4 | 1 | 2 | 0.14076 | 15.424814 | 14.8102 | 14.81549 | T | 119494 | 0.00036 |
| 4 | 1 | 1 | 0.14077 | 15.424814 | 14.8153 | 14.81772 | P | 119512 | 0.00017 |
| 4 | −1 | 0 | 0.14087 | 15.424814 | 14.8602 | 14.85591 | S | 119820 | −0.00029 |
| 4 | −1 | 1 | 0.14088 | 15.424814 | 14.8650 | 14.85975 | O | 119851 | −0.00036 |
| | | | | | | | | Avg. Rel. Error | −0.00035 |

TABLE 56

The geometrical and energy parameters of the triplet excited states of molecular hydrogen compared to the experimental energies [9].

| n | m | l | a ($a_0$) | a (m) | b, c (m) | c' (m) | 2c' (m) | e | $V_e$ (eV) | $V_p$ (eV) |
|---|---|---|---|---|---|---|---|---|---|---|
| 2 | 1 | 1 | 3.02860 | 1.60266E−10 | 1.31165E−10 | 9.20919E−11 | 1.84184E−10 | 0.57462 | −5.11612 | 0 |
| 2 | 1 | 0 | 3.33333 | 1.76392E−10 | 1.47580E−10 | 9.66141E−11 | 1.93228E−10 | 0.54772 | −4.58402 | 0 |
| 3 | 4 | 1 | 3.02860 | 1.60266E−10 | 1.13859E−10 | 1.12789E−10 | 2.25578E−10 | 0.70376 | −3.72248 | 0 |
| 3 | 2 | 2 | 4.63043 | 2.45032E−10 | 2.01471E−10 | 1.39462E−10 | 2.78925E−10 | 0.56916 | −2.22432 | 0 |
| 3 | 2 | 0 | 4.66667 | 2.46949E−10 | 2.03426E−10 | 1.40007E−10 | 2.80014E−10 | 0.56695 | −2.20446 | 0 |
| 3 | 1 | 1 | 5.02860 | 2.66102E−10 | 2.22908E−10 | 1.45335E−10 | 2.90670E−10 | 0.54616 | −2.02419 | 0 |
| 3 | 1 | 2 | 5.29710 | 2.80310E−10 | 2.37326E−10 | 1.49165E−10 | 2.98329E−10 | 0.53214 | −1.90861 | 0 |
| 3 | 1 | 0 | 5.33333 | 2.82228E−10 | 2.39270E−10 | 1.49674E−10 | 2.99348E−10 | 0.53033 | −1.89402 | 0 |
| 4 | 4 | 1 | 5.02860 | 2.66102E−10 | 2.06512E−10 | 1.67818E−10 | 3.35637E−10 | 0.63065 | −1.59277 | 0 |
| 4 | 3 | 1 | 5.69526 | 3.01380E−10 | 2.42762E−10 | 1.78596E−10 | 3.57193E−10 | 0.59260 | −1.37400 | 0 |
| 4 | 3 | 2 | 5.96376 | 3.15589E−10 | 2.57285E−10 | 1.82758E−10 | 3.65516E−10 | 0.57910 | −1.30225 | 0 |
| 4 | 2 | 1 | 6.36193 | 3.36659E−10 | 2.78763E−10 | 1.88760E−10 | 3.77520E−10 | 0.56069 | −1.20882 | 0 |

TABLE 56-continued

The geometrical and energy parameters of the triplet excited states of molecular hydrogen compared to the experimental energies [9].

| | | | | | | | | | | |
|---|---|---|---|---|---|---|---|---|---|---|
| 4 | 2 | 0 | 6.66667 | 3.52785E−10 | 2.95161E−10 | 1.93228E−10 | 3.86456E−10 | 0.54772 | −1.14600 | 0 |
| 4 | 1 | 1 | 7.02860 | 3.71937E−10 | 3.14600E−10 | 1.98404E−10 | 3.96808E−10 | 0.53343 | −1.07948 | 0 |
| 4 | 1 | 0 | 7.33333 | 3.88063E−10 | 3.30941E−10 | 2.02659E−10 | 4.05319E−10 | 0.52223 | −1.02923 | 0 |
| 5 | 3 | 1 | 7.69526 | 4.07216E−10 | 3.34593E−10 | 2.32104E−10 | 4.64208E−10 | 0.56998 | −0.80341 | 0 |
| 5 | 3 | 2 | 7.96376 | 4.21424E−10 | 3.49065E−10 | 2.36119E−10 | 4.72237E−10 | 0.56029 | −0.77238 | 0 |
| 5 | 2 | 1 | 8.36193 | 4.42494E−10 | 3.70488E−10 | 2.41949E−10 | 4.83898E−10 | 0.54679 | −0.73059 | 0 |
| 6 | −4 | 0 | 14.66667 | 7.76126E−10 | 6.92214E−10 | 3.51016E−10 | 7.02033E−10 | 0.45227 | −0.33334 | 0 |

| n | m | l | T (eV) | $V_m$ (eV) | $E_{T(H_2MO)}$ (eV) | $\overline{E}_{Kvib}$ (eV) | ω ($10^{15}$ rad/s) | $E_K$ (eV) | $\overline{E}_D$ (eV) |
|---|---|---|---|---|---|---|---|---|---|
| 2 | 1 | 1 | 1.68927 | −0.42232 | −3.84916 | 0.28479 | 7.30819 | 4.81038 | −1.67016E−02 |
| 2 | 1 | 0 | 1.37520 | −0.34380 | −3.55261 | 0.28479 | 7.30819 | 4.81038 | −1.54149E−02 |
| 3 | 4 | 1 | 1.84367 | −0.30728 | −2.18609 | 0.28479 | 3.24809 | 2.13795 | −6.32367E−03 |
| 3 | 2 | 2 | 0.72056 | −0.12009 | −1.62386 | 0.28479 | 3.24809 | 2.13795 | −4.69732E−03 |
| 3 | 2 | 0 | 0.70858 | −0.11810 | −1.61398 | 0.28479 | 3.24809 | 2.13795 | −4.66874E−03 |
| 3 | 1 | 1 | 0.60380 | −0.10063 | −1.52102 | 0.28479 | 3.24809 | 2.13795 | −4.39984E−03 |
| 3 | 1 | 2 | 0.54047 | −0.09008 | −1.45822 | 0.28479 | 3.24809 | 2.13795 | −4.21816E−03 |
| 3 | 1 | 0 | 0.53269 | −0.08878 | −1.45011 | 0.28479 | 3.24809 | 2.13795 | −4.19471E−03 |
| 4 | 4 | 1 | 0.63349 | −0.07919 | −1.03847 | 0.28479 | 1.82705 | 1.20259 | −2.25298E−03 |
| 4 | 3 | 1 | 0.48251 | −0.06031 | −0.95181 | 0.28479 | 1.82705 | 1.20259 | −2.06497E−03 |
| 4 | 3 | 2 | 0.43672 | −0.05459 | −0.92012 | 0.28479 | 1.82705 | 1.20259 | −1.99621E−03 |
| 4 | 2 | 1 | 0.38002 | −0.04750 | −0.87630 | 0.28479 | 1.82705 | 1.20259 | −1.90115E−03 |
| 4 | 2 | 0 | 0.34380 | −0.04298 | −0.84518 | 0.28479 | 1.82705 | 1.20259 | −1.83363E−03 |
| 4 | 1 | 1 | 0.30717 | −0.03840 | −0.81070 | 0.28479 | 1.82705 | 1.20259 | −1.75884E−03 |
| 4 | 1 | 0 | 0.28070 | −0.03509 | −0.78362 | 0.28479 | 1.82705 | 1.20259 | −1.70007E−03 |
| 5 | 3 | 1 | 0.26101 | −0.02610 | −0.56850 | 0.28479 | 1.16931 | 0.76966 | −9.86698E−04 |
| 5 | 3 | 2 | 0.24247 | −0.02425 | −0.55416 | 0.28479 | 1.16931 | 0.76966 | −9.61808E−04 |
| 5 | 2 | 1 | 0.21843 | −0.02184 | −0.53401 | 0.28479 | 1.16931 | 0.76966 | −9.26832E−04 |
| 6 | −4 | 0 | 0.06818 | −0.00568 | −0.27084 | 0.28479 | 0.812021 | 0.53449 | −3.91731E−04 |

| n | m | l | $\overline{E}_{osc}$ (eV) | $IP_1(H_2)$ (eV) | Cal. $T_e$ (eV) | Exp. $T_e$ (eV) | State | Exp. $T_e$ (cm$^{-1}$) | Relative Error |
|---|---|---|---|---|---|---|---|---|---|
| 2 | 1 | 1 | 0.12570 | 15.424814 | 11.7013 | 11.87084 | c | 95744 | 0.01428 |
| 2 | 1 | 0 | 0.12698 | 15.424814 | 11.9992 | 11.89489 | a | 95938 | −0.00877 |
| 3 | 4 | 1 | 0.13607 | 15.424814 | 13.3748 | 13.36275 | e | 107777 | −0.00090 |
| 3 | 2 | 2 | 0.13770 | 15.424814 | 13.9387 | 13.97338 | d | 112702 | 0.00249 |
| 3 | 2 | 0 | 0.13773 | 15.424814 | 13.9486 | 13.98181 | h | 112770 | 0.00238 |
| 3 | 1 | 1 | 0.13800 | 15.424814 | 14.0418 | 13.98268 | g | 112777 | −0.00423 |
| 3 | 1 | 2 | 0.13818 | 15.424814 | 14.1048 | 14.01132 | i | 113008 | −0.00667 |
| 3 | 1 | 0 | 0.13820 | 15.424814 | 14.1129 | 14.03488 | j | 113198 | −0.00556 |
| 4 | 4 | 1 | 0.14014 | 15.424814 | 14.5265 | 14.47007 | f | 116708 | −0.00390 |
| 4 | 3 | 1 | 0.14033 | 15.424814 | 14.6133 | 14.66658 | v | 118293 | 0.00363 |
| 4 | 3 | 2 | 0.14040 | 15.424814 | 14.6451 | 14.67625 | k | 118371 | 0.00212 |
| 4 | 2 | 1 | 0.14050 | 15.424814 | 14.6890 | 14.68915 | p | 118475 | 0.00001 |
| 4 | 2 | 0 | 0.14056 | 15.424814 | 14.7202 | 14.69250 | s | 118502 | −0.00189 |
| 4 | 1 | 1 | 0.14064 | 15.424814 | 14.7547 | 14.70155 | r | 118575 | −0.00362 |
| 4 | 1 | 0 | 0.14070 | 15.424814 | 14.7819 | 14.79379 | m | 119319 | 0.00080 |
| 5 | 3 | 1 | 0.14141 | 15.424814 | 14.9977 | 14.99651 | n | 120954 | −0.00008 |
| 5 | 3 | 2 | 0.14143 | 15.424814 | 15.0121 | 15.01449 | q | 121099 | 0.00016 |
| 5 | 2 | 1 | 0.14147 | 15.424814 | 15.0323 | 15.03879 | t | 121295 | 0.00043 |
| 6 | −4 | 0 | 14.201 | 15.424814 | 15.2960 | 15.31031 | u | 123485 | 0.00094 |
| | | | | | | | | Avg. Rel. Error | −0.00044 |

REFERENCES

1. D. R. Lide, *CRC Handbook of Chemistry and Physics*, 86th Edition, CRC Press, Taylor & Francis, Boca Raton, (2005-6), pp. 9-19 to 9-45.
2. G. A. Sim, J. M. Robertson, T. H. Goodwin, "The crystal and molecular structure of benzoic acid", Acta Cryst., Vol. 8, (1955), pp. 157-164.
3. G. Herzberg, *Molecular Spectra and Molecular Structure II. Infrared and Raman Spectra of Polyatomic Molecules*, Van Nostrand Reinhold Company, New York, N.Y., (1945), pp. 362-369.
4. acetic acid at http://webbook.nist.gov/.
5. G. Herzberg, *Molecular Spectra and Molecular Structure II. Infrared and Raman Spectra of Polyatomic Molecules*, Krieger Publishing Company, Malabar, Fla., (1991), p. 195.
6. D. Lin-Vien. N. B. Colthup, W. G. Fateley, J. G. Grasselli, *The Handbook of Infrared and Raman Frequencies of Organic Molecules*, Academic Press, Inc., Harcourt Brace Jovanovich, Boston, (1991), p. 138.
7. methyl formate at http://webbook.nist.gov/.
8. methanol at http://webbook.nist.gov/.
9. K. P. Huber, G. Herzberg, *Molecular Spectra and Molecular Structure, IV. Constants of Diatomic Molecules*, Van Nostrand Reinhold Company, New York, (1979).
10. J. Crovisier, Molecular Database—Constants for molecules of astrophysical interest in the gas phase: photodissociation, microwave and infrared spectra, Ver. 4.2, Observatoire de Paris, Section de Meudon, Meudon, France, May 2002, pp. 34-37, available at http://wwwusr.obspm.fr/~crovisie/.
11. J. D. Cox, G. Pilcher, *Thermochemistry of Organometallic Compounds*, Academic Press, New York, (1970), pP. 254-255.

12. W. I. F. David, R. M. Ibberson, G. A. Jeffrey, J. R. Ruble, "The structure analysis of deuterated benzene and deuterated nitromethane by pulsed-neutron powder diffraction: a comparison with single crystal neutron analysis", Physics B (1992), 180 & 181, pp. 597-600.
13. G. A. Jeffrey, J. R. Ruble, R. K. McMullan, J. A. Pople, "The crystal structure of deuterated benzene," Proceedings of the Royal Society of London. Series A, Mathematical and Physical Sciences, Vol. 414, No. 1846, (Nov. 9, 1987), pp. 47-57.
14. H. B. Burgi, S. C. Capelli, "Getting more out of crystal-structure analyses," Helvetica Chimica Acta, Vol. 86, (2003), pp. 1625-1640.
15. D. R. Lide, *CRC Handbook of Chemistry and Physics*, 86th Edition, CRC Press, Taylor & Francis, Boca Raton, (2005-6), pp. 10-202 to 10-204.
16. C. S. Choi, E. Prince, "The crystal structure of cyclotrimethylene-trinitramine" Acta Cryst., Vol. B28, (1972), pp. 2857-2862.
17. D. Lin-Vien. N. B. Colthup, W. G. Fateley, J. G. Grasselli, *The Handbook of Infrared and Raman Frequencies of Organic Molecules*, Academic Press, Inc., Harcourt Brace Jovanovich, Boston, (1991), p. 187.
18. D. Lin-Vien. N. B. Colthup, W. G. Fateley, J. G. Grasselli, *The Handbook of Infrared and Raman Frequencies of Organic Molecules*, Academic Press, Inc., Harcourt Brace Jovanovich, Boston, (1991), p. 194.
19. D. Lin-Vien. N. B. Colthup, W. G. Fateley, J. G. Grasselli, *The Handbook of Infrared and Raman Frequencies of Organic Molecules*, Academic Press, Inc., Harcourt Brace Jovanovich, Boston, (1991), p. 482.
20. D. R. Lide, *CRC Handbook of Chemistry and Physics*, 86th Edition, CRC Press, Taylor & Francis, Boca Raton, (2005-6), pp. 9-82 to 9-86.
21. D. R. Lide, *CRC Handbook of Chemistry and Physics*, 86th Edition, CRC Press, Taylor & Francis, Boca Raton, (2005-6), pp. 9-54 to 9-59.
22. R. J. Fessenden, J. S. Fessenden, *Organic Chemistry*, Willard Grant Press. Boston, Mass., (1979), p. 20.
23. D. R. Lide, *CRC Handbook of Chemistry and Physics*, 86th Edition, CRC Press, Taylor & Francis, Boca Raton, (2005-6), pp. 9-47 to 9-53.
24. D. R. Lide, *CRC Handbook of Chemistry and Physics*, 89th Edition (Internet Version, 2009), CRC Press, Taylor and Francis, Boca Raton, (2009), 9-Dipole Moments.
25. V. H. J. Becher, "Über den Bindungszustand in Bor—Stickstoff-Verbindungen. II. Bindungsmomente in Borazanen und Borazenen," Zeitschrift für anorganische und allgemeine Chemie, Vol. 270, No. 5-6, (1952), pp. 273-286.
26. V. V. Kuznetsov, A. 1. Gren, A. V. Bogatskii, S. P. Egorova, V. I. Sidorov, "Stereochemistry of heterocycles," XLIX. "Investigation of the conformation of alkyl-1,3,2-dioxaborinanes by PMR spectroscopy", Chemistry of Heterocyclic Compounds, Vol. 14, No. 1, (1978), pp. 19-22.
27. É. A. Ishmaeva, A. N. Vereshchagin, N. G. Khusainova, Z. A. Bredikhina, A. N. Pudovik, "Dipole moments of organophosphorous compounds. 15. Polarities and polarizabilities of some acetylenic compounds," Russian Chemical Bulletin, Vol. 27, No. 2, (1978), pp. 310-313.
28. O. A. Varnavskaya-Samarina, É. A. Ishmaeva, O. V. Romanov, R. Ya. Nazmutdinov, A. B. Remizov, A. N. Pudovik, "Dipole moments of organophosphorous compounds. 16. Conformations of trimethylsilyl groups in some phosphites, phosphates, and phosphonates," Russian Chemical Bulletin, Vol. 27, No. 2, (1978), pp. 313-318.
29. A. I. Echeistova, Ya. K. Syrkin, V. 1. Stanko, and A. I. Klimova, "Dipole moments of halogen derivatives of ortho- and meta-carboranes," Journal of Structural Chemistry, Vol. 8, No. 5, (1967), p. 833-834.
30. V. I. Stanko, A. I. Echeistova, I. S. Astakhova, A. I. Klimova, Y. T. Struchkov, Y. K. Syrkin, "Use of dipole moments to determine the structure of halogen derivates of ortho and metacarboranes", J. Struct. Chem., Vol. 8, No. 5, (1967), pp. 829-832.
31. G. J. Moody, J. D. R. Thomas, *Dipole Moments in Inorganic Chemistry*, Edward Arnold, London, (1971), p. 43.
32. V. I. Minkin, O. A. Osipov, Y. A. Zhdanovv, *Dipole Moments in Organic Chemistry*, Plenum, (1970).
33. J. G. Speight, *Lange's Handbook of Chemistry*, Sixteenth Edition, McGraw-Hill Professional, New York, (2004), pp. 1.171 to 1.172.
34. J. A. Dean, *Lange's Handbook of Chemistry*, Fifteenth Edition, McGraw-Hill Professional, New York, (1998), pp. 4.53-4.54.
35. V. I. Minkin, O. A. Osipov, Y. A. Zhdanov, Dipole Moments in Organic Chemistry, Plenum Press, New York, (1956), p. 88.
36. J. M. Bellama, A. G. MacDiarmid, "An electric dipole moment study of methylsilyl and silylmethyl halides", J. Organomet. Chem., Vol. 24, No. 1, (1970), pp. 91-95.
37. R. Varma, A. G. MacDiarmid, J. G. Miller, "Nature of the silicon-phenyl and silicon-oxygen bond in hexaphenyldisiloxane: an electric dipole moment study", J. Organomet. Chem., Vol. 9, No. 1, (1967), pp. 77-81.
38. R. Varma, A. G. MacDiarmid, J. G. Miller, "The dipole moments and structures of disiloxane and methoxysilane", Inorg. Chem., Vol. 3, No. 12, (1964), pp. 1754-1757.
39. A. L. McClellan, *Tables of Experimental Dipole Moments*, W. H. Freeman and Company, San Fransico, (1963), p. 44.
40. A. L. McClellan, *Tables of Experimental Dipole Moments*, Volume 2, Rahara Enterprises, California, (1974).
41. A. L. McClellan, *Tables of Experimental Dipole Moments*, Volume 3, Rahara Enterprises, California, (1989), p. 39.
42. T. Kasuya, W. J. Lafferty, D. R. Lide, J Chem Phys., Vol. 48, (1968), pp. 1-4.
43. J. H. Hand, R. H. Schwendeman, "Microwave spectrum, molecular structure, dipole moment, and ring-bending vibration of 1,3,2-dioxaborolane", J. Chem. Phys., Vol. 45, (1966), pp. 3349-3354.
44. J. R. Weaver, R. W. Perry, "Dipole moment studies. III. The dipole moments of the methylamine boranes", Inorg. Chem., Vol. 5, No. 5, (1966), pp. 713-718.
45. NIST, "Listing of experimental data for $H_2S$ (hydrogen sulfide)", http://cccbdb.nist.gov/exp2.asp?casno-7783064.
46. NIST, "Listing of experimental data for $N(CH_3)_3$ (trimethylamine)", http://cccbdb.nist.gov/exp2.asp?casno-75503.
47. NIST, "Listing of experimental data for $CH_3SCH_3$ (dimethyl sulfide)", http://cccbdb.nist.gov/exp2.asp?casno-75183.
48. http://en.wikipedia.org/wikiTrimethylphosphine.
49. Springer, http://www.springerlink.com/content/t585467172mp2263/fulltext.pdfpage-.

50. NIST, "Listing of experimental data for CH$_3$SiCH$_3$SiCH$_3$ (dimethyl silane)", http//cccbdb.nist.gov/exp2.asp?casno75183.
51. NIST, "Listing of experimental data for SiH$_4$ (silane)", http://cccbdb.nist.gov/exp2.asp?casno=7803625.
52. NIST, "Listing of experimental data for BHF$_2$ (difluoroborane)", http.//cccbdb.nist.gov/exp2.asp?casno=13709836.
53. Springer, http://www.springerlink.com/content/1825370723$^2$16k35/fulltext.pdf?page=1.
54. Springer, http://www.springerlink.com/content/n135855181p714r6/fulltext.pdf?page-1.
55. Springer, http://www.springerlink.com/content/qhl2341h1p157424/fulltext.pdf?page=1.
56. R. D. Nelson Jr., D. R. Lide, A. A. Maryott, "Selected Values of electric dipole moments for molecules in the gas phase" NSRDS-NBS10, (1967), p. 13.
57. R. D. Nelson Jr., D. R. Lide, A. A. Maryott, "Selected Values of electric dipole moments for molecules in the gas phase" NSRDS-NBS10, (1967), p. 26.
58. R. D. Nelson Jr., D. R. Lide, A. A. Maryott, "Selected Values of electric dipole moments for molecules in the gas phase" NSRDS-NBS10, (1967), p. 23.
59. K. K. Chatterjee, J. R. Durig, S. Bell, J. Mol. Struct., Vol. 265, (1992), p. 25.
60. J. L. Duncan, J. L. Harvie, D. C. McKean, S. Cradock, J. Mol. Struct., Vol. 145, (1986), p. 225.
61. M. Wong, 1. Ozier, W. L. Meerts, J. Mol. Spectrosc., Vol. 102, (1983), p. 89.
62. S. D. Hubbard, A. P. Cox, J. Mol. Spectrosc., Vol. 115, (1986), pp. 188.
63. P. R. R. Langridge-Smith, R. Stevens, A. P. Cox, J. Chem. Soc., Faraday Trans. II, Vol.
75, (1979), p. 1620.
64. G. Kodama, J. R. Weaver, J. LaRochelle, R. W. Parry, "Dipole moment studies II. The dipole moments of the ethylphosphines", Inorg. Chem., Vol. 5, No. 5, (1966), pp. 710-713.
65. J. R. Weaver, R. W. Parry, "Dipole moment studies III. The dipole moments of the methylamine boranes", Inorg. Chem., Vol. 5, No. 5, (1966), pp. 713-718.
66. S. Bohm, O. Exner, "Prediction of molecular dipole moments from bond moments: testing of the method by DFT calculations on isolated molecules", Phys. Chem. Chem. Phys., Vol. 6, No. 3, (2004), pp. 510-514.
67. C. W. N. Cumper, "Electric bond and group dipole moments", Tetrahedron, Vol. 25, No.
15, (1969), pp. 3131-3138.
68. O. A. Raevskii, F. G. Khalitov, "The inductive effect in a series of phosphines", Russ. Chem. Bull., Vol. 19, No. 10, (1970), pp. 2222-2224. http://www.springerlink.com/content/uw673505v7064355/.
69. E. Fluck, *The Chemistry of Phosphine*, Topics in Current Chemistry, Vol. 35, (1973). http://www.springerlink.com/content/y17151p8tqnq5772/.
70. M. J. S. Dewar, C. Jie, E. G. Zoebisch, "AM1 calculations for compounds containing boron", J. Organometallics, Vol. 7, No. 2, (1988), pp. 513-521.
71. J. R. Weaver, R. W. Parry, "Dipole moment studies IV. Trends in dipole moments", Inorg. Chem., Vol. 5, No. 5, (1966), pp. 718-723.
72. G. Zhou, W. Chen, Fundamentals of Structural Chemistry, World Scientific, (1993), p. 175.
73. B. A. Arbuzov, O. D. Zolova, L. K. Yuldasheva, "Dipole moments and conformation of cyclic compounds. III. Sulfites", J. Struct. Chem., Vol. 8, No. 2, (1967), pp. 249-252.
74. O. Exner, D. N. Harpp, J. G. Gleason, "Dipole moments and conformation of sultones, thiosultones and sultines", Can. J. Chem., Vol. 50, (1972), pp. 548-552.
75. O. Exner, Z. Fidlerova and V. Jehlicka, Collect. Czech. Chem. Commun., Vol. 33, (1968), pp. 2019.
76. O. Exner, P. Dembech, P. Vivarelli, "Dipole moments and conformation of sulphinic acid esters", J. Chem. Soc. B, (1970), pp. 278-281.
77. A. P. Altshuller, L. Rosenblum, "Dielectric properties of some alkylsilanes", J. Am. Chem. Soc., Vol. 77, No. 2, (1955), pp. 272-274.
78. V. A. Chetverikova, V. A. Kogan, G. I. Zelchan, M. G. Voronkov, O. A. Osipov, "Dipole moments of Si-substituted silatranes", Chem. Heterocycl. Compd., Vol. 5, No. 3, (1969), pp. 332-334.
79. J. M. Bellama, R. S. Evans, J. E. Huheey, "Bond moments, molecular moments, electronegativity, and the dipole moment of methylsilane", J. Am. Chem. Soc., Vol. 95, No. 22, (1973), pp 7242-7244.
80. L. K. Yuldasheva, R. P. Arshinova, Y. Y. Samitov, Y. P. Romadan, M. G. Voronkov, "Steric structure of 5-substituted 2,2-dimethyl-1,3,2-dioxasilanes", Russ. Chem. Bull., Vol. 23, No. 2, (1974), pp. 294-299.
81. M. G. Voronkov, T. N. Aksamentova, V. B. Modonov, L. I. Gubanova, Y. L. Frolov, V. M. Dyakov, "Dipole moments and molecular structure of (aroyloxymethyl)-trifluorosilanes and methyl(aroyloxymethyl)fluorosilanes", Russ. Chem. Bull., Vol. 33, No. 3, (1984), pp. 635-637.
82. L. K. Yuldasheva, R. P. Arshinova, S. G. Vulfson, "Dipole moments of the bonds and the unshared electron pair in sulfites and sulfoxides", Russ. Chem. Bull., Vol. 18, No. 3, (1969), pp. 495-498.
83. Y. Y. Borovikov, V. V. Pirozhenko, "Scale of additive group and bond dipole moments and dipole moments of lone pairs", Theor. Exp. Chem., Vol. 17, No. 2, (1981), pp. 136-146.
84. A. Borba, A. Gómez-Zavaglia, P. N. N. L. Simões, R. Fausto, "Matrix-isolation FT-IR spectra and theoretical study of dimethyl sulfate", Spectrochim. Acts Part A, Vol. 61, (2005), pp. 1461-1470.
85. E. N. Klimovitskii, L. K. Yuldasheva, A. N. Vereshchagin, G. N. Sergeeva, S. G. Vulfson, B. A. Arbuzov, "Sulfate group polarization and polarizability and the conformations of the dimethyl sulfates", Russ. Chem. Bull., Vol. 26, No. 1, (1977), pp. 83-85.
86. G. Wood, J. M. McIntosh, M. H. Miskow, "Conformational analysis of trimethylene sulfites. The vital importance of vicinal unshared electron pairs", Can. J. Chem., Vol. 49, (1971), pp. 1202-1208.
87. B. J. Lindberg, K. Hamrin, G. Johansson, U. Gelius, A. Fahlman, C. Nordling, K. Siegbahn, "Molecular spectroscopy by means of ESCA", Phys. Scr., Vol. 1, (1970), pp. 286-298.
88. D. Eisenberg, W. Kauzmann, *The Structure and Properties of Water*, Oxford University Press, London, (1969), p. 74.
89. K. Ichikawa, Y. Kameda, T. Yamaguchi, H. Wakita and M. Misawa, Neutron diffraction investigation of the intramolecular structure of a water molecule in the liquid phase at high temperatures, Mol. Phys. Vol. 73, (1991), pp. 79-86.
90. D. Eisenberg, W. Kauzmann, *The Structure and Properties of Water*, Oxford University Press, London, (1969), p. 85.

91. D. R. Lide, *CRC Handbook of Chemistry and Physics*, 86th Edition, CRC Press, Taylor & Francis, Boca Raton, (2005-6), p. 4-151.
92. D. Eisenberg, W. Kauzmann, *The Structure and Properties of Water*, Oxford University Press, London, (1969), p. 83.
93. H. A. Haus, J. R. Melcher, *Electromagnetic Fields and Energy*, Department of Electrical Engineering and Computer Science, Massachusetts Institute of Technology, (1985), Sec. 6.3.
94. D. R. Lide, *CRC Handbook of Chemistry and Physics*, 79th Edition, CRC Press, Boca Raton, Fla., (1998-9), p. 6.2.
95. R. L. DeKock, H. B. Gray, *Chemical Structure and Bonding*, The Benjamin/Cummings Publishing Company, Menlo Park, Calif., (1980), pp. 436-439.
96. G. L. Miessler, D. A. Tan, *Inorganic Chemistry*, Third Edition, Pearson Prentice Hall, Upper Saddle River, N.J., (2004), pp. 69-71.
97. D. D. Nelson, Jr., G. T. Fraser, W. Klemperer, "Does ammonia hydrogen bond?", Science, Vol. 238, (1987), pp. 1670-674.
98. R. J. Fessenden, J. S. Fessenden, *Organic Chemistry*, Willard Grant Press. Boston, Mass., (1979), p. 25.
99. P. F. Harris, Z. Lheng, K. Suenaga, "Imaging the atomic structure of activated carbon", J. Phys.: Condens. Matter, Vol. 20, (2008), pp. 362201-362205.
100. R. J. Fessenden, J. S. Fessenden, *Organic Chemistry*, Willard Grant Press. Boston, Mass., (1979), pp. 744-745.
101. R. Zacharia, H. Ulbricht, T. Hertel, "Interlayer cohesive energy of graphite from thermal desorption of polyaromatic hydrocarbons", Phys. Rev. B, Vol. 69, Issue 15, (2004), pp. 155406-155412.
102. D. G. Hurst, D. G. Henshaw, "Atomic distribution in liquid helium by neutron diffraction", Phys. Rev., Vol. 100, No. 4, (1955), pp. 994-1002.
103. D. R. Lide, *CRC Handbook of Chemistry and Physics*, 86th Edition, CRC Press, Taylor & Francis, Boca Raton, (2005-6), pp. 6-119 to 9-120.
104. K. W. Schwarz, R. W. Stark, Phys. Rev. Lett., Vol. 22, No. 24, (1969), pp. 1278-1280.
105. C. J. Pethick, H. Smith, *Bose-Einstein Condensation in Dilute Gases*, Second Edition, Cambridge University Press, Cambridge, UK, (2008), p. 8.
106. D. G. Henshaw, A. D. B. Woods, Phys. Rev. Ltt., Vol. 121, (1961), p. 1266.
107. G. Baym, R. G. Barrera, C. J. Pethick, Phys. Rev. Letters, Vol. 22, No. 1, (1969), pp. 20-23.
108. F. London, *Superfluids* (Dover Publications, New York, 1964), Vol. III.
109. C. Pethick, H. Smith, *Bose-Einstein Condensation in Dilute Gases*, Cambridge University Press, Cambridge, (2008).
110. C. J. Pethick, H. Smith, *Bose-Einstein Condensation in Dilute Gases*, Second Edition, Cambridge University Press, Cambridge, UK, (2008), pp. 1-40.
111. R. Wynar, R. S. Freeland, D. J. Han, C. Ryu, and D. J. Heinzen, "Molecules in a Bose-Einstein Condensate", Science, Vol. 287, February, 11, (2000), pp. 1016-1019.
112. J. A. Dean, *Lange's Handbook of Chemistry*, Fifteenth Edition, McGraw-Hill Professional, New York, (1998).
113. G. L. Pollack, "The solid state of rare gases", Rev. Mod. Phys., Vol. 36, (1964), pp. 748-791.
114. D. G. Henshaw, "Atomic distribution in liquid and solid neon and solid argon by neutron diffraction", Phys. Rev., Vol. 111, No. 6, (1958), pp. 1470-1475.
115. M. L. Klein, J. A. Venables, *Rare Gas Solids*, Volume 1, Academic Press, New York, (1977). p. 242.
116. J. Sugar and A. Musgrove, "Energy levels of krypton, Kr I through Kr XXXVI", J. Phys. Chem. Ref. Data, Vol. 20, No. 5, (1991), pp. 859-915.
117. http://www.nist.gov/srd/PDFfiles/jpcrd422.pdf.
118. E. B. Saloman, "Energy Levels and Observed Spectral Lines of Krypton, Kr I through Kr XXXVI", J. Phys. Chem. Ref. Data, Vol. 36, No. 1, (2007), pp. 215-386.
119. http://link.aip.orglink/?JPCRBU/36/215/1.
120. M. L Klein, J. A. Venables, *Rare Gas Solids*, Volume 1, Academic Press, New York, (1977). p. 245.
121. E. B. Saloman, "Energy levels and observed spectral lines of xenon, Xe I through Xe LIV", J. Phys. Chem. Ref. Data, Vol. 33, No. 3, (2004), pp. 765-921.
122. http://www.nist.gov/srd/PDFfiles/jpcrd661.pdf.
123. M. L. Klein, J. A. Venables, *Rare Gas Solids*, Volume 1, Academic Press, New York, (1977). p. 250.
124. A. Fernández-Ramos, J. A. Miller, S. J. Klipperstein, D. G. Truhlar, "Modeling the Kinetics of Bimolecular Reactions," Chem. Rev., Vol. 106, (2006), pp. 4518-4584.
125. S. C. Tucker, D. G. Truhlar, "Ab initio calculations of the transition-state geometry and vibrational frequencies of the SN2 reaction of chloride with chloromethane," J. Phys. Chem, Vol. 93, No. 25, (1989), pp. 8138-8142.
126. D. R. Lide, *CRC Handbook of Chemistry and Physics*, 86th Edition, CRC Press, Taylor & Francis, Boca Raton, (2005-6), p. 10-156.
127. S. C. Tucker, D. G. Truhlar, "A six-body potential energy surface for the SN2 reaction $Cl^-$ (g)+$CH_3Cl$ (g) and a variational transition-state-theory calculation of the rate constant," J. Am. Chem. Soc., Vol. 112, No. 9, (1990), pp. 3338-3347.
128. S. E. Barlow, J. M. Van Doren, V. M. Bierbaum, "The gas phase displacement reaction of chloride ion with methyl chloride as a function of kinetic energy," J. Am. Chem. Soc., Vol. 110, No. 21, (1988), pp. 7240-7242.
129. $Cl_3^-$ at http://webbook.nist.gov/.
130. R. Mills, B. Holverstott, "Simulation of the gas phase displacement reaction of chloride ion with methyl chloride", at http://www.blacklightpower.com/.
131. L-W. Li, X-K. Kang, M-S Leong, *Spheroidal Wave Functions in Electromagnetic Theory*, Wiley Series in Microwave and Optical Engineering, K. Chang, Editor, John Wiley & Sons, Inc., New York, (2002).
132. G. Herzberg, *Molecular Spectra and Molecular Structure I. Spectra of Diatomic Molecules*, Krieger Publishing Company, Malabar, Fla., Second Edition, (1989), pp. 530-534.

The invention claimed is:

1. A system comprising
at least one processor,
at least one non-transitory computer readable medium, containing instructions that when executed by the at least one processor cause the at least one processor to perform operations for computing and rendering a nature of a chemical bond comprising physical, Maxwellian solutions of charge, mass, and current density functions of molecules, compounds, and materials and solving the dipole moment of at least one bond, the operations comprising:
inputting data into the system regarding the atomic composition, positions, and excitation state of the molecule, compound, or material;
calculating a solution to Maxwellian equations, wherein the solution is a two dimensional spheroidal surface, wherein charge, mass, and current density functions are determined by evaluating the two dimensional spheroidal surface of molecules, compounds, and materials, and solving the dipole moment of at least one bond, and outputting the nature of the chemical bond comprising physical, Maxwellian solutions of charge, mass, and current density functions and the corresponding energy components of molecules, compounds, and materials to an output device in communication with the at least one processor;

wherein at least one processor calculates bond moment $\mu$ of a functional group by considering the charge donation between atoms of the functional group wherein the potential of an MO is that of a point charge at infinity such that an asymmetry in the distribution of charge between nonequivalent HOs or AOs of the MO occurs to maintain an energy match of the MO with the bridged orbitals and the charge redistribution between the spherical orbitals achieves a corresponding current-density that maintains constant current at the equivalent-energy condition according to an energy-matching factor, wherein the dipole moment of a given molecule is given by the vector sum of the bond moments in the molecule wherein the dipole moment is given by taking into account the magnitude and direction of the bond moment of each functional group wherein the function-group bond moment stays constant from molecule to molecule and is in the vector direction of the internuclear axis, and wherein at least one processor creates a molecular model based on the solutions derived from the Maxwellian equations and the dipole moment, and displays a three dimensional representation of the molecular model on the output device.

2. The system of claim 1 comprising an input that comprises at least one of a serial port, usb port, microphone input, camera input, keyboard, an mouse;

wherein the at least one processor is a component of a general purpose computer that comprises at least one of a central processing unit (CPU), one or more specialized processors, system memory, a mass storage device such as a magnetic disk, an optical disk, and other storage device;

computer program products or computer readable medium having embodied therein program code means wherein the computer readable media is any available media which can be accessed by a general purpose or special purpose computer wherein the computer readable media comprises at least one of RAM, ROM, EPROM, CD ROM, DVD or other optical disk storage, magnetic disk storage or other magnetic storage devices, or any other medium which can embody the desired program code means and which can be accessed by the general purpose or special purpose computer wherein the program code means comprises executable instructions and data which cause the general purpose computer or special purpose computer to perform a certain function of a group of functions, and the output device that is a display comprising a monitor, video projector, printer, or three-dimensional rendering device that displays at least one of visual or graphical media wherein at least one of the group of static or dynamic images, vibration and rotation, and reactivity and physical properties are displayed.

3. The system of claim 1 wherein the at least one processor executes instructions to superimpose functional groups comprising at least one of the group of those of alkanes, branched alkanes, alkenes, branched alkenes, alkynes, alkyl fluorides, alkyl chlorides, alkyl bromides, alkyl iodides, alkene halides, primary alcohols, secondary alcohols, tertiary alcohols, ethers, primary amines, secondary amines, tertiary amines, aldehydes, ketones, carboxylic acids, carboxylic esters, amides, N-alkyl amides, N,N-dialkyl amides, ureas, acid halides, acid anhydrides, nitriles, thiols, sulfides, disulfides, sulfoxides, sulfones, sulfites, sulfates, nitro alkanes, nitrites, nitrates, conjugated polyenes, aromatics, heterocyclic aromatics, substituted aromatics.

4. The system of claim 1 wherein the energy matching factor is $c_1$, $c_2$, $C_1$, or $C_2$ of Eqs. (15.51) and (15.61):

$$-\frac{n_1 e^2}{8\pi\varepsilon_0 \sqrt{\frac{aa_0}{2C_1 C_2}}} \left[ \ln \frac{c_1 c_2 \left(2 - \frac{a_0}{a}\right)}{a - \sqrt{\frac{aa_0}{2C_1 C_2}}} - 1 \right] + E_T(\text{AO/HO}) = \tag{15.51}$$

$$E(\text{basis energies})$$

$$E_{T+osc}(\text{Group}) = E_T(\text{MO}) + E_{osc} \tag{15.61}$$

$$= \left( \begin{array}{c} -\frac{n_1 e^2}{8\pi\varepsilon_0 \sqrt{\frac{aa_0}{2C_1 C_2}}} \left[ \ln \frac{c_1 c_2 \left(2 - \frac{a_0}{a}\right)}{a - \sqrt{\frac{aa_0}{2C_1 C_2}}} - 1 \right] \\ E_T(\text{AO/HO}) = + E_T(\text{atom---atom}, msp^3 \cdot \text{AO}) \end{array} \right)$$

$$\left[ 1 + \sqrt{2\hbar \sqrt{\frac{C_{1o} C_{2o} e^2}{4\pi\varepsilon_o R^3}}{m_e c^2}} \right] + n_1 \frac{1}{2} \hbar \sqrt{\frac{k}{\mu}} \right)$$

$$= \left( \begin{array}{c} E(\text{basis energies}) + \\ E_T(\text{atom---atom}, msp^3 \cdot \text{AO}) \end{array} \right)$$

$$\left[ 1 + \sqrt{2\hbar \sqrt{\frac{C_{1o} C_{2o} e^2}{4\pi\varepsilon_o R^3}}{m_e c^2}} \right] + n_1 \frac{1}{2} \hbar \sqrt{\frac{k}{\mu}}.$$

5. The system of claim 4 wherein the orbital energy and radius are reciprocally related such that the contribution scales as the square of the ratio (over unity) of the energy of the resultant net positively-charged orbital and the initial matched energy of the resultant net negatively-charged orbital of the bond multiplied by the energy-matching factor.

6. The system of claim 5 wherein the partial charges on the HOs or AOs corresponding to the charge contribution are equivalent to point charges centered on the nuclei;

due to symmetry, the bond moment p of each functional group is along the internuclear axis whereby it is calculated from the partial changes at the separation distance, the internuclear distance.

7. The system of claim 6, wherein the bond moment of each functional group is along the internuclear axis of A-B, wherein A is the net positively-charged atom, and is calculated using the reciprocal relationship between the orbital energies and radii, the dependence of the orbital area on the radius squared, and the relationship of the partial charge q to the areas with energy matching for each electron of the MO, such that the bond moment is given by $$\mu = qd = n_1 ce \left(1 - \left(\frac{E_A(\text{valence})}{E_B(\text{valence})}\right)^2\right) 2c' \quad (16.15)$$

wherein $n_1$ is the number of equivalent bonds of the MO, c is energy-matching factor, and d is the charge-separation distance, the internuclear distance 2c';

$E_B$(valence) is the initial matched energy of the resultant net negatively-charged orbital of the bond that is further lowered by bonding (Eqs. (15.32) and (15.16)):

$$E(\text{atom}, msp^3) = \frac{-e^2}{8\pi\varepsilon_0 r_{msp^3}} + \frac{2\pi\mu_0 e^2 \hbar^2}{m_e^2 r^3} \quad (15.16)$$

$$r_{mol2sp^3} = \frac{-e^2}{8\pi\varepsilon_0 \left(E_{Coulomb}(C, 2sp^3) + \sum E_{T_{mol}}(MO, 2sp^3)\right)} \quad (15.32)$$

$$= \frac{e^2}{8\pi\varepsilon_0 (e14.825751 \text{ eV} + \sum |E_{T_{mol}}(MO, 2sp^3)|)}$$

to atom A having an energy to which the heteroatom is energy matched.

8. The system of claim 1 wherein the functional group bond moments determined using Eq. (16.15) are substantially given by

| Functional Group[a] | $n_1$ | $(c_1)c_2$ | $(C_1)C_2$ | $E_B$(valence) | $E_A$(valence) | $\frac{q}{e}$ | Bond Length 2c' (Å) | Bond Moment $\mu$ (D) |
|---|---|---|---|---|---|---|---|---|
| H—C (alkyl) | 1 | 0.91771 | 1 | 14.63489 | 15.35946 | 0.070 | 1.11713 | 0.37 |
| H—C (aromatic) | 1 | 0.91771 | 1 | 15.95955 | 15.95955 | 0 | 1.09327 | 0 |
| H—N[b] (amine) | 1 | 0.78896 | 1 | 13.59844 | 15.81768 | 0.279 | 1.00343 | 1.34 |
| H—N[c] (ammonia) | 1 | 0.74230 | 1 | 13.59844 | 15.81768 | 0.262 | 1.03677 | 1.30 |
| H—O[d] (alcohol) | 1 | 0.91771 | 1 | 13.59844 | 15.81768 | 0.324 | 0.97165 | 1.51 |
| H—O[e] (water) | 1 | 0.71419 | 1 | 13.59844 | 15.81768 | 0.323 | 0.97157 | 1.51 |
| C—N | 1 | 0.91140 | 1 | 14.53414 | 14.82575 | 0.037 | 1.46910 | 0.26 |
| C—O | 1 | 0.85395 | 1 | 14.63489 | 15.56407 | 0.112 | 1.41303 | 0.76 |
| C—F[f] | 1 | 1.09254[b] | 1 | 14.63489 | 15.98435 | 0.211 | 1.38858 | 1.41 |
| C—Cl | 1 | 1 | (2)0.81317 | 14.63489 | 15.35946 | 0.165 | 1.79005 | 1.42 |
| C—Br | 1 | 1 | (2)0.74081 | 14.63489 | 15.35946 | 0.150 | 1.93381 | 1.40 |
| C—I[g] | 1 | 1 | (2)0.65537 | 14.63489 | 15.28545 | 0.119 | 2.13662 | 1.22 |
| C=O | 2 | 0.85395 | 1 | 14.63489 | 16.20002 | 0.385 | 1.20628 | 2.23 |
| C≡N | 3 | 0.91140 | 1 | 14.63489 | 16.20002 | 0.616 | 1.16221 | 3.44 |
| H—S[h] | 1 | 0.69878 | 1 | 14.63489 | 15.81768 | 0.118 | 1.34244 | 0.76 |
| C—S | 1 | 1 | 0.91771 | 14.63489 | 15.35946 | 0.093 | 1.81460 | 0.81 |
| S—O | 1 | 1 | 0.77641 | 14.63489 | 15.76868 | 0.125 | 1.56744 | 0.94 |
| S=O[i] | 2 | 0.82897 | 1 | 10.36001 | 11.57099 | 0.410 | 1.49118 | 2.94 |
| N—O | 1 | 1.06727 | 1 | 14.53414 | 14.82575 | 0.943 | 1.40582 | 0.29 |
| N=O (nitro) | 2 | 0.91140 | 1 | 14.63489 | 15.95955 | 0.345 | 1.22157 | 2.02 |
| C—P | 1 | 1 | 0.73885 | 14.63489 | 15.35946 | 0.975 | 1.86534 | 0.67 |
| P—O | 1 | 0.79401 | 1 | 14.63489 | 15.35946 | 0.081 | 1.61423 | 0.62 |
| P=O[j] | 2 | 1.25942 | 1 | 14.63489 | 15.76868 | 0.405 | 1.46521 | 2.85 |
| Si—H | 1 | 1 | 0.75800 | 10.25487 | 11.37682 | 0.131 | 1.48797 | 0.94 |
| Si—C | 1 | 1 | 0.70071 | 14.63489 | 15.35946 | 0.071 | 1.87675 | 0.64 |
| Si—O[k] | 1 | 1 | 1.32796 | 10.25487 | 10.87705 | 0.166 | 1.72480 | 1.38 |
| B—H[l] | 1 | 1.14361 | 1 | 11.80624 | 12.93364 | 0.172 | 1.20235 | 0.99 |
| B—C | 1 | 0.80672 | 1 | 14.63489 | 15.35946 | 0.082 | 1.57443 | 0.62 |
| B—O (alkoxy) | 1 | 1 | 0.79562 | 11.80624 | 12.93364 | 0.159 | 1.37009 | 1.05 |
| B—N | 1 | 1 | 0.81231 | 11.89724 | 14.53414 | 0.400 | 1.36257 | 2.62 |
| B—F[m] | 1 | 0.85447 | 1 | 14.88734 | 17.42282 | 0.316 | 1.29621 | 1.97 |
| B—Cl | 1 | 1 | 0.91044 | 11.80624 | 12.93364 | 0.182 | 1.76065 | 1.54 |

[a] The more positive atom is on the left.
[b] $c_2$ from Eqs. (15.77), (15.79), and Eq. (13.430) and $E_A$(valence) is given by 1/2 two $H_2$-type ellipsoidal MOs (Eq. (11.212)).
[c] $c_2$ from Eqs. (15.77), (15.79), and the product of 0.936127 (Eq. (13.248)) and 0.92235 given by 13.59844 eV/(13.59844 eV + 0.25 · $E_D$) where $E_D$ is the N—H bond energy $E_D$($^{14}$NH$_3$) = 4.57913 eV given by Eq. (13.404) and the energy of H is 13.59844 eV; $E_A$(valence) is given by 1/2 two $H_2$-type ellipsoidal MOs (Eq. (11.212)).
[d] $E_A$(valence) is given by 1/2 two $H_2$-type ellipsoidal MOs (Eq. (11.212)).
[e] $c_2$ from Eqs. (15.77) given by 13.59844 eV/(13.59844 eV + 0.25 · $E_D$) where $E_D$ is the O—H bond energy $E_D$(H$^{16}$OH) = 5.1059 eV given by Eq. (13.222)) and the energy of H is 13.59844 eV; $E_A$(valence) is given by 1/2 two $H_2$-type ellipsoidal MOs (Eq. (11.212)).
[f] Eq. (15.129) with the inverse energy ratio of E(F) = −17.42282 eV and E(C, 2sp$^3$) = −14.63489 eV corresponding to higher binding energy of the former.
[g] $E_A$(valence) is given by 15.35946 eV − 1/2$E_{mag}$ (Eqs. (14.150) and (15.67)).
[h] $c_1$ from Eqs. (15.79), (15.145), and (13.430); $E_A$(valence) is given by 1/2 two $H_2$-type ellipsoidal MOs (Eq. (11.212)).
[i] $c_2$ from the reciprocal of Eq. (15.147), $E_A$(valence) is given by Eq. (15.139), and $E_B$(valence) is E(S) = −10.36001 eV.
[j] $c_2$ from the reciprocal of Eq. (15.182).
[k] $c_2$ from the reciprocal of Eq. (20.49).
[l] $c_2$ from the reciprocal of Eq. (22.29).
[m] $c_2$ from Eq. (15.77) using E(F) = −17.42282 eV and E(B$_{B—Fborane}$, 2sp$^3$) = −14.88734 eV (Eq. (22.61)).

9. The system of claim 1 wherein interatomic and molecular binding is determined by electrical and electrodynamics forces wherein Coulombic-based bonding can be grouped into two main categories, bonding that comprises permanent dipole-dipole interactions further including an extreme case, hydrogen bonding, and bonding regarding reversible mutually induced dipole fields in near-neighbor collision-partner molecules called van der Waals bonding.

10. The system of claim 9 wherein structure and properties of liquids and solids are solved by first solving the unit cell of the condensed solid based on an energy minimum of the molecular interactions and their dependence on the packing.

11. The system of claim 10 wherein bonding in neutral condensed solids and liquids arises from Coulombic interactions between partial charges corresponding to dipoles of the molecules and atoms.

12. The system of claim 11 wherein the energy from the interaction of the partial charges increases as the separation decreases, but concomitantly, the energy of a bond that may form between the interacting species increases as well such that the equilibrium separation distance corresponds to the occurrence of the balance between the Coulombic potential energy of the interacting atoms and the energy of the nascent bond whose formation involves the interacting atoms.

13. The system of claim 12 wherein balance is at the energy threshold for the formation of a nascent bond that would replace the interacting partial charges while also destabilizing the standard bonds of the interacting molecules or cancel the Coulombic potential energy of interacting atoms wherein the general equation for the balance of the Coulombic energy and the nascent bond energy is given by $$\frac{-\delta^+\delta^- e^2}{4\pi\varepsilon_0 r_e} = \left[ \begin{pmatrix} -\frac{n_1 e^2}{8\pi\varepsilon_0 \sqrt{\frac{aa_0}{2C_1C_2}}} \left[ \frac{c_1 c_2 \left(2-\frac{a_0}{a}\right) \ln \frac{a+\sqrt{\frac{aa_0}{2C_1C_2}}}{a-\sqrt{\frac{aa_0}{2C_1C_2}}} -1 }{} \right] \\ E_T(\text{AO/HO}) + E_T(\text{atom—atom, msp}^3 \cdot \text{AO}) \end{pmatrix} \\ \left[ 1 + \sqrt{\frac{2\hbar\sqrt{\frac{C_{1o}C_{2o}e^2}{4\pi\varepsilon_o R^3}}}{m_e c^2}} \right] + \\ n_1 \frac{1}{2}\hbar \sqrt{\frac{\frac{c_1 c_2 e^2}{8\pi\varepsilon_0 a^3} - \frac{e^2}{8\pi\varepsilon_0 \left(a+\sqrt{\frac{aa_0}{2C_1C_2}}\right)^3}}{\mu}} \right]$$

where $\delta^+$ and $\delta^-$ are the partial charges of the interacting atoms, $r_3$, is the internuclear separation distance of the interacting atoms, $n_1$ is the number of equivalent bonds of the MO, $c_1$ is the fraction of the Hz-type ellipsoidal MO basis function, $c_2$ is the factor that results in an equipotential energy match of the participating at least two atomic orbitals of each chemical bond, $C_{1o}$ is the fraction of the $H_2$-type ellipsoidal MO basis function of the oscillatory transition state of a chemical bond of the group, and $C_{2o}$ is the factor that results in an equipotential energy match of the participating at least two atomic orbitals of the transition state of the chemical bond, $E_T(\text{AO/HO})$ is the total energy comprising the difference of the energy $E(\text{AO/HO})$ of at least one atomic or hybrid orbital to which the MO is energy matched and any energy component $\Delta E_{H_2MO}(\text{AO/HO})$ due to the AO or HO's charge donation to the MO, $E_T(\text{atom-atom,msp}^3.\text{AO})$ is the change in the energy of the AOs or HOs upon forming the bond, and p is the reduced mass.

14. The system of claim 13 wherein the a, b, and c parameters of the unit cell are solved, then the unit cell can be proliferated to arbitrary scale to render the solid.

15. The system of claim 14 wherein the liquid is given as linear combinations of units cells based on the solid cell whose structures and populations are based on statistical thermodynamical principles.

16. The system of claim 15 wherein the electric field in the material having an electric polarization density is determined, and in turn, the lattice energy is calculated from the energy of each dipole in the corresponding field using the electrostatic form of Gauss' equation.

17. The system of claim 16 wherein the polarization density corresponding to the aligned dipoles moments determines the electric field E:

$$E = \frac{-\mu \frac{\rho}{MW} N_A}{3\varepsilon_0}$$

wherein $\mu$ is the dipole moment, $\rho$ is the density, $N_A$ is the Avogadro constant, MW is the molecular weight, and $\epsilon_0$ is the permittivity of free space, and in turn, the energy U is calculated from the energy of each dipole in the corresponding field using the electrostatic form of Gauss' equation:

$$U = 2\mu \cdot E(H_2O) = \frac{-2(\mu)^2 \frac{\rho}{MW} N_A}{3\varepsilon_0}.$$

18. The system of claim 1 wherein reaction kinetics are modeled using thermal rate constants by solving the classical equations of motion with the formation of the transition state and any intermediate reaction complexes between the reactants and products on the trajectory between them.

19. The system of claim 18 wherein the transition state is the minimum energy complex involving the reactants; the activation energy $E_a$ can be interpreted as the minimum energy that the reactants must have in order to form the transition state and transform to product molecules, and $E_a$ is calculated from the total energy of the transition state relative to that of the reactants.

20. The system of claim 19 wherein the parameters of the transition state and any intermediate reaction complexes is solved using the equations of the corresponding functional group with the boundary conditions for the transition state and any intermediate reaction complexes.

21. The system of claim 20 wherein the equations of the functional groups are at least one of $$-\frac{n_1 e^2}{8\pi\varepsilon_0 \sqrt{\frac{aa_0}{2C_1C_2}}} \left[ \ln \frac{a+\sqrt{\frac{aa_0}{2C_1C_2}}}{a-\sqrt{\frac{aa_0}{2C_1C_2}}} - 1 \right] + E_T(\text{AO/HO}) = \quad (15.51)$$

$E$(basis energies)

-continued $$E_{T+osc}(\text{Group}) = E_T(\text{MO}) + E_{osc} \quad (15.61)$$

$$= \left( \left( -\frac{n_1 e^2}{8\pi\varepsilon_0 \sqrt{\frac{aa_0}{2C_1C_2}}} \left[ \frac{a + \sqrt{\frac{aa_0}{2C_1C_2}}}{a - \sqrt{\frac{aa_0}{2C_1C_2}}} - 1 \right] \right) \right)$$

$$E_T(\text{AO/HO}) = +E_T(\text{atom—atom, } msp^3 \cdot \text{AO})$$

$$\left[ 1 + \sqrt{\frac{2\hbar\sqrt{\frac{C_{1o}C_{2o}e^2}{4\pi\varepsilon_o R^3}}}{m_e c^2}} \right] + n_1 \frac{1}{2}\hbar\sqrt{\frac{k}{\mu}}$$

$$= \left( \begin{array}{c} E(\text{basis energies}) + \\ E_T(\text{atom—atom, } msp^3 \cdot \text{AO}) \end{array} \right)$$

$$\left[ 1 + \sqrt{\frac{2\hbar\sqrt{\frac{C_{1o}C_{2o}e^2}{4\pi\varepsilon_o R^3}}}{m_e c^2}} \right] + n_1 \frac{1}{2}\hbar\sqrt{\frac{k}{\mu}}.$$

22. A non-transitory computer readable medium containing instructions that when executed by at least one processor cause the at least one processor to perform operations for computing and rendering a nature of a chemical bond comprising physical, Maxwellian solutions of charge, mass, and current density functions of molecules, compounds, and materials and solving the dipole moment of at least one bond, the operations comprising:

inputting data into a system containing at least one processor regarding the atomic composition, positions, and excitation state of the molecule, compound, or material;

calculating a solution to Maxwellian equations, wherein the solution is a two dimensional spheroidal surface, wherein charge, mass, and current density functions are determined by evaluating the two dimensional spheroidal surface of molecules, compounds, and materials, and solving the dipole moment of at least one bond, and outputting the nature of the chemical bond comprising physical, Maxwellian solutions of charge, mass, and current density functions and the corresponding energy components of molecules, compounds, and materials to an output device in communication with the at least one processor;

wherein at least one processor calculates bond moment $\mu$ of a functional group by considering the charge donation between atoms of the functional group wherein the potential of an MO is that of a point charge at infinity such that an asymmetry in the distribution of charge between nonequivalent HOs or AOs of the MO occurs to maintain an energy match of the MO with the bridged orbitals and the charge redistribution between the spherical orbitals achieves a corresponding current-density that maintains constant current at the equivalent-energy condition according to an energy-matching factor, wherein the dipole moment of a given molecule is given by the vector sum of the bond moments in the molecule wherein the dipole moment is given by taking into account the magnitude and direction of the bond moment of each functional group wherein the function-group bond moment stays constant from molecule to molecule and is in the vector direction of the internuclear axis, and wherein at least one processor creates a molecular model based on the solutions derived from the Maxwellian equations and the dipole moment, and displays a three dimensional representation of the molecular model on the output device.

23. A method for computing and rendering a nature of a chemical bond comprising physical, Maxwellian solutions of charge, mass, and current density functions of molecules, compounds, and materials and solving the dipole moment of at least one bond, the method comprising:

inputting data into a system containing at least one processor regarding the atomic composition, positions, and excitation state of the molecule, compound, or material;

calculating a solution to Maxwellian equations, wherein the solution is a two dimensional spheroidal surface, wherein charge, mass, and current density functions are determined by evaluating the two dimensional spheroidal surface of molecules, compounds, and materials, and solving the dipole moment of at least one bond, and outputting the nature of the chemical bond comprising physical, Maxwellian solutions of charge, mass, and current density functions and the corresponding energy components of molecules, compounds, and materials to an output device in communication with the at least one processor;

wherein at least one processor calculates bond moment $\mu$ of a functional group by considering the charge donation between atoms of the functional group wherein the potential of an MO is that of a point charge at infinity such that an asymmetry in the distribution of charge between nonequivalent HOs or AOs of the MO occurs to maintain an energy match of the MO with the bridged orbitals and the charge redistribution between the spherical orbitals achieves a corresponding current-density that maintains constant current at the equivalent-energy condition according to an energy-matching factor, wherein the dipole moment of a given molecule is given by the vector sum of the bond moments in the molecule wherein the dipole moment is given by taking into account the magnitude and direction of the bond moment of each functional group wherein the function-group bond moment stays constant from molecule to molecule and is in the vector direction of the internuclear axis, and wherein at least one processor creates a molecular model based on the solutions derived from the Maxwellian equations and the dipole moment, and displays a three dimensional representation of the molecular model on the output device.

* * * * *